(12) United States Patent
Samal et al.

(10) Patent No.: US 10,383,936 B2
(45) Date of Patent: Aug. 20, 2019

(54) INFECTIOUS LARYNGOTRACHEITIS VIRUS (ILTV) VACCINE USING RECOMBINANT NEWCASTLE DISEASE VIRUS VECTOR

(71) Applicant: UNIVERSITY OF MARYLAND, College Park, MD (US)

(72) Inventors: Siba K. Samal, Hyattsville, MD (US); Mallikarjuna Kanabagatte Basavarajappa, Greenbelt, MD (US); Sweety Samal, Dwarka (IN)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 14/900,834

(22) PCT Filed: Jul. 21, 2014

(86) PCT No.: PCT/US2014/047395
§ 371 (c)(1),
(2) Date: Dec. 22, 2015

(87) PCT Pub. No.: WO2015/013178
PCT Pub. Date: Jan. 29, 2015

(65) Prior Publication Data
US 2017/0049880 A1 Feb. 23, 2017

Related U.S. Application Data

(60) Provisional application No. 61/857,558, filed on Jul. 23, 2013.

(51) Int. Cl.
| | | |
|---|---|---|
| *A61K 39/245* | (2006.01) | |
| *C12N 7/00* | (2006.01) | |
| *C07K 14/005* | (2006.01) | |
| *A61K 39/17* | (2006.01) | |
| *A61K 39/00* | (2006.01) | |

(52) U.S. Cl.
CPC ............ *A61K 39/245* (2013.01); *A61K 39/17* (2013.01); *C07K 14/005* (2013.01); *C12N 7/00* (2013.01); *A61K 2039/5256* (2013.01); *A61K 2039/552* (2013.01); *A61K 2039/70* (2013.01); *C12N 2710/16034* (2013.01); *C12N 2760/18121* (2013.01); *C12N 2760/18134* (2013.01); *C12N 2760/18143* (2013.01); *C12N 2760/18151* (2013.01)

(58) Field of Classification Search
None
See application file for complete search history.

(56) References Cited

U.S. PATENT DOCUMENTS

| | | | |
|---|---|---|---|
| 6,719,979 B2 * | 4/2004 | Peeters | C07K 14/005 424/186.1 |
| 8,932,604 B2 * | 1/2015 | Cook | A61K 39/245 424/184.1 |
| 2013/0101619 A1 * | 4/2013 | Cook | A61K 39/245 424/199.1 |

OTHER PUBLICATIONS

Samal (Role of fusion protein in Newcastle Disease Virus pathogenesis, PhD. Thesis, pp. 1-23, 2012).*
De Leeuw (GenBank accession No. AAC28374.1) Tong et al. (Avian Pathology, 2001, vol. 30, p. 143-148).*
Tong et al. (Avian Pathology, 2001, vol. 30, p. 143-148).*

* cited by examiner

*Primary Examiner* — Agnieszka Boesen
(74) *Attorney, Agent, or Firm* — Hodgson Russ LLP

(57) ABSTRACT

In this study, for the first time, protective efficacy of gD against ILTV challenge was evaluated. Immunization with recombinant Newcastle disease virus expressing ILTV gD induced a higher level of neutralizing antibodies and offered complete protection to chickens against lethal ILTV challenge. Uses of recombinant NDV as a vaccine vector are also described.

18 Claims, 5 Drawing Sheets
Specification includes a Sequence Listing.

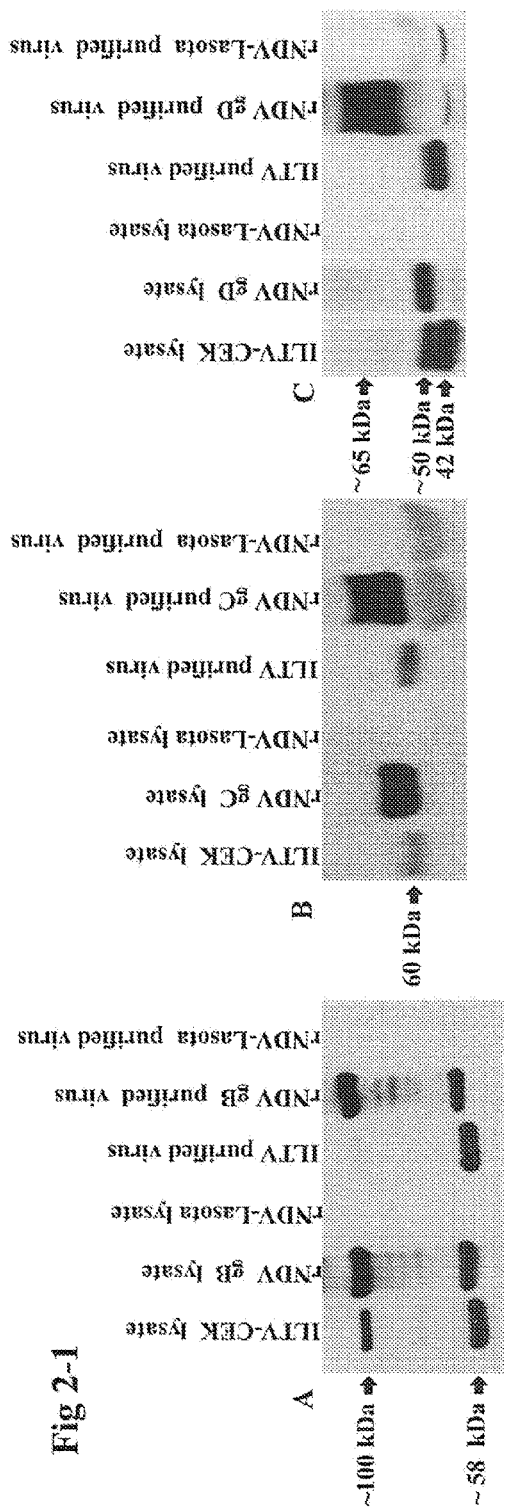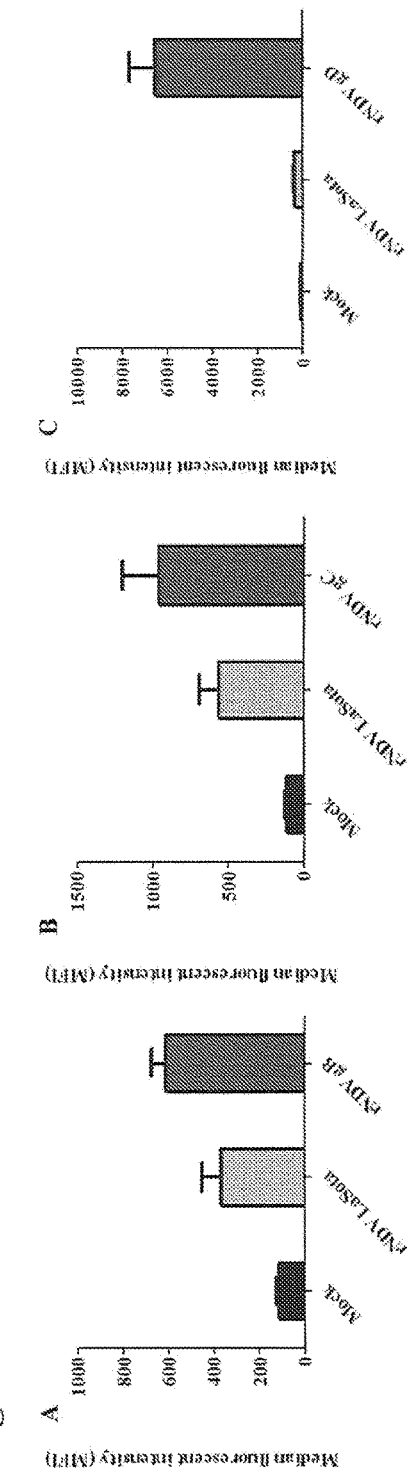
Fig 2-1
Fig 2-2

Virus growth in embryonated eggs

Fig 5-A
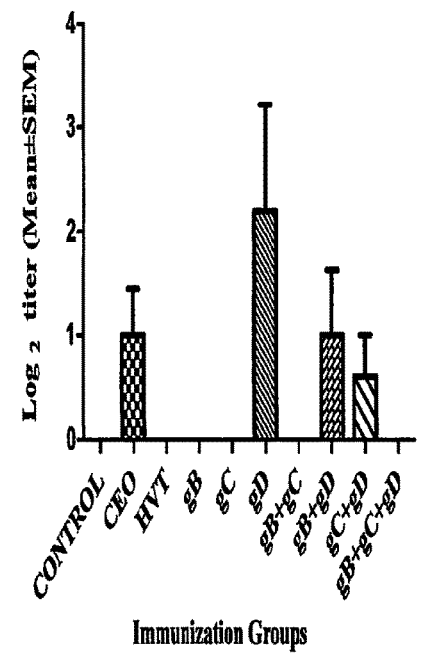
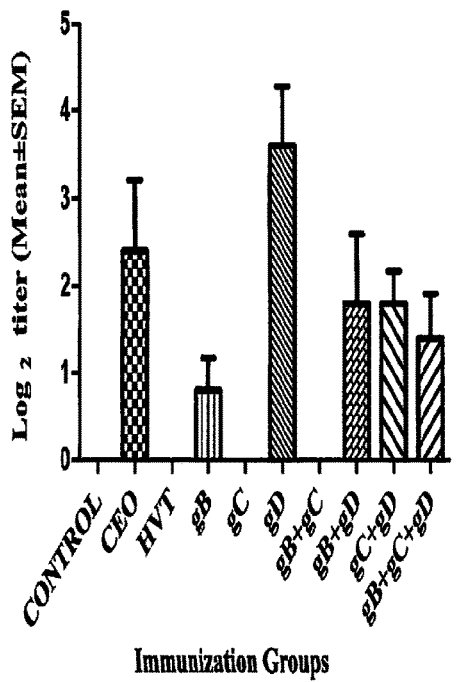
Fig 5-B
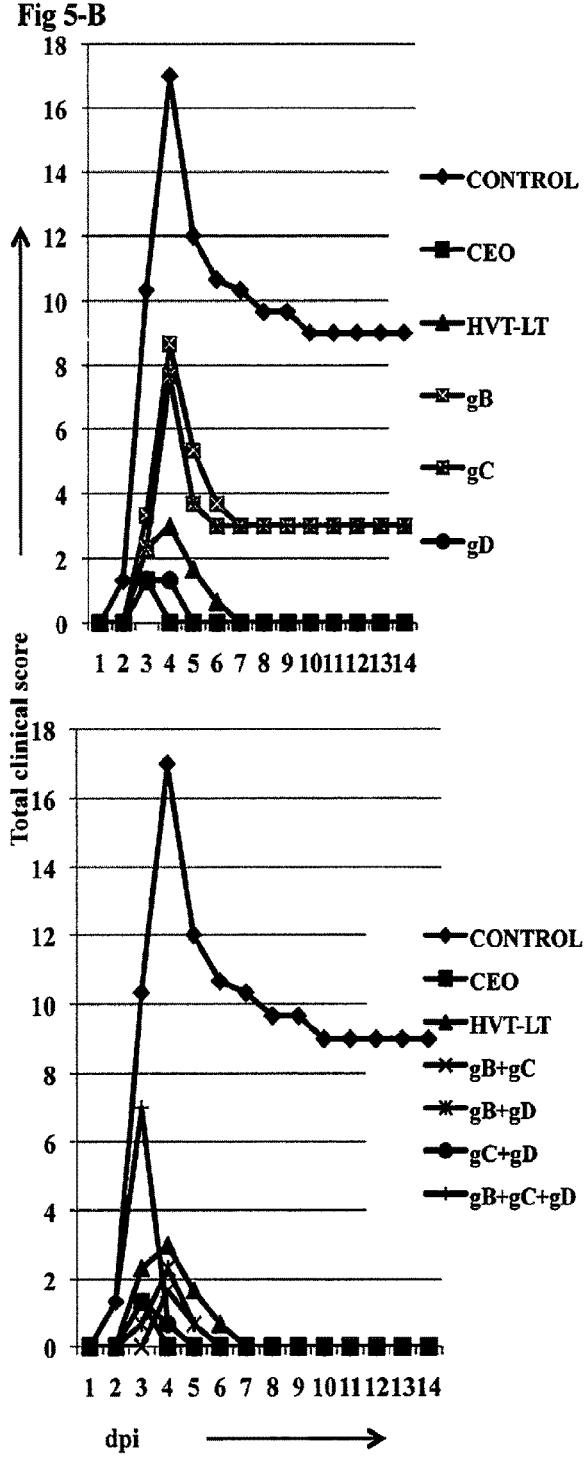

SEQUENCE LISTING

<160> NUMBER OF SEQ ID NOS: 27

<210> SEQ ID NO 1
<211> LENGTH: 2652
<212> TYPE: DNA
<213> ORGANISM: Infectious Laryngotracheitis Virus
<220> FEATURE:
<223> OTHER INFORMATION: gB

<400> SEQUENCE: 1
atgcaatcct acatcgccgt gaacattgac atggctagct tgaaaatgct                50

```
gatctgcgtg tgcgtggcaa tcctgatccc atctacccta tctcaagatt      100
cacacggaat tgctggaata atagaccctc gtgatacagc cagcatggat      150
gttggaaaaa tctctttctc cgaagccatt gggtcggggg caccgaaaga      200
accccagatt agaaacagaa tttttgcgtg ctcatctcca actggcgcca      250
gtgttgcgag gcttgcccag ccacgacatt gtcaccgaca tgccgattcg      300
actaacatga ctgaaggaat tgccgtagtc ttcaagcaaa acattgcccc      350
gtacgtcttt aatgtgactc tatactataa acatataacc acagttacta      400
cgtgggcatt attctcaaga ccccaaataa caaatgagta cgtgaccagg      450
gttccaatag actatcatga aattgtcagg attgatcgat cgggagaatg      500
ctcatccaaa gcaacgtatc ataaaaattt catgtttttt gaagcttacg      550
acaatgatga agcagaaaaa aaattgcccc tggttccatc actgttaaga      600
tcaactgtct ccaaggcgtt tcatacaact aactttacta agcgacatca      650
aaccctggga taccgaacgt ctacatcggt cgactgtgtt gtggaatatc      700
tacaggctag atctgtatac ccgtatgatt actttggaat ggcgacaggt      750
gatacagtag aaatttctcc tttttatacc aaaaacacga ccggaccaag      800
gcgtcacagt gtctacagag actatagatt tctcgaaatc gcaaattatc      850
aagtcaggga tttggaaacc ggacaaataa gaccccctaa aaaagaaac      900
tttctaacag atgaacaatt cactataggc tgggatgcaa tggaagaaaa      950
ggaatctgta tgtactctca gtaaatggat tgaagtcccg gaagcagttc      1000
gtgtttcgta caaaaacagt taccacttt cacttaaaga tatgactatg       1050
acgttctcgt ccgaaaaaca accttttaac atcagcaggc ttcatttggc      1100
tgaatgcgtt cctaccatag ccacggaggc catagatggc atctttgcca      1150
gaaagtatag ttcgactcat gtccgttctg gggacatcga atactatctc      1200
ggtagtggcg gatttctgat cgcatttcag aaactcatga gccatggctt      1250
ggctgaaatg tacctagaag aggcacaaag acaaaatcat ctcccgagag      1300
ggagagagcg tcgccaagcc gcaggtcgcc gcacggcgtc gctgcagtct      1350
ggacctcagg gtgatagaat tactacccac agttctgcaa catttgccat      1400
gttacaattt gcatacgaca aaatccaagc ccatgttaac gagcttatcg      1450
gaaatttgtt ggaagcgtgg tgtcagcttc agaaccgcca actgattgta      1500
tggcatgaga tgaagaaact aaacccgaac tcactgatga catctttgtt      1550
cggacaacct gtaagcgcca ggctattggg agacatcgta gcggtatcaa      1600
aatgtataga aattccaatc gaaaatatta ggatgcagga ttccatgcgc      1650
atgccagggg acccaaccat gtgctatacc agaccagtac ttattttcag      1700
gtattcgtcc tcccctgagt cacagttttc tgcgaactca acagaaaacc      1750
acaatcttga catattaggc caactcggag aacataatga aattttacaa      1800
gggcggaatt tgatagaacc atgcatgatc aatcacagac ggtactttct      1850
gttgggagaa aactaccttc tttacgaaga ctatacattt gttagacaag      1900
taaatgcttc cgagatcgaa gaagtgagca tattcatcaa cttgaacgcc      1950
actatactag aagatttgga ctttgtgccc gtcgaagtat acactcgcga      2000
ggaactcaga gatactggga cttttaaacta tgatgatgtg gtcagatatc      2050
```

```
aaaatattta taacaaaagg ttcagagaca ttgacactgt aatacgtgga      2100
gataggggag atgcaatctt tagagcaata gcagattttt ttggcaacac      2150
tcttggagaa gtaggaaagg cattgggaac tgtagtgatg acagccgcgg      2200
cagcagtaat ttctacagta tctggcatcg cctcatttct ttctaacccg      2250
ttcgccgcac tcggaattgg gatagcggtg gtggtgagca ttattttagg      2300
actgctggcg ttcaaatatg taatgaacct gaaatcaaac ccagttcagg      2350
ttctgttccc aggcgcagtt cccccggccg gaactcctcc acgaccctct      2400
agacgttact acaaggatga ggaggaggtt gaggaggata gtgatgagga      2450
cgacaggata cttgccacca gagttctgaa aggccttgag cttctacaca      2500
aggatgaaca gaaagctcga agacagaaag cgcggttttc tgcttttgct      2550
aaaaatatga gaaacctatt tcgcagaaaa ccccgaacca aggaagatga      2600
ctaccccctg ctcgaatacc cttcgtgggc agaagaaagc gaagacgaat      2650
aa                                                          2652
```

```

<210> SEQ ID NO 2
<211> LENGTH: 883
<212> TYPE: PRT
<213> ORGANISM: Infectious Laryngotracheitis Virus
<220> FEATURE:
<223> OTHER INFORMATION: gB

<400> SEQUENCE: 2

Met Gln Ser Tyr Ile Ala Val Asn Ile Asp Met Ala Ser Leu Lys
  1               5                  10                  15

Met Leu Ile Cys Val Cys Val Ala Ile Leu Ile Pro Ser Thr Leu
                 20                  25                  30

Ser Gln Asp Ser His Gly Ile Ala Gly Ile Ile Asp Pro Arg Asp
                 35                  40                  45

Thr Ala Ser Met Asp Val Gly Lys Ile Ser Phe Ser Glu Ala Ile
                 50                  55                  60

Gly Ser Gly Ala Pro Lys Glu Pro Gln Ile Arg Asn Arg Ile Phe
                 65                  70                  75

Ala Cys Ser Ser Pro Thr Gly Ala Ser Val Ala Arg Leu Ala Gln
                 80                  85                  90

Pro Arg His Cys His Arg His Ala Asp Ser Thr Asn Met Thr Glu
                 95                 100                 105

Gly Ile Ala Val Val Phe Lys Gln Asn Ile Ala Pro Tyr Val Phe
                110                 115                 120

Asn Val Thr Leu Tyr Tyr Lys His Ile Thr Thr Val Thr Thr Trp
                125                 130                 135

Ala Leu Phe Ser Arg Pro Gln Ile Thr Asn Glu Tyr Val Thr Arg
                140                 145                 150

Val Pro Ile Asp Tyr His Glu Ile Val Arg Ile Asp Arg Ser Gly
                155                 160                 165

Glu Cys Ser Ser Lys Ala Thr Tyr His Lys Asn Phe Met Phe Phe
                170                 175                 180

Glu Ala Tyr Asp Asn Asp Glu Ala Glu Lys Lys Leu Pro Leu Val
                185                 190                 195

Pro Ser Leu Leu Arg Ser Thr Val Ser Lys Ala Phe His Thr Thr
                200                 205                 210
```

```
Asn Phe Thr Lys Arg His Gln Thr Leu Gly Tyr Arg Thr Ser Thr
                215                 220                 225

Ser Val Asp Cys Val Val Glu Tyr Leu Gln Ala Arg Ser Val Tyr
                230                 235                 240

Pro Tyr Asp Tyr Phe Gly Met Ala Thr Gly Asp Thr Val Glu Ile
                245                 250                 255

Ser Pro Phe Tyr Thr Lys Asn Thr Thr Gly Pro Arg Arg His Ser
                260                 265                 270

Val Tyr Arg Asp Tyr Arg Phe Leu Glu Ile Ala Asn Tyr Gln Val
                275                 280                 285

Arg Asp Leu Glu Thr Gly Gln Ile Arg Pro Pro Lys Lys Arg Asn
                290                 295                 300

Phe Leu Thr Asp Glu Gln Phe Thr Ile Gly Trp Asp Ala Met Glu
                305                 310                 315

Glu Lys Glu Ser Val Cys Thr Leu Ser Lys Trp Ile Glu Val Pro
                320                 325                 330

Glu Ala Val Arg Val Ser Tyr Lys Asn Ser Tyr His Phe Ser Leu
                335                 340                 345

Lys Asp Met Thr Met Thr Phe Ser Ser Gly Lys Gln Pro Phe Asn
                350                 355                 360

Ile Ser Arg Leu His Leu Ala Glu Cys Val Pro Thr Ile Ala Thr
                365                 370                 375

Glu Ala Ile Asp Gly Ile Phe Ala Arg Lys Tyr Ser Ser Thr His
                380                 385                 390

Val Arg Ser Gly Asp Ile Glu Tyr Tyr Leu Gly Ser Gly Gly Phe
                395                 400                 405

Leu Ile Ala Phe Gln Lys Leu Met Ser His Gly Leu Ala Glu Met
                410                 415                 420

Tyr Leu Glu Glu Ala Gln Arg Gln Asn His Leu Pro Arg Gly Arg
                425                 430                 435

Glu Arg Arg Gln Ala Ala Gly Arg Arg Thr Ala Ser Leu Gln Ser
                440                 445                 450

Gly Pro Gln Gly Asp Arg Ile Thr Thr His Ser Ser Ala Thr Phe
                455                 460                 465

Ala Met Leu Gln Phe Ala Tyr Asp Lys Ile Gln Ala His Val Asn
                470                 475                 480

Glu Leu Ile Gly Asn Leu Leu Glu Ala Trp Cys Glu Leu Gln Asn
                485                 490                 495

Arg Gln Leu Ile Val Trp His Glu Met Lys Lys Leu Asn Pro Asn
                500                 505                 510

Ser Leu Met Thr Ser Leu Phe Gly Gln Pro Val Ser Ala Arg Leu
                515                 520                 525

Leu Gly Asp Ile Val Ala Val Ser Lys Cys Ile Glu Ile Pro Ile
                530                 535                 540

Glu Asn Ile Arg Met Gln Asp Ser Met Arg Met Pro Gly Asp Pro
                545                 550                 555

Thr Met Cys Tyr Thr Arg Pro Val Leu Ile Phe Arg Tyr Ser Ser
                560                 565                 570

Ser Pro Glu Ser Gln Phe Ser Ala Asn Ser Thr Glu Asn His Asn
                575                 580                 585

Leu Asp Ile Leu Gly Gln Leu Gly Glu His Asn Glu Ile Leu Gln
                590                 595                 600

Glu Arg Asn Leu Ile Glu Pro Cys Met Ile Asn His Arg Arg Tyr
```

```
                        605                 610                 615
Phe Leu Leu Gly Glu Asn Tyr Leu Leu Tyr Glu Asp Tyr Thr Phe
                620                 625                 630

Val Arg Gln Val Asn Ala Ser Glu Ile Glu Glu Val Ser Ile Phe
                635                 640                 645

Ile Asn Leu Asn Ala Thr Ile Leu Glu Asp Leu Asp Phe Val Pro
                650                 655                 660

Val Glu Val Tyr Thr Arg Glu Glu Leu Arg Asp Thr Gly Thr Leu
                665                 670                 675

Asn Tyr Asp Asp Val Val Arg Tyr Gln Asn Ile Tyr Asn Lys Arg
                680                 685                 690

Phe Arg Asp Ile Asp Thr Val Ile Arg Gly Asp Arg Gly Asp Ala
                695                 700                 705

Ile Phe Arg Ala Ile Ala Asp Phe Phe Gly Asn Thr Leu Gly Glu
                710                 715                 720

Val Gly Lys Ala Leu Gly Thr Val Val Met Thr Ala Ala Ala Ala
                725                 730                 735

Val Ile Ser Thr Val Ser Gly Ile Ala Ser Phe Leu Ser Asn Pro
                740                 745                 750

Phe Ala Ala Leu Gly Ile Gly Ile Ala Val Val Val Ser Ile Ile
                755                 760                 765

Leu Gly Leu Leu Ala Phe Lys Tyr Val Met Asn Leu Lys Ser Asn
                770                 775                 780

Pro Val Gln Val Leu Phe Pro Gly Ala Val Pro Pro Ala Gly Thr
                785                 790                 795

Pro Pro Arg Pro Ser Arg Arg Tyr Tyr Lys Asp Glu Glu Glu Val
                800                 805                 810

Glu Glu Asp Ser Asp Glu Asp Asp Arg Ile Leu Ala Thr Arg Val
                815                 820                 825

Leu Lys Gly Leu Glu Leu Leu His Lys Asp Glu Gln Lys Ala Arg
                830                 835                 840

Arg Gln Lys Ala Arg Phe Ser Ala Phe Ala Lys Asn Met Arg Asn
                845                 850                 855

Leu Phe Arg Arg Lys Pro Arg Thr Lys Glu Asp Asp Tyr Pro Leu
                860                 865                 870

Leu Glu Tyr Pro Ser Trp Ala Glu Glu Ser Glu Asp Glu
                875                 880

<210> SEQ ID NO 3
<211> LENGTH: 1245
<212> TYPE: DNA
<213> ORGANISM: Infectious Laryngotracheitis Virus
<220> FEATURE:
<223> OTHER INFORMATION: gC

<400> SEQUENCE: 3
atgcagcatc agagtactgc gctagtttcg agtatacttt tgctcttgag         50
cctgcaaagc cttgcgtttg aattttctg tgatccgcca cacgttttc            100 gagggcagct cggtgacccc attctattgc aatgcttcag cgacagacct         150
ctaacccacg aagaatctgt aaaagtagaa gtaattcgac acccagccag         200
cttagttgaa actgcgctaa gcgcctacgg gatcccccct tcgctagatc         250
catggagagc tactccaaga actctctaca catatgatgc cgctactgat         300
tcaatcaagg acctaggata cattggtgaa gatggaatta acccaccata         350
```

-continued

```
tttggacgac tgtcgttcag gttttttcaa tgtctctatc aagtctagca       400
tgagatctca catggcgcgt tatcagtgga ccgcaagtcg agggtctaca       450
aaactaaata gctctttat cgacgtcttt ttggcaagac cacctacaac        500
tgtccgcatc aaatcagaag aactgtacga agactcagat aaggcttcgc      550
acttaagtgt tgaagcgctt ggcgcttatc ctccatctgc tgcgctgggt      600
acatggatga tacataatgc atctcttgct gaaaaataca gtttagaaag      650
aagagttctt tatgcatcag gagagaatgg atcggtggat cagacatggg     700
aactggaaat acgtggagaa gccagccagc ccctcccttc caaaattcaa     750
tttgtatatc gatggacccc tcctgaggac tttgaaatgc tacgacctga     800
aactcgcttg ttaaggttga ctcccagctg gattagcaag ccccgcatca     850
cggtacaatt cgtccctcct gcctatgccc tgtgtagagc agctaatatt     900
atagacggcc gaggatttat tgaatggatc gtagataata gaatttcgac     950
gagcccacac cagaccttg ttttggatga gcccgagggg aaaaatatcg      1000
ttacactaat ggacgtcata aaactaccac cggaggatac atttcaatct     1050
gcctctaatt acgtgtgcgt cataagaggc tatgaacatg catacagata     1100
tctcaacgcc tccttaatga tagataatct gccaatgcgg caaggattcc     1150
ccgcagtcgc tgcgattttt attataatta gtatcgcttt tgtgggtggg     1200
ttactagttg cttgcttggg cgcatggtgc tggaagacaa cataa          1245
```

<210> SEQ ID NO 4
<211> LENGTH: 414
<212> TYPE: PRT
<213> ORGANISM: Infectious Laryngotracheitis Virus
<220> FEATURE:
<223> OTHER INFORMATION: gC

<400> SEQUENCE: 4

```
Met Gln His Gln Ser Thr Ala Leu Val Ser Ser Ile Leu Leu Leu
  1               5                  10                  15

Leu Ser Leu Gln Ser Leu Ala Phe Glu Phe Cys Asp Pro Pro
             20                  25                  30

His Val Phe Arg Gly Gln Leu Gly Asp Pro Ile Leu Leu Gln Cys
             35                  40                  45

Phe Ser Asp Arg Pro Leu Thr His Glu Glu Ser Val Lys Val Glu
             50                  55                  60

Val Ile Arg His Pro Ala Ser Leu Val Glu Thr Ala Leu Ser Ala
             65                  70                  75

Tyr Gly Ile Pro Pro Ser Leu Asp Pro Trp Arg Ala Thr Pro Arg
             80                  85                  90

Thr Leu Tyr Thr Tyr Asp Ala Ala Thr Asp Ser Ile Lys Asp Leu
             95                 100                 105

Gly Tyr Ile Gly Glu Asp Gly Ile Asn Pro Pro Tyr Leu Asp Asp
            110                 115                 120

Cys Arg Ser Gly Phe Phe Asn Val Ser Ile Lys Ser Ser Met Arg
            125                 130                 135

Ser His Met Ala Arg Tyr Gln Trp Thr Ala Ser Arg Gly Ser Thr
            140                 145                 150

Lys Leu Asn Ser Ser Phe Ile Asp Val Phe Leu Ala Arg Pro Pro
            155                 160                 165
```

| | | | | | | | | | | | |
|---|---|---|---|---|---|---|---|---|---|---|---|
|Thr|Thr|Val|Arg|Ile|Lys|Ser|Glu|Glu|Leu|Tyr|Glu Asp Ser Asp|
| | | |170| | |175| | | |180| |

Lys Ala Ser His Leu Ser Val Glu Ala Leu Gly Ala Tyr Pro Pro
            185                 190                 195

Ser Ala Ala Leu Gly Thr Trp Met Ile His Asn Ala Ser Leu Ala
            200                 205                 210

Glu Lys Tyr Ser Leu Glu Arg Arg Val Leu Tyr Ala Ser Gly Glu
            215                 220                 225

Asn Gly Ser Val Asp Gln Thr Trp Glu Leu Glu Ile Arg Gly Glu
            230                 235                 240

Asn Ser Gln Pro Leu Pro Ser Lys Ile Gln Phe Val Tyr Arg Trp
            245                 250                 255

Thr Pro Pro Glu Asp Phe Glu Met Leu Arg Pro Glu Thr Arg Leu
            260                 265                 270

Leu Arg Leu Thr Pro Ser Trp Ile Ser Lys Pro Arg Ile Thr Val
            275                 280                 285

Gln Phe Val Pro Pro Ala Tyr Ala Leu Cys Arg Ala Ala Asn Ile
            290                 295                 300

Ile Asp Gly Arg Gly Phe Ile Glu Trp Ile Val Asp Asn Arg Ile
            305                 310                 315

Ser Thr Ser Pro His Gln Thr Phe Val Leu Asp Glu Pro Glu Gly
            320                 325                 330

Lys Asn Ile Val Thr Leu Met Asp Val Ile Lys Leu Pro Pro Glu
            335                 340                 345

Asp Thr Phe Gln Ser Ala Ser Asn Tyr Val Cys Val Ile Arg Gly
            350                 355                 360

Tyr Glu His Ala Tyr Arg Tyr Leu Asn Ala Ser Leu Met Ile Asp
            365                 370                 375

Asn Leu Pro Met Arg Gln Gly Phe Pro Ala Val Ala Ala Ile Phe
            380                 385                 390

Ile Ile Ile Ser Ile Ala Phe Val Gly Gly Leu Leu Val Ala Cys
            395                 400                 405

Leu Gly Ala Trp Cys Trp Lys Thr Thr
            410

<210> SEQ ID NO 5
<211> LENGTH: 1134
<212> TYPE: DNA
<213> ORGANISM: Infectious Laryngotracheitis Virus
<220> FEATURE:
<223> OTHER INFORMATION: gD

<400> SEQUENCE: 5

```
atggaccgcc atttattttt gaggaatgct ttttggacta tcgtactgct                50
ttcttccttc gctagccaga gcaccgccgc cgtcacgtac gactacattt               100
taggccgtcg cgcgctcgac gcgctaacca taccggcggt tggcccgtat               150
aacagatacc tcactagggt atcaagaggc tgcgacgttg tcgagctcaa               200
cccgatttct aacgtggacg acatgatatc ggcggccaaa gaaaaagaga               250
aggggggccc tttcgaggcc tccgtcgtct ggttctacgt gattaagggc               300
gacgacggcg aggacaagta ctgtccaatc tatagaaaag agtacaggga               350
atgtggcgac gtacaactgc tatctgaatg cgccgttcaa tctgcacaga               400
tgtgggcagt ggactatgtt cctagcaccc ttgtatcgcg aaatggcgcg               450
```

```
ggactgacta tattctcccc cactgctgcg ctctctggcc aatacttgct      500
gaccctgaaa atcgggagat tgcgcaaac agctctcgta actctagaag       550
ttaacgatcg ctgtttaaag atcgggtcgc agcttaactt tttaccgtcg      600
aaatgctgga caacgaaca gtatcagact ggatttcaag gcgaacacct       650
ttatccgatc gcagacacca atacacgaca cgcggacgac gtatatcggg      700
gatacgaaga tattctgcag cgctggaata atttgctgag gaaaaagaat      750
cctagcgcgc cagaccctcg tccagatagc gtcccgcaag aaattccgc       800 tgtaaccaag aaagcggaag gcgcacccc ggacgcagaa agcagcgaaa       850
agaaggcccc tccagaagac tcggaggacg acatgcaggc agaggcttct      900
ggagaaaatc ctgccgccct ccccgaagac gacgaagtcc ccgaggacac      950
cgagcacgat gatccaaact cggatcctga ctattacaat gacatgcccg     1000
ccgtgatccc ggtggaggag actactaaaa gttctaatgc cgtctccatg     1050
cccatattcg cggcgttcgt agcctgcgcg gtcgcgctcg tggggctact     1100
ggtttggagc atcgtaaaat gcgcgcgtag ctaa                      1134
```

```
<210> SEQ ID NO 6
<211> LENGTH: 377
<212> TYPE: PRT
<213> ORGANISM: Infectious Laryngotracheitis Virus
<220> FEATURE:
<223> OTHER INFORMATION: gD

<400> SEQUENCE: 6

Met Asp Arg His Leu Phe Leu Arg Asn Ala Phe Trp Thr Ile Val
  1               5                  10                  15

Leu Leu Ser Ser Phe Ala Ser Gln Ser Thr Ala Ala Val Thr Tyr
                 20                  25                  30

Asp Tyr Ile Leu Gly Arg Arg Ala Leu Asp Ala Leu Thr Ile Pro
                 35                  40                  45

Ala Val Gly Pro Tyr Asn Arg Tyr Leu Thr Arg Val Ser Arg Gly
                 50                  55                  60

Cys Asp Val Val Glu Leu Asn Pro Ile Ser Asn Val Asp Asp Met
                 65                  70                  75

Ile Ser Ala Ala Lys Glu Lys Glu Lys Gly Gly Pro Phe Glu Ala
                 80                  85                  90

Ser Val Val Trp Phe Tyr Val Lys Gly Asp Gly Glu Asp
                 95                 100                 105

Lys Tyr Cys Pro Ile Tyr Arg Lys Glu Tyr Arg Glu Cys Gly Asp
                110                 115                 120

Val Gln Leu Leu Ser Glu Cys Ala Val Gln Ser Ala Gln Met Trp
                125                 130                 135

Ala Val Asp Tyr Val Pro Ser Thr Leu Val Ser Arg Asn Gly Ala
                140                 145                 150

Gly Leu Thr Ile Phe Ser Pro Thr Ala Ala Leu Ser Gly Gln Tyr
                155                 160                 165

Leu Leu Thr Leu Lys Ile Gly Arg Phe Ala Gln Thr Ala Leu Val
                170                 175                 180

Thr Leu Glu Val Asn Asp Arg Cys Leu Lys Ile Gly Ser Gln Leu
                185                 190                 195

Asn Phe Leu Pro Ser Lys Cys Trp Thr Thr Glu Gln Tyr Gln Thr
```

```
                        200                 205                 210
Gly Phe Gln Gly Glu His Leu Tyr Pro Ile Ala Asp Thr Asn Thr
                215                 220                 225

Arg His Ala Asp Asp Val Tyr Arg Gly Tyr Glu Asp Ile Leu Gln
                230                 235                 240

Arg Trp Asn Asn Leu Leu Arg Lys Lys Asn Pro Ser Ala Pro Asp
                245                 250                 255

Pro Arg Pro Asp Ser Val Pro Gln Glu Ile Pro Ala Val Thr Lys
                260                 265                 270

Lys Ala Glu Gly Arg Thr Pro Asp Ala Glu Ser Ser Glu Lys Lys
                275                 280                 285

Ala Pro Pro Glu Asp Ser Glu Asp Asp Met Gln Ala Glu Ala Ser
                290                 295                 300

Gly Glu Asn Pro Ala Ala Leu Pro Glu Asp Asp Glu Val Pro Glu
                305                 310                 315

Asp Thr Glu His Asp Asp Pro Asn Ser Asp Pro Asp Tyr Tyr Asn
                320                 325                 330

Asp Met Pro Ala Val Ile Pro Val Glu Glu Thr Thr Lys Ser Ser
                335                 340                 345

Asn Ala Val Ser Met Pro Ile Phe Ala Ala Phe Val Ala Cys Ala
                350                 355                 360

Val Ala Leu Val Gly Leu Leu Val Trp Ser Ile Val Lys Cys Ala
                365                 370                 375

Arg Ser

<210> SEQ ID NO 7
<211> LENGTH: 61
<212> TYPE: DNA
<213> ORGANISM: Artificial sequence
<220> FEATURE:
<223> OTHER INFORMATION: gBF, forward primer

<400> SEQUENCE: 7
gatcttaatt aattagaaaa aatacgggta gaaggccacc atgcaatcct             50
acatcgccgt g                                                      61

<210> SEQ ID NO 8
<211> LENGTH: 69
<212> TYPE: DNA
<213> ORGANISM: Artificial sequence
<220> FEATURE:
<223> OTHER INFORMATION: gBR, reverse primer

<400> SEQUENCE: 8
gatcttaatt aatcacattt ttgtagtggc tctcatctga tctagagtat             50
tttcgtcttc gctttcttc                                               69

<210> SEQ ID NO 9
<211> LENGTH: 61
<212> TYPE: DNA
<213> ORGANISM: Artificial sequence
<220> FEATURE:
<223> OTHER INFORMATION: gCF, forward primer

<400> SEQUENCE: 9
gatcttaatt aattagaaaa aatacgggta gaaggccacc atgcagcatc             50
agagtactgc g                                                      61
```

<210> SEQ ID NO 10
<211> LENGTH: 46
<212> TYPE: DNA
<213> ORGANISM: Artificial sequence
<220> FEATURE:
<223> OTHER INFORMATION: gC2, forward primer

<400> SEQUENCE: 10
caatgcggca aggattcccc gcagtcagca catctgctct cattac          46

<210> SEQ ID NO 11
<211> LENGTH: 42
<212> TYPE: DNA
<213> ORGANISM: Artificial sequence
<220> FEATURE:
<223> OTHER INFORMATION: gCR, reverse primer

<400> SEQUENCE: 11
gatcttaatt aatcacattt ttgtagtggc tctcatctga tc              42

<210> SEQ ID NO 12
<211> LENGTH: 66
<212> TYPE: DNA
<213> ORGANISM: Artificial sequence
<220> FEATURE:
<223> OTHER INFORMATION: gDF, forward primer

<400> SEQUENCE: 12
gatcttaatt aattagaaaa aatacgggta gaaggccgcc accatggacc       50
gccatttatt tttgag                                           66

<210> SEQ ID NO 13
<211> LENGTH: 24
<212> TYPE: DNA
<213> ORGANISM: Artificial sequence
<220> FEATURE:
<223> OTHER INFORMATION: gD1, reverse primer

<400> SEQUENCE: 13
gggcatggag acggcattag aact                                  24

<210> SEQ ID NO 14
<211> LENGTH: 46
<212> TYPE: DNA
<213> ORGANISM: Artificial sequence
<220> FEATURE:
<223> OTHER INFORMATION: gD2, forward primer

<400> SEQUENCE: 14
agttctaatg ccgtctccat gcccagcaca tctgctctca ttacct          46

<210> SEQ ID NO 15
<211> LENGTH: 42
<212> TYPE: DNA
<213> ORGANISM: Artificial sequence
<220> FEATURE:
<223> OTHER INFORMATION: gDR, reverse primer

<400> SEQUENCE: 15
gatcttaatt aatcacattt ttgtagtggc tctcatctga tc              42

<210> SEQ ID NO 16
<211> LENGTH: 21775
<212> TYPE: DNA
<213> ORGANISM: Artificial sequence
<220> FEATURE:

<223> OTHER INFORMATION: pNDV gB

<400> SEQUENCE: 16

```
ttcggcgcgc ctaatacgac tcactatagg gaccaaacag agaatccgtg      50
atttacgata ttcggcgcgc ctaatacgac tcactatagg gaccaaacag     100
agaatccgtg atttacgata aaaggcgaaa gagcaattga agtcgcacgg     150
gtagaaggtg tgaatctcga gtgcgagccc gaagcacaaa ctcgagaaag     200
ccttctgcca acatgtcttc cgtatttgat gagtacgaac agctcctcgc     250
ggctcagact cgccccaatg gagctcatgg agggggagaa aaagggagta     300
ccttaaaagt agacgtcccg gtattcactc ttaacagtga tgacccagaa     350
gatagatgga gctttgtggt attctgcctc cggattgctg ttagcgaaga     400
tgccaacaaa ccactcaggc aaggtgctct catatctctt ttatgctccc     450
actcacaggt aatgaggaac catgttgccc ttgcagggaa acagaatgaa     500
gccacattgg ccgtgcttga gattgatggc tttgccaacg gcacgcccca     550
gttcaacaat aggagtggag tgtctgaaga gagagcacag agatttgcga     600
tgatagcagg atctctccct cgggcatgca gcaacggaac cccgttcgtc     650
acagccgggg ccgaagatga tgcaccagaa gacatcaccg ataccctgga     700
gaggatcctc tctatccagg ctcaagtatg ggtcacagta gcaaaagcca     750
tgactgcgta tgagactgca gatgagtcgg aaacaaggcg aatcaataag     800
tatatgcagc aaggcagggt ccaaaagaaa tacatcctct accccgtatg     850
caggagcaca atccaactca cgatcagaca gtctcttgca gtccgcatct     900
ttttggttag cgagctcaag agaggccgca acacggcagg tggtacctct     950
acttattata acctggtagg ggacgtagac tcatacatca ggaataccgg    1000
gcttactgca ttcttcttga cactcaagta cggaatcaac accaagacat    1050
cagcccttgc acttagtagc ctctcaggcg acatccagaa gatgaagcag    1100
ctcatgcgtt tgtatcggat gaaaggagat aatgcgccgt acatgacatt    1150
acttggtgat agtgaccaga tgagctttgc gcctgccgag tatgcacaac    1200
tttactccct tgccatgggt atggcatcag tcctagataa aggtactggg    1250
aaataccaat ttgccaggga ctttatgagc acatcattct ggagacttgg    1300
agtagagtac gctcaggctc agggaagtag cattaacgag gatatggctg    1350
ccgagctaaa gctaacccca gcagcaagga ggggcctggc agctgctgcc    1400
caacgggtct ccgaggagac cagcagcata gacatgccta ctcaacaagt    1450
cggagtcctc actgggctta gcgagggggg gtcccaagct ctacaaggcg    1500
gatcgaatag atcgcaaggg caaccagaag ccggggatgg ggagacccaa    1550
ttcctggatc tgatgagagc ggtagcaaat agcatgaggg aggcgccaaa    1600
ctctgcacag ggcactcccc aatcggggcc tcccccaact cctgggccat    1650
cccaagataa cgacaccgac tgggggtatt gatggacaaa acccagcctg    1700
cttccacaaa aacatcccaa tgccctcacc cgtagtcgac ccctcgattt    1750
gcggctctat atgaccacac cctcaaacaa acatccccct ctttcctccc    1800
tcccccctgct gtacaactcc gcacgcccta gataccacag gcacaatgcg    1850
gctcactaac aatcaaaaca gagccgaggg aattagaaaa aagtacgggt    1900
```

| | |
|---|---|
| agaagaggga tattcagaga tcagggcaag tctcccgagt ctctgctctc | 1950 |
| tcctctacct gatagaccag gacaaacatg gccaccttta cagatgcaga | 2000 |
| gatcgacgag ctatttgaga caagtggaac tgtcattgac aacataatta | 2050 |
| cagcccaggt taaaccagca gagactgttg gaaggagtgc aatcccacaa | 2100 |
| ggcaagacca aggtgctgag cgcagcatgg gagaagcatg ggagcatcca | 2150 |
| gccaccggcc agtcaagaca accccgatcg acaggacaga tctgacaaac | 2200 |
| aaccatccac acccgagcaa cgaccccgc atgacagccc gccggccaca | 2250 |
| tccgccgacc agcccccac ccaggccaca gacgaagccg tcgacacaca | 2300 |
| gctcaggacc ggagcaagca actctctgct gttgatgctt gacaagctca | 2350 |
| gcaataaatc gtccaatgct aaaaagggcc catggtcgag cccccaagag | 2400 |
| gggaatcacc aacgtccgac tcaacagcag gggagtcaac ccagccgcgg | 2450 |
| aaacagtcag gaaagaccgc agaaccaagt caaggccgcc cctggaaacc | 2500 |
| agggcacaga cgtgaacaca gcatatcatg gacaatggga ggagtcacaa | 2550 |
| ctatcagctg gtgcaacccc tcatgctctc cgatcaaggc agagccaaga | 2600 |
| caataccctt gtatctgcgg atcatgtcca gccacctgta gactttgtgc | 2650 |
| aagcgatgat gtctatgatg gaggcgatat cacagagagt aagtaaggtc | 2700 |
| gactatcagc tagatcttgt cttgaaacag acatcctcca tccctatgat | 2750 |
| gcggtccgaa atccaacagc tgaaaacatc tgttgcagtc atggaagcca | 2800 |
| acttgggaat gatgaagatt ctggatcccg gttgtgccaa catttcatct | 2850 |
| ctgagtgatc tacgggcagt tgcccgatct cacccggttt tagtttcagg | 2900 |
| ccctggagac ccctctccct atgtgacaca aggaggcgaa atggcactta | 2950 |
| ataaactttc gcaaccagtg ccacatccat ctgaattgat taaacccgcc | 3000 |
| actgcatgcg ggcctgatat aggagtggaa aaggacactg tccgtgcatt | 3050 |
| gatcatgtca cgcccaatgc acccgagttc ttcagccaag ctcctaagca | 3100 |
| agttagatgc agccgggtcg atcgaggaaa tcaggaaaat caagcgcctt | 3150 |
| gctctaaatg gctaattact actgccacac gtagcgggtc cctgtccact | 3200 |
| cggcatcaca cggaatctgc accgagttcc ccccgcaga cccaaggtcc | 3250 |
| aactctccaa gcggcaatcc tctctcgctt cctcagcccc actgaatgat | 3300 |
| cgcgtaaccg tttaattaat tagaaaaaat acgggtagaa ggccaccatg | 3350 |
| caatcctaca tcgccgtgaa cattgacatg gctagcttga aaatgctgat | 3400 |
| ctgcgtgtgc gtggcaatcc tgatcccatc taccctatct caagattcac | 3450 |
| acggaattgc tggaataata gaccctcgtg atacagccag catggatgtt | 3500 |
| ggaaaaatct ctttctccga agccattggg tcggggcac cgaaagaacc | 3550 |
| ccagattaga aacagaattt ttgcgtgctc atctccaact ggcgccagtg | 3600 |
| ttgcgaggct tgcccagcca cgacattgtc accgacatgc cgattcgact | 3650 |
| aacatgactg aaggaattgc cgtagtcttc aagcaaaaca ttgccccgta | 3700 |
| cgtctttaat gtgactctat actataaaca tataaccaca gttactacgt | 3750 |
| gggcattatt ctcaagaccc caaataacaa atgagtacgt gaccagggtt | 3800 |
| ccaatagact atcatgaaat tgtcaggatt gatcgatcgg gagaatgctc | 3850 |
| atccaaagca acgtatcata aaaatttcat gttttttgaa gcttacgaca | 3900 |

| | |
|---|---|
| atgatgaagc agagaagaag ttgcccctgg ttccatcact gttaagatca | 3950 |
| actgtctcca aggcgtttca tacaactaac tttactaagc gacatcaaac | 4000 |
| cctgggatac cgaacgtcta catcggtcga ctgtgttgtg gaatatctac | 4050 |
| aggctagatc tgtatacccg tatgattact ttggaatggc gacaggtgat | 4100 |
| acagtagaaa tttctccttt ttataccaaa aacacgaccg gaccaaggcg | 4150 |
| tcacagtgtc tacagagact atagatttct cgaaatcgca aattatcaag | 4200 |
| tcagggattt ggaaaccgga caaataagac cccctaaaaa agaaacttt | 4250 |
| ctaacagatg aacaattcac tataggctgg gatgcaatgg aagaaaagga | 4300 |
| atctgtatgt actctcagta aatggattga agtcccggaa gcagttcgtg | 4350 |
| tttcgtacaa aaacagttac cacttttcac ttaaagatat gactatgacg | 4400 |
| ttctcgtccg gaaacaacc ttttaacatc agcaggcttc atttggctga | 4450 |
| atgcgttcct accatagcca cggaggccat agatggcatc tttgccagaa | 4500 |
| agtatagttc gactcatgtc cgttctgggg acatcgaata ctatctcggt | 4550 |
| agtggcggat ttctgatcgc atttcagaaa ctcatgagcc atggcttggc | 4600 |
| tgaaatgtac ctagaagagg cacaaagaca aaatcatctc ccgagaggga | 4650 |
| gagagcgtcg ccaagccgca ggtcgccgca cggcgtcgct gcagtctgga | 4700 |
| cctcagggtg atagaattac tacccacagt tctgcaacat ttgccatgtt | 4750 |
| acaatttgca tacgacaaaa tccaagccca tgttaacgag cttatcggaa | 4800 |
| atttgttgga agcgtggtgt gagcttcaga accgccaact gattgtatgg | 4850 |
| catgagatga agaaactaaa cccgaactca ctgatgacat ctttgttcgg | 4900 |
| acaacctgta agcgccaggc tattgggaga catcgtagcg gtatcaaaat | 4950 |
| gtatagaaat tccaatcgaa aatattagga tgcaggattc catgcgcatg | 5000 |
| ccaggggacc caaccatgtg ctataccaga ccagtactta ttttcaggta | 5050 |
| ttcgtcctcc cctgagtcac agtttttctgc gaactcaaca gaaaaccaca | 5100 |
| atcttgacat attaggccaa ctcggagaac ataatgaaat tttacaaggg | 5150 |
| cggaatttga tagaaccatg catgatcaat cacagacggt actttctgtt | 5200 |
| gggagaaaac taccttcttt acgaagacta tacatttgtt agacaagtaa | 5250 |
| atgcttccga gatcgaagaa gtgagcatat tcatcaactt gaacgccact | 5300 |
| atactagaag atttggactt tgtgcccgtc gaagtataca ctcgcgagga | 5350 |
| actcagagat actgggactt taaactatga tgatgtggtc agatatcaaa | 5400 |
| atatttataa caaaaggttc agagacattg acactgtaat acgtggagat | 5450 |
| aggggagatg caatctttag agcaatagca gattttttg gcaacactct | 5500 |
| tggagaagta ggaaaggcat tgggaactgt agtgatgaca gccgcggcag | 5550 |
| cagtaatttc tacagtatct ggcatcgcct catttctttc taacccgttc | 5600 |
| gccgcactcg gaattgggat agcggtggtg gtgagcatta ttttaggact | 5650 |
| gctggcgttc aaatatgtaa tgaacctgaa atcaaaccca gttcaggttc | 5700 |
| tgttcccagg cgcagttccc ccggccggaa ctcctccacg accctctaga | 5750 |
| cgttactaca aggatgagga ggaggttgag gaggatagtg atgaggacga | 5800 |
| caggatactt gccaccagag ttctgaaagg ccttgagctt ctacacaagg | 5850 |

```
atgaacagaa agctcgaaga cagaaagcgc ggttttctgc ttttgctaaa      5900
aatatgagaa acctatttcg cagaaaaccc cgaaccaagg aagatgacta      5950
cccctgctc gaatacccctt cgtgggcaga agaaagcgaa gacgaaaata     6000
ctctagatca gatgagagcc actacaaaaa tgtgattaat taatagctac     6050
atttaagatt aagaaaaaat acgggtagaa ttggagtgcc ccaattgtgc     6100
caagatggac tcatctagga caattgggct gtactttgat tctgcccatt     6150
cttctagcaa cctgttagca tttccgatcg tcctacaaga cacaggagat     6200
gggaagaagc aaatcgcccc gcaatatagg atccagcgcc ttgacttgtg     6250
gactgatagt aaggaggact cagtattcat caccacctat ggattcatct     6300
ttcaagttgg gaatgaagaa gccactgtcg gcatgatcga tgataaaccc     6350
aagcgcgagt tactttccgc tgcgatgctc tgcctaggaa gcgtcccaaa     6400
taccggagac cttattgagc tggcaagggc ctgtctcact atgatagtca     6450
catgcaagaa gagtgcaact aatactgaga gaatggtttt ctcagtagtg     6500
caggcacccc aagtgctgca aagctgtagg gttgtggcaa acaaatactc     6550
atcagtgaat gcagtcaagc acgtgaaagc gccagagaag attcccggga     6600
gtggaaccct agaatacaag gtgaactttg tctccttgac tgtggtaccg     6650
aagaaggatg tctacaagat cccagctgca gtattgaagg tttctggctc     6700
gagtctgtac aatcttgcgc tcaatgtcac tattaatgtg gaggtagacc     6750
cgaggagtcc tttggttaaa tctctgtcta agtctgacag cggatactat     6800
gctaacctct tcttgcatat tggacttatg accaccgtag ataggaaggg     6850
gaagaaagtg acatttgaca agctggaaaa gaaaataagg agccttgatc     6900
tatctgtcgg gctcagtgat gtgctcgggc cttccgtgtt ggtaaaagca     6950
agaggtgcac ggactaagct tttggcacct ttcttctcta gcagtgggac     7000
agcctgctat cccatagcaa atgcttctcc tcaggtggcc aagatactct     7050
ggagtcaaac cgcgtgcctg cggagcgtta aaatcattat ccaagcaggt     7100
acccaacgcg ctgtcccagt gacccccaac caccaggtta cctctactaa     7150
gctggagaag gggcacaccc ttgccaaata caatccttt aagaaataag      7200
ctgcgtctct gagattgcgc tccgcccact cacccggatc atcatgacac     7250
aaaaaactaa tctgtcttga ttatttacag ttagtttacc tgtctatcaa     7300
gttagaaaaa acacgggtag aagattctgg atcccggttg gcgccctcca     7350
ggtgcaagat gggctccaga ccttctacca agaacccagc acctatgatg     7400
ctgactatcc gggttgcgct ggtactgagt tgcatctgtc cggcaaactc     7450
cattgatggc aggcctcttg cagctgcagg aattgtggtt acaggagaca     7500
aagccgtcaa catatacacc tcatcccaga caggatcaat catagttaag     7550
ctcctcccga atctgcccaa ggataaggag gcatgtgcga aagccccctt     7600
ggatgcatac aacaggacat tgaccacttt gctcaccccc cttggtgact     7650
ctatccgtag gatacaagag tctgtgacta catctggagg ggggagacag     7700
gggcgcctta taggcgccat tattggcggt gtggctcttg gggttgcaac     7750
tgccgcacaa ataacagcgg ccgcagctct gatacaagcc aaacaaaatg     7800
ctgccaacat cctccgactt aaagagagca ttgccgcaac caatgaggct     7850
```

-continued

```
gtgcatgagg tcactgacgg attatcgcaa ctagcagtgg cagttgggaa         7900
gatgcagcag tttgttaatg accaatttaa taaaacagct caggaattag         7950
actgcatcaa aattgcacag caagttggtg tagagctcaa cctgtaccta         8000
accgaattga ctacagtatt cggaccacaa atcacttcac ctgctttaaa         8050
caagctgact attcaggcac tttacaatct agctggtgga aatatggatt         8100
acttattgac taagttaggt gtagggaaca atcaactcag ctcattaatc         8150
ggtagcggct taatcaccgg taaccctatt ctatacgact cacagactca         8200
actcttgggt atacaggtaa ctctaccttc agtcggaaac ctaaataata         8250
tgcgtgccac ctacttggaa accttatccg taagcacaac caggggattt         8300
gcctcggcac ttgtcccaaa agtggtgaca caggtcggtt ctgtgataga         8350
agaacttgac acctcatact gtatagaaac tgacttagat ttatattgta         8400
caagaatagt aacgttccct atgtcccctg gtatttattc ctgcttgagc         8450
ggcaatacgt cggcctgtat gtactcaaag accgaaggcg cacttactac         8500
accatacatg actatcaaag gttcagtcat cgccaactgc aagatgacaa         8550
catgtagatg tgtaaacccc ccgggtatca tatcgcaaaa ctatggagaa         8600
gccgtgtctc taatagataa acaatcatgc aatgttttat ccttaggcgg         8650
gataacttta aggctcagtg gggaattcga tgtaacttat cagaagaata         8700
tctcaataca agattctcaa gtaataataa caggcaatct tgatatctca         8750
actgagcttg ggaatgtcaa caactcgatc agtaatgctt tgaataagtt         8800
agaggaaagc aacagaaaac tagacaaagt caatgtcaaa ctgaccagca         8850
catctgctct cattacctat atcgttttga ctatcatatc tcttgttttt         8900
ggtatactta gcctgattct agcatgctac ctaatgtaca agcaaaaggc         8950
gcaacaaaag accttattat ggcttgggaa taatactcta gatcagatga         9000
gagccactac aaaaatgtga acacagatga ggaacgaagg tttccctaat         9050
agtaatttgt gtgaaagttc tggtagtctg tcagttcaga gagttaagaa         9100
aaaactacgc gttgtagatg accaaaggac gatatacggg tagaacggta         9150
agagaggccg cccctcaatt gcgagccagg cttcacaacc tccgttctac         9200
cgcttcaccg acaacagtcc tcaatcatgg accgcgccgt tagccaagtt         9250
gcgttagaga atgatgaaag agaggcaaaa atacatggc gcttgatatt         9300 ccggattgca atcttattct taacagtagt gaccttggct atatctgtag         9350
cctccctttt atatagcatg ggggctagca cacctagcga tcttgtaggc         9400
ataccgacta ggatttccag ggcagaagaa aagattacat ctacacttgg         9450
ttccaatcaa gatgtagtag ataggatata taagcaagtg gcccttgagt         9500
ctccgttggc attgttaaaa actgagacca caattatgaa cgcaataaca         9550
tctctctctt atcagattaa tggagctgca acaacagtg ggtgggggc          9600 acctatccat gacccagatt atatagggg gataggcaaa gaactcattg          9650
tagatgatgc tagtgatgtc acatcattct atccctctgc atttcaagaa         9700
catctgaatt ttatcccggc gcctactaca ggatcaggtt gcactcgaat         9750
accctcattt gacatgagtg ctacccatta ctgctacacc cataatgtaa         9800
```

```
tattgtctgg atgcagagat cactcacatt catatcagta tttaggactt      9850
ggtgtgctcc ggacatctgc aacagggagg gtattcttt ctactctgcg       9900 ttccatcaac ctggacgaca cccaaaatcg gaagtcttgc agtgtgagtg      9950
caactcccct gggttgtgat atgctgtgct cgaaagtcac ggagacagag     10000
gaagaagatt ataactcagc tgtccctacg cggatggtac atgggaggtt    10050
agggttcgac ggccagtacc acgaaaagga cctagatgtc acaacattat     10100
tcggggactg ggtggccaac tacccaggag taggggtgg atctttat       10150 gacagccgcg tatggttctc agtctacgga gggttaaaac ccaattcacc    10200
cagtgacact gtacaggaag ggaaatatgt gatatacaag cgatacaatg    10250
acacatgccc agatgagcaa gactaccaga ttcgaatggc caagtcttcg    10300
tataagcctg gacggtttgg tgggaaacgc atacagcagg ctatcttatc    10350
tatcaaggtg tcaacatcct taggcgaaga cccggtactg actgtaccgc    10400
ccaacacagt cacactcatg ggggccgaag gcagaattct cacagtaggg    10450
acatctcatt tcttgtatca acgagggtca tcatacttct ctcccgcgtt    10500
attatatcct atgacagtca gcaacaaaac agccactctt catagtcctt    10550
atacattcaa tgccttcact cggccaggta gtatcccttg ccaggcttca    10600
gcaagatgcc ccaacccgtg tgttactgga ctctatacag atccatatcc    10650
cctaatcttc tatagaaacc acaccttgcg aggggtattc gggacaatgc    10700
ttgatggtgt acaagcaaga cttaaccctg cgtctgcagt attcgatagc    10750
acatcccgca gtcgcattac tcgagtgagt tcaagcagta ccaaagcagc    10800
atacacaaca tcaacttgtt ttaaagtggt caagactaat aagacctatt    10850
gtctcagcat tgctgaaata tctaatactc tcttcggaga attcagaatc    10900
gtcccgttac tagttgagat cctcaaagat gacggggtta gagaagccag    10950
gtctggctag ttgagtcaat tataaaggag ttggaaagat ggcattgtat    11000
cacctatctt ctgcgacatc aagaatcaaa ccgaatgccg gcgcgtgctc    11050
gaattccatg ttgccagttg accacaatca gccagtgctc atgcgatcag    11100
attaagcctt gtcaatagtc tcttgattaa gaaaaaatgt aagtggcaat    11150
gagatacaag gcaaaatacg taccggtaaa taatacgggt aggacatggc    11200
gagctccggt cctgaaaggg cagagcatca gattatccta ccagagtcac    11250
acctgtcttc accattggtc aagcacaaac tactctatta ctggaaatta    11300
actgggctac cgcttcctga tgaatgtgac ttcgaccacc tcattctcag    11350
ccgacaatgg aaaaaaatac ttgaatcggc ctctcctgat actgagagaa    11400
tgataaaact cggaagggca gtacaccaaa ctcttaacca caattccaga    11450
ataaccggag tgctccaccc caggtgttta aagaactgg ctaatattga     11500 ggtcccagat tcaaccaaca aatttcggaa gattgagaag aagatccaaa    11550
ttcacaacac gagatatgga gaactgttca caaggctgtg tacgcatata    11600
gagaagaaac tgctggggtc atcttggtct aacaatgtcc cccggtcaga    11650
ggagttcagc agcattcgta cggatccggc attctggttt cactcaaaat    11700
ggtccacagc caagtttgca tggctccata taaaacagat ccagaggcat    11750
ctgatggtgg cagctaggac aaggtctgcg gccaacaaat tggtgatgct    11800
```

```
aacccataag gtaggccaag tctttgtcac tcctgaactt gtcgttgtga    11850
cgcatacgaa tgagaacaag ttcacatgtc ttacccagga acttgtattg    11900
atgtatgcag atatgatgga gggcagagat atggtcaaca taatatcaac    11950
cacggcggtg catctcagaa gcttatcaga gaaaattgat gacattttgc    12000
ggttaataga cgctctggca aaagacttgg gtaatcaagt ctacgatgtt    12050
gtatcactaa tggagggatt tgcatacgga gctgtccagc tactcgagcc    12100
gtcaggtaca tttgcaggag atttcttcgc attcaacctg caggagctta    12150
aagacattct aattggcctc ctccccaatg atatagcaga atccgtgact    12200
catgcaatcg ctactgtatt ctctggttta gaacagaatc aagcagctga    12250
gatgttgtgt ctgttgcgtc tgtggggtca cccactgctt gagtcccgta    12300
ttgcagcaaa ggcagtcagg agccaaatgt gcgcaccgaa aatggtagac    12350
tttgatatga tccttcaggt actgtctttc ttcaagggaa caatcatcaa    12400
cgggtacaga aagaagaatg caggtgtgtg gccgcgagtc aaagtggata    12450
caatatatgg gaaggtcatt gggcaactac atgcagattc agcagagatt    12500
tcacacgata tcatgttgag agagtataag agtttatctg cacttgaatt    12550
tgagccatgt atagaatatg accctgtcac aaacctgagc atgttcctaa    12600
aagacaaggc aatcgcacac cccaacgata attggcttgc ctcgtttagg    12650
cggaaccttc tctccgaaga ccagaagaaa catgtaaaag aagcaacttc    12700
gactaatcgc ctcttgatag agttttttaga gtcaaatgat tttgatccat    12750
ataaagagat ggaatatctg acgacccttg agtaccttag agatgacaat    12800
gtggcagtat catactcgct caaggagaag gaagtgaaag ttaatggacg    12850
gatcttcgct aagctgacaa agaagttaag gaactgtcag gtcatggcgg    12900
aagggatcct agccgatcag attgcacctt tctttcaggg aaatggagtc    12950
attcaggata gcatatcctt gaccaagagt atgctagcga tgagtcaact    13000
gtcttttaac agcaataaga aacgtatcac tgactgtaaa gaaagagtat    13050
cttcaaaccg caatcatgat ccgaaaagca agaaccgtcg gagagttgca    13100
accttcataa caactgacct gcaaaagtac tgtcttaatt ggagatatca    13150
gacaatcaaa ttgttcgctc atgccatcaa tcagttgatg ggcctacctc    13200
acttcttcga atggattcac ctaagactga tggacactac gatgttcgta    13250
ggagacccct tcaatcctcc aagtgacccct actgactgtg acctctcaag    13300
agtccctaat gatgacatat atattgtcag tgccagaggg ggtatcgaag    13350
gattatgcca gaagctatgg acaatgatct caattgctgc aatccaactt    13400
gctgcagcta gatcgcattg tcgtgttgcc tgtatggtac agggtgataa    13450
tcaagtaata gcagtaacga gagaggtaag atcagacgac tgtccggaga    13500
tggtgttgac acagttgcat caagccagtg ataatttctt caaggaatta    13550
attcatgtca atcatttgat tggccataat ttgaaggatc gtgaaaccat    13600
caggtcagac acattcttca tatacagcaa acgaatcttc aaagatggag    13650
caatcctcag tcaagtcctc aaaaattcat ctaaattagt gctagtgtca    13700
ggtgatctca gtgaaaacac cgtaatgtcc tgtgccaaca ttgcctctac    13750
```

```
tgtagcacgg ctatgcgaga acgggcttcc caaagacttc tgttactatt    13800
taaactatat aatgagttgt gtgcagacat actttgactc tgagttctcc    13850
atcaccaaca attcgcaccc cgatcttaat cagtcgtgga ttgaggacat    13900
ctcttttgtg cactcatatg ttctgactcc tgcccaatta gggggactga    13950
gtaaccttca atactcaagg ctctacacta gaaatatcgg tgacccgggg    14000
actactgctt ttgcagagat caagcgacta gaagcagtgg gattactgag    14050
tcctaacatt atgactaata tcttaactag gccgcctggg aatggagatt    14100
gggccagtct gtgcaacgac ccatactctt tcaattttga gactgttgca    14150
agcccaaata ttgttcttaa gaaacatacg caaagagtcc tatttgaaac    14200
ttgttcaaat cccttattgt ctggagtgca cacagaggat aatgaggcag    14250
aagagaaggc attggctgaa ttcttgctta atcaagaggt gattcatccc    14300
cgcgttgcgc atgccatcat ggaggcaagc tctgtaggta ggagaaagca    14350
aattcaaggg cttgttgaca caacaaacac cgtaattaag attgcgctta    14400
ctaggaggcc attaggcatc aagaggctga tgcggatagt caattattct    14450
agcatgcatg caatgctgtt tagagacgat gttttttcct ccagtagatc    14500
caaccacccc ttagtctctt ctaatatgtg ttctctgaca ctggcagact    14550
atgcacggaa tagaagctgg tcacctttga cgggaggcag gaaaatactg    14600
ggtgtatcta atcctgatac gatagaactc gtagagggtg agattcttag    14650
tgtaagcgga gggtgtacaa gatgtgacag cggagatgaa caatttactt    14700
ggttccatct tccaagcaat atagaattga ccgatgacac cagcaagaat    14750
cctccgatga gggtaccata tctcgggtca aagacacagg agaggagagc    14800
tgcctcactt gcaaaaatag ctcatatgtc gccacatgta aaggctgccc    14850
taagggcatc atccgtgttg atctgggctt atggggataa tgaagtaaat    14900
tggactgctg ctcttacgat tgcaaaatct cggtgcaatg taaacttaga    14950
gtatcttcgg ttactgtccc ctttacccac ggctgggaat cttcaacata    15000
gactagatga tggtataact cagatgacat tcacccctgc atctctctac    15050
agggtgtcac cttacattca catatccaat gattctcaaa ggctgttcac    15100
tgaagaagga gtcaaagagg ggaatgtggt ttaccaacag atcatgctct    15150
tgggtttatc tctaatcgaa tcgatctttc caatgacaac aaccaggaca    15200
tatgatgaga tcacactgca cctacatagt aaatttagtt gctgtatcag    15250
agaagcacct gttgcggttc ctttcgagct acttggggtg gtaccggaac    15300
tgaggacagt gacctcaaat aagtttatgt atgatcctag ccctgtatcg    15350
gagggagact ttgcgagact tgacttagct atcttcaaga gttatgagct    15400
taatctggag tcatatccca cgatagagct aatgaacatt ctttcaatat    15450
ccagcgggaa gttgattggc cagtctgtgg tttcttatga tgaagatacc    15500
tccataaaga atgacgccat aatagtgtat gacaataccc gaaattggat    15550
cagtgaagct cagaattcag atgtggtccg cctatttgaa tatgcagcac    15600
ttgaagtgct cctcgactgt tcttaccaac tctattatct gagagtaaga    15650
ggcctagaca atattgtctt atatatgggt gatttataca agaatatgcc    15700
aggaattcta ctttccaaca ttgcagctac aatatctcat cccgtcattc    15750
```

```
attcaaggtt acatgcagtg ggcctggtca accatgacgg atcacaccaa      15800
cttgcagata cggattttat cgaaatgtct gcaaaactat tagtatcttg      15850
cacccgacgt gtgatatccg gcttatattc aggaaataag tatgatctgc      15900
tgttcccatc tgtcttagat gataacctga atgagaagat gcttcagctg      15950
atatcccggt tatgctgtct gtacacggta ctctttgcta caacaagaga      16000
aatcccgaaa ataagaggct taactgcaga agagaaatgt tcaatactca      16050
ctgagtattt actgtcggat gctgtgaaac cattacttag ccccgatcaa      16100
gtgagctcta tcatgtctcc taacataatt acattcccag ctaatctgta      16150
ctacatgtct cggaagagcc tcaatttgat cagggaaagg aggacaggg       16200
atactatcct ggcgttgttg ttcccccaag agccattatt agagttccct      16250
tctgtgcaag atattggtgc tcgagtgaaa gatccattca cccgacaacc      16300
tgcggcattt ttgcaagagt tagatttgag tgctccagca aggtatgacg      16350
cattcacact tagtcagatt catcctgaac tcacatctcc aaatccggag      16400
gaagactact tagtacgata cttgttcaga gggatagga ctgcatcttc       16450
ctcttggtat aaggcatctc atctcctttc tgtacccgag gtaagatgtg      16500
caagacacgg gaactcctta tacttagctg aagggagcgg agccatcatg      16550
agtcttctcg aactgcatgt accacatgaa actatctatt acaatacgct      16600
cttttcaaat gagatgaacc ccccgcaacg acatttcggg ccgaccccaa      16650
ctcagttttt gaattcggtt gtttatagga atctacaggc ggaggtaacc      16700
tgcaaagatg gatttgtcca agagttccgt ccattatgga gagaaaatac      16750
agaggaaagt gacctgacct cagataaagc agtggggtat attacatctg      16800
cagtgcccta cagatctgta tcattgctgc attgtgacat tgaaattcct      16850
ccagggtcca atcaaagctt actagatcaa ctagctatca atttatctct      16900
gattgccatg cattctgtaa gggagggcgg ggtagtaatc atcaaagtgt      16950
tgtatgcaat gggatactac tttcatctac tcatgaactt gtttgctccg      17000
tgttccacaa aaggatatat tctctctaat ggttatgcat gtcgaggaga      17050
tatggagtgt tacctggtat ttgtcatggg ttacctgggc gggcctacat      17100
ttgtacatga ggtggtgagg atggcaaaaa ctctggtgca gcggcacggt      17150
acgcttttgt ctaaatcaga tgagatcaca ctgaccaggt tattcacctc      17200
acagcggcag cgtgtgacag acatcctatc cagtccttta ccaagattaa      17250
taaagtactt gaggaagaat attgacactg cgctgattga agccggggga      17300
cagcccgtcc gtccattctg tgcggagagt ctggtgagca cgctagcgaa      17350
cataactcag ataacccaga tcatcgctag ccacattgac acagttatcc      17400
ggtctgtgat atatatggaa gctgagggtg atctcgctga cacagtattt      17450
ctatttaccc cttacaatct ctctactgac gggaaaaaga ggacatcact      17500
taaacagtgc acgagacaga tcctagaggt tacaatacta ggtcttagag      17550
tcgaaaatct caataaaata ggcgatataa tcagcctagt gcttaaaggc      17600
atgatctcca tggaggacct tatcccacta aggacatact tgaagcatag      17650
tacctgccct aaatatttga aggctgtcct aggtattacc aaactcaaag      17700
```

```
aaatgtttac agacacttct gtactgtact tgactcgtgc tcaacaaaaa      17750
ttctacatga aaactatagg caatgcagtc aaaggatatt acagtaactg      17800
tgactcttaa cgaaaatcac atattaatag gctcctttt tggccaattg       17850 tattcttgtt gatttaatca tattatgtta gaaaaaagtt gaaccctgac      17900
tccttaggac tcgaattcga actcaaataa atgtcttaaa aaaggttgc       17950 gcacaattat tcttgagtgt agtctcgtca ttcaccaaat cttggttggg      18000
tcggcatggc atctccacct cctcgcggtc cgacctgggc atccgaagga      18050
ggacgcacgt ccactcggat ggctaaggga gagcctgcag tagcataacc      18100
ccttggggcc tctaaacggg tcttgagggg ttttttgctg aaaggaggaa      18150
ctatatactc gagctgcagc aatggcaaca acgttgcgca aactattaac      18200
tggcgaacta cttactctag cttcccggca acaattaata gactggatgg      18250
aggcggataa agttgcagga ccacttctgc gctcggccct tccggctggc      18300
tggtttattg ctgataaatc tggagccggt gagcgtgggt ctcgcggtat      18350
cattgcagca ctggggccag atggtaagcc ctcccgtatc gtagttatct      18400
acacgacggg gagtcaggca actatggatg aacgaaatag acagatcgct      18450
gagataggtg cctcactgat taagcattgg taactgtcag accaagttta      18500
ctcatatata ctttagattg atttaaaact tcatttttaa tttaaaagga      18550
tctaggtgaa gatcctttt gataatctca tgaccaaaat cccttaacgt       18600
gagttttcgt tccactgagc gtcagacccc gtagaaaaga tcaaaggatc      18650
ttcttgagat ccttttttc tgcgcgtaat ctgctgcttg caaacaaaaa       18700
aaccaccgct accagcggtg gtttgtttgc cggatcaaga gctaccaact      18750
ctttttccga aggtaactgg cttcagcaga gcgcagatac caaatactgt      18800
ccttctagtg tagccgtagt taggccacca cttcaagaac tctgtagcac      18850
cgcctacata cctcgctctg ctaatcctgt taccagtggc tgctgccagt      18900
ggcgataagt cgtgtcttac cgggttggac tcaagacgat agttaccgga      18950
taaggcgcag cggtcgggct gaacggggg ttcgtgcaca cagcccagct       19000
tggagcgaac gacctacacc gaactgagat acctacagcg tgagctatga      19050
gaaagcgcca cgcttcccga agggagaaag gcggacaggt atccggtaag      19100
cggcagggtc ggaacaggag agcgcacgag ggagcttcca gggggaaacg      19150
cctggtatct ttatagtcct gtcgggtttc gccacctctg acttgagcgt      19200
cgatttttgt gatgctcgtc aggggggcgg agcctatgga aaaacgccag      19250
caacgcggcc tttttacggt tcctggcctt ttgctggcct tttgctcaca      19300
tgttctttcc tgcgttatcc cctgattctg tggataaccg tattaccgcc      19350
tttgagtgag ctgataccgc tcgccgcagc cgaacgaccg agcgcagcga      19400
gtcagtgagc gaggaagcgg aagagcgcct gatgcggtat tttctcctta      19450
cgcatctgtg cggtatttca caccgcatat ggtgcactct cagtacaatc      19500
tgctctgatg ccgcatagtt aagccagtat acactccgct atcgctacgt      19550
gactgggtca tggctgcgcc ccgacacccg ccaacacccg ctgacgcgcc      19600
ctgacgggct tgtctgctcc cggcatccgc ttacagacaa gctgtgaccg      19650
tctccgggag ctgcatgtgt cagaggtttt caccgtcatc accgaaacgc      19700
```

```
gcgaggcagc tgcggtaaag ctcatcagcg tggtcgtgaa gcgattcaca    19750
gatgtctgcc tgttcatccg cgtccagctc gttgagtttc tccagaagcg    19800
ttaatgtctg gcttctgata aagcgggcca tgttaagggc ggtttttcc     19850 tgtttggtca ctgatgcctc cgtgtaaggg ggatttctgt tcatgggggt    19900
aatgataccg atgaaacgag agaggatgct cacgatacgg gttactgatg    19950
atgaacatgc ccggttactg gaacgttgtg agggtaaaca actggcggta    20000
tggatgcggc gggaccagag aaaaatcact caggtcaat gccagcgctt     20050 cgttaataca gatgtaggtg ttccacaggg tagccagcag catcctgcga    20100
tgcagatccg gaacataatg gtgcagggcg ctgacttccg cgtttccaga    20150
ctttacgaaa cacggaaacc gaagaccatt catgttgttg ctcaggtcgc    20200
agacgttttg cagcagcagt cgcttcacgt tcgctcgcgt atcggtgatt    20250
cattctgcta accagtaagg caaccccgcc agcctagccg ggtcctcaac    20300
gacaggagca cgatcatgcg cacccgtggc caggacccaa cgctgcccga    20350
gatgcgccgc gtgcggctgc tggagatggc ggacgcgatg gatatgttct    20400
gccaagggtt ggtttgcgca ttcacagttc tccgcaagaa ttgattggct    20450
ccaattcttg gagtggtgaa tccgttagcg aggtgccgcc ggcttccatt    20500
caggtcgagg tggcccggct ccatgcaccg cgacgcaacg cggggaggca    20550
gacaaggtat agggcggcgc ctacaatcca tgccaacccg ttccatgtgc    20600
tcgccgaggc ggcataaatc gccgtgacga tcagcggtcc agtgatcgaa    20650
gttaggctgg taagagccgc gagcgatcct tgaagctgtc cctgatggtc    20700
gtcatctacc tgcctggaca gcatggcctg caacgcgggc atcccgatgc    20750
cgccggaagc gagaagaatc ataatgggga aggccatcca gcctcgcgtc    20800
gcgaacgcca gcaagacgta gcccagcgcg tcggccgcca tgccggcgat    20850
aatggcctgc ttctcgccga aacgtttggt ggcgggacca gtgacgaagg    20900
cttgagcgag ggcgtgcaag attccgaata ccgcaagcga caggccgatc    20950
atcgtcgcgc tccagcgaaa gcggtcctcg ccgaaaatga cccagagcgc    21000
tgccggcacc tgtcctacga gttgcatgat aaagaagaca gtcataagtg    21050
cggcgacgat agtcatgccc cgcgcccacc ggaaggagct gactgggttg    21100
aaggctctca agggcatcgg tcgacgctct cccttatgcg actcctgcat    21150
taggaagcag cccagtagta ggttgaggcc gttgagcacc ccgccgcaa    21200 ggaatggtgc atgcaaggag atggcgccca acagtccccc ggccacgggg    21250
cctgccacca tacccacgcc gaaacaagcg ctcatgagcc cgaagtggcg    21300
agcccgatct tccccatcgg tgatgtcggc gatataggcg ccagcaaccg    21350
cacctgtggc gccggtgatg ccggccacga tgcgtccggc gtagaggatc    21400
cacaggacgg gtgtggtcgc catgatcgcg tagtcgatag tggctccaag    21450
tagcgaagcg agcaggactg gcggcgcc aaagcggtcg acagtgctc       21500 cgagaacggg tgcgcataga aattgcatca acgcatatag cgctagcagc    21550
acgccatagt gactggcgat gctgtcggaa tggacgatat cccgcaagag    21600
gcccggcagt accggcataa ccaagcctat gcctacagca tccagggtga    21650
```

| | |
|---|---|
| cggtgccgag gatgacgatg agcgcattgt tagatttcat acacggtgcc | 21700 |
| tgactgcgtt agcaatttaa ctgtgataaa ctaccgcatt aaagcttatc | 21750 |
| gatgataagc tgtcaaacat gagaa | 21775 |

<210> SEQ ID NO 17
<211> LENGTH: 20359
<212> TYPE: DNA
<213> ORGANISM: Artificial sequence
<220> FEATURE:
<223> OTHER INFORMATION: pNDV gC

<400> SEQUENCE: 17

| | |
|---|---|
| ttcggcgcgc ctaatacgac tcactatagg gaccaaacag agaatccgtg | 50 |
| atttacgata aaaggcgaaa gagcaattga agtcgcacgg gtagaaggtg | 100 |
| tgaatctcga gtgcgagccc gaagcacaaa ctcgagaaag ccttctgcca | 150 |
| acatgtcttc cgtatttgat gagtacgaac agctcctcgc ggctcagact | 200 |
| cgccccaatg gagctcatgg aggggagaa aaagggagta cccttaaagt | 250 |
| agacgtcccg gtattcactc ttaacagtga tgacccagaa gatagatgga | 300 |
| gctttgtggt attctgcctc cggattgctg ttagcgaaga tgccaacaaa | 350 |
| ccactcaggc aaggtgctct catatctctt ttatgctccc actcacaggt | 400 |
| aatgaggaac catgttgccc ttgcagggaa acagaatgaa gccacattgg | 450 |
| ccgtgcttga gattgatggc tttgccaacg gcacgcccca gttcaacaat | 500 |
| aggagtggag tgtctgaaga gagagcacag agatttgcga tgatagcagg | 550 |
| atctctccct cgggcatgca gcaacggaac cccgttcgtc acagccgggg | 600 |
| ccgaagatga tgcaccagaa gacatcaccg atacccctgga gaggatcctc | 650 |
| tctatccagg ctcaagtatg ggtcacagta gcaaaagcca tgactgcgta | 700 |
| tgagactgca gatgagtcgg aaacaaggcg aatcaataag tatatgcagc | 750 |
| aaggcagggt ccaaaagaaa tacatcctct accccgtatg caggagcaca | 800 |
| atccaactca cgatcagaca gtctcttgca gtccgcatct ttttggttag | 850 |
| cgagctcaag agaggccgca acacggcagg tggtacctct acttattata | 900 |
| acctggtagg ggacgtagac tcatacatca ggaataccgg gcttactgca | 950 |
| ttcttcttga cactcaagta cggaatcaac accaagacat cagcccttgc | 1000 |
| acttagtagc ctctcaggcg acatccagaa gatgaagcag ctcatgcgtt | 1050 |
| tgtatcggat gaaaggagat aatgcgccgt acatgacatt acttggtgat | 1100 |
| agtgaccaga tgagctttgc gcctgccgag tatgcacaac tttactccct | 1150 |
| tgccatgggt atggcatcag tcctagataa aggtactggg aaataccaat | 1200 |
| ttgccaggga ctttatgagc acatcattct ggagacttgg agtagagtac | 1250 |
| gctcaggctc agggaagtag cattaacgag gatatggctg ccgagctaaa | 1300 |
| gctaaccca gcagcaagga ggggcctggc agctgctgcc ccacgggtct | 1350 |
| ccgaggagac cagcagcata gacatgccta ctcaacaagt cggagtcctc | 1400 |
| actgggctta gcgaggggggg gtcccaagct ctacaaggcg gatcgaatag | 1450 |
| atcgcaaggg caaccagaag ccggggatgg ggagacccaa ttcctggatc | 1500 |
| tgatgagagc ggtagcaaat agcatgaggg aggcgcaaa ctctgcacag | 1550 |
| ggcactcccc aatcggggcc tccccccaact cctgggccat cccaagataa | 1600 |

| | |
|---|---|
| cgacaccgac tgggggtatt gatggacaaa acccagcctg cttccacaaa | 1650 |
| aacatcccaa tgccctcacc cgtagtcgac ccctcgattt gcggctctat | 1700 |
| atgaccacac cctcaaacaa acatccccct ctttcctccc tcccctgct | 1750 |
| gtacaactcc gcacgcccta gataccacag gcacaatgcg gctcactaac | 1800 |
| aatcaaaaca gagccgaggg aattagaaaa aagtacgggt agaagaggga | 1850 |
| tattcagaga tcagggcaag tctcccgagt ctctgctctc tcctctacct | 1900 |
| gatagaccag gacaaacatg gccacctttt cagatgcaga gatcgacgag | 1950 |
| ctatttgaga caagtggaac tgtcattgac aacataatta cagcccaggg | 2000 |
| taaaccagca gagactgttg gaaggagtgc aatcccacaa ggcaagacca | 2050 |
| aggtgctgag cgcagcatgg gagaagcatg ggagcatcca gccaccggcc | 2100 |
| agtcaagaca acccgatcg acaggacaga tctgacaaac aaccatccac | 2150 |
| acccgagcaa acgaccccgc atgacagccc gccggccaca tccgccgacc | 2200 |
| agccccccac ccaggccaca gacgaagccg tcgacacaca gctcaggacc | 2250 |
| ggagcaagca actctctgct gttgatgctt gacaagctca gcaataaatc | 2300 |
| gtccaatgct aaaaagggcc catggtcgag cccccaagag gggaatcacc | 2350 |
| aacgtccgac tcaacagcag gggagtcaac ccagccgcgg aaacagtcag | 2400 |
| gaaagaccgc agaaccaagt caaggccgcc cctggaaacc agggcacaga | 2450 |
| cgtgaacaca gcatatcatg cacaatggga ggagtcacaa ctatcagctg | 2500 |
| gtgcaacccc tcatgctctc cgatcaaggc agagccaaga caatacccctt | 2550 |
| gtatctgcgg atcatgtcca gccacctgta gactttgtgc aagcgatgat | 2600 |
| gtctatgatg gaggcgatat cacagagagt aagtaaggtc gactatcagc | 2650 |
| tagatcttgt cttgaaacag acatcctcca tccctatgat gcggtccgaa | 2700 |
| atccaacagc tgaaaacatc tgttgcagtc atggaagcca acttgggaat | 2750 |
| gatgaagatt ctggatcccg gttgtgccaa catttcatct ctgagtgatc | 2800 |
| tacgggcagt tgcccgatct cacccggttt tagtttcagg ccctggagac | 2850 |
| ccctctccct atgtgacaca aggaggcgaa atggcactta ataaactttc | 2900 |
| gcaaccagtg ccacatccat ctgaattgat taaacccgcc actgcatgcg | 2950 |
| ggcctgatat aggagtggaa aaggacactg tccgtgcatt gatcatgtca | 3000 |
| cgcccaatgc acccgagttc ttcagccaag ctcctaagca agttagatgc | 3050 |
| agccgggtcg atcgaggaaa tcaggaaaat caagcgcctt gctctaaatg | 3100 |
| gctaattact actgccacac gtagcgggtc cctgtccact cggcatcaca | 3150 |
| cggaatctgc accgagttcc ccccgcaga cccaaggtcc aactctccaa | 3200 |
| gcggcaatcc tctctcgctt cctcagcccc actgaatgat cgcgtaaccg | 3250 |
| tttaattaat tagaaaaaat acgggtagaa ggccaccatg cagcatcaga | 3300 |
| gtactgcgct agtttcgagt atacttttgc tcttgagcct gcaaagcctt | 3350 |
| gcgtttgaat ttttctgtga tccgccacac gttttttcgag ggcagctcgg | 3400 |
| tgaccccatt ctattgcaat gcttcagcga cagacctcta acccacgaag | 3450 |
| aatctgtaaa agtagaagta attcgacacc cagccagctt agttgaaact | 3500 |
| gcgctaagcg cctacgggat ccccccttcg ctagatccat ggagagctac | 3550 |

```
tccaagaact ctctacacat atgatgccgc tactgattca atcaaggacc    3600
taggatacat tggtgaagat ggaattaacc caccatattt ggacgactgt    3650
cgttcaggtt ttttcaatgt ctctatcaag tctagcatga gatctcacat    3700
ggcgcgttat cagtggaccg caagtcgagg gtctacaaaa ctaaatagct    3750
cttttatcga cgtctttttg gcaagaccac ctacaactgt ccgcatcaaa    3800
tcagaagaac tgtacgaaga ctcagataag gcttcgcact taagtgttga    3850
agcgcttggc gcttatcctc catctgctgc gctgggtaca tggatgatac    3900
ataatgcatc tcttgctgaa aaatacagtt tagaaagaag agttctttat    3950
gcatcaggag agaatggatc ggtggatcag acatgggaac tggaaatacg    4000
tggagaagcc agccagcccc tcccttccaa aattcaattt gtatatcgat    4050
ggacccctcc tgaggacttt gaaatgctac gacctgaaac tcgcttgtta    4100
aggttgactc ccagctggat tagcaagccc cgcatcacgg tacaattcgt    4150
ccctcctgcc tatgccctgt gtagagcagc taatattata gacggccgag    4200
gatttattga atggatcgta gataatagaa tttcgacgag cccacaccag    4250
acctttgttt tggatgagcc cgaggggaaa atatcgttta cactaatgga    4300
cgtcataaaa ctaccaccgg aggatacatt tcaatctgcc tctaattacg    4350
tgtgcgtcat aagaggctat gaacatgcat acagatatct caacgcctcc    4400
ttaatgatag ataatctgcc aatgcggcaa ggattccccg cagtcagcac    4450
atctgctctc attacctata tcgttttgac tatcatatct cttgttttttg    4500
gtatacttag cctgattcta gcatgctacc taatgtacaa gcaaaaggcg    4550
caaaaaaaga cctattatg gcttgggaat aatactctag atcagatgag    4600
agccactaca aaaatgtgat taattaatag ctacatttaa gattaagaaa    4650
aaatacgggt agaattggag tgccccaatt gtgccaagat ggactcatct    4700
aggacaattg ggctgtactt tgattctgcc cattcttcta gcaacctgtt    4750
agcatttccg atcgtcctac aagacacagg agatgggaag aagcaaatcg    4800
ccccgcaata taggatccag cgccttgact tgtggactga tagtaaggag    4850
gactcagtat tcatcaccac ctatggattc atctttcaag ttgggaatga    4900
agaagccact gtcggcatga tcgatgataa acccaagcgc gagttacttt    4950
ccgctgcgat gctctgccta ggaagcgtcc caaataccgg agaccttatt    5000
gagctggcaa gggcctgtct cactatgata gtcacatgca agaagagtgc    5050
aactaatact gagagaatgg ttttctcagt agtgcaggca ccccaagtgc    5100
tgcaaagctg tagggttgtg gcaaacaaat actcatcagt gaatgcagtc    5150
aagcacgtga aagcgccaga gaagattccc gggagtggaa ccctagaata    5200
caaggtgaac tttgtctcct tgactgtggt accgaagaag gatgtctaca    5250
agatcccagc tgcagtattg aaggtttctg gctcgagtct gtacaatctt    5300
gcgctcaatg tcactattaa tctggaggta gacccgagga gtccctttggt   5350
taaatctctg tctaagtctg acagcggata ctatgctaac ctcttcttgc    5400
atattggact tatgaccacc gtagatagga aggggaagaa agtgacattt    5450
gacaagctgg aaaagaaaat aaggagcctt gatctatctg tcgggctcag    5500
tgatgtgctc gggccttccg tgttggtaaa agcaagaggt gcacggacta    5550
```

```
agcttttggc accttctcttc tctagcagtg ggacagcctg ctatcccata    5600
gcaaatgctt ctcctcaggt ggccaagata ctctggagtc aaaccgcgtg    5650
cctgcggagc gttaaaatca ttatccaagc aggtacccaa cgcgctgtcc    5700
cagtgacccc caaccaccag gttacctcta ctaagctgga aaggggcac     5750
acccttgcca aatacaatcc ttttaagaaa taagctgcgt ctctgagatt    5800
gcgctccgcc cactcacccg gatcatcatg acacaaaaaa ctaatctgtc    5850
ttgattattt acagttagtt tacctgtcta tcaagttaga aaaaacacgg    5900
gtagaagatt ctggatcccg gttggcgccc tccaggtgca agatgggctc    5950
cagaccttct accaagaacc cagcacctat gatgctgact atccgggttg    6000
cgctggtact gagttgcatc tgtccggcaa actccattga tggcaggcct    6050
cttgcagctg caggaattgt ggttacagga gacaaagccg tcaacatata    6100
cacctcatcc cagacaggat caatcatagt taagctcctc ccgaatctgc    6150
ccaaggataa ggaggcatgt gcgaaagccc ccttggatgc atacaacagg    6200
acattgacca cttttgctcac cccccttggt gactctatcc gtaggataca   6250
agagtctgtg actacatctg gagggggag acaggggcgc cttataggcg     6300
ccattattgg cggtgtggct cttgggggttg caactgccgc acaaataaca   6350
gcggccgcag ctctgataca agccaaacaa aatgctgcca acatcctccg    6400
acttaaagag agcattgccg caaccaatga ggctgtgcat gaggtcactg    6450
acggattatc gcaactagca gtggcagttg ggaagatgca gcagtttgtt    6500
aatgaccaat ttaataaaac agctcaggaa ttagactgca tcaaaattgc    6550
acagcaagtt ggtgtagagc tcaacctgta cctaaccgaa ttgactacag    6600
tattcggacc acaaatcact tcacctgctt taaacaagct gactattcag    6650
gcactttaca atctagctgg tggaaatatg gattacttat tgactaagtt    6700
aggtgtaggg aacaatcaac tcagctcatt aatcggtagc ggcttaatca    6750
ccggtaaccc tattctatac gactcacaga ctcaactctt gggtatacag    6800
gtaactctac cttcagtcgg gaacctaaat aatatgcgtg ccacctactt    6850
ggaaacctta tccgtaagca caaccagggg atttgcctcg gcacttgtcc    6900
caaaagtggt gacacaggtc ggttctgtga tagaagaact tgacacctca    6950
tactgtatag aaactgactt agatttatat tgtacaagaa tagtaacgtt    7000
ccctatgtcc cctggtattt attcctgctt gagcggcaat acgtcggcct    7050
gtatgtactc aaagaccgaa ggcgcactta ctacaccata catgactatc    7100
aaaggttcag tcatcgccaa ctgcaagatg acaacatgta gatgtgtaaa    7150
cccccgggt atcatatcgc aaaactatgg agaagccgtg tctctaatag     7200
ataaacaatc atgcaatgtt ttatccttag gcgggataac tttaaggctc    7250
agtggggaat tcgatgtaac ttatcagaag aatatctcaa tacaagattc    7300
tcaagtaata ataacaggca atcttgatat ctcaactgag cttgggaatg    7350
tcaacaactc gatcagtaat gctttgaata agttagagga aagcaacaga    7400
aaactagaca aagtcaatgt caaactgacc agcacatctg ctctcattac    7450
ctatatcgtt ttgactatca tatctcttgt ttttggtata cttagcctga    7500
```

| | |
|---|---|
| ttctagcatg ctacctaatg tacaagcaaa aggcgcaaca aaagaccttc | 7550 |
| ttatggcttg ggaataatac tctagatcag atgagagcca ctacaaaat | 7600 |
| gtgaacacag atgaggaacg aaggtttccc taatagtaat ttgtgtgaaa | 7650 |
| gttctggtag tctgtcagtt cagagagtta agaaaaaact acgcgttgta | 7700 |
| gatgaccaaa ggacgatata cgggtagaac ggtaagagag gccgcccctc | 7750 |
| aattgcgagc caggcttcac aacctccgtt ctaccgcttc accgacaaca | 7800 |
| gtcctcaatc atggaccgcg ccgttagcca agttcgtta gagaatgatg | 7850 |
| aaagagaggc aaaaaataca tggcgcttga tattccggat tgcaatctta | 7900 |
| ttcttaacag tagtgacctt ggctatatct gtagcctccc ttttatatag | 7950 |
| catgggggct agcacaccta gcgatcttgt aggcataccg actaggattt | 8000 |
| ccagggcaga agaaaagatt acatctacac ttggttccaa tcaagatgta | 8050 |
| gtagatagga tatataagca agtggcccttc gagtctccgt tggcattgtt | 8100 |
| aaaaactgag accacaatta tgaacgcaat aacatctctc tcttatcaga | 8150 |
| ttaatggagc tgcaaacaac agtgggtggg gggcacctat ccatgaccca | 8200 |
| gattatatag gggggatagg caaagaactc attgtagatg atgctagtga | 8250 |
| tgtcacatca ttctatccct ctgcatttca agaacatctg aattttatcc | 8300 |
| cggcgcctac tacaggatca ggttgcactc gaatacctc atttgacatg | 8350 |
| agtgctaccc attactgcta cacccataat gtaatattgt ctggatgcag | 8400 |
| agatcactca cattcatatc agtatttagc acttggtgtg ctggggacat | 8450 |
| ctgcaacagg gagggtattc ttttctactc tgcgttccat caacctggac | 8500 |
| gacacccaaa atcggaagtc ttgcagtgtg agtgcaactc ccctgggttg | 8550 |
| tgatatgctg tgctcgaaag tcacggagac agaggaagaa gattataact | 8600 |
| cagctgtccc tacgcggatg gtacatggga ggttagggtt cgacggccag | 8650 |
| taccacgaaa aggacctaga tgtcacaaca ttattcgggg actgggtggc | 8700 |
| caactaccca ggagtagggg gtggatcttt tattgacagc cgcgtatggt | 8750 |
| tctcagtcta cggagggtta aaacccaatt cacccagtga cactgtacag | 8800 |
| gaagggaaat atgtgatata caagcgatac aatgacacat gcccagatga | 8850 |
| gcaagactac cagattcgaa tggccaagtc ttcgtataag cctggacggt | 8900 |
| ttggtgggaa acgcatacag caggctatct tatctatcaa ggtgtcaaca | 8950 |
| tccttaggcg aagacccggt actgactgta ccgcccaaca cagtcacact | 9000 |
| catggggggcc gaaggcagaa ttctcacagt agggacatct catttcttgt | 9050 |
| atcaacgagg gtcatcatac ttctctcccg cgttattata tcctatgaca | 9100 |
| gtcagcaaca aaacagccac tcttcatagt cctttatacat tcaatgcctt | 9150 |
| cactcggcca ggtagtatcc cttgccaggc ttcagcaaga tgccccaacc | 9200 |
| cgtgtgttac tggagtctat acagatccat atccctaat cttctataga | 9250 |
| aaccacacct tgcgaggggt attcgggaca atgcttgatg gtgtacaagc | 9300 |
| aagacttaac cctgcgtctg cagtattcga tagcacatcc cgcagtcgca | 9350 |
| ttactcgagt gagttcaagc agtaccaaag cagcatacac aacatcaact | 9400 |
| tgttttaaag tggtcaagac taataagacc tattgtctca gcattgctga | 9450 |
| aatatctaat actctcttcg gagaattcag aatcgtcccg ttactagttg | 9500 |

```
agatcctcaa agatgacggg gttagagaag ccaggtctgg ctagttgagt      9550
caattataaa ggagttggaa agatggcatt gtatcaccta tcttctgcga      9600
catcaagaat caaaccgaat gccggcgcgt gctcgaattc catgttgcca      9650
gttgaccaca atcagccagt gctcatgcga tcagattaag ccttgtcaat      9700
agtctcttga ttaagaaaaa atgtaagtgg caatgagata caaggcaaaa      9750
tacgtaccgg taaataatac gggtaggaca tggcgagctc cggtcctgaa      9800
agggcagagc atcagattat cctaccagag tcacacctgt cttcaccatt      9850
ggtcaagcac aaactactct attactggaa attaactggg ctaccgcttc      9900
ctgatgaatg tgacttcgac cacctcattc tcagccgaca atggaaaaaa      9950
atacttgaat cggcctctcc tgatactgag agaatgataa aactcggaag     10000
ggcagtacac caaactctta accacaattc cagaataacc ggagtgctcc     10050
accccaggtg tttagaagaa ctggctaata ttgaggtccc agattcaacc     10100
aacaaatttc ggaagattga gaagaagatc caaattcaca cacgagata     10150
tggagaactg ttcacaaggc tgtgtacgca tatagagaag aaactgctgg     10200
ggtcatcttg gtctaacaat gtcccccggt cagaggagtt cagcagcatt     10250
cgtacggatc cggcattctg gtttcactca aaatggtcca cagccaagtt     10300
tgcatggctc catataaaac agatccagag gcatctgatg gtggcagcta     10350
ggacaaggtc tgcggccaac aaattggtga tgctaaccca taaggtaggc     10400
caagtctttg tcactcctga acttgtcgtt gtgacgcata cgaatgagaa     10450
caagttcaca tgtcttaccc aggaacttgt attgatgtat gcagatatga     10500
tggagggcag agatatggtc aacataatat caaccacggc ggtgcatctc     10550
agaagcttat cagagaaaat tgatgacatt ttgcggttaa tagacgctct     10600
ggcaaaagac ttgggtaatc aagtctacga tgttgtatca ctaatggagg     10650
gatttgcata cggagctgtc cagctactcg agccgtcagg tacatttgca     10700
ggagatttct tcgcattcaa cctgcaggag cttaaagaca ttctaattgg     10750
cctcctcccc aatgatatag cagaatccgt gactcatgca atcgctactg     10800
tattctctgg tttagaacag aatcaagcag ctgagatgtt gtgtctgttg     10850
cgtctgtggg gtcacccact gcttgagtcc cgtattgcag caaaggcagt     10900
caggagccaa atgtgcgcac cgaaaatggt agactttgat atgatccttc     10950
aggtactgtc tttcttcaag ggaacaatca tcaacgggta cagaaagaag     11000
aatgcaggtg tgtggccgcg agtcaaagtg gatacaatat atgggaaggt     11050
cattgggcaa ctacatgcag attcagcaga gatttcacac gatatcatgt     11100
tgagagagta taagagtttta tctgcacttg aatttgagcc atgtatagaa     11150
tatgaccctg tcacaaacct gagcatgttc ctaaaagaca aggcaatcgc     11200
acaccccaac gataattggc ttgcctcgtt taggcggaac cttctctccg     11250
aagaccagaa gaaacatgta aaagaagcaa cttcgactaa tcgcctcttg     11300
atagagtttt tagagtcaaa tgattttgat ccatataaag agatggaata     11350
tctgacgacc cttgagtacc ttagagatga caatgtggca gtatcatact     11400
cgctcaagga gaaggaatgt aaagttaatg gacggatctt cgctaagctg     11450
```

-continued

| | |
|---|---|
| acaaagaagt taaggaactg tcaggtgatg gcggaaggga tcctagccga | 11500 |
| tcagattgca cctttctttc agggaaatgg agtcattcag catagcatat | 11550 |
| ccttgaccaa gagtatgcta gcgatgagtc aactgtcttt taacagcaat | 11600 |
| aagaaacgta tcactgactg taaagaaaga gtatcttcaa accgcaatca | 11650 |
| tgatccgaaa agcaagaacc gtcggagagt tgcaaccttc ataacaactg | 11700 |
| acctgcaaaa gtactgtctt aattggagat atcagacaat caaattgttc | 11750 |
| gctcatgcca tcaatcagtt gatgggccta cctcacttct tcgaatggat | 11800 |
| tcacctaaga ctgatggaca ctacgatgtt cgtaggagac cctttcaatc | 11850 |
| ctccaagtga ccctactgac tgtgacctct caagagtccc taatgatgac | 11900 |
| atatatattg tcagtgccag agggggtatc gaaggattat gccagaagct | 11950 |
| atggacaatg atctcaattg ctgcaatcca acttgctgca gctagatcgc | 12000 |
| attgtcgtgt tgcctgtatg gtacaggggtg ataatcaagt aatagcagta | 12050 |
| acgagagagg taagatcaga cgactctccg gagatggtgt tgacacagtt | 12100 |
| gcatcaagcc agtgataatt tcttcaagga attaattcat gtcaatcatt | 12150 |
| tgattggcca taatttgaag gatcgtgaaa ccatcaggtc agacacattc | 12200 |
| ttcatataca gcaaacgaat cttcaaagat ggagcaatcc tcagtcaagt | 12250 |
| cctcaaaaat tcatctaaat tagtgctagt gtcaggtgat ctcagtgaaa | 12300 |
| acaccgtaat gtcctgtgcc aacattgcct ctactgtagc acggctatgc | 12350 |
| gagaacgggc ttcccaaaga cttctgttac tatttaaact atataatgag | 12400 |
| ttgtgtgcag acatactttg actctgagtt ctccatcacc aacaattcgc | 12450 |
| accccgatct taatcagtcg tggattgagg acatctcttt tgtgcactca | 12500 |
| tatgttctga ctcctgccca attaggggga ctgagtaacc ttcaatactc | 12550 |
| aaggctctac actagaaata tcggtgaccc ggggactact gcttttgcag | 12600 |
| agatcaagcg actagaagca gtgggattac tgagtcctaa cattatgact | 12650 |
| aatatcttaa ctaggccgcc tgggaatgga gattgggcca gtctgtgcaa | 12700 |
| cgacccatac tctttcaatt ttgagactgt tgcaagccca aatattgttc | 12750 |
| ttaagaaaca tacgcaaaga gtcctatttg aaacttgttc aaatccctta | 12800 |
| ttgtctggag tgcacacaga ggataatgag gcagaagaga aggcattggc | 12850 |
| tgaattcttg cttaatcaag aggtgattca tccccgcgtt gcgcatgcca | 12900 |
| tcatggaggc aagctctgta ggtaggagaa agcaaattca agggcttgtt | 12950 |
| gacacaacaa acaccgtaat taagattgcg cttactagga ggccattagg | 13000 |
| catcaagagg ctgatgcgga tagtcaatta ttctagcatg catgcaatgc | 13050 |
| tgtttagaga cgatgttttt tcctccagta gatccaacca cccccttagtc | 13100 |
| tcttctaata tgtgttctct gacactggca gactatgcac ggaatagaag | 13150 |
| ctggtcacct ttgacgggag gcaggaaaat actgggtgta tctaatcctg | 13200 |
| atacgataga actcgtagag ggtgagattc ttagtgtaag cggagggtgt | 13250 |
| acaagatgtg acagcggaga tgaacaattt acttggttcc atcttccaag | 13300 |
| caatatagaa ttgaccgatg acaccagcaa gaatcctccg atgagggtac | 13350 |
| catatctcgg gtcaaagaca caggagagga cagctgcctc acttgcaaaa | 13400 |
| atagctcata tgtcgccaca tgtaaaggct gccctaaggg catcatccgt | 13450 |

```
gttgatctgg gcttatgggg ataatgaagt aaattggact gctgctctta    13500
cgattgcaaa atctcggtgc aatgtaaact tagagtatct tcggttactg    13550
tccccttac  ccacggctgg gaatcttcaa catagactag atgatggtat    13600
aactcagatg acattcaccc ctgcatctct ctacagggtg tcaccttaca    13650
ttcacatatc caatgattct caaaggctgt tcactgaaga aggagtcaaa    13700
gaggggaatg tggtttacca acagatcatg ctcttgggtt tatctctaat    13750
cgaatcgatc tttccaatga caacaaccag gacatatgat gagatcacac    13800
tgcacctaca tagtaaattt agttgctgta tcagagaagc acctgttgcg    13850
gttcctttcg agctacttgg ggtggtaccg gaactgagga cagtgacctc    13900
aaataagttt atgtatgatc ctagccctgt atcggaggga gactttgcga    13950
gacttgactt agctatcttc aagagttatg agcttaatct ggagtcatat    14000
cccacgatag agctaatgaa cattctttca atatccagcg ggaagttgat    14050
tggccagtct gtggtttctt atgatgaaga tacctccata aagaatgacg    14100
ccataatagt gtatgacaat acccgaaatt ggatcagtga agctcagaat    14150
tcagatgtgg tccgcctatt tgaatatgca gcacttgaag tgctcctcga    14200
ctgttcttac caactctatt atctgagagt aagaggccta gacaatattg    14250
tcttatatat gggtgattta tacaagaata tgccaggaat tctactttcc    14300
aacattgcag ctacaatatc tcatcccgtc attcattcaa ggttacatgc    14350
agtgggcctg gtcaaccatg acggatcaca ccaacttgca gatacggatt    14400
ttatcgaaat gtctgcaaaa ctattagtat cttgcacccg acgtgtgata    14450
tccggcttat attcaggaaa taagtatgat ctgctgttcc catctgtctt    14500
agatgataac ctgaatgaga agatgcttca gctgatatcc cggttatgct    14550
gtctgtacac ggtactcttt gctacaacaa gagaaatccc gaaaataaga    14600
ggcttaactg cagaagagaa atgttcaata ctcactgagt atttactgtc    14650
ggatgctgtg aaaccattac ttagccccga tcaagtgagc tctatcatgt    14700
ctcctaacat aattacattc ccagctaatc tgtactacat gtctcggaag    14750
agcctcaatt tgatcaggga aagggaggac agggatacta tcctggcgtt    14800
gttgttcccc caagagccat tattagagtt cccttctgtg caagatattg    14850
gtgctcgagt gaaagatcca ttcacccgac aacctgcggc attttttgcaa   14900
gagttagatt tgagtgctcc agcaaggtat gacgcattca cacttagtca    14950
gattcatcct gaactcacat ctccaaatcc ggaggaagac tacttagtac    15000
gatacttgtt cagagggata gggactgcat cttcctcttg gtataaggca    15050
tctcatctcc tttctgtacc cgaggtaaga tgtgcaagac acgggaactc    15100
cttatactta gctgaaggga gcggagccat catgagtctt ctcgaactgc    15150
atgtaccaca tgaaactatc tattacaata cgctcttttc aaatgagatg    15200
aaccccccgc aacgacattt cgggccgacc ccaactcagt ttttgaattc    15250
ggttgtttat aggaatctac aggcggaggt aacctgcaaa gatggatttg    15300
tccaagagtt ccgtccatta tggagagaaa atacagagga aagtgacctg    15350
acctcagata aagcagtggg gtatattaca tctgcagtgc cctacagatc    15400
```

```
tgtatcattg ctgcattgtg acattgaaat tcctccaggg tccaatcaaa      15450
gcttactaga tcaactagct atcaatttat ctctgattgc catgcattct      15500
gtaagggagg gcggggtagt aatcatcaaa gtgttgtatg caatgggata      15550
ctactttcat ctactcatga acttgtttgc tccgtgttcc acaaaaggat      15600
atattctctc taatggttat gcatgtcgag gagatatgga gtgttacctg      15650
gtatttgtca tgggttacct gggcgggcct acatttgtac atgaggtggt      15700
gaggatggca aaaactctgg tgcagcggca cggtacgctt ttgtctaaat      15750
cagatgagat cacactgacc aggttattca cctcacagcg gcagcgtgtg      15800
acagacatcc tatccagtcc tttaccaaga ttaataaagt acttgaggaa      15850
gaatattgac actgcgctga ttgaagccgg gggacagccc gtccgtccat      15900
tctgtgcgga gagtctggtg agcacgctag cgaacataac tcagataacc      15950
cagatcatcg ctagccacat tgacacagtt atccggtctg tgatatatat      16000
ggaagctgag ggtgatctcg ctgacacagt atttctattt accccttaca      16050
atctctctac tgacgggaaa aagaggacat cacttaaaca gtgcacgaga      16100
cagatcctag aggttacaat actaggtctt agagtcgaaa atctcaataa      16150
aataggcgat ataatcagcc tagtgcttaa aggcatgatc tccatggagg      16200 acctatccc actaaggaca tacttgaagc atagtacctg ccctaaatat       16250
ttgaaggctg tcctaggtat taccaaactc aaagaaatgt ttacagacac      16300
ttctgtactg tacttgactc gtgctcaaca aaaattctac atgaaaacta      16350
taggcaatgc agtcaaagga tattacagta actgtgactc ttaacgaaaa      16400
tcacatatta ataggctcct tttttggcca attgtattct tgttgattta      16450
atcatattat gttagaaaaa agttgaaccc tgactcctta ggactcgaat      16500
tcgaactcaa ataaatgtct taaaaaaagg ttgcgcacaa ttattcttga      16550
gtgtagtctc gtcattcacc aaatcttggt tgggtcggca tggcatctcc      16600
acctcctcgc ggtccgacct gggcatccga aggaggacgc acgtccactc      16650
ggatggctaa gggagagcct gcagtagcat aaccccttgg ggcctctaaa      16700
cgggtcttga ggggtttttt gctgaaagga ggaactatat actcgagctg      16750
cagcaatggc aacaacgttg cgcaaactat taactggcga actacttact      16800
ctagcttccc ggcaacaatt aatagactgg atggaggcgg ataaagttgc      16850
aggaccactt ctgcgctcgg cccttccggc tggctggttt attgctgata      16900
aatctggagc cggtgagcgt gggtctcgcg gtatcattgc agcactgggg      16950
ccagatggta agccctcccg tatcgtagtt atctacacga cggggagtca      17000
ggcaactatg gatgaacgaa atagacagat cgctgagata ggtgcctcac      17050
tgattaagca ttggtaactg tcagaccaag tttactcata tatactttag      17100
attgatttaa aacttcattt ttaatttaaa aggatctagg tgaagatcct      17150
ttttgataat ctcatgacca aaatccctta acgtgagttt tcgttccact      17200
gagcgtcaga ccccgtagaa aagatcaaag gatcttcttg agatcctttt      17250
tttctgcgcg taatctgctg cttgcaaaca aaaaaaccac cgctaccagc      17300
ggtggtttgt ttgccggatc aagagctacc aactcttttt ccgaaggtaa      17350
ctggcttcag cagagcgcag ataccaaata ctgtccttct agtgtagccg      17400
```

```
tagttaggcc accacttcaa gaactctgta gcaccgccta catacctcgc    17450
tctgctaatc ctgttaccag tggctgctgc cagtggcgat aagtcgtgtc    17500
ttaccgggtt ggactcaaga cgatagttac cggataaggc gcagcggtcg    17550
ggctgaacgg ggggttcgtg cacacagccc agcttggagc gaacgaccta    17600
caccgaactg agatacctac agcgtgagct atgagaaagc gccacgcttc    17650
ccgaagggag aaaggcggac aggtatccgg taagcggcag ggtcggaaca    17700
ggagagcgca cgagggagct tccaggggga aacgcctggt atctttatag    17750
tcctgtcggg tttcgccacc tctgacttga gcgtcgattt ttgtgatgct    17800
cgtcaggggg gcggagccta tggaaaaacg ccagcaacgc ggccttttta    17850
cggttcctgg ccttttgctg ccttttgct cacatgttct ttcctgcgtt     17900
atcccctgat tctgtggata accgtattac cgcctttgag tgagctgata    17950
ccgctcgccg cagccgaacg accgagcgca gcgagtcagt gagcgaggaa    18000
gcggaagagc gcctgatgcg gtattttctc cttacgcatc tgtgcggtat    18050
ttcacaccgc atatggtgca ctctcagtac aatctgctct gatgccgcat    18100
agttaagcca gtatacactc cgctatcgct acgtgactgg gtcatggctg    18150
cgccccgaca cccgccaaca cccgctgacg cgccctgacg ggcttgtctg    18200
ctcccggcat ccgcttacag acaagctgtg accgtctccg ggagctgcat    18250
gtgtcagagg ttttcaccgt catcaccgaa acgcgcgagg cagctgcggt    18300
aaagctcatc agcgtggtcg tgaagcgatt cacagatgtc tgcctgttca    18350
tccgcgtcca gctcgttgag tttctccaga agcgttaatg tctggcttct    18400
gataaagcgg gccatgttaa gggcggtttt ttcctgtttg gtcactgatg    18450
cctccgtgta aggggattt ctgttcatgg ggtaatgat accgatgaaa      18500
cgagagagga tgctcacgat acgggttact gatgatgaac atgcccggtt    18550
actggaacgt tgtgagggta aacaactggc ggtatgatg cggcgggacc     18600
agagaaaaat cactcagggt caatgccagc gcttcgttaa tacagatgta    18650
ggtgttccac agggtagcca gcagcatcct gcgatgcaga tccggaacat    18700
aatggtgcag ggcgctgact tccgcgtttc cagactttac gaaacacgga    18750
aaccgaagac cattcatgtt gttgctcagg tcgcagacgt tttgcagcag    18800
cagtcgcttc acgttcgctc gcgtatcggt gattcattct gctaaccagt    18850
aaggcaaccc cgccagccta gccgggtcct caacgacagg agcacgatca    18900
tgcgcacccg tggccaggac ccaacgctgc ccgagatgcg ccgcgtgcgg    18950
ctgctggaga tggcggacgc gatggatatg ttctgccaag ggttggtttg    19000
cgcattcaca gttctccgca agaattgatt ggctccaatt cttggagtgg    19050
tgaatccgtt agcgaggtgc cgccggcttc cattcaggtc gaggtggccc    19100
ggctccatgc accgcgacgc aacgcgggga ggcagacaag gtatagggcg    19150
gcgcctacaa tccatgccaa cccgttccat gtgctcgccg aggcggcata    19200
aatcgccgtg acgatcagcg gtccagtgat cgaagttagg ctggtaagag    19250
ccgcgagcga tccttgaagc tgtccctgat ggtcgtcatc tacctgcctg    19300
gacagcatgg cctgcaacgc gggcatcccg atgccgccgg aagcgagaag    19350
```

| | |
|---|---|
| aatcataatg gggaaggcca tccagcctcg cgtcgcgaac gccagcaaga | 19400 |
| cgtagcccag cgcgtcggcc gccatgccgg cgataatggc ctgcttctcg | 19450 |
| ccgaaacgtt tggtggcggg accagtgacg aaggcttgag cgagggcgtg | 19500 |
| caagattccg aataccgcaa gcgacaggcc gatcatcgtc gcgctccagc | 19550 |
| gaaagcggtc ctcgccgaaa atgacccaga gcgctgccgg cacctgtcct | 19600 |
| acgagttgca tgataaagaa gacagtcata agtgcggcga cgatagtcat | 19650 |
| gccccgcgcc caccggaagg agctgactgg gttgaaggct ctcaagggca | 19700 |
| tcggtcgacg ctctccctta tgcgactcct gcattaggaa gcagcccagt | 19750 |
| agtaggttga ggccgttgag caccgccgcc gcaaggaatg gtgcatgcaa | 19800 |
| ggagatggcg cccaacagtc ccccggccac ggggcctgcc accataccca | 19850 |
| cgccgaaaca gcgctcatg agcccgaagt ggcgagcccg atcttcccca | 19900 |
| tcggtgatgt cggcgatata ggcgccagca accgcacctg tggcgccggt | 19950 |
| gatgccggcc acgatgcgtc cggcgtagag gatccacagg acgggtgtgg | 20000 |
| tcgccatgat cgcgtagtcg atagtggctc caagtagcga agcgagcagg | 20050 |
| actgggcggc ggccaaagcg gtcggacagt gctccgagaa cgggtgcgca | 20100 |
| tagaaattgc atcaacgcat atagcgctag cagcacgcca tagtgactgg | 20150 |
| cgatgctgtc ggaatggacg atatcccgca agaggcccgg cagtaccggc | 20200 |
| ataaccaagc ctatgcctac agcatccagg gtgacggtgc cgaggatgac | 20250 |
| gatgagcgca ttgttagatt tcatacacgg tgcctgactg cgttagcaat | 20300 |
| ttaactgtga taaactaccg cattaaagct tatcgatgat aagctgtcaa | 20350 |
| acatgagaa | 20359 |

<210> SEQ ID NO 18
<211> LENGTH: 20307
<212> TYPE: DNA
<213> ORGANISM: Artificial sequence
<220> FEATURE:
<223> OTHER INFORMATION: pNDV gD

<400> SEQUENCE: 18
ttcggcgcgc ctaatacgac tcactatagg gaccaaacag agaatccgtg 50
atttacgata aaaggcgaaa gagcaattga agtcgcacgg gtagaaggtg 100
tgaatctcga gtgcgagccc gaagcacaaa ctcgagaaag ccttctgcca 150
acatgtcttc cgtatttgat gagtacgaac agctcctcgc ggctcagact 200
cgccccaatg gagctcatgg agggggagaa aaagggagta ccttaaaagt 250
agacgtcccg gtattcactc ttaacagtga tgacccagaa gatagatgga 300
gctttgtggt attctgcctc cggattgctg ttagcgaaga tgccaacaaa 350
ccactcaggc aaggtgctct catatctctt ttatgctccc actcacaggt 400
aatgaggaac catgttgccc ttgcagggaa acagaatgaa gccacattgg 450
ccgtgcttga gattgatggc tttgccaacg gcacgcccca gttcaacaat 500
aggagtggag tgtctgaaga gagagcacag agatttgcga tgatagcagg 550
atctctccct cgggcatgca gcaacggaac cccgttcgtc acagccgggg 600
ccgaagatga tgcaccagaa gacatcaccg ataccctgga gaggatcctc 650
tctatccagg ctcaagtatg ggtcacagta gcaaaagcca tgactgcgta 700

```
tgagactgca gatgagtcgg aaacaaggcg aatcaataag tatatgcagc        750
aaggcagggt ccaaaagaaa tacatcctct accccgtatg caggagcaca        800
atccaactca cgatcagaca gtctcttgca gtccgcatct ttttggttag        850
cgagctcaag agaggccgca acacggcagg tggtacctct acttattata        900
acctggtagg ggacgtagac tcatacatca ggaataccgg gcttactgca        950
ttcttcttga cactcaagta cggaatcaac accaagacat cagcccttgc       1000
acttagtagc ctctcaggcg acatccagaa gatgaagcag ctcatgcgtt       1050
tgtatcggat gaaaggagat aatgcgccgt acatgacatt acttggtgat       1100
agtgaccaga tgagctttgc gcctgccgag tatgcacaac tttactccct       1150
tgccatgggt atggcatcag tcctagataa aggtactggg aaataccaat       1200
ttgccaggga ctttatgagc acatcattct ggagacttgg agtagagtac       1250
gctcaggctc agggaagtag cattaacgag gatatggctg ccgagctaaa       1300 gctaaccccca gcagcaagga ggggcctggc agctgctgcc caacgggtct       1350
ccgaggagac cagcagcata gacatgccta ctcaacaagt cggagtcctc       1400
actgggctta gcgaggggggg gtcccaagct ctacaaggcg gatcgaatag       1450
atcgcaaggg caaccagaag ccggggatgg ggagacccaa ttcctggatc       1500
tgatgagagc ggtagcaaat agcatgaggg aggcgccaaa ctctgcacag       1550
ggcactcccc aatcggggcc tcccccaact cctgggccat cccaagataa       1600
cgacaccgac tgggggtatt gatggacaaa acccagcctg cttccacaaa       1650
aacatcccaa tgccctcacc cgtagtcgac ccctcgattt gcggctctat       1700
atgaccacac cctcaaacaa acatccccct cttcctccc tcccctgct         1750 gtacaactcc gcacgcccta gataccacag gcacaatgcg gctcactaac       1800
aatcaaaaca gagccgaggg aattagaaaa aagtacgggt agaagaggga       1850
tattcagaga tcagggcaag tctcccgagt ctctgctctc tcctctacct       1900
gatagaccag gacaaacatg gccacccttta cagatgcaga gatcgacgag     1950
ctatttgaga caagtggaac tgtcattgac aacataatta cagcccaggg       2000
taaaccagca gagactgttg gaaggagtgc aatcccacaa ggcaagacca       2050
aggtgctgag cgcagcatgg gagaagcatg ggagcatcca gccaccggcc       2100
agtcaagaca accccgatcg acaggacaga tctgacaaac aaccatccac       2150
acccgagcaa acgacccgc atgacagccc gccggccaca tccgccgacc        2200
agccccccac ccaggccaca gacgaagccg tcgacacaca gctcaggacc       2250
ggagcaagca actctctgct gttgatgctt gacaagctca gcaataaatc       2300
gtccaatgct aaaaagggcc catggtcgag ccccccaagag gggaatcacc      2350 aacgtccgac tcaacagcag gggagtcaac ccagccgcgg aaacagtcag      2400
gaaagaccgc agaaccaagt caaggccgcc cctggaaacc agggcacaga     2450
cgtgaacaca gcatatcatg gacaatggga ggagtcacaa ctatcagctg      2500
gtgcaacccc tcatgctctc cgatcaaggc agagccaaga caatacccttt      2550 gtatctgcgg atcatgtcca gccacctgta gactttgtgc aagcgatgat       2600
gtctatgatg gaggcgatat cacagagagt aagtaaggtc gactatcagc       2650
```

-continued

```
tagatcttgt cttgaaacag acatcctcca tccctatgat gcggtccgaa    2700
atccaacagc tgaaaacatc tgttgcagtc atggaagcca acttgggaat    2750
gatgaagatt ctggatcccg gttgtgccaa catttcatct ctgagtgatc    2800
tacgggcagt tgcccgatct cacccggttt tagtttcagg ccctggagac    2850
ccctctccct atgtgacaca aggaggcgaa atggcactta ataaactttc    2900
gcaaccagtg ccacatccat ctgaattgat taaacccgcc actgcatgcg    2950
ggcctgatat aggagtggaa aaggacactg tccgtgcatt gatcatgtca    3000
cgcccaatgc acccgagttc ttcagccaag ctcctaagca agttagatgc    3050
agccgggtcg atcgaggaaa tcaggaaaat caagcgcctt gctctaaatg    3100
gctaattact actgccacac gtagcgggtc cctgtccact cggcatcaca    3150
cggaatctgc accgagttcc cccccgcaga cccaaggtcc aactctccaa    3200
gcggcaatcc tctctcgctt cctcagcccc actgaatgat cgcgtaaccg    3250
tttaattaat tagaaaaaat acgggtagaa ggccgccacc atggaccgcc    3300
atttattttt gaggaatgct ttttggacta tcgtactgct ttcttccttc    3350
gctagccaga gcaccgccgc cgtcacgtac gactacattt taggccgtcg    3400
cgcgctcgac gcgctaacca taccggcggt tgggcccgta tcagcctacc    3450
tcactagggt atcaagaggc tgcgacgttg tcgagctcaa cccgatttct    3500
aacgtggacg acatgatatc ggcggccaaa gaaaaagaga aggggggccc    3550
tttcgaggcc tccgtcgtct ggttctacgt gattaagggc gacgacggcg    3600
aggacaagta ctgtccaatc tatagaaaag agtacaggga atgtggcgac    3650
gtacaactgc tatctgaatg cgccgttcaa tctgcacaga tgtgggcagt    3700
ggactatgtt cctagcaccc ttgtatcgcg aaatggcgcg ggactgacta    3750
tattctcccc cactgctgcg ctctctggcc aatacttgct gaccctgaaa    3800
atcgggagat ttgcgcaaac agctctcgta actctagaag ttaacgatcg    3850
ctgtttaaag atcgggtcgc agcttaactt tttaccgtcg aaatgctgga    3900
caacagaaca gtatcagact ggatttcaag gcgaacacct ttatccgatc    3950
gcagacacca atacacgaca cgcggacgac gtatatcggg gatacgaaga    4000
tattctgcag cgctggaata atttgctgag gaaaaagaat cctagcgcgc    4050
cagaccctcg tccagatagc gtcccgcaag aaattcccgc tgtaaccaag    4100
aaagcggaag ggcgcacccc ggacgcagaa agcagcgaaa agaaggcccc    4150
tccagaagac tcggaggacg acatgcaggc agaggcttct ggagaaaatc    4200
ctgccgccct ccccgaagac gacgaagtcc ccgaggacac cgagcacgat    4250
gatccaaact cggatcctga ctattacaat gacatgcccg ccgtgatccc    4300
ggtggaggag actactaaaa gttctaatgc cgtctccatg cccagcacat    4350
ctgctctcat tacctatatc gttttgacta tcatatctct tgttttggt    4400
atacttagcc tgattctagc atgctaccta atgtacaagc aaaaggcgca    4450
acaaaagacc ttattatggc ttgggaataa tactctagat cagatgagag    4500
acaaaagacc ttattatggc ttgggaataa tactctagat cagatgagag    4550
ccactacaaa aatgtgatta attaaatagct acatttaaga ttaagaaaaa    4600
atacgggtag aattggagtg ccccaattgt gccaagatgg actcatctag    4650
```

```
gacaattggg ctgtactttg attctgccca ttcttctagc aacctgttag      4700
catttccgat cgtcctacaa gacacaggag atgggaagaa gcaaatcgcc      4750
ccgcaatata ggatccagcg ccttgacttg tggactgata gtaaggagga      4800
ctcagtattc atcaccacct atggattcat ctttcaagtt gggaatgaag      4850
aagccactgt cggcatgatc gatgataaac ccaagcgcga gttactttcc      4900
gctgcgatgc tctgcctagg aagcgtccca aataccggag accttattga      4950
gctggcaagg gcctgtctca ctatgatagt cacatgcaag aagagtgcaa      5000
ctaatactga gagaatggtt ttctcagtag tgcaggcacc ccaagtgctg      5050
caaagctgta gggttgtggc aaacaaatac tcatcagtga atgcagtcaa      5100
gcacgtgaaa gcgccagaga agattcccgg gagtggaacc ctagaataca      5150
aggtgaactt tgtctccttg actgtggtac cgaagaagga tgtctacaag      5200
atcccagctg cagtattgaa ggtttctggc tcgagtctgt acaatcttgc      5250
gctcaatgtc actattaatg tggaggtaga cccgaggagt cctttggtta      5300
aatctctgtc taagtctgac agcggatact atgctaacct cttcttgcat      5350
attggactta tgaccaccgt agataggaag gggaagaaag tgacatttga      5400
caagctggaa aagaaaataa ggagccttga tctatctgtc gggctcagtg      5450
atgtgctcgg gccttccgtg ttggtaaaag caagaggtgc acggactaag      5500
cttttggcac ctttcttctc tagcagtggg acagcctgct atcccatagc      5550
aaatgcttct cctcaggtgg ccaagatact ctggagtcaa accgcgtgcc      5600
tgcggagcgt taaaatcatt atccaagcag gtacccaacg cgctgtccca      5650
gtgaccccca accaccaggt tacctctact aagctggaga aggggcacag      5700
ccttgccaaa tacaatcctt ttaagaaata agctgcgtct ctgagattgc      5750
gctccgccca ctcacccgga tcatcatgac acaaaaaact aatctgtctt      5800
gattatttac agttagttta cctgtctatc aagttagaaa aaacacgggt      5850
agaagattct ggatcccggt tggcgccctc caggtgcaag atgggctcca      5900
gaccttctac caagaaccca gcacctatga tgctgactat ccgggttgcg      5950
ctggtactga gttgcatctg tccggcaaac tccattgatg gcaggcctct      6000
tgcagctgca ggaattgtgg ttacaggaga caaagccgtc aacatataca      6050
cctcatccca gacaggatca atcatagtta agctcctccc gaatctgccc      6100
aaggataagg aggcatgtgc gaaagccccc ttggatgcat acaacaggac      6150
attgaccact ttgctcaccc cccttggtga ctctatccgt aggatacaag      6200
agtctgtgac tacatctgga ggggggagac aggggcgcct tataggcgcc      6250
attattggcg gtgtggctct tggggttgca actgccgcac aaataacagc      6300
ggccgcagct ctgatacaag ccaaacaaaa tgctgccaac atcctccgac      6350
ttaaagagag cattgccgca accaatgagg ctgtgcatga ggtcactgac      6400
ggattatcgc aactagcagt ggcagttggg aagatgcagc agtttgttaa      6450
tgaccaattt aataaaacag ctcaggaatt agactgcatc aaaattgcac      6500
agcaagttgg tgtagagctc aacctgtacc taaccgaatt gactacagta      6550
ttcggaccac aaatcacttc acctgcttta aacaagctga ctattcaggc      6600
```

```
actttacaat ctagctggtg gaaatatgga ttacttattg actaagttag      6650
gtgtagggaa caatcaactc agctcattaa tcggtagcgg cttaatcacc      6700
ggtaacccta ttctatacga ctcacagact caactcttgg gtatacaggt      6750
aactctacct tcagtcggga acctaaataa tatgcgtgcc acctacttgg      6800
aaaccttatc cgtaagcaca accaggggat ttgcctcggc acttgtccca      6850
aaagtggtga cacaggtcgg ttctgtgata gaagaacttg acacctcata      6900
ctgtatagaa actgacttag atttatattg tacaagaata gtaacgttcc      6950
ctatgtcccc tggtatttat tcctgcttga gcggcaatac gtcggcctgt      7000
atgtactcaa agaccgaagg cgcacttact acaccataca tgactatcaa      7050
aggttcagtc atcgccaact gcaagatgac aacatgtaga tgtgtaaacc      7100
ccccgggtat catatcgcaa aactatggag aagccgtgtc tctaatagat      7150
aaacaatcat gcaatgtttt atccttaggc gggataactt taaggctcag      7200
tggggaattc gatgtaactt atcagaagaa tatctcaata caagattctc      7250
aagtaataat aacaggcaat cttgatatct caactgagct tgggaatgtc      7300
aacaactcga tcagtaatgc tttgaataag ttagaggaaa gcaacagaaa      7350
actagacaaa gtcaatgtca aactgaccag cacatctgct ctcattacct      7400
atatcgtttt gactatcata tctcttgttt ttggtatact tagcctgatt      7450
ctagcatgct acctaatgta caagcaaaag gcgcaacaaa agaccttatt      7500
atggcttggg aataatactc tagatcagat gagagccact acaaaaatgt      7550
gaacacagat gaggaacgaa ggtttcccta atagtaattt gtgtgaaagt      7600
tctggtagtc tgtcagttca gagagttaag aaaaaactac gcgttgtaga      7650
tgaccaaagg acgatatacg ggtagaacgg taagagaggc cgcccctcaa      7700
ttgcgagcca ggcttcacaa cctccgttct accgcttcac cgacaacagt      7750
cctcaatcat ggaccgcgcc gttagccaag ttgcgttaga gaatgatgaa      7800
agagaggcaa aaaatacatg gcgcttgata ttccggattg caatcttatt      7850
cttaacagta gtgaccttgg ctatatctgt agcctcccct ttatatagca      7900
tgggggctag cacacctagc gatcttgtag gcataccgac taggatttcc      7950
agggcagaag aaaagattac atctacactt ggttccaatc aagatgtagt      8000
agataggata tataagcaag tggcccttga gtctccgttg gcattgttaa      8050
aaactgagac cacaattatg aacgcaataa catctctctc ttatcagatt      8100
aatggagctg caaacaacag tgggtggggg gcacctatcc atgacccaga      8150
ttatataggg gggataggca aagaactcat tgtagatgat gctagtgatg      8200
tcacatcatt ctatccctct gcatttcaag aacatctgaa ttttatcccg      8250
gcgcctacta caggatcagg ttgcactcga ataccctcat ttgacatgag      8300
tgctacccat tactgctaca cccataatgt aatattgtct ggatgcagag      8350
atcactcaca ttcatatcag tatttagcac ttggtgtgct ccggacatct      8400
gcaacaggga gggtattctt ttctactctg cgttccatca acctggacga      8450
cacccaaaat cggaagtctt gcagtgtgag tgcaactccc ctgggttgtg      8500
atatgctgtg ctcgaaagtc acggagacag aggaagaaga ttataactca      8550
gctgtcccta cgcggatggt acatgggagg ttagggttcg acggccagta      8600
```

-continued

```
ccacgaaaag gacctagatg tcacaacatt attcggggac tgggtggcca        8650
actacccagg agtaggggt ggatcttta ttgacagccg cgtatggttc          8700
```

```
ccacgaaaag gacctagatg tcacaacatt attcggggac tgggtggcca        8650
actacccagg agtaggggt ggatctttta ttgacagccg cgtatggttc         8700
tcagtctacg gagggttaaa acccaattca cccagtgaca ctgtacagga        8750
agggaaatat gtgatataca agcgatacaa tgacacatgc ccagatgagc        8800
aagactacca gattcgaatg gccaagtctt cgtataagcc tggacggttt        8850
ggtgggaaac gcatacagca ggctatctta tctatcaagg tgtcaacatc        8900
cttaggcgaa gacccggtac tgactgtacc gcccaacaca gtcacactca        8950
tgggggccga aggcagaatt ctcacagtag ggacatctca tttcttgtat        9000
caacgagggt catcatactt ctctcccgcg ttattatatc ctatgacagt        9050
cagcaacaaa acagccactc ttcatagtcc ttatacattc aatgccttca        9100
ctcggccagg tagtatccct tgccaggctt cagcaagatg ccccaacccg        9150
tgtgttactg gagtctatac agatccatat cccctaatct tctatagaaa        9200
ccacaccttg cgagggtat tcgggacaat gcttgatggt gtacaagcaa         9250
gacttaaccc tgcgtctgca gtattcgata gcacatcccg cagtcgcatt        9300
actcgagtga gttcaagcag taccaaagca gcatacacaa catcaacttg        9350
ttttaaagtg gtcaagacta ataagaccta ttgtctcagc attgctgaaa        9400
tatctaatac tctcttcgga gaattcagaa tcgtcccgtt actagttgag        9450
atcctcaaag atgacgggt tagagaagcc aggtctggct agttgagtca         9500
attataaagg agttggaaag atggcattgt atcacctatc ttctgcgaca        9550
tcaagaatca aaccgaatgc cggcgcgtgc tcgaattcca tgttgccagt        9600
tgaccacaat cagccagtgc tcatgcgatc agattaagcc ttgtcaatag        9650
tctcttgatt aagaaaaaat gtaagtggca atgagataca aggcaaaata        9700
cgtaccggta aataatacgg gtaggacatg gcgagctcgc gtcctgaaag        9750
ggcagagcat cagattatcc taccagagtc acacctgtct tcaccattgg        9800
tcaagcacaa actactctat tactggaaat taactgggct accgcttcct        9850
gatgaatgtg acttcgacca cctcattctc agccgacaat ggaaaaaaat        9900
acttgaatcg gcctctcctg atactgagag aatgataaaa ctcggaaggg        9950
cagtacacca aactcttaac cacaattcca gaataaccgg agtgctccac        10000
cccaggtgtt tagaagaact ggctaatatt gaggtcccag attcaaccaa        10050
caaatttcgg aagattgaga agaagatcca aattcacaac acgagatatg        10100
gagaactgtt cacaaggctg tgtacgcata tagagaagaa actgctgggg        10150
tcatcttggt ctaacaatgt cccccggtca gaggagttca gcagcattcg        10200
tacggatccg gcattctggt ttcactcaaa atggtccaca gccaagtttg        10250
catggctcca tataaaacag atccagaggc atctgatggt ggcagctagg        10300
acaaggtctg cggccaacaa attggtgatg ctaacccata aggtaggcca        10350
agtctttgtc actcctgaac ttgtcgttgt gacgcatacg aatgagaaca        10400
agttcacatg tcttacccag gaacttgtat tgatgtatgc agatatgatg        10450
gagggcagag atatggtcaa cataatatca accacggcgg tgcatctcag        10500
aagcttatca gagaaaattg atgacatttt gcggttaata gacgctctgg        10550
```

-continued

| | |
|---|---|
| caaaagactt gggtaatcaa gtctacgatg ttgtatcact aatggaggga | 10600 |
| tttgcatacg gagctgtcca gctactcgag ccgtcaggta catttgcagg | 10650 |
| agatttcttc gcattcaacc tgcaggagct aaaagacatt ctaattggcc | 10700 |
| tcctccccaa tgatatagca gaatccgtga ctcatgcaat cgctactgta | 10750 |
| ttctctggtt tagaacagaa tcaagcagct gagatgttgt gtctgttgcg | 10800 |
| tctgtggggt cacccactgc ttgagtcccg tattgcagca aaggcagtca | 10850 |
| ggagccaaat gtgcgcaccg aaaatggtag actttgatat gatccttcag | 10900 |
| gtactgtctt tcttcaaggg aacaatcatc aacgggtaca gaaagaagaa | 10950 |
| tgcaggtgtg tggccgcgag tcaaagtgga tacaatatat gggaaggtca | 11000 |
| ttgggcaact acatgcagat tcagcagaga tttcacacga tatcatgttg | 11050 |
| agagagtata agagtttatc tgcacttgaa tttgagccat gtatagaata | 11100 |
| tgaccctgtc acaaacctga gcatgttcct aaaagacaag gcaatcgcac | 11150 |
| accccaacga taattggctt gcctcgttta ggcggaacct tctctccgaa | 11200 |
| gaccagaaga aacatgtaaa agaagcaact tcgactaatc gcctcttgat | 11250 |
| agagtttta gagtcaaatg attttgatcc atataaagag atggaatatc | 11300 |
| tgacgaccct tgagtacctt agagatgaca atgtggcagt atcatactcg | 11350 |
| ctcaaggaga aggaagtgaa agttaatgga cggatcttcg ctaagctgac | 11400 |
| aaagaagtta aggaactgtc aggtgatggc ggaagggatc ctagccgatc | 11450 |
| agattgcacc tttctttcag ggaaatggag tcattcagga tagcatatcc | 11500 |
| ttgaccaaga gtatgctagc gatgagtcaa ctgtctttta acagcaataa | 11550 |
| gaaacgtatc actgactgta aagaaagagt atcttcaaac cgcaatcatg | 11600 |
| atccgaaaag caagaaccgt cggagagttg caaccttcat aacaactgac | 11650 |
| ctgcaaaagt actgtcttaa ttggagatat cagacaatca aattgttcgc | 11700 |
| tcatgccatc aatcagttga tgggcctacc tcacttcttc gaatggattc | 11750 |
| acctaagact gatggacact acgatgttcg taggagaccc tttcaatcct | 11800 |
| ccaagtgacc ctactgactg tgacctctca agagtcccta atgatgacat | 11850 |
| atatattgtc agtgccagag gggtatcga aggattatgc cagaagctat | 11900 |
| ggacaatgat ctcaattgct gcaatccaac ttgctgcagc tagatcgcat | 11950 |
| tgtcgtgttg cctgtatggt acagggtgat aatcaagtaa tagcagtaac | 12000 |
| gagagaggta agatcagacg actctccgga gatggtgttg acacagttgc | 12050 |
| atcaagccag tgataatttc ttcaaggaat taattcatgt caatcatttg | 12100 |
| attggccata atttgaagga tcgtgaaacc atcaggtcag acacattctt | 12150 |
| catatacagc aaacgaatct tcaaagatgg agcaatcctc agtcaagtcc | 12200 |
| tcaaaaattc atctaaatta gtgctagtgt caggtgatct cagtgaaaac | 12250 |
| accgtaatgt cctgtgccaa cattgcctct actgtagcac ggctatgcga | 12300 |
| gaacgggctt cccaaaagact tctgttacta tttaaactat ataatgagtt | 12350 |
| gtgtgcagac atactttgac tctgagttct ccatcaccaa caattcgcac | 12400 |
| cccgatctta atcagtcgtg gattgaggac atctcttttg tgcactcata | 12450 |
| tgttctgact cctgcccaat tagggggact gagtaacctt caatactcaa | 12500 |
| ggctctacac tagaaatatc ggtgacccgg ggactactgc ttttgcagag | 12550 |

```
atcaagcgac tagaagcagt gggattactg agtcctaaca ttatgactaa        12600
tatcttaact aggccgcctg ggaatggaga ttgggccagt ctgtgcaacg        12650
acccatactc tttcaatttt gagactgttg caagcccaaa tattgttctt        12700
aagaaacata cgcaaagagt cctatttgaa acttgttcaa atcccttatt        12750
gtctggagtg cacacagagg ataatgaggc agaagagaag gcattggctg        12800
aattcttgct taatcaagag gtgattcatc cccgcgttgc gcatgccatc        12850
atggaggcaa gctctgtagg taggagaaag caaattcaag ggcttgttga        12900
cacaacaaac accgtaatta agattgcgct tactaggagg ccattaggca        12950
tcaagaggct gatgcggata gtcaattatt ctagcatgca tgcaatgctg        13000
tttagagacg atgttttttc ctccagtaga tccaaccacc ccttagtctc        13050
ttctaatatg tgttctctga cactggcaga ctatgcacgg aatagaagct        13100
ggtcaccttt gacgggaggc aggaaaatac tgggtgtatc taatcctgat        13150
acgatagaac tcgtagaggg tgagattctt agtgtaagcg gagggtgtac        13200
aagatgtgac agcggagatg aacaatttac ttggttccat cttccaagca        13250
atatagaatt gaccgatgac accagcaaga atcctccgat gagggtacca        13300
tatctcgggt caaagacaca ggagaggaga gctgcctcac ttgcaaaaat        13350
agctcatatg tcgccacatg taaaggctgc cctaagggca tcatccgtgt        13400
tgatctgggc ttatggggat aatgaagtaa attggactgc tgctcttacg        13450
attgcaaaat ctcggtgcaa tgtaaactta gagtatcttc ggttactgtc        13500
ccctttaccc acggctggga atcttcaaca tagactagat gatggtataa        13550
ctcagatgac attcacccct gcatctctct acagggtgtc accttacatt        13600
cacatatcca atgattctca aaggctgttc actgaagaag gagtcaaaga        13650
ggggaatgtg gtttaccaac agatcatgct cttgggttta tctctaatcg        13700
aatcgatctt tccaatgaca acaaccagga catatgatga gatcacactg        13750
cacctacata gtaaatttag ttgctgtatc agagaagcac ctgttgcggt        13800
tcctttcgag ctacttgggg tggtaccgga actgaggaca gtgacctcaa        13850
ataagtttat gtatgatcct agccctgtat cggagggaga ctttgcgaga        13900
cttgacttag ctatcttcaa gagttatgag cttaatctgg agtcatatcc        13950
cacgatagag ctaatgaaca ttcttttcaat atccagcggg aagttgattg        14000
gccagtctgt ggtttcttat gatgaagata cctccataaa gaatgacgcc        14050
ataatagtgt atgacaatac ccgaaattgg atcagtgaag ctcagaattc        14100
agatgtggtc cgcctatttg aatatgcagc acttgaagtg ctccctcgact        14150 gttcttacca actctattat ctgagagtaa gaggcctaga caatattgtc        14200
ttatatatgg gtgatttata caagaatatg ccaggaattc tactttccaa        14250
cattgcagct acaatatctc atcccgtcat tcattcaagg ttacatgcag        14300
tgggcctggt caaccatgac ggatcacacc aacttgcaga tacggatttt        14350
atcgaaatgt ctgcaaaact attagtatct tgcacccgac gtgtgatatc        14400
cggcttatat tcaggaaata agtatgatct gctgttccca tctgtcttag        14450 atgataaccct gaatgagaag atgcttcagc tgatatcccg gttatgctgt        14500
```

```
ctgtacacgg tactctttgc tacaacaaga gaaatcccga aaataagagg      14550
cttaactgca gaagagaaat gttcaatact cactgagtat ttactgtcgg      14600
atgctgtgaa accattactt agccccgatc aagtgagctc tatcatgtct      14650
cctaacataa ttacattccc agctaatctg tactacatgt ctcggaagag      14700
cctcaatttg atcagggaaa gggaggacag ggatactatc ctggcgttgt      14750 tgttcccca agagccatta ttagagttcc cttctgtgca agatattggt       14800
gctcgagtga aagatccatt cacccgacaa cctgcggcat ttttgcaaga      14850
gttagatttg agtgctccag caaggtatga cgcattcaca cttagtcaga      14900
ttcatcctga actcacatct ccaaatccgg aggaagacta cttagtacga      14950
tacttgttca gagggatagg gactgcatct tcctcttggt ataaggcatc      15000
tcatctcctt tctgtacccg aggtaagatg tgcaagacac gggaactcct      15050
tatacttagc tgaagggagc ggagccatca tgagtcttct cgaactgcat      15100
gtaccacatg aaactatcta ttacaatacg ctcttttcaa atgagatgaa      15150
ccccccgcaa cgacatttcg ggccgacccc aactcagttt ttgaattcgg      15200
ttgtttatag gaatctacag gcggaggtaa cctgcaaaga tggatttgtc      15250
caagagttcc gtccattatg gagagaaaat acagaggaaa gtgacctgac      15300
ctcagataaa gcagtggggt atattacatc tgcagtgccc tacagatctg      15350
tatcattgct gcattgtgac attgaaattc ctccagggtc caatcaaagc      15400
ttactagatc aactagctat caatttatct ctgattgcca tgcattctgt      15450
aagggagggc ggggtagtaa tcatcaaagt gttgtatgca atgggatact      15500
actttcatct actcatgaac ttgtttgctc cgtgttccac aaaaggatat      15550
attctctcta atggttatgc atgtcgagga gatatggagt gttacctggt      15600
atttgtcatg ggttacctgg gcgggcctac atttgtacat gaggtggtga      15650
ggatggcaaa aactctggtg cagcggcacg gtacgctttt gtctaaatca      15700
gatgagatca cactgaccag gttattcacc tcacagcggc agcgtgtgac      15750
agacatccta tccagtcctt taccaagatt aataaagtac ttgaggaaga      15800
atattgacac tgcgctgatt gaagccgggg gacagcccgt ccgtccattc      15850
tgtgcggaga gtctggtgag cacgctagcg aacataactc agataaccca      15900
gatcatcgct agccacattg acacagttat ccggtctgtg atatatatgg      15950
aagctgaggg tgatctcgct gacacagtat ttctatttac cccttacaat      16000
ctctctactg acgggaaaaa gaggacatca cttaaacagt gcacgagaca      16050
gatcctagag gttacaatac taggtcttag agtcgaaaat ctcaataaaa      16100
taggcgatat aatcagccta gtgcttaaag gcatgatctc catggaggac      16150
cttatcccac taaggacata cttgaagcat agtacctgcc ctaaatattt      16200
gaaggctgtc ctaggtatta ccaaactcaa agaaatgttt acagacactt      16250
ctgtactgta cttgactcgt gctcaacaaa aattctacat gaaaactata      16300
ggcaatgcag tcaaaggata ttacagtaac tgtgactctt aacgaaaatc      16350
acatattaat aggctccttt tttggccaat tgtattcttg ttgatttaat      16400
catattatgt tagaaaaaag ttgaaccctg actcctaggg actcgaattc      16450
gaactcaaat aaatgtctta aaaaaggtt gcgcacaatt attcttgagt       16500
```

-continued

```
gtagtctcgt cattcaccaa atcttggttg ggtcggcatg gcatctccac      16550
ctcctcgcgg tccgacctgg gcatccgaag gaggacgcac gtccactcgg      16600
atggctaagg gagagcctgc agtagcataa ccccttgggg cctctaaacg      16650
ggtcttgagg ggttttttgc tgaaaggagg aactatatac tcgagctgca      16700
gcaatggcaa caacgttgcg caaactatta actggcgaac tacttactct      16750
agcttcccgg caacaattaa tagactggat ggaggcggat aaagttgcag      16800
gaccacttct gcgctcggcc cttccggctg gctggtttat tgctgataaa      16850
tctggagccg gtgagcgtgg gtctcgcggt atcattgcag cactggggcc      16900
agatggtaag ccctcccgta tcgtagttat ctacacgacg gggagtcagg      16950
caactatgga tgaacgaaat agacagatcg ctgagatagg tgcctcactg      17000
attaagcatt ggtaactgtc agaccaagtt tactcatata tactttagat      17050
tgatttaaaa cttcattttt aatttaaaag gatctaggtg aagatccttt      17100
ttgataatct catgaccaaa atcccttaac gtgagttttc gttccactga      17150
gcgtcagacc ccgtagaaaa gatcaaagga tcttcttgag atccttttttt      17200 tctgcgcgta atctgctgct tgcaaacaaa aaaaccaccg ctaccagcgg      17250
tggtttgttt gccggatcaa gagctaccaa ctctttttcc gaaggtaact      17300
ggcttcagca gagcgcagat accaaatact gtccttctag tgtagccgta      17350
gttaggccac cacttcaaga actctgtagc accgcctaca tacctcgctc      17400
tgctaatcct gttaccagtg gctgctgcca gtggcgataa gtcgtgtctt      17450
accgggttgg actcaagacg atagttaccg gataaggcgc agcggtcggg      17500
ctgaacgggg ggttcgtgca cacagcccag cttggagcga acgacctaca      17550
ccgaactgag atacctacag cgtgagctat gagaaagcgc cacgcttccc      17600
gaagggagaa aggcggacag gtatccggta agcggcaggg tcggaacagg      17650
agagcgcacg agggagcttc caggggggaaa cgcctggtat ctttatagtc      17700
ctgtcgggtt tcgccacctc tgacttgagc gtcgattttt gtgatgctcg      17750 tcagggggc ggagcctatg gaaaaacgcc agcaacgcgg cctttttacg      17800
gttcctggcc ttttgctggc cttttgctca catgttcttt cctgcgttat      17850
cccctgattc tgtggataac cgtattaccg cctttgagtg agctgatacc      17900
gctcgccgca gccgaacgac cgagcgcagc gagtcagtga gcgaggaagc      17950
ggaagagcgc ctgatgcggt attttctcct tacgcatctg tgcggtattt      18000
cacaccgcat atggtgcact ctcagtacaa tctgctctga tgccgcatag      18050
ttaagccagt atacactccg ctatcgctac gtgactgggt catggctgcg      18100
ccccgacacc cgccaacacc cgctgacgcg ccctgacggg cttgtctgct      18150
cccggcatcc gcttacagac aagctgtgac cgtctccggg agctgcatgt      18200
gtcagaggtt ttcaccgtca tcaccgaaac gcgcgaggca gctgcggtaa      18250
agctcatcag cgtggtcgtg aagcgattca cagatgtctg cctgttcatc      18300
cgcgtccagc tcgttgagtt tctccagaag cgttaatgtc tggcttctga      18350
taaagcgggc catgttaagg gcggtttttt cctgtttggt cactgatgcc      18400
tccgtgtaag ggggatttct gttcatgggg gtaatgatac cgatgaaacg      18450
```

-continued

```
agagaggatg ctcacgatac gggttactga tgatgaacat gcccggttac      18500
tggaacgttg tgagggtaaa caactggcgg tatggatgcg gcgggaccag      18550
agaaaaatca ctcagggtca atgccagcgc ttcgttaata cagatgtagg      18600
tgttccacag ggtagccagc agcatcctgc gatgcagatc cggaacataa      18650
tggtgcaggg cgctgacttc cgcgtttcca gactttacga aacacggaaa      18700
ccgaagacca ttcatgttgt tgctcaggtc gcagacgttt tgcagcagca      18750
gtcgcttcac gttcgctcgc gtatcggtga ttcattctgc taaccagtaa      18800
ggcaaccccg ccagcctagc cgggtcctca acgacaggag cacgatcatg      18850
cgcacccgtg gccaggaccc aacgctgccc gagatgcgcc gcgtgcggct      18900
gctggagatg gcggacgcga tggatatgtt ctgccaaggg ttggtttgcg      18950
cattcacagt tctccgcaag aattgattgg ctccaattct tggagtggtg      19000
aatccgttag cgaggtgccg ccggcttcca ttcaggtcga ggtggccggg      19050
ctccatgcac cgcgacgcaa cgcggggagg cagacaaggt atagggcggc      19100
gcctacaatc catgccaacc cgttccatgt gctcgccgag gcggcataaa      19150
tcgccgtgac gatcagcggt ccagtgatcg aagttaggct ggtaagagcc      19200
gcgagcgatc cttgaagctg tccctgatgg tcgtcatcta cctgcctgga      19250
cagcatggcc tgcaacgcgg gcatcccgat gccgccggaa gcgagaagaa      19300
tcataatggg gaaggccatc cagcctcgcg tcgcgaacgc cagcaagacg      19350
tagcccagcg cgtcggccgc catgccggcg ataatggcct gcttctcgcc      19400
gaaacgtttg gtggcgggac cagtgacgaa ggcttgagcg agggcgtgca      19450
agattccgaa taccgcaagc gacaggccga tcatcgtcgc gctccagcga      19500
aagcggtcct cgccgaaaat gacccagagc gctgccggca cctgtcctac      19550
gagttgcatg ataaagaaga cagtcataag tgcggcgacg atagtcatgc      19600
cccgcgccca ccggaaggag ctgactgggt tgaaggctct caagggcatc      19650
ggtcgacgct ctcccttatg cgactcctgc attaggaagc agcccagtag      19700
taggttgagg ccgttgagca ccgccgccgc aaggaatggt gcatgcaagg      19750
agatggcgcc caacagtccc ccggccacgg ggcctgccac catacccacg      19800
ccgaaacaag cgctcatgag cccgaagtgg cgagcccgat cttccccatc      19850
ggtgatgtcg gcgatatagg cgccagcaac cgcacctgtg gcgccggtga      19900
tgccggccac gatgcgtccg gcgtagagga tccacaggac gggtgtggtc      19950
gccatgatcg cgtagtcgat agtggctcca agtagcgaag cgagcaggac      20000
tgggcggcgg ccaaagcggt cggacagtgc tccgagaacg ggtgcgcata      20050
gaaattgcat caacgcatat agcgctagca gcacgccata gtgactggcg      20100
atgctgtcgg aatggacgat atcccgcaag aggcccggca gtaccggcat      20150
aaccaagcct atgcctacag catccagggt gacggtgccg aggatgacga      20200
tgagcgcatt gttagatttc atacacggtg cctgactgcg ttagcaattt      20250
aactgtgata aactaccgca ttaaagctta tcgatgataa gctgtcaaac      20300
atgagaa                                                     20307
```

<210> SEQ ID NO 19
<211> LENGTH: 17870

<212> TYPE: DNA

<213> ORGANISM: Artificial sequence
<220> FEATURE:
<223> OTHER INFORMATION: rNDV gB

<400> SEQUENCE: 19

| | |
|---|---:|
| accaaacaga gaatccgtga tttacgataa aaggcgaaag agcaattgaa | 50 |
| gtcgcacggg tagaaggtgt gaatctcgag tgcgagcccg aagcacaaac | 100 |
| tcgagaaagc cttctgccaa catgtcttcc gtatttgatg agtacgaaca | 150 |
| gctcctcgcg gctcagactc gccccaatgg agctcatgga gggggagaaa | 200 |
| aagggagtac cttaaaagta gacgtcccgg tattcactct taacagtgat | 250 |
| gacccagaag atagatggag ctttgtggta ttctgcctcc ggattgctgt | 300 |
| tagcgaagat gccaacaaac cactcaggca aggtgctctc atatctcttt | 350 |
| tatgctccca ctcacaggta atgaggaacc atgttgccct tgcagggaaa | 400 |
| cagaatgaag ccacattggc cgtgcttgag attgatggct tgccaacgg | 450 |
| cacgccccag ttcaacaata ggagtggagt gtctgaagag agagcacaga | 500 |
| gatttgcgat gatagcagga tctctcccctc gggcatgcag caacggaacc | 550 |
| ccgttcgtca cagccggggc cgaagatgat gcaccagaag acatcaccga | 600 |
| taccctggag aggatcctct ctatccaggc tcaagtatgg gtcacagtag | 650 |
| caaaagccat gactgcgtat gagactgcag atgagtcgga acaaggcga | 700 |
| atcaataagt atatgcagca aggcagggtc caaaagaaat acatcctcta | 750 |
| ccccgtatgc aggagcacaa tccaactcac gatcagacag tctcttgcag | 800 |
| tccgcatctt tttggttagc gagctcaaga gaggccgcaa cacggcaggt | 850 |
| ggtacctcta cttattataa cctggtaggg gacgtagact catacatcag | 900 |
| gaataccggg cttactgcat tcttcttgac actcaagtac ggaatcaaca | 950 |
| ccaagacatc agcccttgca cttagtagcc tctcaggcga catccagaag | 1000 |
| atgaagcagc tcatgcgttt gtatcggatg aaaggagata atgcgccgta | 1050 |
| catgacatta cttggtgata gtgaccagat gagctttgcg cctgccgagt | 1100 |
| atgcacaact ttactccctt gccatgggta tggcatcagt cctagataaa | 1150 |
| ggtactggga ataccaatt tgccagggac tttatgagca catcattctg | 1200 |
| gagacttgga gtagagtacg ctcaggctca gggaagtagc attaacgagg | 1250 |
| atatggctgc cgagctaaag ctaaccccag cagcaaggag gggcctggca | 1300 |
| gctgctgccc aacgggtctc cgaggagacc agcagcatag acatgcctac | 1350 |
| tcaacaagtc ggagtcctca ctgggcttag cgagggggggg tcccaagctc | 1400 |
| tacaaggcgg atcgaataga tcgcaagggc aaccagaagc cggggatggg | 1450 |
| gagacccaat tcctggatct gatgagagcg gtagcaaata gcatgaggga | 1500 |
| ggcgccaaac tctgcacagg gcactcccca atcggggcct cccccaactc | 1550 |
| ctgggccatc ccaagataac gacaccgact gggggtattg atggacaaaa | 1600 |
| cccagcctgc ttcacaaaaa acatcccaat gccctcaccc gtagtcgacc | 1650 |
| cctcgatttg cggctctata tgaccacacc ctcaaacaaa catccccctc | 1700 |
| tttcctccct cccctgctg tacaactccg cacgccctag ataccacagg | 1750 |
| cacaatgcgg ctcactaaca atcaaaacag agccgaggga attagaaaaa | 1800 |

| | |
|---|---|
| agtacgggta gaagagggat attcagagat cagggcaagt ctcccgagtc | 1850 |
| tctgctctct cctctacctg atagaccagg acaaacatgg ccacctttac | 1900 |
| agatgcagag atcgacgagc tatttgagac aagtggaact gtcattgaca | 1950 |
| acataattac agcccagggt aaaccagcag agactgttgg aaggagtgca | 2000 |
| atcccacaag gcaagaccaa ggtgctgagc gcagcatggg agaagcatgg | 2050 |
| gagcatccag ccaccggcca gtcaagacaa ccccgatcga caggacagat | 2100 |
| ctgacaaaca accatccaca cccgagcaaa cgaccccgca tgacagcccg | 2150 |
| ccggccacat ccgccgacca gccccccacc caggccacag acgaagccgt | 2200 |
| cgacacacag ctcaggaccg gagcaagcaa ctctctgctg ttgatgcttg | 2250 |
| acaagctcag caataaatcg tccaatgcta aaaagggccc atggtcgagc | 2300 |
| ccccaagagg ggaatcacca acgtccgact caacagcagg ggagtcaacc | 2350 |
| cagccgcgga aacagtcagg aaagaccgca gaaccaagtc aaggccgccc | 2400 |
| ctggaaacca gggcacagac gtgaacacag catatcatgg acaatgggag | 2450 |
| gagtcacaac tatcagctgg tgcaacccct catgctctcc gatcaaggca | 2500 |
| gagccaagac aataccccttg tatctgcgga tcatgtccag ccacctgtag | 2550 |
| actttgtgca agcgatgatg tctatgatgg aggcgatatc acagagagta | 2600 |
| agtaaggtcg actatcagct agatcttgtc ttgaaacaga catcctccat | 2650 |
| ccctatgatg cggtccgaaa tccaacagct gaaaacatct gttgcagtca | 2700 |
| tggaagccaa cttgggaatg atgaagattc tggatcccgg ttgtgccaac | 2750 |
| atttcatctc tgagtgatct acgggcagtt gcccgatctc accggttttt | 2800 |
| agtttcaggc cctggagacc cctctcccta tgtgacacaa ggaggcgaaa | 2850 |
| tggcacttaa taaactttcg caaccagtgc cacatccatc tgaattgatt | 2900 |
| aaacccgcca ctgcatgcgg gcctgatata ggagtggaaa aggacactgt | 2950 |
| ccgtgcattg atcatgtcac gcccaatgca cccgagttct tcagccaagc | 3000 |
| tcctaagcaa gttagatgca gccgggtcga tcgaggaaat caggaaaatc | 3050 |
| aagcgccttg ctctaaatgg ctaattacta ggaatctgca ccgagttccc | 3100 |
| ccccgcagac ccaaggtcca actctccaag cggcaatcct ctctcgcttc | 3150 |
| ctcagcccca ctgaatgatc gcgtaaccgt ttaattaatt agaaaaaata | 3200 |
| cgggtagaag gccaccatgc aatcctacat cgccgtgaac attgacatgg | 3250 |
| ctagcttgaa aatgctgatc tgcgtgtgcg tggcaatcct gatcccatct | 3300 |
| accctatctc aagattcaca cggaattgct ggaataatag accctcgtga | 3350 |
| tacagccagc atggatgttg aaaaatctc tttctccgaa gccattgggt | 3400 |
| cgggggcacc gaaagaaccc cagattagaa acagaatttt tgcgtgctca | 3450 |
| tctccaactg gcgccagtgt tgcgaggctt gcccagccac gacattgtca | 3500 |
| ccgacatgcc gattcgacta acatgactga aggaattgcc gtagtcttca | 3550 |
| agcaaaacat tgccccgtac gtctttaatg tgactctata ctataaacat | 3600 |
| ataaccacag ttactacgtg gcattattc tcaagacccc aaataacaaa | 3650 |
| tgagtacgtg accagggttc caatagacta tcatgaaatt gtcaggattg | 3700 |
| atcgatcggg agaatgctca tccaaagcaa cgtatcataa aaatttcatg | 3750 |

-continued

| | |
|---|---|
| tttttttgaag cttacgacaa tgatgaagca gagaagaagt tgcccctggt | 3800 |
| tccatcactg ttaagatcaa ctgtctccaa ggcgtttcat acaactaact | 3850 |
| ttactaagcg acatcaaacc ctgggatacc gaacgtctac atcggtcgac | 3900 |
| tgtgttgtgg aatatctaca ggctagatct gtatacccgt atgattactt | 3950 |
| tggaatggcg acaggtgata cagtagaaat ttctccttttt tataccaaaa | 4000 |
| acacgaccgg accaaggcgt cacagtgtct acagagacta tagatttctc | 4050 |
| gaaatcgcaa attatcaagt cagggatttg gaaaccggac aaataagacc | 4100 |
| ccctaaaaaa agaaactttc taacagatga acaattcact ataggctggg | 4150 |
| atgcaatgga agaaaaggaa tctgtatgta ctctcagtaa atggattgaa | 4200 |
| gtcccggaag cagttcgtgt ttcgtacaaa aacagttacc acttttcact | 4250 |
| taaagatatg actatgacgt tctcgtccgg aaaacaacct tttaacatca | 4300 |
| gcaggcttca tttggctgaa tgcgttccta ccatagccac ggaggccata | 4350 |
| gatggcatct ttgccagaaa gtatagttcg actcatgtcc gttctgggga | 4400 |
| catcgaatac tatctcggta gtggcggatt tctgatcgca tttcagaaac | 4450 |
| tcatgagcca tggcttggct gaaatgtacc tagaagaggc acaaagacaa | 4500 |
| aatcatctcc cgagagggag agagcgtcgc caagccgcag gtcgccgcac | 4550 |
| ggcgtcgctg cagtctggac ctcagggtga tagaattact acccacagtt | 4600 |
| ctgcaacatt tgccatgtta caatttgcat acgacaaaat ccaagcccat | 4650 |
| gttaacgagc ttatcggaaa tttgttggaa gcgtggtgtg agcttcagaa | 4700 |
| ccgccaactg attgtatggc atgagatgaa gaaactaaac ccgaactcac | 4750 |
| tgatgacatc tttgttcgga caacctgtaa gcgccaggct attgggagac | 4800 |
| atcgtagcgg tatcaaaatg tatagaaatt ccaatcgaaa atattaggat | 4850 |
| gcaggattcc atgcgcatgc caggggaccc aaccatgtgc tataccagac | 4900 |
| cagtacttat tttcaggtat tcgtcctccc ctgagtcaca gttttctgcg | 4950 |
| aactcaacag aaaaccacaa tcttgacata ttaggccaac tcggagaaca | 5000 |
| taatgaaatt ttacaagggc ggaatttgat agaaccatgc atgatcaatc | 5050 |
| acagacggta ctttctgttg ggagaaaact accttcttta cgaagactat | 5100 |
| acatttgtta gacaagtaaa tgcttccgag atcgaagaag tgagcatatt | 5150 |
| catcaacttg aacgccacta tactagaaga tttggacttt gtgcccgtcg | 5200 |
| aagtatacac tcgcgaggaa ctcagagata ctgggacttt aaactatgat | 5250 |
| gatgtggtca gatatcaaaa tatttataac aaaaggttca gagacattga | 5300 |
| cactgtaata cgtggagata ggggagatgc aatctttaga gcaatagcag | 5350 |
| attttttttgg caacactctt ggagaagtag gaaaggcatt gggaactgta | 5400 |
| gtgatgacag ccgcggcagc agtaatttct acagtatctg gcatcgcctc | 5450 |
| atttctttct aacccgttcg ccgcactcgg aattgggata gcggtggtgg | 5500 |
| tgagcattat tttaggactg ctggcgttca aatatgtaat gaacctgaaa | 5550 |
| tcaaacccag ttcaggttct gttcccaggc gcagttcccc cggccggaac | 5600 |
| tcctccacga ccctctagac gttactacaa ggatgaggag gaggttgagg | 5650 |
| aggatagtga tgaggacgac aggatacttg ccaccagagt tctgaaaggc | 5700 |
| cttgagcttc tacacaagga tgaacagaaa gctcgaagac agaaagcgcg | 5750 |

```
gttttctgct tttgctaaaa atatgagaaa cctatttcgc agaaaacccc        5800
gaaccaagga agatgactac cccctgctcg aatacccttc gtgggcagaa        5850
gaaagcgaag acgaaaatac tctagatcag atgagagcca ctacaaaaat        5900
gtgattaatt aatagctaca tttaagatta agaaaaaata cgggtagaat        5950
tggagtgccc caattgtgcc aagatggact catctaggac aattgggctg        6000
tactttgatt ctgcccattc ttctagcaac ctgttagcat ttccgatcgt        6050
cctacaagac acaggagatg ggaagaagca aatcgccccg caatatagga        6100
tccagcgcct tgacttgtgg actgatagta aggaggactc agtattcatc        6150
accacctatg gattcatctt tcaagttggg aatgaagaag ccactgtcgg        6200
catgatcgat gataaaccca agcgcgagtt actttccgct gcgatgctct        6250
gcctaggaag cgtcccaaat accggagacc ttattgagct ggcaagggcc        6300
tgtctcacta tgatagtcac atgcaagaag agtgcaacta atactgagag        6350
aatggttttc tcagtagtgc aggcacccca agtgctgcaa agctgtaggg        6400
ttgtggcaaa caaatactca tcagtgaatg cagtcaagca cgtgaaagcg        6450
ccagagaaga ttcccgggag tggaacccta gaatacaagg tgaactttgt        6500
ctccttgact gtggtaccga agaaggatgt ctacaagatc ccagctgcag        6550
tattgaaggt ttctggctcg agtctgtaca atcttgcgct caatgtcact        6600
attaatgtgg aggtagaccc gaggagtcct ttggttaaat ctctgtctaa        6650
gtctgacagc ggatactatg ctaacctctt cttgcatatt ggacttatga        6700
ccaccgtaga taggaagggg aagaaagtga catttgacaa gctggaaaag        6750
aaaataagga gccttgatct atctgtcggg ctcagtgatg tgctcgggcc        6800
ttccgtgttg gtaaaagcaa gaggtgcacg gactaagctt ttggcacctt        6850
tcttctctag cagtgggaca gcctgctatc ccatagcaaa tgcttctcct        6900
caggtggcca agatactctg gagtcaaacc gcgtgcctgc ggagcgttaa        6950
aatcattatc caagcaggta cccaacgcgc tgtcccagtg acccccaacc        7000
accaggttac ctctactaag ctggagaagg ggcacaccct tgccaaatac        7050
aatcctttta agaaataagc tgcgtctctg agattgcgct ccgcccactc        7100
acccggatca tcatgacaca aaaaactaat ctgtcttgat tatttacagt        7150
tagtttacct gtctatcaag ttagaaaaaa cacgggtaga agattctgga        7200
tcccggttgg cgccctccag gtgcaagatg ggctccagac cttctaccaa        7250
gaacccagca cctatgatgc tgactatccg ggttgcgctg gtactgagtt        7300
gcatctgtcc ggcaaactcc attgatggca ggcctcttgc agctgcagga        7350
attgtggtta caggagacaa agccgtcaac atatacacct catcccagac        7400
aggatcaatc atagttaagc tcctcccgaa tctgcccaag gataaggagg        7450
catgtgcgaa agccccttg gatgcataca acaggacatt gaccactttg        7500
ctcacccccc ttggtgactc tatccgtagg atacaagagt ctgtgactac        7550
atctggaggg gggagacagg ggcgccttat aggcgccatt attggcggtg        7600
tggctcttgg ggttgcaact gccgcacaaa taacagcggc cgcagctctg        7650
atacaagcca aacaaaatgc tgccaacatc ctccgactta aagagagcat        7700
```

| | |
|---|---|
| tgccgcaacc aatgaggctg tgcatgaggt cactgacgga ttatcgcaac | 7750 |
| tagcagtggc agttgggaag atgcagcagt ttgttaatga ccaatttaat | 7800 |
| aaaacagctc aggaattaga ctgcatcaaa attgcacagc aagttggtgt | 7850 |
| agagctcaac ctgtacctaa ccgaattgac tacagtattc ggaccacaaa | 7900 |
| tcacttcacc tgctttaaac aagctgacta ttcaggcact ttacaatcta | 7950 |
| gctggtggaa atatggatta cttattgact aagttaggtg tagggaacaa | 8000 |
| tcaactcagc tcattaatcg gtagcggctt aatcaccggt aaccctattc | 8050 |
| tatacgactc acagactcaa ctcttgggta tacaggtaac tctaccttca | 8100 |
| gtcgggaacc taaataatat gcgtgccacc tacttggaaa ccttatccgt | 8150 |
| aagcacaacc aggggatttg cctcggcact tgtcccaaaa gtggtgacac | 8200 |
| aggtcggttc tgtgatagaa gaacttgaca cctcatactg tatagaaact | 8250 |
| gacttagatt tatattgtac aagaatagta acgttcccta tgtccectgg | 8300 |
| tatttattcc tgcttgagcg gcaatacgtc ggcctgtatg tactcaaaga | 8350 |
| ccgaaggcgc acttactaca ccatacatga ctatcaaagg ttcagtcatc | 8400 |
| gccaactgca agatgacaac atgtagatgt gtaaaccccc cgggtatcat | 8450 |
| atcgcaaaac tatggagaag ccgtgtctct aatagataaa caatcatgca | 8500 |
| atgttttatc cttaggcggg ataactttaa ggctcagtgg ggaattcgat | 8550 |
| gtaacttatc agaagaatat ctcaatacaa gattctcaag taataataac | 8600 |
| aggcaatctt gatatctcaa ctgagcttgg gaatgtcaac aactcgatca | 8650 |
| gtaatgcttt gaataagtta gaggaaagca acagaaaact agacaaagtc | 8700 |
| aatgtcaaac tgaccagcac atctgctctc attacctata tcgttttgac | 8750 |
| tatcatatct cttgtttttg gtatacttag cctgattcta gcatgctacc | 8800 |
| taatgtacaa gcaaaaggcg caacaaaaga ccttattatg gcttgggaat | 8850 |
| aatactctag atcagatgag agccactaca aaaatgtgaa cacagatgag | 8900 |
| gaacgaaggt ttccctaata gtaatttgtg tgaaagttct ggtagtctgt | 8950 |
| cagttcagag agttaagaaa aaactacgcg ttgtagatga ccaaaggacg | 9000 |
| atatacgggt agaacggtaa gagaggccgc ccctcaattg cgagccaggc | 9050 |
| ttcacaacct ccgttctacc gcttcaccga caacagtcct caatcatgga | 9100 |
| ccgcgccgtt agccaagttg cgttagagaa tgatgaaaga gaggcaaaaa | 9150 |
| atacatggcg cttgatattc cggattgcaa tcttattctt aacagtagtg | 9200 |
| accttggcta tatctgtagc ctccctttta tatagcatgg gggctagcac | 9250 |
| acctagcgat cttgtaggca taccgactag gatttccagg gcagaagaaa | 9300 |
| agattacatc tacacttggt tccaatcaag atgtagtaga taggatatat | 9350 |
| aagcaagtgg cccttgagtc tccgttggca ttgttaaaaa ctgagaccac | 9400 |
| aattatgaac gcaataacat ctctctctta tcagattaat ggagctgcaa | 9450 |
| acaacagtgg gtgggggca cctatccatg acccagatta tataggggggg | 9500 |
| ataggcaaag aactcattgt agatgatgct agtgatgtca catcattcta | 9550 |
| tccctctgca tttcaagaac atctgaattt tatcccggcg cctactacag | 9600 |
| gatcaggttg cactcgaata ccctcatttg acatgagtgc tacccattac | 9650 |
| tgctacaccc ataatgtaat attgtctgga tgcagagatc actcacattc | 9700 |

```
atatcagtat ttagcacttg gtgtgctccg gacatctgca acagggaggg    9750
tattcttttc tactctgcgt tccatcaacc tggacgacac ccaaaatcgg    9800
aagtcttgca gtgtgagtgc aactcccctg ggttgtgata tgctgtgctc    9850
gaaagtcacg gagacagagg aagaagatta taactcagct gtccctacgc    9900
ggatggtaca tgggaggtta gggttcgacg gccagtacca cgaaaaggac    9950
ctagatgtca caacattatt cggggactgg gtggccaact acccaggagt   10000
aggggtgga tcttttattg acagccgcgt atggttctca gtctacggag    10050
ggttaaaacc caattcaccc agtgacactg tacaggaagg gaaatatgtg   10100
atatacaagc gatacaatga cacatgccca gatgagcaag actaccagat   10150
tcgaatggcc aagtcttcgt ataagcctgg acggtttggt gggaaacgca   10200
tacagcaggc tatcttatct atcaaggtgt caacatcctt aggcgaagac   10250
ccggtactga ctgtaccgcc caacacagtc acactcatgg gggccgaagg   10300
cagaattctc acagtaggga catctcattt cttgtatcaa cgagggtcat   10350
catacttctc tcccgcgtta ttatatccta tgacagtcag caacaaaaca   10400
gccactcttc atagtcctta tacattcaat gccttcactc ggccaggtag   10450
tatcccttgc caggcttcag caagatgccc caacccgtgt gttactggag   10500
tctatacaga tccatatccc ctaatcttct atagaaacca caccttgcga   10550
ggggtattcg ggacaatgct tgatggtgta caagcaagac ttaaccctgc   10600
gtctgcagta ttcgatagca catcccgcag tcgcattact cgagtgagtt   10650
caagcagtac caaagcagca tacacaacat caacttgttt taaagtggtc   10700
aagactaata agaccatttg tctcagcatt gctgaaatat ctaatactct   10750
cttcggagaa ttcagaatcg tcccgttact agttgagatc ctcaaagatg   10800
acggggttag agaagccagg tctggctagt tgagtcaatt ataaaggagt   10850
tggaaagatg gcattgtatc acctatcttc tgcgacatca agaatcaaac   10900
cgaatgccgg cgcgtgctcg aattccatgt tgccagttga ccacaatcag   10950
ccagtgctca tgcgatcaga ttaagccttg tcaatagtct cttgattaag   11000
aaaaaatgta agtggcaatg agatacaagg caaaatacgt accggtaaat   11050
aatacgggta ggacatggcg agctccggtc ctgaaagggc agagcatcag   11100
attatcctac cagagtcaca cctgtcttca ccattggtca agcacaaact   11150
actctattac tggaaattaa ctgggctacc gcttcctgat gaatgtgact   11200
tcgaccacct cattctcagc cgacaatgga aaaaaatact tgaatcggcc   11250
tctcctgata ctgagagaat gataaaactc ggaagggcag tacaccaaac   11300
tcttaaccac aattccagaa taaccggagt gctccacccc aggtgtttag   11350
aagaactggc taatattgag gtcccagatt caaccaacaa atttcggaag   11400
attgagaaga agatccaaat tcacaacacg agatatggag aactgttcac   11450
aaggctgtgt acgcatatag agaagaaact gctggggtca tcttggtcta   11500
acaatgtccc ccggtcagag gagttcagca gcattcgtac ggatccggca   11550
ttctggtttc actcaaaatg gtccacagcc aagtttgcat ggctcccatat  11600
aaaacagatc cagaggcatc tgatggtggc agctaggaca aggtctgcgg   11650
```

```
ccaacaaatt ggtgatgcta acccataagg taggccaagt ctttgtcact         11700
cctgaacttg tcgttgtgac gcatacgaat gagaacaagt tcacatgtct         11750
tacccaggaa cttgtattga tgtatgcaga tatgatggag ggcagagata         11800
tggtcaacat aatatcaacc acggcggtgc atctcagaag cttatcagag         11850
aaaattgatg acattttgcg gttaatagac gctctggcaa aagacttggg         11900
taatcaagtc tacgatgttg tatcactaat ggagggattt gcatacggag         11950
ctgtccagct actcgagccg tcaggtacat ttgcaggaga tttcttcgca         12000
ttcaacctgc aggagcttaa agacattcta attggcctcc tccccaatga         12050
tatagcagaa tccgtgactc atgcaatcgc tactgtattc tctggtttag         12100
aacagaatca agcagctgag atgttgtgtc tgttgcgtct gtggggtcac         12150
ccactgcttg agtcccgtat tgcagcaaag gcagtcagga gccaaatgtg         12200
cgcaccgaaa atggtagact ttgatatgat ccttcaggta ctgtctttct         12250
tcaagggaac aatcatcaac gggtacagaa agaagaatgc aggtgtgtgg         12300
ccgcgagtca aagtggatac aatatatggg aaggtcattg gcaactaca          12350 tgcagattca gcagagattt cacacgatat catgttgaga gagtataaga         12400
gtttatctgc acttgaattt gagccatgta tagaatatga ccctgtcaca         12450
aacctgagca tgttcctaaa agacaaggca atcgcacacc ccaacgataa         12500
ttggcttgcc tcgtttaggc ggaaccttct ctccgaagac cagaagaaac         12550
atgtaaaaga agcaacttcg actaatcgcc tcttgataga gttttagag          12600 tcaaatgatt ttgatccata taagagatg gaatatctga cgacccttga          12650
gtaccttaga gatgacaatg tggcagtatc atactcgctc aaggagaagg         12700
aagtgaaagt taatggacgg atcttcgcta agctgacaaa gaagttaagg         12750
aactgtcagg tgatggcgga agggatccta gccgatcaga ttgcaccttt         12800 cttttcaggga aatggagtca ttcaggatag catatccttg accaagagta        12850
tgctagcgat gagtcaactg tcttttaaca gcaataagaa acgtatcact         12900
gactgtaaag aaagagtatc ttcaaaccgc aatcatgatc cgaaaagcaa         12950
gaaccgtcgg agagttgcaa ccttcataac aactgacctg caaaagtact         13000
gtcttaattg gagatatcag acaatcaaat tgttcgctca tgccatcaat         13050
cagttgatgg gcctacctca cttcttcgaa tggattcacc taagactgat         13100
ggacactacg atgttcgtag gagacccttt caatcctcca agtgaccta          13150 ctgactgtga cctctcaaga gtccctaatg atgacatata tattgtcagt         13200
gccagagggg gtatcgaagg attatgccag aagctatgga caatgatctc         13250
aattgctgca atccaacttg ctgcagctag atcgcattgt cgtgttgcct         13300
gtatggtaca gggtgataat caagtaatag cagtaacgag agaggtaaga         13350
tcagacgact ctccggagat ggtgttgaca cagttgcatc aagccagtga         13400
taatttcttc aaggaattaa ttcatgtcaa tcatttgatt ggccataatt         13450
tgaaggatcg tgaaccatc aggtcagaca cattcttcat atacagcaaa          13500
cgaatcttca aagatggagc aatcctcagt caagtcctca aaaattcatc         13550
taaattagtg ctagtgtcag gtgatctcag tgaaaacacc gtaatgtcct         13600
gtgccaacat tgcctctact gtagcacggc tatgcgagaa cgggcttccc         13650
```

```
aaagacttct gttactattt aaactatata atgagttgtg tgcagacata    13700
ctttgactct gagttctcca tcaccaacaa ttcgcacccc gatcttaatc    13750
agtcgtggat tgaggacatc tcttttgtgc actcatatgt tctgactcct    13800
gcccaattag ggggactgag taaccttcaa tactcaaggc tctacactag    13850
aaatatcggt gacccgggga ctactgcttt tgcagagatc aagcgactag    13900
aagcagtggg attactgagt cctaacatta tgactaatat cttaactagg    13950
ccgcctggga atggagattg ggccagtctg tgcaacgacc catactcttt    14000
caattttgag actgttgcaa gcccaaatat tgttcttaag aaacatacgc    14050
aaagagtcct atttgaaact tgttcaaatc ccttattgtc tggagtgcac    14100
acagaggata atgaggcaga agagaaggca ttggctgaat tcttgcttaa    14150
tcaagaggtg attcatcccc gcgttgcgca tgccatcatg gaggcaagct    14200
ctgtaggtag gagaaagcaa attcaagggc ttgttgacac aacaaacacc    14250
gtaattaaga ttgcgcttac taggaggcca ttaggcatca agaggctgat    14300
gcggatagtc aattattcta gcatgcatgc aatgctgttt agagacgatg    14350
ttttttcctc cagtagatcc aaccaccect tagtctcttc taatatgtgt    14400
tctctgacac tggcagacta tgcacggaat agaagctggt cacctttgac    14450
gggaggcagg aaaatactgg gtgtatctaa tcctgatacg atagaactcg    14500
tagagggtga gattcttagt gtaagcggag ggtgtacaag atgtgacagc    14550
ggagatgaac aatttacttg gttccatctt ccaagcaata tagaattgac    14600
cgatgacacc agcaagaatc ctccgatgag ggtaccatat ctcgggtcaa    14650
agacacagga gaggagagct gcctcacttg caaaaatagc tcatatgtcg    14700
ccacatgtaa aggctgccct aagggcatca tccgtgttga tctgggctta    14750
tggggataat gaagtaaatt ggactgctgc tcttacgatt gcaaaatctc    14800
ggtgcaatgt aaacttagag tatcttcggt tactgtcccc tttacccacg    14850
gctgggaatc ttcaacatag actagatgat ggtataactc agatgacatt    14900 caccectgca tctctctaca gggtgtcacc ttacattcac atatccaatg    14950
attctcaaag gctgttcact gaagaaggag tcaaagaggg gaatgtggtt    15000
taccaacaga tcatgctctt gggtttatct ctaatcgaat cgatctttcc    15050
aatgacaaca accaggacat atgatgagat cacactgcac ctacatagta    15100
aatttagttg ctgtatcaga gaagcacctg ttgcggttcc tttcgagcta    15150
cttggggtgg taccggaact gaggacagtg acctcaaata agtttatgta    15200
tgatcctagc cctgtatcgg agggagactt tgcgagactt gacttagcta    15250
tcttcaagag ttatgagctt aatctggagt catatcccac gatagagcta    15300
atgaacattc tttcaatatc cagcgggaag ttgattggcc agtctgtggt    15350
ttcttatgat gaagatacct ccataaagaa tgacgccata atagtgtatg    15400
acaatacccg aaattggatc agtgaagctc agaattcaga tgtggtccgc    15450
ctatttgaat atgcagcact tgaagtgctc ctcgactgtt cttaccaact    15500
ctattatctg agagtaagag gcctagacaa tattgtctta tatatgggtg    15550
atttatacaa gaatatgcca ggaattctac tttccaacat tgcagctaca    15600
```

```
atatctcatc ccgtcattca ttcaaggtta catgcagtgg gcctggtcaa      15650
ccatgacgga tcacaccaac ttgcagatac ggattttatc gaaatgtctg      15700
caaaactatt agtatcttgc acccgacgtg tgatatccgg cttatattca      15750
ggaaataagt atgatctgct gttcccatct gtcttagatg ataacctgaa      15800
tgagaagatg cttcagctga tatcccggtt atgctgtctg tacacggtac      15850
tctttgctac aacaagagaa atcccgaaaa taagaggctt aactgcagaa      15900
gagaaatgtt caatactcac tgagtattta ctgtcggatg ctgtgaaacc      15950
attacttagc cccgatcaag tgagctctat catgtctcct aacataatta      16000
cattcccagc taatctgtac tacatgtctc ggaagagcct caatttgatc      16050
agggaaaggg aggacaggga tactatcctg gcgttgttgt tcccccaaga      16100
gccattatta gagttcccct ctgtgcaaga tattggtgct cgagtgaaag      16150
atccattcac ccgacaacct gcggcatttt tgcaagagtt agatttgagt      16200
gctccagcaa ggtatgacgc attcacactt agtcagattc atcctgaact      16250
cacatctcca aatccggagg aagactactt agtacgatac ttgttcagag      16300
ggatagggac tgcatcttcc tcttggtata aggcatctca tctcctttct      16350
gtacccgagg taagatgtgc aagacacggg aactccttat acttagctga      16400
agggagcgga gccatcatga gtcttctcga actgcatgta ccacatgaaa      16450
ctatctatta caatacgctc ttttcaaatg agatgaaccc ccgcaacga      16500 catttcgggc cgaccccaac tcagttttg aattcggttg tttataggaa       16550
tctacaggcg gaggtaacct gcaaagatgg atttgtccaa gagttccgtc      16600
cattatggag agaaaataca gaggaaagtg acctgacctc agataaagca      16650
gtggggtata ttacatctgc agtgccctac agatctgtat cattgctgca      16700
ttgtgacatt gaaattcctc cagggtccaa tcaaagctta ctagatcaac      16750
tagctatcaa tttatctctg attgccatgc attctgtaag ggagggcggg      16800
gtagtaatca tcaaagtgtt gtatgcaatg ggatactact ttcatctact      16850
catgaacttg tttgctccgt gttccacaaa aggatatatt ctctctaatg      16900
gttatgcatg tcgaggagat atggagtgtt acctggtatt tgtcatgggt      16950
tacctgggcg ggcctacatt tgtacatgag gtggtgagga tggcaaaaac      17000
tctggtgcag cggcacggta cgcttttgtc taaatcagat gagatcacac      17050
tgaccaggtt attcacctca cagcggcagc gtgtgacaga catcctatcc      17100
agtcctttac caagattaat aaagtacttg aggaagaata ttgacactgc      17150
gctgattgaa gccgggggac agcccgtccg tccattctgt gcggagagtc      17200
tggtgagcac gctagcgaac ataactcaga taacccagat catcgctagc      17250
cacattgaca cagttatccg gtctgtgata tatatggaag ctgagggtga      17300
tctcgctgac acagtatttc tatttacccc ttacaatctc tctactgacg      17350
ggaaaaagag gacatcactt aaacagtgca cgagacagat cctagaggtt      17400
acaatactag gtcttagagt cgaaaatctc aataaaatag gcgatataat      17450
cagcctagtg cttaaaggca tgatctccat ggaggacctt atcccactaa      17500
ggacatactt gaagcatagt acctgcccta aatatttgaa ggctgtccta      17550
ggtattacca aactcaaaga aatgtttaca gacacttctg tactgtactt      17600
```

```
gactcgtgct caacaaaaat tctacatgaa aactataggc aatgcagtca        17650
aaggatatta cagtaactgt gactcttaac gaaaatcaca tattaatagg        17700
ctcctttttt ggccaattgt attcttgttg atttaatcat attatgttag        17750
aaaaaagttg aaccctgact ccttaggact cgaattcgaa ctcaaataaa        17800
tgtcttaaaa aaaggttgcg cacaattatt cttgagtgta gtctcgtcat        17850
tcaccaaatc ttggttgggt                                        17870
```

<210> SEQ ID NO 20
<211> LENGTH: 16554
<212> TYPE: DNA

<213> ORGANISM: Artificial sequence
<220> FEATURE:
<223> OTHER INFORMATION: rNDV gC
<400> SEQUENCE: 20

```
accaaacaga gaatccgtga tttacgataa aaggcgaaag agcaattgaa          50
gtcgcacggg tagaaggtgt gaatctcgag tgcgagcccg aagcacaaac         100
tcgagaaagc cttctgccaa catgtcttcc gtatttgatg agtacgaaca         150
gctcctcgcg gctcagactc gccccaatgg agctcatgga gggggagaaa         200
aagggagtac cttaaaagta gacgtcccgg tattcactct taacagtgat         250
gacccagaag atagatggag ctttgtggta ttctgcctcc ggattgctgt         300
tagcgaagat gccaacaaac cactcaggca aggtgctctc atatctcttt         350
tatgctccca ctcacaggta atgaggaacc atgttgccct tgcagggaaa         400
cagaatgaag ccacattggc cgtgcttgag attgatggct ttgccaacgg         450
cacgccccag ttcaacaata ggagtggagt gtctgaagag agagcacaga         500
gatttgcgat gatagcagga tctctccctc gggcatgcag caacggaacc         550
ccgttcgtca cagccggggc cgaagatgat gcaccagaag acatcaccga         600
taccctggag aggatcctct ctatccaggc tcaagtatgg gtcacagtag         650
caaaagccat gactgcgtat gagactgcag atgagtcgga aacaaggcga         700
atcaataagt atatgcagca aggcagggtc caaaagaaat acatcctcta         750
ccccgtatgc aggagcacaa tccaactcac gatcagacag tctcttgcag         800
tccgcatctt tttggttagc gagctcaaga gaggccgcaa cacggcaggt         850
ggtacctcta cttattataa cctggtaggg gacgtagact catacatcag         900
gaataccggg cttactgcat tcttcttgac actcaagtac ggaatcaaca         950
ccaagacatc agcccttgca cttagtagcc tctcaggcga catccagaag        1000
atgaagcagc tcatgcgttt gtatcggatg aaaggagata atgcgccgta        1050
catgacatta cttggtgata gtgaccagat gagctttgcg cctgccgagt        1100
atgcacaact ttactccctt gccatgggta tggcatcagt cctagataaa        1150
ggtactggga ataccaatt tgccagggac tttatgagca catcattctg        1200
gagacttgga gtagagtacg ctcaggctca gggaagtagc attaacgagg        1250
atatggctgc cgagctaaag ctaaccccag cagcaaggag gggcctggca        1300
gctgctgccc aacgggtctc cgaggagacc agcagcatag acatgcctac        1350
```

-continued

| | |
|---|---|
| tcaacaagtc ggagtcctca ctgggcttag cgaggggggg tcccaagctc | 1400 |
| tacaaggcgg atcgaataga tcgcaagggc aaccagaagc cggggatggg | 1450 |
| gagacccaat tcctggatct gatgagagcg gtagcaaata gcatgaggga | 1500 |
| ggcgccaaac tctgcacagg gcactcccca atcggggcct cccccaactc | 1550 |
| ctgggccatc ccaagataac gacaccgact gggggtattg atggacaaaa | 1600 |
| cccagcctgc ttccacaaaa acatcccaat gccctcaccc gtagtcgacc | 1650 |
| cctcgatttg cggctctata tgaccacacc ctcaaacaaa catcccctc | 1700 |
| tttcctccct cccctgctg tacaactccg cacgccctag ataccacagg | 1750 |
| cacaatgcgg ctcactaaca atcaaaacag agccgaggga attagaaaaa | 1800 |
| agtacgggta gaagagggat attcagagat cagggcaagt ctcccgagtc | 1850 |
| tctgctctct cctctacctg atagaccagg acaaacatgg ccacctttac | 1900 |
| agatgcagag atcgacgagc tatttgagac aagtggaact gtcattgaca | 1950 |
| acataattac agcccagggt aaaccagcag agactgttgg aaggagtgca | 2000 |
| atcccacaag gcaagaccaa ggtgctgagc gcagcatggg agaagcatgg | 2050 |
| gagcatccag ccaccggcca gtcaagacaa ccccgatcga caggacagat | 2100 |
| ctgacaaaca accatccaca cccgagcaaa cgaccccgca tgacagcccg | 2150 |
| ccggccacat ccgccgacca gccccccacc caggccacag acgaagccgt | 2200 |
| cgacacacag ctcaggaccg gagcaagcaa ctctctgctg ttgatgcttg | 2250 |
| acaagctcag caataaatcg tccaatgcta aaaagggccc atggtcgagc | 2300 |
| ccccaagagg ggaatcacca acgtccgact caacagcagg ggagtcaacc | 2350 |
| cagccgcgga aacagtcagg aaagaccgca gaaccaagtc aaggccgccc | 2400 |
| ctggaaacca gggcacagac gtgaacacag catatcatgg acaatgggag | 2450 |
| gagtcacaac tatcagctgg tgcaacccct catgctctcc gatcaaggca | 2500 |
| gagccaagac aatacccttg tatctgcgga tcatgtccag ccacctgtag | 2550 |
| actttgtgca agcgatgatg tctatgatgg aggcgatatc acagagagta | 2600 |
| agtaaggtcg actatcagct agatcttgtc ttgaaacaga catcctccat | 2650 |
| ccctatgatg cggtccgaaa tccaacagct gaaaacatct gttgcagtca | 2700 |
| tggaagccaa cttgggaatg atgaagattc tggatcccgg ttgtgccaac | 2750 |
| atttcatctc tgagtgatct acgggcagtt gcccgatctc acccggtttt | 2800 |
| agtttcaggc cctggagacc cctctcccta tgtgacacaa ggaggcgaaa | 2850 |
| tggcacttaa taaactttcg caaccagtgc cacatccatc tgaattgatt | 2900 |
| aaacccgcca ctgcatgcgg gcctgatata ggagtggaaa aggacactgt | 2950 |
| ccgtgcattg atcatgtcac gcccaatgca cccgagttct tcagccaagc | 3000 |
| tcctaagcaa gttagatgca gccgggtcga tcgaggaaat caggaaaatc | 3050 |
| aagcgccttg ctctaaatgg ctaattacta ctgccacacg tagcgggtcc | 3100 |
| ctgtccactc ggcatcacac ggaatctgca ccgagttccc ccccgcagac | 3150 |
| ccaaggtcca actctccaag cggcaatcct ctctcgcttc ctcagcccca | 3200 |
| ctgaatgatc gcgtaaccgt ttaattaatt agaaaaaata cgggtagaag | 3250 |
| gccaccatgc agcatcagag tactgcgcta gtttcgagta tacttttgct | 3300 |
| cttgagcctg caaagccttg cgtttgaatt tttctgtgat ccgccacacg | 3350 |

| | |
|---|---|
| tttttcgagg gcagctcggt gacccccattc tattgcaatg cttcagcgac | 3400 |
| agacctctaa cccacgaaga atctgtaaaa gtagaagtaa ttcgacaccc | 3450 |
| agccagctta gttgaaactg cgctaagcgc ctacgggatc cccccttcgc | 3500 |
| tagatccatg gagagctact ccaagaactc tctacacata tgatgccgct | 3550 |
| actgattcaa tcaaggacct aggatacatt ggtgaagatg gaattaaccc | 3600 |
| accatatttg gacgactgtc gttcaggttt tttcaatgtc tctatcaagt | 3650 |
| ctagcatgag atctcacatg gcgcgttatc agtggaccgc aagtcgaggg | 3700 |
| tctacaaaac taaatagctc tttttatcgac gtcttttttgg caagaccacc | 3750 |
| tacaactgtc cgcatcaaat cagaagaact gtacgaagac tcagataagg | 3800 |
| cttcgcactt aagtgttgaa gcgcttggcg cttatcctcc atctgctgcg | 3850 |
| ctgggtacat ggatgataca taatgcatct cttgctgaaa aatacagttt | 3900 |
| agaaagaaga gttctttatg catcaggaga gaatggatcg gtggatcaga | 3950 |
| catgggaact ggaaatacgt ggagaagcca gccagcccct cccttccaaa | 4000 |
| attcaatttg tatatcgatg gacccctcct gaggactttg aaatgctacg | 4050 |
| acctgaaact cgcttgttaa ggttgactcc cagctggatt agcaagcccc | 4100 |
| gcatcacggt acaattcgtc cctcctgcct atgccctgtg tagagcagct | 4150 |
| aatattatag acggccgagg atttattgaa tggatcgtag ataatagaat | 4200 |
| ttcgacgagc ccacaccaga cctttgtttt ggatgagccc gaggggaaaa | 4250 |
| atatcgttac actaatggac gtcataaaac taccaccgga ggatacattt | 4300 |
| caatctgcct ctaattacgt gtgcgtcata agaggctatg aacatgcata | 4350 |
| cagatatctc aacgcctcct taatgataga taatctgcca atgcggcaag | 4400 |
| gattccccgc agtcagcaca tctgctctca ttacctatat cgttttgact | 4450 |
| atcatatctc ttgttttttgg tatacttagc ctgattctag catgctacct | 4500 |
| aatgtacaag caaaaggcgc aacaaaagac cttattatgg cttgggaata | 4550 |
| atactctaga tcagatgaga gccactacaa aaatgtgatt aattaatagc | 4600 |
| tacatttaag attaagaaaa aatacgggta gaattggagt gccccaattg | 4650 |
| tgccaagatg gactcatcta ggacaattgg gctgtacttt gattctgccc | 4700 |
| attcttctag caacctgtta gcatttccga tcgtcctaca agacacagga | 4750 |
| gatgggaaga agcaaatcgc cccgcaatat aggatccagc gccttgactt | 4800 |
| gtggactgat agtaaggagg actcagtatt catcaccacc tatggattca | 4850 |
| tctttcaagt tggaatgaa gaagccactg tcggcatgat cgatgataaa | 4900 |
| cccaagcgcg agttactttc cgctgcgatg ctctgcctag gaagcgtccc | 4950 |
| aaataccgga gaccttattg agctggcaag ggcctgtctc actatgatag | 5000 |
| tcacatgcaa gaagagtgca actaatactg agagaatggt tttctcagta | 5050 |
| gtgcaggcac cccaagtgct gcaaagctgt agggttgtgg caaacaaata | 5100 |
| ctcatcagtg aatgcagtca agcacgtgaa agcgccagag aagattcccg | 5150 |
| ggagtggaac cctagaatac aaggtgaact ttgtctcctt gactgtggta | 5200 |
| ccgaagaagt atgtctacaa gatcccagct gcagtattga aggtttctgg | 5250 |
| ctcgagtctg tacaatcttg cgctcaatgt cactattaat gtggaggtag | 5300 |

```
acccgaggag tcctttggtt aaatctctgt ctaagtctga cagcggatac      5350
tatgctaacc tcttcttgca tattggactt atgaccaccg tagataggaa      5400
ggggaagaaa gtgacatttg acaagctgga aaagaaaata aggagccttg      5450
atctatctgt cgggctcagt gatgtgctcg ggccttccgt gttggtaaaa      5500
gcaagaggtg cacggactaa gcttttggca cctttcttct ctagcagtgg      5550
gacagcctgc tatcccatag caaatgcttc tcctcaggtg gccaagatac      5600
tctggagtca aaccgcgtgc ctgcggagcg ttaaaatcat tatccaagca      5650
ggtacccaac gcgctgtccc agtgaccccc aaccaccagg ttacctctac      5700
taagctggag aaggggcaca cccttgccaa atacaatcct tttaagaaat      5750
aagctgcgtc tctgagattg cgctccgccc actcacccgg atcatcatga      5800
cacaaaaaac taatctgtct tgattattta cagttagttt acctgtctat      5850
caagttagaa aaaacacggg tagaagattc tggatcccgg ttggcgccct      5900
ccaggtgcaa gatgggctcc agaccttcta ccaagaaccc agcacctatg      5950
atgctgacta tccgggttgc gctggtactg agttgcatct gtccggcaaa      6000
ctccattgat ggcaggcctc ttgcagctgc aggaattgtg gttacaggag      6050
acaaagccgt caacatatac acctcatccc agacaggatc aatcatagtt      6100
aagctcctcc cgaatctgcc caaggataag gaggcatgtg cgaaagcccc      6150
cttggatgca tacaacagga cattgaccac tttgctcacc cccttggtg      6200 actctatccg taggatacaa gagtctgtga ctacatctgg aggggggaga      6250
caggggcgcc ttataggcgc cattattggc ggtgtggctc ttggggttgc      6300
aactgccgca caaataacag cggccgcagc tctgatacaa gccaaacaaa      6350
atgctgccaa catcctccga cttaaagaga gcattgccgc aaccaatgag      6400
gctgtgcatg aggtcactga cggattatcg caactagcag tggcagttgg      6450
gaagatgcag cagtttgtta atgaccaatt taataaaaca gctcaggaat      6500
tagactgcat caaaattgca cagcaagttg gtgtagagct caacctgtac      6550
ctaaccgaat tgactacagt attcggacca caaatcactt cacctgcttt      6600
aaacaagctg actattcagg cactttacaa tctagctggt ggaaatatgg      6650
attacttatt gactaagtta ggtgtaggga acaatcaact cagctcatta      6700
atcggtagcg gcttaatcac cggtaaccct attctatacg actcacagac      6750
tcaactcttg ggtatacagg taactctacc ttcagtcggg aacctaaata      6800
atatgcgtgc cacctacttg gaaaccttat ccgtaagcac aaccagggga      6850
tttgcctcgg cacttgtccc aaaagtggtg acacaggtcg gttctgtgat      6900
agaagaactt gacacctcat actgtataga aactgactta gatttatatt      6950
gtacaagaat agtaacgttc cctatgtccc ctggtattta ttcctgcttg      7000
agcggcaata cgtcggcctg tatgtactca aagaccgaag gcgcacttac      7050
tacaccatac atgactatca aaggttcagt catcgccaac tgcaagatga      7100
caacatgtag atgtgtaaac cccccgggta tcatatcgca aaactatgga      7150
gaagccgtgt ctctaataga taaacaatca tgcaatgttt tatccttagg      7200
cgggataact ttaaggctca gtggggaatt cgatgtaact tatcagaaga      7250
atatctcaat acaagattct caagtaataa taacaggcaa tcttgatatc      7300
```

-continued

| | |
|---|---|
| tcaactgagc ttgggaatgt caacaactcg atcagtaatg ctttgaataa | 7350 |
| gttagaggaa agcaacagaa aactagacaa agtcaatgtc aaactgacca | 7400 |
| gcacatctgc tctcattacc tatatcgttt tgactatcat atctcttgtt | 7450 |
| tttggtatac ttagcctgat tctagcatgc tacctaatgt acaagcaaaa | 7500 |
| ggcgcaacaa aagaccttat tatggcttgg gaataatact ctagatcaga | 7550 |
| tgagagccac tacaaaaatg tgaacacaga tgaggaacga aggtttccct | 7600 |
| aatagtaatt tgtgtgaaag ttctggtagt ctgtcagttc agagagttaa | 7650 |
| gaaaaaacta cgcgttgtag atgaccaaag gacgatatac gggtagaacg | 7700 |
| gtaagagagg ccgcccctca attgcgagcc aggcttcaca acctccgttc | 7750 |
| taccgcttca ccgacaacag tcctcaatca tggaccgcgc cgttagccaa | 7800 |
| gttgcgttag agaatgatga agagaggca aaaatacat ggcgcttgat | 7850 |
| attccggatt gcaatcttat tcttaacagt agtgaccttg gctatatctg | 7900 |
| tagcctccct tttatatagc atgggggcta gcacacctag cgatcttgta | 7950 |
| ggcataccga ctaggatttc cagggcagaa gaaaagatta catctacact | 8000 |
| tggttccaat caagatgtag tagataggat atataagcaa gtggcccttg | 8050 |
| agtctccgtt ggcattgtta aaaactgaga ccacaattat gaacgcaata | 8100 |
| acatctctct cttatcagat taatggagct gcaaacaaca gtgggtgggg | 8150 |
| ggcacctatc catgacccag attatatagg ggggatagge aaagaactca | 8200 |
| ttgtagatga tgctagtgat gtcacatcat tctatccctc tgcatttcaa | 8250 |
| gaacatctga attttatccc ggcgcctact acaggatcag gttgcactcg | 8300 |
| aataccctca tttgacatga gtgctaccca ttactgctac acccataatg | 8350 |
| taatattgtc tggatgcaga gatcactcac attcatatca gtatttagca | 8400 |
| cttggtgtgc tccggacatc tgcaacaggg agggtattct tttctactct | 8450 |
| gcgttccatc aacctggacg acacccaaaa tcggaagtct tgcagtgtga | 8500 |
| gtgcaactcc cctgggttgt gatatgctgt gctcgaaagt cacggagaca | 8550 |
| gaggaagaag attataactc agctgtccct acgcggatgg tacatgggag | 8600 |
| gttagggttc gacggccagt accacgaaaa ggacctagat gtcacaacat | 8650 |
| tattcgggga ctgggtggcc aactacccag gagtaggggg tggatctttt | 8700 |
| attgacagcc gcgtatggtt ctcagtctac ggagggttaa acccaattc | 8750 |
| acccagtgac actgtacagg aagggaaata tgtgatatac aagcgataca | 8800 |
| atgacacatg cccagatgag caagactacc agattcgaat ggccaagtct | 8850 |
| tcgtataagc ctggacggtt tggtgggaaa cgcatacagc aggctatctt | 8900 |
| atctatcaag gtgtcaacat ccttaggcga agacccggta ctgactgtac | 8950 |
| cgcccaacac agtcacactc atgggggccg aaggcagaat tctcacagta | 9000 |
| gggacatctc atttcttgta tcaacgaggg tcatcatact tctctcccgc | 9050 |
| gttattatat cctatgacag tcagcaacaa aacagccact cttcatagtc | 9100 |
| cttatacatt caatgccttc actcggccag gtagtatccc ttgccaggct | 9150 |
| tcagcaagat gccccaaccc gtgtgttact ggagtctata cagatccata | 9200 |
| tccccctaatc ttctatagaa accacacctt gcgagggta ttcgggacaa | 9250 |

```
tgcttgatgg tgtacaagca agacttaacc ctgcgtctgc agtattcgat         9300
agcacatccc gcagtcgcat tactcgagtg agttcaagca gtaccaaagc         9350
agcatacaca acatcaactt gttttaaagt ggtcaagact aataagacct         9400
attgtctcag cattgctgaa atatctaata ctctcttcgg agaattcaga         9450
atcgtcccgt tactagttga gatcctcaaa gatgacgggg ttagagaagc         9500
caggtctggc tagttgagtc aattataaag gagttggaaa gatggcattg         9550
tatcacctat cttctgcgac atcaagaatc aaaccgaatg ccggcgcgtg         9600
ctcgaattcc atgttgccag ttgaccacaa tcagccagtg ctcatgcgat         9650
cagattaagc cttgtcaata gtctcttgat taagaaaaaa tgtaagtggc         9700
aatgagatac aaggcaaaat acgtaccggt aaataatacg ggtaggacat         9750
ggcgagctcc ggtcctgaaa gggcagagca tcagattatc ctaccagagt         9800
cacacctgtc ttcaccattg gtcaagcaca aactactcta ttactggaaa         9850
ttaactgggc taccgcttcc tgatgaatgt gacttcgacc acctcattct         9900
cagccgacaa tggaaaaaaa tacttgaatc ggcctctcct gatactgaga         9950
gaatgataaa actcggaagg gcagtacacc aaactcttaa ccacaattcc        10000
agaataaccg gagtgctcca ccccaggtgt ttagaagaac tggctaatat        10050
tgaggtccca gattcaacca acaaatttcg gaagattgag aagaagatcc        10100
aaattcacaa cacgagatat ggagaactgt tcacaaggct gtgtacgcat        10150
atagagaaga aactgctggg gtcatcttgg tctaacaatg tcccccggtc        10200
agaggagttc agcagcattc gtacggatcc ggcattctgg tttcactcaa        10250
aatggtccac agccaagttt gcatggctcc atataaaaca gatccagagg        10300
catctgatgg tggcagctag gacaaggtct gcggccaaca aattggtgat        10350
gctaacccat aaggtaggcc aagtctttgt cactcctgaa cttgtcgttg        10400
tgacgcatac gaatgagaac aagttcacat gtcttaccca ggaacttgta        10450
ttgatgtatg cagatatgat ggagggcaga gatatggtca acataatatc        10500
aaccacggcg gtgcatctca gaagcttatc agagaaaatt gatgacattt        10550
tgcggttaat agacgctctg gcaaaagact tgggtaatca agtctacgat        10600
gttgtatcac taatggaggg atttgcatac ggagctgtcc agctactcga        10650
gccgtcaggt acatttgcag gagatttctt cgcattcaac ctgcaggagc        10700
ttaaagacat tctaattggc ctcctcccca atgatatagc agaatccgtg        10750
actcatgcaa tcgctactgt attctctggt ttagaacaga atcaagcagc        10800
tgagatgttg tgtctgttgc gtctgtgggg tcacccactg cttgagtccc        10850
gtattgcagc aaaggcagtc aggagccaaa tgtgcgcacc gaaaatggta        10900
gactttgata tgatccttca ggtactgtct ttcttcaagg gaacaatcat        10950
caacgggtac agaaagaaga atgcaggtgt gtggccgcga gtcaaagtgg        11000
atacaatata tgggaaggtc attgggcaac tacatgcaga ttcagcagag        11050
atttcacacg atatcatgtt gagagagtat aagagtttat ctgcacttga        11100
atttgagcca tgtatagaat atgaccctgt cacaaacctg agcatgttcc        11150
taaaagacaa ggcaatcgca caccccaacg ataattggct tgcctcgttt        11200
aggcggaacc ttctctccga agaccagaag aaacatgtaa aagaagcaac        11250
```

```
ttcgactaat cgcctcttga tagagttttt agagtcaaat gattttgatc    11300
catataaaga gatggaatat ctgacgaccc ttgagtacct tagagatgac    11350
aatgtggcag tatcatactc gctcaaggag aaggaagtga aagttaatgg    11400
acggatcttc gctaagctga caaagaagtt aaggaactgt caggtgatgg    11450
cggaagggat cctagccgat cagattgcac ctttctttca gggaaatgga    11500
gtcattcagg atagcatatc cttgaccaag agtatgctag cgatgagtca    11550
actgtctttt aacagcaata agaaacgtat cactgactgt aaagaaagag    11600
tatcttcaaa ccgcaatcat gatccgaaaa gcaagaaccg tcggagagtt    11650
gcaaccttca taacaactga cctgcaaaag tactgtctta attggagata    11700
tcagacaatc aaattgttcg ctcatgccat caatcagttg atgggcctac    11750
ctcacttctt cgaatggatt cacctaagac tgatggacac tacgatgttc    11800
gtaggagacc ctttcaatcc tccaagtgac cctactgact gtgacctctc    11850
aagagtccct aatgatgaca tatatattgt cagtgccaga gggggtatcg    11900
aaggattatg ccagaagcta tggacaatga tctcaattgc tgcaatccaa    11950
cttgctgcag ctagatcgca ttgtcgtgtt gcctgtatgg tacagggtga    12000
taatcaagta atagcagtaa cgagagaggt aagatcagac gactctccgg    12050
agatggtgtt gacacagttg catcaagcca gtgataattt cttcaaggaa    12100
ttaattcatg tcaatcattt gattggccat aatttgaagg atcgtgaaac    12150
catcaggtca gacacattct tcatatacag caaacgaatc ttcaaagatg    12200
gagcaatcct cagtcaagtc ctcaaaaatt catctaaatt agtgctagtg    12250
tcaggtgatc tcagtgaaaa caccgtaatg tcctgtgcca acattgcctc    12300
tactgtagca cggctatgcg agaacgggct tcccaaagac ttctgttact    12350
atttaaacta tataatgagt tgtgtgcaga catactttga ctctgagttc    12400
tccatcacca acaattcgca ccccgatctt aatcagtcgt ggattgagga    12450
catctctttt gtgcactcat atgttctgac tcctgcccaa ttaggggac    12500 tgagtaacct tcaatactca aggctctaca ctagaaatat cggtgacccg    12550
gggactactg cttttgcaga gatcaagcga ctagaagcag tgggattact    12600
gagtcctaac attatgacta atatcttaac taggccgcct gggaatggag    12650
attgggccag tctgtgcaac gacccatact cttttcaattt tgagactgtt    12700 gcaagcccaa atattgttct taagaaacat acgcaaagag tcctatttga    12750
aacttgttca aatcccttat tgtctggagt gcacacagag gataatgagg    12800
cagaagagaa ggcattggct gaattcttgc ttaatcaaga ggtgattcat    12850
ccccgcgttg cgcatgccat catggaggca agctctgtag gtaggagaaa    12900
gcaaattcaa gggcttgttg acacaacaaa caccgtaatt aagattgcgc    12950
ttactaggag gccattaggc atcaagaggc tgatgcggat agtcaattat    13000
tctagcatgc atgcaatgct gtttagagac gatgtttttt cctccagtag    13050
atccaaccac cccttagtct cttctaatat gtgttctctg acactggcag    13100
actatgcacg gaatagaagc tggtcacctt gacgggagg caggaaaata    13150 ctgggtgtat ctaatcctga tacgatagaa ctcgtagagg gtgagattct    13200
```

```
tagtgtaagc ggagggtgta caagatgtga cagcggagat gaacaattta       13250
cttggttcca tcttccaagc aatatagaat tgaccgatga caccagcaag       13300
aatcctccga tgagggtacc atatctcggg tcaaagacac aggagaggag       13350
agctgcctca cttgcaaaaa tagctcatat gtcgccacat gtaaaggctg       13400
ccctaagggc atcatccgtg ttgatctggg cttatgggga taatgaagta       13450
aattggactg ctgctcttac gattgcaaaa tctcggtgca atgtaaactt       13500
agagtatctt cggttactgt cccctttacc cacggctggg aatcttcaac       13550
atagactaga tgatggtata actcagatga cattcacccc tgcatctctc       13600
tacagggtgt caccttacat tcacatatcc aatgattctc aaaggctgtt       13650
cactgaagaa ggagtcaaag aggggaatgt ggtttaccaa cagatcatgc       13700
tcttgggttt atctctaatc gaatcgatct ttccaatgac aacaaccagg       13750
acatatgatg agatcacact gcacctacat agtaaattta gttgctgtat       13800
cagagaagca cctgttgcgg ttcctttcga gctacttggg gtggtaccgg       13850
aactgaggac agtgacctca aataagttta tgtatgatcc tagccctgta       13900
tcggagggag acttttgcgag acttgactta gctatcttca agagttatga       13950
gcttaatctg gagtcatatc ccacgataga gctaatgaac attctttcaa       14000
tatccagcgg gaagttgatt ggccagtctg tggtttctta tgatgaagat       14050
acctccataa agaatgacgc cataatagtg tatgacaata cccgaaattg       14100
gatcagtgaa gctcagaatt cagatgtggt ccgcctattt gaatatgcag       14150
cacttgaagt gctcctcgac tgttcttacc aactctatta tctgagagta       14200
agaggcctag acaatattgt cttatatatg ggtgatttat acaagaatat       14250
gccaggaatt ctactttcca acattgcagc tacaatatct catcccgtca       14300
ttcattcaag gttacatgca gtgggcctgg tcaaccatga cggatcacac       14350
caacttgcag atacggattt tatcgaaatg tctgcaaaac tattagtatc       14400
ttgcacccga cgtgtgatat ccggcttata ttcaggaaat aagtatgatc       14450
tgctgttccc atctgtctta gatgataacc tgaatgagaa gatgcttcag       14500
ctgtatatccc ggttatgctg tctgtacacg gtactctttg ctacaacaag       14550
agaaatcccg aaaataagag cttaactgc agaagagaaa tgttcaatac        14600
tcactgagta tttactgtcg gatgctgtga accattact agcccccgat        14650
caagtgagct ctatcatgtc tcctaacata attacattcc cagctaatct       14700
gtactacatg tctcggaaga gcctcaattt gatcagggaa agggaggaca       14750
gggatactat cctggcgttg ttgttccccc aagagccatt attagagttc       14800
ccttctgtgc aagatattgg tgctcgagtg aaagatccat tcacccgaca       14850
acctgcggca tttttgcaag agttagattt gagtgctcca gcaaggtatg       14900
acgcattcac acttagtcag attcatcctg aactcacatc tccaaatccg       14950
gaggaagact acttagtacg atacttgttc agagggatag ggactgcatc       15000
ttcctcttgg tataaggcat ctcatctcct ttctgtaccc gaggtaagat       15050
gtgcaagaca cggggaactcc ttatacttag ctgaagggag cggagccatc      15100
atgagtcttc tcgaactgca tgtaccacat gaaactatct attacaatac       15150
gctcttttca aatgagatga accccccgca acgacatttc gggccgaccc       15200
```
caactcagtt tttgaattcg gttgtttata ggaatctaca ggcggaggta 15250
acctgcaaag atggatttgt ccaagagttc cgtccattat ggagagaaaa 15300
tacagaggaa agtgacctga cctcagataa agcagtgggg tatattacat 15350
ctgcagtgcc ctacagatct gtatcattgc tgcattgtga cattgaaatt 15400
cctccagggt ccaatcaaag cttactagat caactagcta tcaatttatc 15450
tctgattgcc atgcattctg taagggaggg cggggtagta atcatcaaag 15500
tgttgtatgc aatgggatac tactttcatc tactcatgaa cttgtttgct 15550
ccgtgttcca caaaaggata tattctctct aatggttatg catgtcgagg 15600
agatatggag tgttacctgg tatttgtcat gggttacctg ggcgggccta 15650
catttgtaca tgaggtggtg aggatggcaa aaactctggt gcagcggcac 15700
ggtacgcttt tgtctaaatc agatgagatc acactgacca ggttattcac 15750
ctcacagcgg cagcgtgtga cagacatcct atccagtcct ttaccaagat 15800
taataaagta cttgaggaag aatattgaca ctgcgctgat tgaagccggg 15850
ggacagcccg tccgtccatt ctgtgcggag agtctggtga gcacgctagc 15900
gaacataact cagataaccc agatcatcgc tagccacatt gacacagtta 15950
tccggtctgt gatatatatg gaagctgagg gtgatctcgc tgacacagta 16000
tttctattta ccccttacaa tctctctact gacgggaaaa agaggacatc 16050
acttaaacag tgcacgagac agatcctaga ggttacaata ctaggtctta 16100
gagtcgaaaa tctcaataaa ataggcgata taatcagcct agtgcttaaa 16150
ggcatgatct ccatggagga ccttatccca ctaaggacat acttgaagca 16200
tagtacctgc cctaaatatt tgaaggctgt cctaggtatt accaaactca 16250
aagaaatgtt tacagacact tctgtactgt acttgactcg tgctcaacaa 16300
aaattctaca tgaaaactat aggcaatgca gtcaaaggat attacagtaa 16350
ctgtgactct taacgaaaat cacatattaa taggctcctt ttttggccaa 16400
ttgtattctt gttgatttaa tcatattatg ttagaaaaaa gttgaaccct 16450
gactccttag gactcgaatt cgaactcaaa taaatgtctt aaaaaaaggt 16500
tgcgcacaat tattcttgag tgtagtctcg tcattcacca aatcttggtt 16550
gggt 16554

<210> SEQ ID NO 21
<211> LENGTH: 16452
<212> TYPE: DNA
<213> ORGANISM: Artificial sequence
<220> FEATURE:
<223> OTHER INFORMATION: rNDV gD

<400> SEQUENCE: 21
accaaacaga gaatccgtga tttacgataa aaggcgaaag agcaattgaa 50
gtcgcacggg tagaaggtgt gaatctcgag tgcgagcccg aagcacaaac 100
tcgagaaagc cttctgccaa catgtcttcc gtatttgatg agtacgaaca 150
gctcctcgcg gctcagactc gccccaatgg agctcatgga gggggagaaa 200
aagggagtac cttaaaagta gacgtcccgg tattcactct taacagtgat 250
gacccagaag atagatggag ctttgtggta ttctgcctcc ggattgctgt 300

| | |
|---|---|
| tagcgaagat gccaacaaac cactcaggca aggtgctctc atatctcttt | 350 |
| tatgctccca ctcacaggta atgaggaacc atgttgccct tgcagggaaa | 400 |
| cagaatgaag ccacattggc cgtgcttgag attgatggct ttgccaacgg | 450 |
| cacgccccag ttcaacaata ggagtggagt gtctgaagag agagcacaga | 500 |
| gatttgcgat gatagcagga tctctccctc gggcatgcag caacggaacc | 550 |
| ccgttcgtca cagccggggc cgaagatgat gcaccagaag acatcaccga | 600 |
| taccctggag aggatcctct ctatccaggc tcaagtatgg gtcacagtag | 650 |
| caaaagccat gactgcgtat gagactgcag atgagtcgga aacaaggcga | 700 |
| atcaataagt atatgcagca aggcagggtc caaaagaaat acatcctcta | 750 |
| ccccgtatgc aggagcacaa tccaactcac gatcagacag tctcttgcag | 800 |
| tccgcatctt tttggttagc gagctcaaga gaggccgcaa cacggcaggt | 850 |
| ggtacctcta cttattataa cctggtaggg gacgtagact catacatcag | 900 |
| gaataccggg cttactgcat tcttcttgac actcaagtac ggaatcaaca | 950 |
| ccaagacatc agcccttgca cttagtagcc tctcaggcga catccagaag | 1000 |
| atgaagcagc tcatgcgttt gtatcggatg aaaggagata atgcgccgta | 1050 |
| catgacatta cttggtgata gtgaccagat gagctttgcg cctgccgagt | 1100 |
| atgcacaact ttactccctt gccatgggta tggcatcagt cctagataaa | 1150 |
| ggtactggga ataccaatt tgccagggac tttatgagca catcattctg | 1200 |
| gagacttgga gtagagtacg ctcaggctca gggaagtagc attaacgagg | 1250 |
| atatggctgc cgagctaaag ctaaccccag cagcaaggag gggcctggca | 1300 |
| gctgctgccc aacgggtctc cgaggagacc agcagcatag acatgcctac | 1350 |
| tcaacaagtc ggagtcctca ctgggcttag cgagggggg tcccaagctc | 1400 |
| tacaaggcgg atcgaataga tcgcaagggc aaccagaagc cggggatggg | 1450 |
| gagacccaat tcctggatct gatgagagcg gtagcaaata gcatgaggga | 1500 |
| ggcgccaaac tctgcacagg gcactcccca atcggggcct cccccaactc | 1550 |
| ctgggccatc ccaagataac gacaccgact gggggtattg atggacaaaa | 1600 |
| cccagcctgc ttccacaaaa acatcccaat gccctcaccc gtagtcgacc | 1650 |
| cctcgatttg cggctctata tgaccacacc ctcaaacaaa catcccctc | 1700 |
| tttcctccct ccccctgctg tacaactccg cacgccctag ataccacagg | 1750 |
| cacaatgcgg ctcactaaca atcaaaacag agccgaggga attagaaaaa | 1800 |
| agtacgggta gaagagggat attcagagat cagggcaagt ctcccgagtc | 1850 |
| tctgctctct cctctacctg atagaccagg acaaacatgg ccacctttac | 1900 |
| agatgcagag atcgacgagc tatttgagac aagtggaact gtcattgaca | 1950 |
| acataattac agcccagggt aaaccagcag agactgttgg aaggagtgca | 2000 |
| atcccacaag gcaagaccaa ggtgctgagc gcagcatggg agaagcatgg | 2050 |
| gagcatccag ccaccggcca gtcaagacaa ccccgatcga caggacagat | 2100 |
| ctgacaaaca accatccaca cccgagcaaa cgaccccgca tgacagcccg | 2150 |
| ccggccacat ccgccgacca gccccccacc caggccacag acgaagccgt | 2200 |
| cgacacacag ctcaggaccg gagcaagcaa ctctctgctg ttgatgcttg | 2250 |
| acaagctcag caataaatcg tccaatgcta aaaagggccc atggtcgagc | 2300 |

```
ccccaagagg ggaatcacca acgtccgact caacagcagg ggagtcaacc      2350
cagccgcgga aacagtcagg aaagaccgca gaaccaagtc aaggccgccc      2400
ctggaaacca gggcacagac gtgaacacag catatcatgg acaatgggag      2450
gagtcacaac tatcagctgg tgcaacccct catgctctcc gatcaaggca      2500
gagccaagac aataccccttg tatctgcgga tcatgtccag ccacctgtag     2550
actttgtgca agcgatgatg tctatgatgg aggcgatatc acagagagta     2600
agtaaggtcg actatcagct agatcttgtc ttgaaacaga catcctccat      2650
ccctatgatg cggtccgaaa tccaacagct gaaaacatct gttgcagtca      2700
tggaagccaa cttgggaatg atgaagattc tggatcccgg ttgtgccaac      2750
atttcatctc tgagtgatct acgggcagtt gcccgatctc accggttttt      2800
agtttcaggc cctggagacc cctctcccta tgtgacacaa ggaggcgaaa      2850
tggcacttaa taaactttcg caaccagtgc cacatccatc tgaattgatt      2900
aaacccgcca ctgcatgcgg gcctgatata ggagtggaaa aggacactgt      2950
ccgtgcattg atcatgtcac gcccaatgca cccgagttct tcagccaagc      3000
tcctaagcaa gttagatgca gccgggtcga tcgaggaaat caggaaaatc      3050
aagcgccttg ctctaaatgg ctaattacta ctgccacacg tagcgggtcc      3100
ctgtccactc ggcatcacac ggaatctgca ccgagttccc ccccgcagac      3150
ccaaggtcca actctccaag cggcaatcct ctctcgcttc ctcagcccca      3200
ctgaatgatc gcgtaaccgt ttaattaatt agaaaaaata cgggtagaag      3250
gccgccacca tggaccgcca tttattttg aggaatgctt tttggactat      3300
cgtactgctt tcttccttcg ctagccagag caccgccgcc gtcacgtacg      3350
actacatttt aggccgtcgc gcgctcgacg cgctaaccat accggcggtt      3400
ggcccgtata acagataccct cactagggta tcaagaggct gcgacgttgt      3450
cgagctcaac ccgatttcta acgtggacga catgatatcg gcggccaaag      3500
aaaaagagaa gggggggccct ttcgaggcct ccgtcgtctg gttctacgtg      3550
attaagggcg acgacggcga ggacaagtac tgtccaatct atagaaaaga      3600
gtacagggaa tgtggcgacg tacaactgct atctgaatgc gccgttcaat      3650
ctgcacagat gtgggcagtg gactatgttc ctagcaccct tgtatcgcga      3700
aatggcgcgg gactgactat attctccccc actgctgcgc tctctggcca      3750
atacttgctg accctgaaaa tcgggagatt tgcgcaaaca gctctcgtaa      3800
ctctagaagt taacgatcgc tgtttaaagat cgggtcgca gcttaacttt      3850 ttaccgtcga aatgctggac aacagaacag tatcagactg gatttcaagg      3900 cgaacaccctt tatccgatcg cagacaccaa tacacgacac gcggacgacg      3950
tatatcgggg atacgaagat attctgcagc gctggaataa tttgctgagg      4000
aaaaagaatc ctagcgcgcc agaccctcgt ccagatagcg tcccgcaaga      4050
aattcccgct gtaaccaaga aagcggaagg gcgcacccccg gacgcagaaa      4100 gcagcgaaaa gaaggcccct ccagaagact cggaggacga catgcaggca      4150
gaggcttctg gagaaaatcc tgccgccctc cccgaagacg acgaagtccc      4200
cgaggacacc gagcacgatg atccaaactc ggatcctgac tattacaatg      4250
```

```
acatgcccgc cgtgatcccg gtggaggaga ctactaaaag ttctaatgcc      4300
gtctccatgc ccagcacatc tgctctcatt acctatatcg ttttgactat      4350
catatctctt gttttggta tacttagcct gattctagca tgctacctaa       4400
tgtacaagca aaaggcgcaa caaaagacct tattatggct tgggaataat      4450
actctagatc agatgagagc cactacaaaa atgtgattaa ttaatagcta      4500
catttaagat taagaaaaaa tacgggtaga attggagtgc cccaattgtg      4550
ccaagatgga ctcatctagg acaattgggc tgtactttga ttctgcccat      4600
tcttctagca acctgttagc atttccgatc gtcctacaag acacaggaga      4650
tgggaagaag caaatcgccc cgcaatatag gatccagcgc cttgacttgt      4700
ggactgatag taaggaggac tcagtattca tcaccaccta tggattcatc      4750
tttcaagttg ggaatgaaga agccactgtc ggcatgatcg atgataaacc      4800
caagcgcgag ttactttccg ctgcgatgct ctgcctagga agcgtcccaa      4850
ataccggaga ccttattgag ctggcaaggg cctgtctcac tatgatagtc      4900
acatgcaaga agagtgcaac taatactgag agaatggttt tctcagtagt      4950
gcaggcaccc caagtgctgc aaagctgtag ggttgtggca aacaaatact      5000
catcagtgaa tgcagtcaag cacgtgaaag cgccagagaa gattcccggg      5050
agtggaaccc tagaatacaa ggtgaacttt gtctccttga ctgtggtacc      5100
gaagaaggat gtctacaaga tcccagctgc agtattgaag gtttctggct      5150
cgagtctgta caatcttgcg ctcaatgtca ctattaatgt ggaggtagac      5200
ccgaggagtc ctttggttaa atctctgtct aagtctgaca gcggatacta      5250
tgctaacctc ttcttgcata ttggacttat gaccaccgta gataggaagg      5300
ggaagaaagt gacatttgac aagctggaaa agaaaataag gagccttgat      5350
ctatctgtcg ggctcagtga tgtgctcggg ccttccgtgt tggtaaaagc      5400
aagaggtgca cggactaagc ttttggcacc tttcttctct agcagtggga      5450
cagcctgcta tcccatagca aatgcttctc ctcaggtggc caagatactc      5500
tggagtcaaa ccgcgtgcct gcggagcgtt aaaatcatta tccaagcagg      5550
tacccaacgc gctgtcccag tgaccccaa ccaccaggtt acctctacta      5600
agctggagaa ggggcacacc cttgccaaat acaatccttt taagaaataa      5650
gctgcgtctc tgagattgcg ctccgcccac tcacccggat catcatgaca      5700
caaaaaacta atctgtcttg attatttaca gttagtttac ctgtctatca      5750
agttagaaaa aacacgggta gaagattctg gatcccggtt ggcgccctcc      5800
aggtgcaaga tgggctccag accttctacc aagaacccag cacctatgat      5850
gctgactatc cggggtgcgc tggtactgag ttgcatctgt ccggcaaact      5900
ccattgatgg caggcctctt gcagctgcag gaattgtggt tacaggagac      5950
aaagccgtca acatatacac ctcatcccag acaggatcaa tcatagttaa      6000
gctcctcccg aatctgccca aggataagga ggcatgtgcg aaagccccct      6050
tggatgcata caacaggaca ttgaccactt tgctcacccc ccttggtgac      6100
tctatccgta ggatacaaga gtctgtgact acatctggag gggggagaca      6150
ggggcgcctt ataggcgcca ttattggcgg tgtggctctt ggggttgcaa      6200
ctgccgcaca ataacagcg gccgcagctc tgatacaagc caaacaaaat      6250
```

```
gctgccaaca tcctccgact taaagagagc attgccgcaa ccaatgaggc      6300
tgtgcatgag gtcactgacg gattatcgca actagcagtg gcagttggga      6350
agatgcagca gtttgttaat gaccaattta ataaaacagc tcaggaatta      6400
gactgcatca aaattgcaca gcaagttggt gtagagctca acctgtacct      6450
aaccgaattg actacagtat tcggaccaca aatcacttca cctgctttaa      6500
acaagctgac tattcaggca ctttacaatc tagctggtgg aaatatggat      6550
tacttattga ctaagttagg tgtagggaac aatcaactca gctcattaat      6600
cggtagcggc ttaatcaccg gtaaccctat tctatacgac tcacagactc      6650
aactcttggg tatacaggta actctacctt cagtcgggaa cctaaataat      6700
atgcgtgcca cctacttgga aaccttatcc gtaagcacaa ccaggggatt      6750
tgcctcggca cttgtcccaa agtggtgac acaggtcggt tctgtgatag       6800
aagaacttga cacctcatac tgtatagaaa ctgacttaga tttatattgt      6850
acaagaatag taacgttccc tatgtcccct ggtatttatt cctgcttgag      6900
cggcaatacg tcggcctgta tgtactcaaa gaccgaaggc gcacttacta      6950
caccatacat gactatcaaa ggttcagtca tcgccaactg caagatgaca      7000
acatgtagat gtgtaaaccc cccgggtatc atatcgcaaa actatggaga      7050
agccgtgtct ctaatagata aacaatcatg caatgtttta tccttaggcg      7100
ggataacttt aaggctcagt ggggaattcg atgtaactta tcagaagaat      7150
atctcaatac aagattctca agtaataata acaggcaatc ttgatatctc      7200
aactgagctt gggaatgtca acaactcgat cagtaatgct ttgaataagt      7250
tagaggaaag caacagaaaa ctagacaaag tcaatgtcaa actgaccagc      7300
acatctgctc tcattaccta tatcgttttg actatcatat ctcttgtttt      7350
tggtatactt agcctgattc tagcatgcta cctaatgtac aagcaaaagg      7400
cgcaacaaaa gaccttatta tggcttggga ataatactct agatcagatg      7450
agagccacta caaaaatgtg aacacagatg aggaacgaag gtttccctaa      7500
tagtaatttg tgtgaaagtt ctggtagtct gtcagttcag agagttaaga      7550
aaaaactacg cgttgtagat gaccaaagga cgatatacgg gtagaacggt      7600
aagagaggcc gccccctcaat tgcgagccag gcttcacaac ctccgttcta      7650
ccgcttcacc gacaacagtc ctcaatcatg gaccgcgccg ttagccaagt      7700
tgcgttagag aatgatgaaa gagaggcaaa aaatacatgg cgcttgatat      7750
tccggattgc aatcttattc ttaacagtag tgaccttggc tatatctgta      7800
gcctcccttt tatatagcat gggggctagc acacctagcg atcttgtagg      7850
cataccgact aggatttcca gggcagaaga aaagattaca tctacacttg      7900
gttccaatca agatgtagta gataggatat ataagcaagt ggcccttgag      7950
tctccgttgg cattgttaaa aactgagacc acaattatga acgcaataac      8000
atctctctct tatcagatta atggagctgc aaacaacagt gggtgggggg      8050
cacctatcca tgacccagat tatataggg ggataggcaa agaactcatt       8100
gtagatgatg ctagtgatgt cacatcattc tatccctctg catttcaaga      8150
acatctgaat tttatcccgg cgcctactac aggatcaggt tgcactcgaa      8200
```

| | |
|---|---|
| taccctcatt tgacatgagt gctacccatt actgctacac ccataatgta | 8250 |
| atattgtctg gatgcagaga tcactcacat tcatatcagt atttagcact | 8300 |
| tggtgtgctc cggacatctg caacagggag ggtattcttt tctactctgc | 8350 |
| gttccatcaa cctggacgac acccaaaatc ggaagtcttg cagtgtgagt | 8400 |
| gcaactcccc tgggttgtga tatgctgtgc tcgaaagtca cggagacaga | 8450 |
| ggaagaagat tataactcag ctgtccctac gcggatggta catgggaggt | 8500 |
| tagggttcga cggccagtac cacgaaaagg acctagatgt cacaacatta | 8550 |
| ttcggggact gggtggccaa ctacccagga gtaggggggtg gatcttttat | 8600 |
| tgacagccgc gtatggttct cagtctacgg agggttaaaa cccaattcac | 8650 |
| ccagtgacac tgtacaggaa gggaaatatg tgatatacaa gcgatacaat | 8700 |
| gacacatgcc cagatgagca agactaccag attcgaatgg ccaagtcttc | 8750 |
| gtataagcct ggacggtttg gtgggaaacg catacagcag gctatcttat | 8800 |
| ctatcaaggt gtcaacatcc ttaggcgaag acccggtact gactgtaccg | 8850 |
| cccaacacag tcacactcat gggggccgaa ggcagaattc tcacagtagg | 8900 |
| gacatctcat ttcttgtatc aacgagggtc atcatacttc tctcccgcgt | 8950 |
| tattatatcc tatgcagtc agcaacaaaa cagccactct tcatagtcct | 9000 |
| tatacattca atgccttcac tcggccaggt agtatccctt gccaggcttc | 9050 |
| agcaagatgc cccaacccgt gtgttactgg agtctataca gatccatatc | 9100 |
| ccctaatctt ctatagaaac cacaccttgc gagggtatt cgggacaatg | 9150 |
| cttgatggtg tacaagcaag acttaacccct gcgtctgcag tattcgatag | 9200 |
| cacatcccgc agtcgcatta ctcgagtgag ttcaagcagt accaaagcag | 9250 |
| catacacaac atcaacttgt tttaaagtgg tcaagactaa taagacctat | 9300 |
| tgtctcagca ttgctgaaat atctaatact ctcttcggag aattcagaat | 9350 |
| cgtcccgtta ctagttgaga tcctcaaaga tgacggggtt agagaagcca | 9400 |
| ggtctggcta gttgagtcaa ttataaagga gttggaaaga tggcattgta | 9450 |
| tcacctatct tctgcgacat caagaatcaa accgaatgcc ggcgcgtgct | 9500 |
| cgaattccat gttgccagtt gaccacaatc agccagtgct catgcgatca | 9550 |
| gattaagcct tgtcaatagt ctcttgatta agaaaaaatg taagtggcaa | 9600 |
| tgagatacaa ggcaaaatac gtaccggtaa ataatacggg taggacatgg | 9650 |
| cgagctccgg tcctgaaagg gcagagcatc agattatcct accagagtca | 9700 |
| cacctgtctt caccattggt caagcacaaa ctactctatt actggaaatt | 9750 |
| aactgggcta ccgcttcctg atgaatgtga cttcgaccac ctcattctca | 9800 |
| gccgacaatg gaaaaaaata cttgaatcgg cctctcctga tactgagaga | 9850 |
| atgataaaac tcggaagggc agtacaccaa actcttaacc acaattccag | 9900 |
| aataaccgga gtgctccacc ccaggtgttt agaagaactg gctaatattg | 9950 |
| aggtcccaga ttcaaccaac aaatttcgga agattgagaa gaagatccaa | 10000 |
| attcacaaca cgagatatgg agaactgttc acaaggctgt gtacgcatat | 10050 |
| agagaagaaa ctgctgggggt catcttggtc taacaatgtc ccccggtcag | 10100 |
| aggagttcag cagcattcgt acggatccgg cattctggtt tcactcaaaa | 10150 |
| tggtccacag ccaagtttgc atggctccat ataaaacaga tccagaggca | 10200 |

```
tctgatggtg gcagctagga caaggtctgc ggccaacaaa ttggtgatgc        10250
taacccataa ggtaggccaa gtctttgtca ctcctgaact tgtcgttgtg        10300
acgcatacga atgagaacaa gttcacatgt cttacccagg aacttgtatt        10350
gatgtatgca gatatgatgg agggcagaga tatggtcaac ataatatcaa        10400
ccacggcggt gcatctcaga agcttatcag agaaaattga tgacattttg        10450
cggttaatag acgctctggc aaaagacttg ggtaatcaag tctacgatgt        10500
tgtatcacta atggagggat ttgcatacgg agctgtccag ctactcgagc        10550
cgtcaggtac atttgcagga gatttcttcg cattcaacct gcaggagctt        10600
aaagacattc taattggcct cctccccaat gatatagcag aatccgtgac        10650
tcatgcaatc gctactgtat tctctggttt agaacagaat caagcagctg        10700
agatgttgtg tctgttgcgt ctgtggggtc acccactgct tgagtcccgt        10750
attgcagcaa aggcagtcag gagccaaatg tgcgcaccga aaatggtaga        10800
ctttgatatg atccttcagg tactgtcttt cttcaaggga acaatcatca        10850
acgggtacag aaagaagaat gcaggtgtgt ggccgcgagt caaagtggat        10900
acaatatatg ggaaggtcat tgggcaacta catgcagatt cagcagagat        10950
ttcacacgat atcatgttga gagagtataa gagtttatct gcacttgaat        11000
ttgagccatg tatagaatat gaccctgtca caaacctgag catgttccta        11050
aaagacaagg caatcgcaca ccccaacgat aattggcttg cctcgtttag        11100
gcggaacctt ctctccgaag accagaagaa acatgtaaaa gaagcaactt        11150
cgactaatcg cctcttgata gagtttttag agtcaaatga ttttgatcca        11200
tataaagaga tggaatatct gacgacccct gagtaccttt gagatgacaa        11250
tgtggcagta tcatactcgc tcaaggagaa ggaagtgaaa gttaatggac        11300
ggatcttcgc taagctgaca aagaagttaa ggaactgtca ggtgatggcg        11350
gaagggatcc tagccgatca gattgcacct ttctttcagg gaaatggagt        11400
cattcaggat agcatatcct tgaccaagag tatgctagcg atgagtcaac        11450
tgtcttttaa cagcaataag aaacgtatca ctgactgtaa agaaagagta        11500
tcttcaaacc gcaatcatga tccgaaaagc aagaaccgtc ggagagttgc        11550
aaccttcata acaactgacc tgcaaaagta ctgtcttaat tggagatatc        11600
agacaatcaa attgttcgct catgccatca atcagttgat gggcctacct        11650
cacttcttcg aatggattca cctaagactg atggacacta cgatgttcgt        11700
aggagaccct ttcaatcctc caagtgaccc tactgactgt gacctctcaa        11750
gagtccctaa tgatgacata tatattgtca gtgccagagg gggtatcgaa        11800
ggattatgcc agaagctatg gacaatgatc tcaattgctg caatccaact        11850
tgctgcagct agatcgcatt gtcgtgttgc ctgtatggta cagggtgata        11900
atcaagtaat agcagtaacg agagaggtaa gatcagacga ctctccggag        11950
atggtgttga cacagttgca tcaagccagt gataatttct tcaaggaatt        12000
aattcatgtc aatcatttga ttggccataa tttgaaggat cgtgaaacca        12050
tcaggtcaga cacattcttc atatacagca aacgaatctt caaagatgga        12100
gcaatcctca gtcaagtcct caaaaattca tctaaattag tgctagtgtc        12150
```

```
aggtgatctc agtgaaaaca ccgtaatgtc ctgtgccaac attgcctcta    12200
ctgtagcacg gctatgcgag aacgggcttc ccaaagactt ctgttactat    12250
ttaaactata taatgagttg tgtgcagaca tactttgact ctgagttctc    12300
catcaccaac aattcgcacc ccgatcttaa tcagtcgtgg attgaggaca    12350
tctcttttgt gcactcatat gttctgactc ctgcccaatt agggggactg    12400
agtaaccttc aatactcaag gctctacact agaaatatcg gtgacccggg    12450
gactactgct tttgcagaga tcaagcgact agaagcagtg ggattactga    12500
gtcctaacat tatgactaat atcttaacta ggccgcctgg gaatggagat    12550
tgggccagtc tgtgcaacga cccatactct ttcaattttg agactgttgc    12600
aagcccaaat attgttctta agaaacatac gcaaagagtc ctatttgaaa    12650
cttgttcaaa tcccttattg tctggagtgc acacagagga taatgaggca    12700
gaagagaagg cattggctga attcttgctt aatcaagagg tgattcatcc    12750
ccgcgttgcg catgccatca tggaggcaag ctctgtaggt aggagaaagc    12800
aaattcaagg gcttgttgac acaacaaaca ccgtaattaa gattgcgctt    12850
actaggaggc cattaggcat caagaggctg atgcggatag tcaattattc    12900
tagcatgcat gcaatgctgt ttagagacga tgttttttcc tccagtagat    12950
ccaaccaccc cttagtctct tctaatatgt gttctctgac actggcagac    13000
tatgcacgga atagaagctg gtcacctttg acgggaggca ggaaaatact    13050
gggtgtatct aatcctgata cgatagaact cgtagagggt gagattctta    13100
gtgtaagcgg agggtgtaca agatgtgaca gcggagatga acaatttact    13150
tggttccatc ttccaagcaa tatagaattg accgatgaca ccagcaagaa    13200
tcctccgatg agggtaccat atctcgggtc aaagacacag gagaggagag    13250
ctgcctcact tgcaaaaata gctcatatgt cgccacatgt aaaggctgcc    13300
ctaagggcat catccgtgtt gatctgggct tatggggata atgaagtaaa    13350
ttggactgct gctcttacga ttgcaaaatc tcggtgcaat gtaaacttag    13400
agtatcttcg gttactgtcc cctttaccca cggctgggaa tcttcaacat    13450
agactagatg atggtataac tcagatgaca ttcaccccctg catctctcta    13500
cagggtgtca ccttacattc acatatccaa tgattctcaa aggctgttca    13550
ctgaagaagg agtcaaagag gggaatgtgg tttaccaaca gatcatgctc    13600
ttgggtttat ctctaatcga atcgatcttt ccaatgacaa caaccaggac    13650
atatgatgag atcacactgc acctacatag taaatttagt tgctgtatca    13700
gagaagcacc tgttgcggtt cctttcgagc tacttggggt ggtaccggaa    13750
ctgaggacag tgacctcaaa taagtttatg tatgatccta gccctgtatc    13800
ggagggagac tttgcgagac ttgacttagc tatcttcaag agttatgagc    13850
ttaatctgga gtcatatccc acgatagagc taatgaacat tctttcaata    13900
tccagcggga agttgattgg ccagtctgtg gtttcttatg atgaagatac    13950
ctccataaag aatgacgcca taatagtgta tgacaatacc cgaaattgga    14000
tcagtgaagc tcagaattca gatgtggtcc gcctatttga atatgcagca    14050
cttgaagtgc tcctcgactg ttcttaccaa ctctattatc tgagagtaag    14100
aggcctagac aatattgtct tatatatggg tgatttatac aagaatatgc    14150
```

```
caggaattct actttccaac attgcagcta caatatctca tcccgtcatt      14200
cattcaaggt tacatgcagt gggcctggtc aaccatgacg gatcacacca      14250
acttgcagat acggatttta tcgaaatgtc tgcaaaacta ttagtatctt      14300
gcacccgacg tgtgatatcc ggcttatatt caggaaataa gtatgatctg      14350
ctgttcccat ctgtcttaga tgataacctg aatgagaaga tgcttcagct      14400
gatatcccgg ttatgctgtc tgtacacggt actctttgct acaacaagag      14450
aaatcccgaa aataagaggc ttaactgcag aagagaaatg ttcaatactc      14500
actgagtatt tactgtcgga tgctgtgaaa ccattactta gccccgatca      14550
agtgagctct atcatgtctc ctaacataat tacattccca gctaatctgt      14600
actacatgtc tcggaagagc ctcaatttga tcagggaaag ggaggacagg      14650
gatactatcc tggcgttgtt gttcccccaa gagccattat tagagttccc      14700
ttctgtgcaa gatattggtg ctcgagtgaa agatccattc acccgacaac      14750
ctgcggcatt tttgcaagag ttagatttga gtgctccagc aaggtatgac      14800
gcattcacac ttagtcagat tcatcctgaa ctcacatctc caaatccgga      14850
ggaagactac ttagtacgat acttgttcag agggataggg actgcatctt      14900
cctcttggta taaggcatct catctccttt ctgtacccga ggtaagatgt      14950
gcaagacacg ggaactcctt atacttagct gaagggagcg gagccatcat      15000
gagtcttctc gaactgcatg taccacatga aactatctat tacaatacgc      15050
tcttttcaaa tgagatgaac cccccgcaac gacatttcgg gccgacccca      15100
actcagtttt tgaattcggt tgtttatagg aatctacagg cggaggtaac      15150
ctgcaaagat ggatttgtcc aagagttccg tccattatgg agagaaaata      15200
cagaggaaag tgacctgacc tcagataaag cagtggggta tattacatct      15250
gcagtgccct acagatctgt atcattgctg cattgtgaca ttgaaattcc      15300
tccagggtcc aatcaaagct tactagatca actagctatc aatttatctc      15350
tgattgccat gcattctgta agggagggcg gggtagtaat catcaaagtg      15400
ttgtatgcaa tgggatacta cttttcatcta ctcatgaact tgtttgctcc      15450
gtgttccaca aaaggatata ttctctctaa tggttatgca tgtcgaggag      15500
atatggagtg ttacctggta tttgtcatgg gttacctggg cgggcctaca      15550
tttgtacatg aggtggtgag gatggcaaaa actctggtgc agcggcacgg      15600
tacgcttttg tctaaatcag atgagatcac actgaccagg ttattcacct      15650
cacagcggca gcgtgtgaca gacatcctat ccagtccttt accaagatta      15700
ataaagtact tgaggaagaa tattgacact gcgctgattg aagccggggg      15750
acagcccgtc cgtccattct gtgcggagag tctggtgagc acgctagcga      15800
acataactca gataacccag atcatcgcta gccacattga cacagttatc      15850
cggtctgtga tatatatgga agctgagggt gatctcgctg acacagtatt      15900
tctatttacc ccttacaatc tctctactga cgggaaaaag aggacatcac      15950
ttaaacagtg cacgagacag atcctagagg ttacaatact aggtcttaga      16000
gtcgaaaatc tcaataaaat aggcgatata atcagcctag tgcttaaagg      16050
catgatctcc atggaggacc ttatcccact aaggacatac ttgaagcata      16100
```

```
gtacctgccc taaatatttg aaggctgtcc taggtattac caaactcaaa      16150
gaaatgttta cagacacttc tgtactgtac ttgactcgtg ctcaacaaaa      16200
attctacatg aaaactatag gcaatgcagt caaaggatat tacagtaact      16250
gtgactctta acgaaaatca catattaata ggctccttt ttggccaatt       16300 gtattcttgt tgatttaatc atattatgtt agaaaaaagt tgaaccctga      16350
ctccttagga ctcgaattcg aactcaaata aatgtcttaa aaaaaggttg      16400
cgcacaatta ttcttgagtg tagtctcgtc attcaccaaa tcttggttgg      16450
gt                                                          16452

<210> SEQ ID NO 22
<211> LENGTH: 42
<212> TYPE: DNA
<213> ORGANISM: Artificial sequence
<220> FEATURE:
<223> OTHER INFORMATION: gB sequence

<400> SEQUENCE: 22
aatgatgaag cagaaaaaaa attgcccctg gttccatcac tg              42

<210> SEQ ID NO 23
<211> LENGTH: 42
<212> TYPE: DNA
<213> ORGANISM: Artificial sequence
<220> FEATURE:
<223> OTHER INFORMATION: gB sequence with mutations

<400> SEQUENCE: 23
aatgatgaag cagagaagaa gttgcccctg gttccatcac tg              42

<210> SEQ ID NO 24
<211> LENGTH: 10
<212> TYPE: DNA
<213> ORGANISM: Artificial sequence
<220> FEATURE:
<223> OTHER INFORMATION: Newcastle Disease Virus gene end
      transcriptional signal

<400> SEQUENCE: 24
ttagaaaaaa                                                  10

<210> SEQ ID NO 25
<211> LENGTH: 553
<212> TYPE: PRT
<213> ORGANISM: Newcastle Disease Virus
<220> FEATURE:
<223> OTHER INFORMATION: NDV F gene

<400> SEQUENCE: 25
```

Met Gly Ser Arg Pro Ser Thr Lys Asn Pro
 1               5                  10

Ala Pro Met Met Leu Thr Ile Arg Val Ala
             15                  20

Leu Val Leu Ser Cys Ile Cys Pro Ala Asn
             25                  30

Ser Ile Asp Gly Arg Pro Leu Ala Ala Ala
             35                  40

Gly Ile Val Val Thr Gly Asp Lys Ala Val
             45                  50

Asn Ile Tyr Thr Ser Ser Gln Thr Gly Ser

```
                55                  60
Ile Ile Val Lys Leu Leu Pro Asn Leu Pro
                65                  70
Lys Asp Lys Glu Ala Cys Ala Lys Ala Pro
                75                  80
Leu Asp Ala Tyr Asn Arg Thr Leu Thr Thr
                85                  90
Leu Leu Thr Pro Leu Gly Asp Ser Ile Arg
                95                 100
Arg Ile Gln Glu Ser Val Thr Thr Ser Gly
               105                 110
Gly Gly Arg Gln Gly Arg Leu Ile Gly Ala
               115                 120
Ile Ile Gly Gly Val Ala Leu Gly Val Ala
               125                 130
Thr Ala Ala Gln Ile Thr Ala Ala Ala Ala
               135                 140
Leu Ile Gln Ala Lys Gln Asn Ala Ala Asn
               145                 150
Ile Leu Arg Leu Lys Glu Ser Ile Ala Ala
               155                 160
Thr Asn Glu Ala Val His Glu Val Thr Asp
               165                 170
Gly Leu Ser Gln Leu Ala Val Ala Val Gly
               175                 180
Lys Met Gln Gln Phe Val Asn Asp Gln Phe
               185                 190
Asn Lys Thr Ala Gln Glu Leu Asp Cys Ile
               195                 200
Lys Ile Ala Gln Gln Val Gly Val Glu Leu
               205                 210
Asn Leu Tyr Leu Thr Glu Leu Thr Thr Val
               215                 220
Phe Gly Pro Gln Ile Thr Ser Pro Ala Leu
               225                 230
Asn Lys Leu Thr Ile Gln Ala Leu Tyr Asn
               235                 240
Leu Ala Gly Gly Asn Met Asp Tyr Leu Leu
               245                 250
Thr Lys Leu Gly Val Gly Asn Asn Gln Leu
               255                 260
Ser Ser Leu Ile Gly Ser Gly Leu Ile Thr
               265                 270
Gly Asn Pro Ile Leu Tyr Asp Ser Gln Thr
               275                 280
Gln Leu Leu Gly Ile Gln Val Thr Leu Pro
               285                 290
Ser Val Gly Asn Leu Asn Asn Met Arg Ala
               295                 300
Thr Tyr Leu Glu Thr Leu Ser Val Ser Thr
               305                 310
Thr Arg Gly Phe Ala Ser Ala Leu Val Pro
               315                 320
```

```
Lys Val Val Thr Gln Val Gly Ser Val Ile
                325                 330

Glu Glu Leu Asp Thr Ser Tyr Cys Ile Glu
                335                 340

Thr Asp Leu Asp Leu Tyr Cys Thr Arg Ile
                345                 350

Val Thr Phe Pro Met Ser Pro Gly Ile Tyr
                355                 360

Ser Cys Leu Ser Gly Asn Thr Ser Ala Cys
                365                 370

Met Tyr Ser Lys Thr Glu Gly Ala Leu Thr
                375                 380

Thr Pro Tyr Met Thr Ile Lys Gly Ser Val
                385                 390

Ile Ala Asn Cys Lys Met Thr Thr Cys Arg
                395                 400

Cys Val Asn Pro Pro Gly Ile Ile Ser Gln
                405                 410

Asn Tyr Gly Glu Ala Val Ser Leu Ile Asp
                415                 420

Lys Gln Ser Cys Asn Val Leu Ser Leu Gly
                425                 430

Gly Ile Thr Leu Arg Leu Ser Gly Glu Phe
                435                 440

Asp Val Thr Tyr Gln Lys Asn Ile Ser Ile
                445                 450

Gln Asp Ser Gln Val Ile Ile Thr Gly Asn
                455                 460

Leu Asp Ile Ser Thr Glu Leu Gly Asn Val
                465                 470

Asn Asn Ser Ile Ser Asn Ala Leu Asn Lys
                475                 480

Leu Glu Glu Ser Asn Arg Lys Leu Asp Lys
                485                 490

Val Asn Val Lys Leu Thr Ser Thr Ser Ala
                495                 500

Leu Ile Thr Tyr Ile Val Leu Thr Ile Ile
                505                 510

Ser Leu Val Phe Gly Ile Leu Ser Leu Ile
                515                 520

Leu Ala Cys Tyr Leu Met Tyr Lys Gln Lys
                525                 530

Ala Gln Gln Lys Thr Leu Leu Trp Leu Gly
                535                 540

Asn Asn Thr Leu Asp Gln Met Arg Ala Thr
                545                 550

Thr Lys Met

<210> SEQ ID NO 26
<211> LENGTH: 18991
<212> TYPE: DNA
<213> ORGANISM: Artificial sequence
<220> FEATURE:
<223> OTHER INFORMATION: pNDVY527A
```

<400> SEQUENCE: 26

```
ttcggcgcgc ctaatacgac tcactatagg gaccaaacag agaatccgtg         50
atttacgata aaaggcgaaa gagcaattga agtcgcacgg gtagaaggtg        100
tgaatctcga gtgcgagccc gaagcacaaa ctcgagaaag ccttctgcca        150
acatgtcttc cgtatttgat gagtacgaac agctcctcgc ggctcagact        200
cgccccaatg gagctcatgg aggggagaa aaagggagta ccttaaaagt         250
agacgtcccg gtattcactc ttaacagtga tgacccagaa gatagatgga        300
gctttgtggt attctgcctc cggattgctg ttagcgaaga tgccaacaaa        350
ccactcaggc aaggtgctct catatctctt ttatgctccc actcacaggt        400
aatgaggaac catgttgccc ttgcagggaa acagaatgaa gccacattgg        450
ccgtgcttga gattgatggc tttgccaacg gcacgcccca gttcaacaat        500
aggagtggag tgtctgaaga gagcacag agatttgcga tgatagcagg          550
atctctccct cgggcatgca gcaacggaac cccgttcgtc acagccgggg        600
ccgaagatga tgcaccagaa gacatcaccg ataccctgga gaggatcctc        650
tctatccagg ctcaagtatg ggtcacagta gcaaaagcca tgactgcgta        700
tgagactgca gatgagtcgg aaacaaggcg aatcaataag tatatgcagc        750
aaggcagggt ccaaaagaaa tacatcctct accccgtatg caggagcaca        800
atccaactca cgatcagaca gtctcttgca gtccgcatct ttttggttag        850
cgagctcaag agaggccgca acacggcagg tggtacctct acttattata        900
acctggtagg ggacgtagac tcatacatca ggaataccgg gcttactgca        950
ttcttcttga cactcaagta cggaatcaac accaagacat cagcccttgc       1000
acttagtagc ctctcaggcg acatccagaa gatgaagcag ctcatgcgtt       1050
tgtatcggat gaaaggagat aatgcgccgt acatgacatt acttggtgat       1100
agtgaccaga tgagctttgc gcctgccgag tatgcacaac tttactcct        1150
tgccatgggt atggcatcag tcctagataa aggtactggg aaataccaat       1200
ttgccaggga ctttatgagc acatcattct ggagacttgg agtagagtac       1250
gctcaggctc agggaagtag cattaacgag gatatggctg ccgagctaaa       1300
gctaacccca gcagcaagga ggggcctggc agctgctgcc caacgggtct       1350
ccgaggagac cagcagcata gacatgccta ctcaacaagt cggagtcctc       1400
actgggctta gcgaggggg gtcccaagct ctacaaggcg gatcgaatag        1450
atcgcaaggg caaccagaag ccggggatgg ggagacccaa ttcctggatc       1500
tgatgagagc ggtagcaaat agcatgaggg aggcgccaaa ctctgcacag       1550
ggcactcccc aatcggggcc tccccaact cctgggccat cccaagataa         1600
cgacaccgac tgggggtatt gatggacaaa acccagcctg cttccacaaa       1650
aacatcccaa tgccctcacc cgtagtcgac ccctcgattt gcggctctat       1700
atgaccacac cctcaaacaa acatcccct ctttcctccc tccccctgct        1750
gtacaactcc gcacgcccta gataccacag gcacaatgcg gctcactaac       1800
aatcaaaaca gagccgaggg aattagaaaa aagtacgggt agaagaggga       1850
tattcagaga tcagggcaag tctcccgagt ctctgctctc tcctctacct       1900
```

```
gatagaccag gacaaacatg gccacctttta cagatgcaga gatcgacgag      1950
ctatttgaga caagtggaac tgtcattgac aacataatta cagcccaggg      2000
taaaccagca gagactgttg gaaggagtgc aatcccacaa ggcaagacca      2050
aggtgctgag cgcagcatgg gagaagcatg ggagcatcca gccaccggcc      2100
agtcaagaca accccgatcg acaggacaga tctgacaaac aaccatccac      2150
acccgagcaa acgaccccgc atgacagccc gccggccaca tccgccgacc      2200 agcccccccac ccaggccaca gacgaagccg tcgacacaca gctcaggacc      2250
ggagcaagca actctctgct gttgatgctt gacaagctca gcaataaatc      2300
gtccaatgct aaaaagggcc catggtcgag cccccaagag gggaatcacc      2350
aacgtccgac tcaacagcag gggagtcaac ccagccgcgg aaacagtcag      2400
gaaagaccgc agaaccaagt caaggccgcc cctggaaacc agggcacaga      2450
cgtgaacaca gcatatcatg gacaatggga ggagtcacaa ctatcagctg      2500
gtgcaacccc tcatgctctc cgatcaaggc agagccaaga caatacccct      2550
gtatctgcgg atcatgtcca gccacctgta gactttgtgc aagcgatgat      2600
gtctatgatg gaggcgatat cacagagagt aagtaaggtc gactatcagc      2650
tagatcttgt cttgaaacag acatcctcca tccctatgat gcggtccgaa      2700
atccaacagc tgaaaacatc tgttgcagtc atggaagcca acttgggaat      2750
gatgaagatt ctggatcccg gttgtgccaa catttcatct ctgagtgatc      2800
tacgggcagt tgcccgatct cacccggttt tagtttcagg ccctggagac      2850
ccctctccct atgtgacaca aggaggcgaa atggcactta ataaactttc      2900
gcaaccagtg ccacatccat ctgaattgat taaacccgcc actgcatgcg      2950
ggcctgatat aggagtggaa aaggacactg tccgtgcatt gatcatgtca      3000
cgcccaatgc acccgagttc ttcagccaag ctcctaagca agttagatgc      3050
agccgggtcg atcgaggaaa tcaggaaaat caagcgcctt gctctaaatg      3100
gctaattact actgccacac gtagcgggtc cctgtccact cggcatcaca      3150
cggaatctgc accgagttcc cccccgcaga cccaaggtcc aactctccaa      3200
gcggcaatcc tctctcgctt cctcagcccc actgaatgat cgcgtaaccg      3250
tttaattaat agctacattt aagattaaga aaaaatacgg gtagaattgg      3300
agtgccccaa ttgtgccaag atggactcat ctaggacaat tgggctgtac      3350
tttgattctg cccattcttc tagcaacctg ttagcatttc cgatcgtcct      3400
acaagacaca ggagatggga agaagcaaat cgccccgcaa tataggatcc      3450
agcgccttga cttgtggact gatagtaagg aggactcagt attcatcacc      3500
acctatggat tcatctttca agttgggaat gaagaagcca ctgtcggcat      3550
gatcgatgat aaacccaagc gcgagttact ttccgctgcg atgctctgcc      3600
taggaagcgt cccaaatacc ggagacctta ttgagctggc aagggcctgt      3650
ctcactatga tagtcacatg caagaagagt gcaactaata ctgagagaat      3700
ggttttctca gtagtgcagg cacccccaagt gctgcaaagc tgtagggttg      3750
tggcaaacaa atactcatca gtgaatgcag tcaagcacgt gaaagcgcca      3800
gagaagattc ccgggagtgg aacccctagaa tacaaggtga actttgtctc      3850
cttgactgtg gtaccgaaga aggatgtcta caagatccca gctgcagtat      3900
```

```
tgaaggtttc tggctcgagt ctgtacaatc ttgcgctcaa tgtcactatt        3950
aatgtggagg tagacccgag gagtcctttg gttaaatctc tgtctaagtc        4000
tgacagcgga tactatgcta acctcttctt gcatattgga cttatgacca        4050
ccgtagatag gaaggggaag aaagtgacat ttgacaagct ggaaaagaaa        4100
ataaggagcc ttgatctatc tgtcgggctc agtgatgtgc tcgggccttc        4150
cgtgttggta aaagcaagag gtgcacggac taagcttttg gcacctttct        4200
tctctagcag tgggacagcc tgctatccca tagcaaatgc ttctcctcag        4250
gtggccaaga tactctggag tcaaaccgcg tgcctgcgga gcgttaaaat        4300
cattatccaa gcaggtaccc aacgcgctgt cccagtgacc cccaaccacc        4350
aggttacctc tactaagctg gagaaggggc acacccttgc caaatacaat        4400 cctttaaga aataagctgc gtctctgaga ttgcgctccg cccactcacc         4450
cggatcatca tgcacaaaa aactaatctg tcttgattat ttacagttag         4500
tttacctgtc tatcaagtta gaaaaaacac gggtagaaga ttctggatcc        4550
cggttggcgc cctccaggtg caagatgggc tccagaccct ctaccaagaa        4600
cccagcacct atgatgctga ctatccgggt tgcgctggta ctgagttgca        4650
tctgtccggc aaactccatt gatggcaggc ctcttgcagc tgcaggaatt        4700
gtggttacag gagacaaagc cgtcaacata tacacctcat cccagacagg        4750
atcaatcata gttaagctcc tcccgaatct gcccaaggat aaggaggcat        4800
gtgcgaaagc ccccttggat gcatacaaca ggacattgac cactttgctc        4850
accccccttg gtgactctat ccgtaggata caagagtctg tgactacatc        4900 tggaggggggg agacagggggc gccttatagg cgccattatt ggcggtgtgg       4950 ctcttgggt tgcaactgcc gcacaaataa cagcggccgc agctctgata         5000
caagccaaac aaaatgctgc caacatcctc cgacttaaag agagcattgc        5050
cgcaaccaat gaggctgtgc atgaggtcac tgacggatta tcgcaactag        5100
cagtggcagt tgggaagatg cagcagtttg ttaatgacca atttaataaa        5150
acagctcagg aattgactg catcaaaatt gcacagcaag ttggtgtaga         5200
gctcaacctg tacctaaccg aattgactac agtattcgga ccacaaatca        5250
cttcacctgc tttaaacaag ctgactattc aggcacttta caatctagct        5300
ggtggaaata tggattactt attgactaag ttaggtgtag ggaacaatca        5350
actcagctca ttaatcggta gcggcttaat caccggtaac cctattctat        5400
acgactcaca gactcaactc ttgggtatac aggtaactct accttcagtc        5450
gggaacctaa ataatatgcg tgccacctac ttggaaacct tatccgtaag        5500
cacaaccagg ggatttgcct cggcacttgt cccaaaagtg gtgacacagg        5550
tcggttctgt gatagaagaa cttgacacct catactgtat agaaactgac        5600
ttagatttat attgtacaag aatagtaacg ttccctatgt cccctggtat        5650
ttattcctgc ttgagcggca atacgtcggc ctgtatgtac tcaaagaccg        5700
aaggcgcact tactacacca tacatgacta tcaaaggttc agtcatcgcc        5750
aactgcaaga tgcaacatg tagatgtgta aaccccccgg gtatcatatc         5800
gcaaaactat ggagaagccg tgtctctaat agataaacaa tcatgcaatg        5850
```

```
ttttatccctt aggcgggata actttaaggc tcagtgggga attcgatgta      5900
acttatcaga agaatatctc aatacaagat tctcaagtaa taataacagg      5950
caatcttgat atctcaactg agcttgggaa tgtcaacaac tcgatcagta      6000
atgcttgaa taagttagag gaaagcaaca gaaaactaga caaagtcaat       6050
gtcaaactga ccagcacatc tgctctcatt acctatatcg ttttgactat      6100
catatctctt gttttggta tacttagcct gattctagca tgctacctaa       6150
tggctaagca aaaggcgcaa caaaagacct tattatggct tgggaataat      6200
actctagatc agatgagagc cactacaaaa atgtgaacac agatgaggaa      6250
cgaaggtttc cctaatagta atttgtgtga aagttctggt agtctgtcag      6300
ttcagagagt taagaaaaaa ctacgcgttg tagatgacca aaggacgata      6350
tacgggtaga acggtaagag aggccgcccc tcaattgcga gccaggcttc      6400
acaacctccg ttctaccgct tcaccgacaa cagtcctcaa tcatggaccg      6450
cgccgttagc caagttgcgt tagagaatga tgaaagagag gcaaaaaata      6500
catggcgctt gatattccgg attgcaatct tattcttaac agtagtgacc      6550
ttggctatat ctgtagcctc ccttttatat agcatggggg ctagcacacc      6600
tagcgatctt gtaggcatac cgactaggat ttccagggca gaagaaaaga      6650
ttacatctac acttggttcc aatcaagatg tagtagatag gatatataag      6700
caagtggccc ttgagtctcc gttggcattg ttaaaaactg agaccacaat      6750
tatgaacgca ataacatctc tctcttatca gattaatgga gctgcaaaca      6800
acagtgggtg gggggcacct atccatgacc cagattatat agggggata       6850
ggcaaagaac tcattgtaga tgatgctagt gatgtcacat cattctatcc      6900
ctctgcattt caagaacatc tgaatttat cccggcgcct actacaggat       6950
caggttgcac tcgaataccc tcatttgaca tgagtgctac ccattactgc      7000
tacacccata atgtaatatt gtctggatgc agagatcact cacattcata      7050
tcagtattta gcacttggtg tgctccggac atctgcaaca gggagggtat      7100
tcttttctac tctgcgttcc atcaacctgg acgacaccca aaatcggaag      7150
tcttgcagtg tgagtgcaac tcccctgggt tgtgatatgc tgtgctcgaa      7200
agtcacggag acagaggaag aagattataa ctcagctgtc cctacgcgga      7250
tggtacatgg gaggttaggg ttcgacggcc agtaccacga aaaggaccta      7300
gatgtcacaa cattattcgg ggactgggtg gccaactacc caggagtagg      7350
gggtggatct tttattgaca gccgcgtatg gttctcagtc tacggagggt      7400
taaaacccaa ttcacccagt gacactgtac aggaagggaa atatgtgata      7450
tacaagcgat acaatgacac atgcccagat gagcaagact accagattcg      7500
aatggccaag tcttcgtata agcctggacg gtttggtggg aaacgcatac      7550
agcaggctat cttatctatc aaggtgtcaa catccttagg cgaagacccg      7600
gtactgactg taccgcccaa cacagtcaca ctcatggggg ccgaaggcag      7650
aattctcaca gtagggacat ctcatttctt gtatcaacga gggtcatcat      7700
acttctctcc cgcgttatta tatcctatga cagtcagcaa caaaacagcc      7750
actcttcata gtccttatac attcaatgcc ttcactcggc caggtagtat      7800
cccttgccag gcttcagcaa gatgccccaa cccgtgtgtt actggagtct      7850
```

```
atacagatcc atatcccta atcttctata gaaaccacac cttgcgaggg      7900
gtattcggga caatgcttga tggtgtacaa gcaagactta accctgcgtc      7950
tgcagtattc gatagcacat cccgcagtcg cattactcga gtgagttcaa      8000
gcagtaccaa agcagcatac acaacatcaa cttgttttaa agtggtcaag      8050
actaataaga cctattgtct cagcattgct gaaatatcta atactctctt      8100
cggagaattc agaatcgtcc cgttactagt tgagatcctc aaagatgacg      8150
gggttagaga agccaggtct ggctagttga gtcaattata aaggagttgg      8200
aaagatggca ttgtatcacc tatcttctgc gacatcaaga atcaaaccga      8250
atgccggcgc gtgctcgaat tccatgttgc cagttgacca caatcagcca      8300
gtgctcatgc gatcagatta agccttgtca atagtctctt gattaagaaa      8350
aaatgtaagt ggcaatgaga tacaaggcaa aatacgtacc ggtaaataat      8400
acgggtagga catggcgagc tccggtcctg aaagggcaga gcatcagatt      8450
atcctaccag agtcacacct gtcttcacca ttggtcaagc acaaactact      8500
ctattactgg aaattaactg ggctaccgct tcctgatgaa tgtgacttcg      8550
accacctcat tctcagccga caatggaaaa aaatacttga atcggcctct      8600
cctgatactg agagaatgat aaaactcgga agggcagtac accaaactct      8650
taaccacaat tccagaataa ccggagtgct ccaccccagg tgtttagaag      8700
aactggctaa tattgaggtc ccagattcaa ccaacaaatt tcggaagatt      8750
gagaagaaga tccaaattca caacacgaga tatggagaac tgttcacaag      8800
gctgtgtacg catatagaga agaaactgct ggggtcatct tggtctaaca      8850
atgtcccccg gtcagaggag ttcagcagca ttcgtacgga tccggcattc      8900
tggtttcact caaaatggtc cacagccaag tttgcatggc tccatataaa      8950
acagatccag aggcatctga tggtggcagc taggacaagg tctgcggcca      9000
acaaattggt gatgctaacc cataaggtag gccaagtctt tgtcactcct      9050
gaacttgtcg ttgtgacgca tacgaatgag aacaagttca catgtcttac      9100
ccaggaactt gtattgatgt atgcagatat gatggagggc agagatatgg      9150
tcaacataat atcaaccacg gcggtgcatc tcagaagctt atcagagaaa      9200
attgatgaca ttttgcggtt aatagacgct ctggcaaaag acttgggtaa      9250
tcaagtctac gatgttgtat cactaatgga gggatttgca tacggagctg      9300
tccagctact cgagccgtca ggtacatttg caggagattt cttcgcattc      9350
aacctgcagg agcttaaaga cattctaatt ggcctcctcc ccaatgatat      9400
agcagaatcc gtgactcatg caatcgctac tgtattctct ggtttagaac      9450
agaatcaagc agctgagatg ttgtgtctgt tgcgtctgtg gggtcaccca      9500
ctgcttgagt cccgtattgc agcaaaggca gtcaggagcc aaatgtgcgc      9550
accgaaaatg gtagactttg atatgatcct tcaggtactg tctttcttca      9600
agggaacaat catcaacggg tacagaaaga agaatgcagg tgtgtggccg      9650
cgagtcaaag tggatacaat atatgggaag gtcattgggc aactacatgc      9700
agattcagca gagatttcac acgatatcat gttgagagag tataagagtt      9750
tatctgcact tgaatttgag ccatgtatag aatatgaccc tgtcacaaac      9800
```

-continued

```
ctgagcatgt tcctaaaaga caaggcaatc gcacacccca acgataattg      9850
gcttgcctcg tttaggcgga accttctctc cgaagaccag aagaaacatg      9900
taaaagaagc aacttcgact aatcgcctct tgatagagtt tttagagtca      9950
aatgattttg atccatataa agagatggaa tatctgacga cccttgagta     10000
ccttagagat gacaatgtgg cagtatcata ctcgctcaag gagaaggaag     10050
tgaaagttaa tggacggatc ttcgctaagc tgacaaagaa gttaaggaac     10100
tgtcaggtga tggcggaagg gatcctagcc gatcagattg cacctttctt     10150
tcagggaaat ggagtcattc aggatagcat atccttgacc aagagtatgc     10200
tagcgatgag tcaactgtct tttaacagca ataagaaacg tatcactgac     10250
tgtaaagaaa gagtatcttc aaaccgcaat catgatccga aaagcaagaa     10300
ccgtcggaga gttgcaacct tcataacaac tgacctgcaa aagtactgtc     10350
ttaattggag atatcagaca atcaaattgt tcgctcatgc catcaatcag     10400
ttgatgggcc tacctcactt cttcgaatgg attcacctaa gactgatgga     10450
cactacgatg ttcgtaggag acccttcaa tcctccaagt gaccctactg      10500
actgtgacct ctcaagagtc cctaatgatg acatatatat tgtcagtgcc     10550
agaggggta tcgaaggatt atgccagaag ctatggacaa tgatctcaat      10600
tgctgcaatc caacttgctg cagctagatc gcattgtcgt gttgcctgta     10650
tggtacaggg tgataatcaa gtaatagcag taacgagaga ggtaagatca     10700
gacgactctc cggagatggt gttgacacag ttgcatcaag ccagtgataa     10750
tttcttcaag gaattaattc atgtcaatca tttgattggc cataatttga     10800
aggatcgtga aaccatcagg tcagacacat tcttcatata cagcaaacga     10850
atcttcaaag atggagcaat cctcagtcaa gtcctcaaaa attcatctaa     10900
attagtgcta gtgtcaggtg atctcagtga aaacaccgta atgtcctgtg     10950
ccaacattgc ctctactgta gcacggctat gcgagaacgg gcttcccaaa     11000
gacttctgtt actatttaaa ctatataatg agttgtgtgc agacatactt     11050
tgactctgag ttctccatca ccaacaattc gcaccccgat cttaatcagt     11100
cgtggattga ggacatctct tttgtgcact catatgttct gactcctgcc     11150
caattagggg gactgagtaa ccttcaatac tcaaggctct acactagaaa     11200
tatcggtgac ccggggacta ctgcttttgc agagatcaag cgactagaag     11250
cagtgggatt actgagtcct aacattatga ctaatatctt aactaggccg     11300
cctgggaatg gagattgggc cagtctgtgc aacgacccat actctttcaa     11350
ttttgagact gttgcaagcc caaatattgt tcttaagaaa catacgcaaa     11400
gagtcctatt tgaaacttgt tcaaatccct tattgtctgg agtgcacaca     11450
gaggataatg aggcagaaga gaaggcattg gctgaattct tgcttaatca     11500
agaggtgatt catccccgcg ttgcgcatgc catcatggag gcaagctctg     11550
taggtaggag aaagcaaatt caagggcttg ttgacacaac aaacaccgta     11600
attaagattg cgcttactag gaggccatta ggcatcaaga ggctgatgcg     11650
gatagtcaat tattctagca tgcatgcaat gctgtttaga gacgatgttt     11700
tttcctccag tagatccaac caccccttag tctcttctaa tatgtgttct     11750
ctgacactgg cagactatgc acggaataga agctggtcac ctttgacggg     11800
```

```
aggcaggaaa atactgggtg tatctaatcc tgatacgata gaactcgtag      11850
agggtgagat tcttagtgta agcggagggt gtacaagatg tgacagcgga      11900
gatgaacaat ttacttggtt ccatcttcca agcaatatag aattgaccga      11950
tgacaccagc aagaatcctc cgatgagggt accatatctc gggtcaaaga      12000
cacaggagag gagagctgcc tcacttgcaa aaatagctca tatgtcgcca      12050
catgtaaagg ctgccctaag ggcatcatcc gtgttgatct gggcttatgg      12100
ggataatgaa gtaaattgga ctgctgctct tacgattgca aaatctcggt      12150
gcaatgtaaa cttagagtat cttcggttac tgtccccttt acccacggct      12200
gggaatcttc aacatagact agatgatggt ataactcaga tgacattcac      12250
ccctgcatct ctctacaggg tgtcacctta cattcacata tccaatgatt      12300
ctcaaaggct gttcactgaa gaaggagtca agagggggaa tgtggtttac      12350
caacagatca tgctcttggg tttatctcta atcgaatcga tctttccaat      12400
gacaacaacc aggacatatg atgagatcac actgcaccta catagtaaat      12450
ttagttgctg tatcagagaa gcacctgttg cggttccttt cgagctactt      12500
ggggtggtac cggaactgag gacagtgacc tcaaataagt ttatgtatga      12550
tcctagccct gtatcggagg gagactttgc gagacttgac ttagctatct      12600
tcaagagtta tgagcttaat ctggagtcat atcccacgat agagctaatg      12650
aacattcttt caatatccag cgggaagttg attggccagt ctgtggtttc      12700
ttatgatgaa gatacctcca taaagaatga cgccataata gtgtatgaca      12750
atacccgaaa ttggatcagt gaagctcaga attcagatgt ggtccgccta      12800
tttgaatatg cagcacttga agtgctcctc gactgttctt accaactcta      12850
ttatctgaga gtaagaggcc tagacaatat tgtcttatat atgggtgatt      12900
tatacaagaa tatgccagga attctacttt ccaacattgc agctacaata      12950
tctcatcccg tcattcattc aaggttacat gcagtgggcc tggtcaacca      13000
tgacggatca caccaacttg cagatacgga ttttatcgaa atgtctgcaa      13050
aactattagt atcttgcacc cgacgtgtga tatccggctt atattcagga      13100
aataagtatg atctgctgtt cccatctgtc ttagatgata acctgaatga      13150
gaagatgctt cagctgatat cccggttatg ctgtctgtac acggtactct      13200
ttgctacaac aagagaaatc ccgaaaataa gaggcttaac tgcagaagag      13250
aaatgttcaa tactcactga gtatttactg tcggatgctg tgaaaccatt      13300
acttagcccc gatcaagtga gctctatcat gtctcctaac ataattacat      13350
tcccagctaa tctgtactac atgtctcgga agagcctcaa tttgatcagg      13400
gaaagggagg acaggggatac tatcctggcg ttgttgttcc cccaagagcc      13450
attattagag ttcccttctg tgcaagatat tggtgctcga gtgaaagatc      13500
cattcacccg acaacctgcg gcattttttgc aagagttaga tttgagtgct      13550
ccagcaaggt atgacgcatt cacacttagt cagattcatc ctgaactcac      13600
atctccaaat ccggaggaag actacttagt acgatacttg ttcagaggga      13650
tagggactgc atcttcctct tggtataagg catctcatct cctttctgta      13700
cccgaggtaa gatgtgcaag acacgggaac tccttatact tagctgaagg      13750
```

```
gagcggagcc atcatgagtc ttctcgaact gcatgtacca catgaaacta      13800
tctattacaa tacgctcttt tcaaatgaga tgaaccccc gcaacgacat       13850
ttcgggccga ccccaactca gttttttgaat tcggttgttt ataggaatct     13900
acaggcggag gtaacctgca aagatggatt tgtccaagag ttccgtccat      13950
tatggagaga aaatacagag gaaagtgacc tgacctcaga taaagcagtg      14000
gggtatatta catctgcagt gccctacaga tctgtatcat tgctgcattg      14050
tgacattgaa attcctccag ggtccaatca aagcttacta gatcaactag      14100
ctatcaattt atctctgatt gccatgcatt ctgtaaggga gggcggggta      14150
gtaatcatca aagtgttgta tgcaatggga tactactttc atctactcat      14200
gaacttgttt gctccgtgtt ccacaaaagg atatattctc tctaatggtt      14250
atgcatgtcg aggagatatg gagtgttacc tggtatttgt catgggttac      14300
ctgggcgggc ctacatttgt acatgaggtg gtgaggatgg caaaaactct      14350
ggtgcagcgg cacggtacgc ttttgtctaa atcagatgag atcacactga      14400
ccaggttatt cacctcacag cggcagcgtg tgacagacat cctatccagt      14450
cctttaccaa gattaataaa gtacttgagg aagaatattg acactgcgct      14500
gattgaagcc gggggacagc ccgtccgtcc attctgtgcg gagagtctgg      14550
tgagcacgct agcgaacata actcagataa cccagatcat cgctagccac      14600
attgacacag ttatccggtc tgtgatatat atggaagctg agggtgatct      14650
cgctgacaca gtatttctat ttaccccta caatctctct actgacggga      14700
aaagaggac atcacttaaa cagtgcacga gacagatcct agaggttaca       14750
atactaggtc ttagagtcga aaatctcaat aaaataggcg atataatcag      14800
cctagtgctt aaaggcatga tctccatgga ggaccttatc ccactaagga      14850
catacttgaa gcatagtacc tgccctaaat atttgaaggc tgtcctaggt      14900
attaccaaac tcaaagaaat gtttacagac acttctgtac tgtacttgac      14950
tcgtgctcaa caaaaattct acatgaaaac tataggcaat gcagtcaaag      15000
gatattacag taactgtgac tcttaacgaa atcacatat taataggctc       15050
cttttttggc caattgtatt cttgttgatt taatcatatt atgttagaaa      15100
aaagttgaac cctgactcct taggactcga attcgaactc aaataaatgt      15150
cttaaaaaaa ggttgcgcac aattattctt gagtgtagtc tcgtcattca      15200
ccaaatcttg gttgggtcgg catggcatct ccacctcctc gcggtccgac      15250
ctgggcatcc gaaggaggac gcacgtccac tcggatggct aagggagagc      15300
ctgcagtagc ataaccccctt ggggcctcta acgggtctt gagggttttt     15350
ttgctgaaag gaggaactat atactcgagc tgcagcaatg gcaacaacgt      15400
tgcgcaaact attaactggc gaactactta ctctagcttc ccggcaacaa      15450
ttaatagact ggatggaggc ggataaagtt gcaggaccac ttctgcgctc      15500
ggcccttccg gctggctggt ttattgctga taaatctgga gccggtgagc      15550
gtgggtctcg cggtatcatt gcagcactgg ggccagatgg taagccctcc      15600
cgtatcgtag ttatctacac gacggggagt caggcaacta tggatgaacg      15650
aaatagacag atcgctgaga taggtgcctc actgattaag cattggtaac      15700
tgtcagacca agtttactca tatatacttt agattgattt aaaacttcat      15750
```

```
ttttaattta aaaggatcta ggtgaagatc cttttttgata atctcatgac      15800
caaaatccct taacgtgagt tttcgttcca ctgagcgtca gaccccgtag      15850
aaaagatcaa aggatcttct tgagatcctt tttttctgcg cgtaatctgc      15900
tgcttgcaaa caaaaaaacc accgctacca gcggtggttt gtttgccgga      15950
tcaagagcta ccaactcttt ttccgaaggt aactggcttc agcagagcgc      16000
agataccaaa tactgtcctt ctagtgtagc cgtagttagg ccaccacttc      16050
aagaactctg tagcaccgcc tacatacctc gctctgctaa tcctgttacc      16100
agtggctgct gccagtggcg ataagtcgtg tcttaccggg ttggactcaa      16150
gacgatagtt accggataag gcgcagcggt cgggctgaac ggggggttcg      16200
tgcacacagc ccagcttgga gcgaacgacc tacaccgaac tgagatacct      16250
acagcgtgag ctatgagaaa gcgccacgct tcccgaaggg agaaaggcgg      16300
acaggtatcc ggtaagcggc agggtcggaa caggagagcg cacgagggag      16350
cttccagggg gaaacgcctg gtatctttat agtcctgtcg ggtttcgcca      16400
cctctgactt gagcgtcgat ttttgtgatg ctcgtcaggg gggcggagcc      16450
tatggaaaaa cgccagcaac gcggccttttt tacggttcct ggccttttgc      16500
tggccttttg ctcacatgtt ctttcctgcg ttatccctg attctgtgga      16550
taaccgtatt accgcctttg agtgagctga taccgctcgc cgcagccgaa      16600
cgaccgagcg cagcgagtca gtgagcgagg aagcggaaga gcgcctgatg      16650
cggtattttc tccttacgca tctgtgcggt atttcacacc gcatatggtg      16700
cactctcagt acaatctgct ctgatgccgc atagttaagc cagtatacac      16750
tccgctatcg ctacgtgact gggtcatggc tgcgccccga cacccgccaa      16800
cacccgctga cgcgccctga cgggcttgtc tgctcccggc atccgcttac      16850
agacaagctg tgaccgtctc cgggagctgc atgtgtcaga ggttttcacc      16900
gtcatcaccg aaacgcgcga ggcagctgcg gtaaagctca tcagcgtggt      16950
cgtgaagcga ttcacagatg tctgcctgtt catccgcgtc cagctcgttg      17000
agtttctcca gaagcgttaa tgtctggctt ctgataaagc gggccatgtt      17050
aagggcggtt ttttcctgtt tggtcactga tgcctccgtg taaggggat       17100
ttctgttcat gggggtaatg ataccgatga acgagagag gatgctcacg      17150
atacgggtta ctgatgatga acatgcccgg ttactggaac gttgtgaggg      17200
taaacaactg gcggtatgga tgcggcggga ccagagaaaa atcactcagg      17250
gtcaatgcca gcgcttcgtt aatacagatg taggtgttcc acagggtagc      17300
cagcagcatc ctgcgatgca gatccggaac ataatggtgc agggcgctga      17350
cttccgcgtt tccagacttt acgaaacacg gaaaccgaag accattcatg      17400
ttgttgctca ggtcgcagac gttttgcagc agcagtcgct tcacgttcgc      17450
tcgcgtatcg gtgattcatt ctgctaacca gtaaggcaac cccgccagcc      17500
tagccgggtc ctcaacgaca ggagcacgat catgcgcacc cgtggccagg      17550
acccaacgct gcccgagatg cgccgcgtgc ggctgctgga gatggcggac      17600
gcgatggata tgttctgcca agggttggtt tgcgcattca cagttctccg      17650
caagaattga ttggctccaa ttcttggagt ggtgaatccg ttagcgaggt      17700
```
gccgccggct tccattcagg tcgaggtggc ccggctccat gcaccgcgac 17750
gcaacgcggg gaggcagaca aggtataggg cggcgcctac aatccatgcc 17800
aacccgttcc atgtgctcgc cgaggcggca taaatcgccg tgacgatcag 17850
cggtccagtg atcgaagtta ggctggtaag agccgcgagc gatccttgaa 17900
gctgtccctg atggtcgtca tctacctgcc tggacagcat ggcctgcaac 17950
gcgggcatcc cgatgccgcc ggaagcgaga agaatcataa tggggaaggc 18000
catccagcct cgcgtcgcga acgccagcaa gacgtagccc agcgcgtcgg 18050
ccgccatgcc ggcgataatg gcctgcttct cgccgaaacg tttggtggcg 18100
ggaccagtga cgaaggcttg agcgagggcg tgcaagattc cgaataccgc 18150
aagcgacagg ccgatcatcg tcgcgctcca gcgaaagcgg tcctcgccga 18200
aaatgaccca gagcgctgcc ggcacctgtc ctacgagttg catgataaag 18250
aagacagtca taagtgcggc gacgatagtc atgccccgcg cccaccggaa 18300
ggagctgact gggttgaagg ctctcaaggg catcggtcga cgctctccct 18350
tatgcgactc ctgcattagg aagcagccca gtagtaggtt gaggccgttg 18400
agcaccgccg ccgcaaggaa tggtgcatgc aaggagatgg cgcccaacag 18450
tcccccggcc acggggcctg ccaccatacc cacgccgaaa caagcgctca 18500
tgagcccgaa gtggcgagcc cgatcttccc catcggtgat gtcggcgata 18550
taggcgccag caaccgcacc tgtggcgccg gtgatgccgg ccacgatgcg 18600
tccggcgtag aggatccaca ggacgggtgt ggtcgccatg atcgcgtagt 18650
cgatagtggc tccaagtagc gaagcgagca ggactgggcg gcggccaaag 18700
cggtcggaca gtgctccgag aacgggtgcg catagaaatt gcatcaacgc 18750
atatagcgct agcagcacgc catagtgact ggcgatgctg tcggaatgga 18800
cgatatcccg caagaggccc ggcagtaccg gcataaccaa gcctatgcct 18850
acagcatcca gggtgacggt gccgaggatg acgatgagcg cattgttaga 18900
tttcatacac ggtgcctgac tgcgttagca atttaactgt gataaactac 18950
cgcattaaag cttatcgatg ataagctgtc aaacatgaga a 18991

<210> SEQ ID NO 27
<211> LENGTH: 15186
<212> TYPE: DNA
<213> ORGANISM: Artificial sequence
<220> FEATURE:
<223> OTHER INFORMATION: rNDVY527A

<400> SEQUENCE: 27
accaaacaga gaatccgtga tttacgataa aaggcgaaag agcaattgaa 50
gtcgcacggg tagaaggtgt gaatctcgag tgcgagcccg aagcacaaac 100
tcgagaaagc cttctgccaa catgtcttcc gtatttgatg agtacgaaca 150
gctcctcgcg gctcagactc gccccaatgg agctcatgga gggggagaaa 200
aagggagtac cttaaaagta gacgtcccgg tattcactct taacagtgat 250
gacccagaag atagatggag ctttgtggta ttctgcctcc ggattgctgt 300
tagcgaagat gccaacaaac cactcaggca aggtgctctc atatctcttt 350
tatgctccca ctcacaggta atgaggaacc atgttgccct tgcagggaaa 400
cagaatgaag ccacattggc cgtgcttgag attgatggct ttgccaacgg 450

```
cacgccccag ttcaacaata ggagtggagt gtctgaagag agagcacaga        500
gatttgcgat gatagcagga tctctccctc gggcatgcag caacggaacc        550
ccgttcgtca cagccggggc cgaagatgat gcaccagaag acatcaccga        600
taccctggag aggatcctct ctatccaggc tcaagtatgg gtcacagtag        650
caaaagccat gactgcgtat gagactgcag atgagtcgga aacaaggcga        700
atcaataagt atatgcagca aggcagggtc caaaagaaat acatcctcta        750
ccccgtatgc aggagcacaa tccaactcac gatcagacag tctcttgcag        800
tccgcatctt tttggttagc gagctcaaga gaggccgcaa cacggcaggt        850
ggtacctcta cttattataa cctggtaggg gacgtagact catacatcag        900
gaataccggg cttactgcat tcttcttgac actcaagtac ggaatcaaca        950
ccaagacatc agcccttgca cttagtagcc tctcaggcga catccagaag       1000
atgaagcagc tcatgcgttt gtatcggatg aaaggagata atgcgccgta       1050
catgacatta cttggtgata gtgaccagat gagctttgcg cctgccgagt       1100
atgcacaact ttactccctt gccatgggta tggcatcagt cctagataaa       1150
ggtactggga ataccaattt tgccagggac tttatgagca catcattctg       1200
gagacttgga gtagagtacg ctcaggctca gggaagtagc attaacgagg       1250
atatggctgc cgagctaaag ctaaccccag cagcaaggag gggcctggca       1300
gctgctgccc aacgggtctc cgaggagacc agcagcatag acatgcctac       1350
tcaacaagtc ggagtcctca ctgggcttag cgaggggggg tcccaagctc       1400
tacaaggcgg atcgaataga tcgcaagggc aaccagaagc cggggatggg       1450
gagacccaat tcctggatct gatgagagcg gtagcaaata gcatgaggga       1500
ggcgccaaac tctgcacagg gcactcccca atcggggcct cccccaactc       1550
ctgggccatc ccaagataac gacaccgact gggggtattg atggacaaaa       1600
cccagcctgc ttccacaaaa acatcccaat gccctcaccc gtagtcgacc       1650
cctcgatttg cggctctata tgaccacacc ctcaaacaaa catccccctc       1700
tttcctccct cccctgctg tacaactccg cacgccctag ataccacagg        1750
cacaatgcgg ctcactaaca atcaaaacag agccgaggga attagaaaaa       1800
agtacgggta gaagagggat attcagagat cagggcaagt ctcccgagtc       1850
tctgctctct cctctacctg atagaccagg acaaacatgg ccacctttac       1900
agatgcagag atcgacgagc tatttgagac aagtggaact gtcattgaca       1950
acataattac agcccagggt aaaccagcag agactgttgg aaggagtgca       2000
atcccacaag gcaagaccaa ggtgctgagc gcagcatggg agaagcatgg       2050
gagcatccag ccaccggcca gtcaagacaa ccccgatcga caggacagat       2100
ctgacaaaca accatccaca cccgagcaaa cgaccccgca tgacagcccg       2150
ccggccacat ccgccgacca gcccccacc caggccacag acgaagccgt        2200
cgacacacag ctcaggaccg gagcaagcaa ctctctgctg ttgatgcttg       2250
acaagctcag caataaatcg tccaatgcta aaaagggccc atggtcgagc       2300
ccccaagagg ggaatcacca acgtccgact caacagcagg ggagtcaacc       2350
cagccgcgga aacagtcagg aaagaccgca gaaccaagtc aaggccgccc       2400
```

```
ctggaaacca gggcacagac gtgaacacag catatcatgg acaatgggag      2450
gagtcacaac tatcagctgg tgcaacccct catgctctcc gatcaaggca      2500
gagccaagac aataccctttg tatctgcgga tcatgtccag ccacctgtag     2550
actttgtgca agcgatgatg tctatgatgg aggcgatatc acagagagta      2600
agtaaggtcg actatcagct agatcttgtc ttgaaacaga catcctccat      2650
ccctatgatg cggtccgaaa tccaacagct gaaaacatct gttgcagtca      2700
tggaagccaa cttgggaatg atgaagattc tggatcccgg ttgtgccaac      2750
atttcatctc tgagtgatct acgggcagtt gcccgatctc acccggtttt      2800
agtttcaggc cctggagacc cctctcccta tgtgacacaa ggaggcgaaa      2850
tggcacttaa taaactttcg caaccagtgc cacatccatc tgaattgatt      2900
aaacccgcca ctgcatgcgg gcctgatata ggagtggaaa aggacactgt      2950
ccgtgcattg atcatgtcac gcccaatgca cccgagttct tcagccaagc      3000
tcctaagcaa gttagatgca gccgggtcga tcgaggaaat caggaaaatc      3050
aagcgccttg ctctaaatgg ctaattacta ctgccacacg tagcgggtcc      3100
ctgtccactc ggcatcacac ggaatctgca ccgagttccc ccccgcagac      3150
ccaaggtcca actctccaag cggcaatcct ctctcgcttc ctcagcccca      3200
ctgaatgatc gcgtaaccgt ttaattaata gctacattta agattaagaa      3250
aaaatacggg tagaattgga gtgccccaat tgtgccaaga tggactcatc      3300
taggacaatt gggctgtact ttgattctgc ccattcttct agcaacctgt      3350
tagcatttcc gatcgtccta caagacacag gagatgggaa gaagcaaatc      3400
gccccgcaat ataggatcca gcgccttgac ttgtggactg atagtaagga      3450
ggactcagta ttcatcacca cctatggatt catctttcaa gttgggaatg      3500
aagaagccac tgtcggcatg atcgatgata acccaagcg cgagttactt       3550
tccgctgcga tgctctgcct aggaagcgtc ccaaataccg gagaccttat      3600
tgagctggca agggcctgtc tcactatgat agtcacatgc aagaagagtg      3650
caactaatac tgagagaatg gtttttctcag tagtgcaggc accccaagtg     3700
ctgcaaagct gtagggttgt ggcaaacaaa tactcatcag tgaatgcagt      3750
caagcacgtg aaagcgccag agaagattcc cgggagtgga accctagaat      3800
acaaggtgaa ctttgtctcc ttgactgtgg taccgaagaa ggatgtctac      3850
aagatcccag ctgcagtatt gaaggtttct ggctcgagtc tgtacaatct      3900
tgcgctcaat gtcactatta atgtggaggt agacccgagg agtcctttgg      3950
ttaaatctct gtctaagtct gacagcggat actatgctaa cctcttcttg      4000
catattggac ttatgaccac cgtagatagg aaggggaaga aagtgacatt      4050
tgacaagctg gaaaagaaaa taaggagcct tgatctatct gtcgggctca      4100
gtgatgtgct cgggccttcc gtgttggtaa aagcaagagg tgcacggact      4150
aagcttttgg caccttttctt ctctagcagt gggacagcct gctatcccat     4200
agcaaatgct tctcctcagg tggccaagat actctggagt caaaccgcgt      4250
gcctgcggag cgttaaaatc attatccaag caggtaccca acgcgctgtc      4300
ccagtgaccc ccaaccacca ggttacctct actaagctgg agaaggggca      4350
cacccttgcc aaatacaatc ctttaagaa ataagctgcg tctctgagat        4400
```

```
tgcgctccgc ccactcaccc ggatcatcat gacacaaaaa actaatctgt      4450
cttgattatt tacagttagt ttacctgtct atcaagttag aaaaaacacg      4500
ggtagaagat tctggatccc ggttggcgcc ctccaggtgc aagatgggct      4550
ccagaccttc taccaagaac ccagcaccta tgatgctgac tatccgggtt      4600
gcgctggtac tgagttgcat ctgtccggca aactccattg atggcaggcc      4650
tcttgcagct gcaggaattg tggttacagg agacaaagcc gtcaacatat      4700
acacctcatc ccagacagga tcaatcatag ttaagctcct cccgaatctg      4750
cccaaggata aggaggcatg tgcgaaagcc cccttggatg catacaacag      4800
gacattgacc actttgctca ccccccttgg tgactctatc cgtaggatac      4850
aagagtctgt gactacatct ggaggggga  gacaggggcg ccttataggc      4900
gccattattg gcggtgtggc tcttggggtt gcaactgccg cacaaataac      4950
agcggccgca gctctgatac aagccaaaca aaatgctgcc aacatcctcc      5000
gacttaaaga gagcattgcc gcaaccaatg aggctgtgca tgaggtcact      5050
gacggattat cgcaactagc agtggcagtt gggaagatgc agcagtttgt      5100
taatgaccaa tttaataaaa cagctcagga attagactgc atcaaaattg      5150
cacagcaagt tggtgtagag ctcaacctgt acctaaccga attgactaca      5200
gtattcggac cacaaatcac ttcacctgct ttaaacaagc tgactattca      5250
ggcactttac aatctagctg gtggaaatat ggattactta ttgactaagt      5300
taggtgtagg gaacaatcaa ctcagctcat taatcggtag cggcttaatc      5350
accggtaacc ctattctata cgactcacag actcaactct tgggtataca      5400
ggtaactcta ccttcagtcg ggaacctaaa taatatgcgt gccacctact      5450
tggaaaccct atccgtaagc acaaccaggg gatttgcctc ggcacttgtc      5500
ccaaaagtgg tgacacaggt cggttctgtg atagaagaac ttgacacctc      5550
atactgtata gaaactgact tagatttata ttgtacaaga atagtaacgt      5600
tccctatgtc ccctggtatt tattcctgct tgagcggcaa tacgtcggcc      5650
tgtatgtact caaagaccga aggcgcactt actacaccat acatgactat      5700
caaaggttca gtcatcgcca actgcaagat gacaacatgt agatgtgtaa      5750
accccccggg tatcatatcg caaaactatg gagaagccgt gtctctaata      5800
gataaacaat catgcaatgt tttatcctta ggcgggataa cttaaggct      5850
cagtggggaa ttcgatgtaa cttatcagaa gaatatctca atacaagatt      5900
ctcaagtaat aataacaggc aatcttgata tctcaactga gcttgggaat      5950
gtcaacaact cgatcagtaa tgctttgaat aagttagagg aaagcaacag      6000
aaaactagac aaagtcaatg tcaaactgac cagcacatct gctctcatta      6050
cctatatcgt tttgactatc atatctcttg ttttttggtat acttagcctg      6100
attctagcat gctacctaat ggctaagcaa aaggcgcaac aaaagaccctt     6150
attatggctt gggaataata ctctagatca gatgagagcc actacaaaaa      6200
tgtgaacaca gatgaggaac gaaggtttcc ctaatagtaa tttgtgtgaa      6250
agttctggta gtctgtcagt tcagagagtt aagaaaaaac tacgcgttgt      6300
agatgaccaa aggacgatat acgggtagaa cggtaagaga ggccgcccct      6350
```

```
caattgcgag ccaggcttca caacctccgt tctaccgctt caccgacaac    6400
agtcctcaat catggaccgc gccgttagcc aagttgcgtt agagaatgat    6450
gaaagagagg caaaaaatac atggcgcttg atattccgga ttgcaatctt    6500
attcttaaca gtagtgacct tggctatatc tgtagcctcc cttttatata    6550
gcatggggc  tagcacacct agcgatcttg taggcatacc gactaggatt    6600
tccagggcag aagaaaagat tacatctaca cttggttcca atcaagatgt    6650
agtagatagg atatataagc aagtggccct tgagtctccg ttggcattgt    6700
taaaaactga gaccacaatt atgaacgcaa taacatctct ctcttatcag    6750
attaatggag ctgcaaacaa cagtgggtgg ggggcaccta tccatgaccc    6800
agattatata gggggatag  gcaaagaact cattgtagat gatgctagtg    6850
atgtcacatc attctatccc tctgcatttc aagaacatct gaattttatc    6900
ccggcgccta ctacaggatc aggttgcact cgaatacccct catttgacat   6950
gagtgctacc cattactgct acacccataa tgtaatattg tctggatgca    7000
gagatcactc acattcatat cagtatttag cacttggtgt gctccggaca    7050
tctgcaacag ggagggtatt cttttctact ctgcgttcca tcaacctgga    7100
cgacacccaa aatcggaagt cttgcagtgt gagtgcaact cccctgggtt    7150
gtgatatgct gtgctcgaaa gtcacggaga cagaggaaga agattataac    7200
tcagctgtcc ctacgcggat ggtacatggg aggttagggt tcgacggcca    7250
gtaccacgaa aaggacctag atgtcacaac attattcggg gactgggtgg    7300
ccaactaccc aggagtaggg ggtggatctt ttattgacag ccgcgtatgg    7350
ttctcagtct acgagggtt  aaaacccaat tcacccagtg acactgtaca    7400
ggaagggaaa tatgtgatat acaagcgata caatgacaca tgcccagatg    7450
agcaagacta ccagattcga atggccaagt cttcgtataa gcctggacgg    7500
tttggtggga aacgcataca gcaggctatc ttatctatca aggtgtcaac    7550
atccttaggc gaagacccgg tactgactgt accgcccaac acagtcacac    7600
tcatgggggc cgaaggcaga attctcacag tagggacatc tcatttcttg    7650
tatcaacgag ggtcatcata cttctctccc gcgttattat atcctatgac    7700
agtcagcaac aaaacagcca ctcttcatag tccttataca ttcaatgcct    7750
tcactcggcc aggtagtatc ccttgccagg cttcagcaag atgccccaac    7800
ccgtgtgtta ctggagtcta tacagatcca tatcccctaa tcttctatag    7850
aaaccacacc ttgcgagggg tattcgggac aatgcttgat ggtgtacaag    7900
caagacttaa ccctgcgtct gcagtattcg atagcacatc ccgcagtcgc    7950
attactcgag tgagttcaag cagtaccaaa gcagcataca caacatcaac    8000
ttgttttaaa gtggtcaaga ctaataagac ctattgtctc agcattgctg    8050
aaatatctaa tactctcttc ggagaattca gaatcgtccc gttactagtt    8100
gagatcctca aagatgacgg ggttagaaga gccaggtctg gctagttgag    8150
tcaattataa aggagttgga aagatggcat tgtatcacct atcttctgcg    8200
acatcaagaa tcaaaccgaa tgccggcgcg tgctcgaatt ccatgttgcc    8250
agttgaccac aatcagccag tgctcatgcg atcagattaa gccttgtcaa    8300
tagtctcttg attaagaaaa aatgtaagtg gcaatgagat acaaggcaaa    8350
```

```
atacgtaccg gtaaataata cgggtaggac atggcgagct ccggtcctga      8400
aagggcagag catcagatta tcctaccaga gtcacacctg tcttcaccat      8450
tggtcaagca caaactactc tattactgga aattaactgg gctaccgctt      8500
cctgatgaat gtgacttcga ccacctcatt ctcagccgac aatggaaaaa      8550
aatacttgaa tcggcctctc ctgatactga gagaatgata aaactcggaa      8600
gggcagtaca ccaaactctt aaccacaatt ccagaataac cggagtgctc      8650
caccccaggt gtttagaaga actggctaat attgaggtcc cagattcaac      8700
caacaaattt cggaagattg agaagaagat ccaaattcac aacacgagat      8750
atggagaact gttcacaagg ctgtgtacgc atatagagaa gaaactgctg      8800
gggtcatctt ggtctaacaa tgtccccccgg tcagaggagt tcagcagcat     8850
tcgtacggat ccggcattct ggtttcactc aaaatggtcc acagccaagt      8900
ttgcatggct ccatataaaa cagatccaga ggcatctgat ggtggcagct      8950
aggacaaggt ctgcggccaa caaattggtg atgctaaccc ataaggtagg      9000
ccaagtcttt gtcactcctg aacttgtcgt tgtgacgcat acgaatgaga      9050
acaagttcac atgtcttacc caggaacttg tattgatgta tgcagatatg      9100
atggagggca gagatatggt caacataata tcaaccacgg cggtgcatct      9150
cagaagctta tcagagaaaa ttgatgacat tttgcggtta atagacgctc      9200
tggcaaaaga cttgggtaat caagtctacg atgttgtatc actaatggag      9250
ggatttgcat acggagctgt ccagctactc gagccgtcag gtacatttgc      9300
aggagatttc ttcgcattca acctgcagga gcttaaagac attctaattg      9350
gcctcctccc caatgatata gcagaatccg tgactcatgc aatcgctact      9400
gtattctctg gtttagaaca gaatcaagca gctgagatgt tgtgtctgtt      9450
gcgtctgtgg ggtcacccac tgcttgagtc ccgtattgca gcaaaggcag      9500
tcaggagcca aatgtgcgca ccgaaaatgg tagactttga tatgatcctt      9550
caggtactgt ctttcttcaa gggaacaatc atcaacgggt acagaaagaa      9600
gaatgcaggt gtgtggccgc gagtcaaagt ggatacaata tatgggaagg      9650
tcattgggca actacatgca gattcagcag agatttcaca cgatatcatg      9700
ttgagagagt ataagagttt atctgcactt gaatttgagc catgtataga      9750
atatgaccct gtcacaaacc tgagcatgtt cctaaaagac aaggcaatcg      9800
cacaccccaa cgataattgg cttgcctcgt ttaggcggaa ccttctctcc      9850
gaagaccaga agaaacatgt aaaagaagca acttcgacta atcgcctctt      9900
gatagagttt ttagagtcaa atgattttga tccatataaa gagatggaat      9950
atctgacgac ccttgagtac cttagagatg acaatgtggc agtatcatac     10000
tcgctcaagg agaaggaagt gaaagttaat ggacggatct tcgctaagct     10050
gacaaagaag ttaaggaact gtcaggtgat ggcggaaggg atcctagccg     10100
atcagattgc accttttcttt cagggaaatg gagtcattca ggatagcata    10150
tccttgacca agagtatgct agcgatgagt caactgtctt ttaacagcaa     10200
taagaaacgt atcactgact gtaaagaaag agtatcttca aaccgcaatc     10250
atgatccgaa aagcaagaac cgtcggagag ttgcaacctt cataacaact     10300
```

```
gacctgcaaa agtactgtct taattggaga tatcagacaa tcaaattgtt        10350
cgctcatgcc atcaatcagt tgatgggcct acctcacttc ttcgaatgga        10400
ttcacctaag actgatggac actacgatgt tcgtaggaga ccctttcaat        10450
cctccaagtg accctactga ctgtgacctc tcaagagtcc ctaatgatga        10500
catatatatt gtcagtgcca gaggggggtat cgaaggatta tgccagaagc       10550
tatggacaat gatctcaatt gctgcaatcc aacttgctgc agctagatcg        10600
cattgtcgtg ttgcctgtat ggtacagggt gataatcaag taatagcagt        10650
aacgagagag gtaagatcag acgactctcc ggagatggtg ttgacacagt        10700
tgcatcaagc cagtgataat ttcttcaagg aattaattca tgtcaatcat        10750
ttgattggcc ataatttgaa ggatcgtgaa accatcaggt cagacacatt        10800
cttcatatac agcaaacgaa tcttcaaaga tggagcaatc ctcagtcaag        10850
tcctcaaaaa ttcatctaaa ttagtgctag tgtcaggtga tctcagtgaa        10900
aacaccgtaa tgtcctgtgc caacattgcc tctactgtag cacggctatg        10950
cgagaacggg cttcccaaag acttctgtta ctatttaaac tatataatga        11000
gttgtgtgca gacatacttt gactctgagt tctccatcac caacaattcg        11050
caccccgatc ttaatcagtc gtggattgag gacatctctt ttgtgcactc        11100
atatgttctg actcctgccc aattaggggg actgagtaac cttcaatact        11150
caaggctcta cactagaaat atcggtgacc cggggactac tgcttttgca        11200
gagatcaagc gactagaagc agtgggatta ctgagtccta acattatgac        11250
taatatctta actaggccgc ctgggaatgg agattgggcc agtctgtgca        11300
acgacccata ctctttcaat tttgagactg ttgcaagccc aaatattgtt        11350
cttaagaaac atacgcaaag agtcctattt gaaacttgtt caaatcccctt       11400
attgtctgga gtgcacacag aggataatga ggcagaagag aaggcattgg        11450
ctgaattctt gcttaatcaa gaggtgattc atccccgcgt tgcgcatgcc        11500
atcatggagg caagctctgt aggtaggaga aagcaaattc aagggcttgt        11550
tgacacaaca aacaccgtaa ttaagattgc gcttactagg aggccattag        11600
gcatcaagag gctgatgcgg atagtcaatt attctagcat gcatgcaatg        11650
ctgtttagag acgatgtttt ttcctccagt agatccaacc accccttagt        11700
ctcttctaat atgtgttctc tgacactggc agactatgca cggaatagaa        11750
gctggtcacc tttgacggga ggcaggaaaa tactgggtgt atctaatcct        11800
gatacgatag aactcgtaga gggtgagatt cttagtgtaa gcggagggtg        11850
tacaagatgt gacagcggag atgaacaatt tacttggttc catcttccaa        11900
gcaatataga attgaccgat gacaccagca agaatcctcc gatgagggta        11950
ccatatctcg ggtcaaagac acaggagagg agagctgcct cacttgcaaa        12000
aatagctcat atgtcgccac atgtaaaggc tgccctaagg gcatcatccg        12050
tgttgatctg ggcttatggg gataatgaag taaattggac tgctgctctt        12100
acgattgcaa aatctcggtg caatgtaaac ttagagtatc ttcggttact        12150
gtccccttta cccacggctg ggaatcttca acatagacta gatgatggta        12200
taactcagat gacattcacc cctgcatctc tctacgggt gtcaccttac        12250
attcacatat ccaatgattc tcaaaggctg ttcactgaag aaggagtcaa        12300
```

```
agagggaat gtggtttacc aacagatcat gctcttgggt ttatctctaa        12350
tcgaatcgat ctttccaatg acaacaacca ggacatatga tgagatcaca        12400
ctgcacctac atagtaaatt tagttgctgt atcagagaag cacctgttgc        12450
ggttcctttc gagctacttg gggtggtacc ggaactgagg acagtgacct        12500
caaataagtt tatgtatgat cctagccctg tatcggaggg agactttgcg        12550
agacttgact tagctatctt caagagttat gagcttaatc tggagtcata        12600
tcccacgata gagctaatga acattctttc aatatccagc gggaagttga        12650
ttggccagtc tgtggtttct tatgatgaag atacctccat aaagaatgac        12700
gccataatag tgtatgacaa tacccgaaat tggatcagtg aagctcagaa        12750
ttcagatgtg gtccgcctat ttgaatatgc agcacttgaa gtgctcctcg        12800
actgttctta ccaactctat tatctgagag taagaggcct agacaatatt        12850
gtcttatata tgggtgattt atacaagaat atgccaggaa ttctactttc        12900
caacattgca gctacaatat ctcatcccgt cattcattca aggttacatg        12950
cagtgggcct ggtcaaccat gacgatcac accaacttgc agatacggat         13000
tttatcgaaa tgtctgcaaa actattagta tcttgcaccc gacgtgtgat        13050
atccggctta tattcaggaa ataagtatga tctgctgttc ccatctgtct        13100
tagatgataa cctgaatgag aagatgcttc agctgatatc ccggttatgc        13150
tgtctgtaca cggtactctt tgctacaaca agagaaatcc cgaaaataag        13200
aggcttaact gcagaagaga aatgttcaat actcactgag tatttactgt        13250
cggatgctgt gaaaccatta cttagccccg atcaagtgag ctctatcatg        13300
tctcctaaca taattacatt cccagctaat ctgtactaca tgtctcggaa        13350
gagcctcaat ttgatcaggg aaagggagga cagggatact atcctggcgt        13400
tgttgttccc ccaagagcca ttattagagt tcccttctgt gcaagatatt        13450
ggtgctcgag tgaaagatcc attcacccga caacctgcgg cattttttgca       13500 agagttagat ttgagtgctc cagcaaggta tgacgcattc acacttagtc        13550
agattcatcc tgaactcaca tctccaaatc cggaggaaga ctacttagta        13600
cgatacttgt tcagagggat agggactgca tcttcctctt ggtataaggc        13650
atctcatctc ctttctgtac ccgaggtaag atgtgcaaga cacgggaact        13700
ccttatactt agctgaaggg agcggagcca tcatgagtct tctcgaactg        13750
catgtaccac atgaaactat ctattacaat acgctctttt caaatgagat        13800
gaaccccccg caacgacatt tcgggccgac cccaactcag tttttgaatt        13850
cggttgttta taggaatcta caggcggagg taacctgcaa agatggatt         13900 gtccaagagt tccgtccatt atggagagaa aatacagagg aaagtgacct        13950
gacctcagat aaagcagtgg ggtatattac atctgcagtg ccctacagat        14000
ctgtatcatt gctgcattgt gacattgaaa ttcctccagg gtccaatcaa        14050
agcttactag atcaactagc tatcaattta tctctgattg ccatgcattc        14100
tgtaagggag ggcggggtag taatcatcaa agtgttgtat gcaatgggat        14150
actactttca tctactcatg aacttgtttg ctccgtgttc cacaaaagga        14200
tatattctct ctaatggtta tgcatgtcga ggagatatgg agtgttacct        14250
```

```
ggtatttgtc atgggttacc tgggcgggcc tacatttgta catgaggtgg         14300
tgaggatggc aaaaactctg gtgcagcggc acggtacgct tttgtctaaa         14350
tcagatgaga tcacactgac caggttattc acctcacagc ggcagcgtgt         14400
gacagacatc ctatccagtc ctttaccaag attaataaag tacttgagga         14450
agaatattga cactgcgctg attgaagccg ggggacagcc cgtccgtcca         14500
ttctgtgcgg agagtctggt gagcacgcta gcgaacataa ctcagataac         14550
ccagatcatc gctagccaca ttgacacagt tatccggtct gtgatatata         14600
tggaagctga gggtgatctc gctgacacag tatttctatt tacccottac         14650 aatctctcta ctgacgggaa aaagaggaca tcacttaaac agtgcacgag         14700
acagatccta gaggttacaa tactaggtct tagagtcgaa aatctcaata         14750
aaataggcga tataatcagc ctagtgctta aaggcatgat ctccatggag         14800
gaccttatcc cactaaggac atacttgaag catagtacct gccctaaata         14850
tttgaaggct gtcctaggta ttaccaaact caaagaaatg tttacagaca         14900
cttctgtact gtacttgact cgtgctcaac aaaaattcta catgaaaact         14950
ataggcaatg cagtcaaagg atattacagt aactgtgact cttaacgaaa         15000
atcacatatt aataggctcc ttttttggcc aattgtattc ttgttgattt         15050
aatcatatta tgttagaaaa aagttgaacc ctgactcctt aggactcgaa         15100
ttcgaactca aataaatgtc ttaaaaaaag gttgcgcaca attattcttg         15150
agtgtagtct cgtcattcac caaatcttgg ttgggt                        15186
```

INFECTIOUS LARYNGOTRACHEITIS VIRUS (ILTV) VACCINE USING RECOMBINANT NEWCASTLE DISEASE VIRUS VECTOR

CROSS REFERENCE TO RELATED APPLICATIONS

This application is a National Stage entry of International Application No. PCT/US2014/047395, filed on Jul. 21, 2014, which claims the benefit of U.S. Provisional Patent Application No. 61/857,558 filed on Jul. 23, 2013. The disclosures of each of these applications are hereby incorporated in their entirety by reference.

STATEMENT OF FEDERALLY SPONSORED RESEARCH AND DEVELOPMENT

This invention was made with government support under 20116701530136 awarded by USDA. The Government has certain rights in the invention.

INTRODUCTION

The present application relates to recombinant Newcastle disease viruses useful as vaccine vectors, which when carrying one or more foreign genes, i.e. genes not found naturally in the Newcastle disease virus, are also useful as bivalent or multivalent vaccines.

BACKGROUND OF THE INVENTION

Newcastle disease is a highly contagious viral disease affecting all species of birds. The disease can vary from an asymptomatic infection to a highly fatal disease, depending on the virus strain and the host species. Newcastle disease has a worldwide distribution and is a major threat to the poultry industries of all countries. Based on the severity of the disease produced in chickens, Newcastle disease virus (NDV) strains are grouped into three main pathotypes: lentogenic (strains that do not usually cause disease in adult chickens), mesogenic (strains of intermediate virulence) and velogenic (strains that cause high mortality).

NDV is a member of the genus *Rubulavirus* in the family Paramyxoviridae. The genome of NDV is a non-segmented, single-stranded, negative-sense RNA of 15186 nucleotides (Krishnamurthy & Samal, 1998, J Gen Virol 79, 2419-2424; Phillips et al., 1998, Arch Virol 143, 1993-2002; de Leeuw and Peeters, 1999, J Gen Virol 80, 131-136). The genomic RNA contains six genes that encode the following proteins in the order of: the nucleocapsid protein (NP), phosphoprotein (P), matrix protein (M), fusion protein (F), haemagglutinin-neuraminidase (HN) and large polymerase protein (L). Two additional proteins, V and W, of unknown function are produced by RNA editing during P gene transcription (Steward et al., 1993, J Gen Virol 74, 2539-2547).

Three proteins, i.e. NP, P and L proteins, constitute the nucleocapsid. The genomic RNA is tightly bound by the NP protein and together with the P and L proteins form the functional nucleocapsid within which resides the viral transcriptive and replicative activities. The F and HN proteins form the external envelope spikes, where the HN glycoprotein is responsible for attachment of the virus to host cell receptors and the F glycoprotein mediates fusion of the viral envelope with the host cell plasma membrane thereby enabling penetration of the viral genome into the cytoplasm of the host cell. The HN and F proteins are the main targets for the immune response. The M protein forms the inner layer of the virion.

NDV follows the general scheme of transcription and replication of other non-segmented negative-strand RNA viruses. The polymerase enters the genome at a promoter in the 3' extragenic leader region and proceeds along the entire length by a sequential stop-start mechanism during which the polymerase remains template bound and is guided by short consensus gene start (GS) and gene end (GE) signals. This generates a free leader RNA and six non-overlapping subgenomic mRNAs. The abundance of the various mRNAs decreases with increasing gene distance from the promoter. The genes are separated by short intergenic regions (1-47 nucleotides) which are not copied into the individual mRNAs. RNA replication occurs when the polymerase somehow switches to a read-through mode in which the transcription signals are ignored. This produces a complete encapsulated positive-sense replicative intermediate which serves as the template for progeny genomes.

Reverse-genetic techniques have been reported to recover negative-sense viruses from cloned cDNA (Conzelmann, 1996, J Gen Virol 77, 381-389). For NDV, reverse-genetic technology is currently available for avirulent strain LaSota (Römer-Oberdörfer et al., 1999, J Gen Virol 80, 2987-2995; Peeters et al., 1999, J Gen Virol 73, 5001-5009).

Infectious laryngotracheitis (ILT) is an acute respiratory disease of chickens that causes significant economic losses to poultry industry worldwide (Bagust et al., 2000, Rev Sci Tech 19, 483-492; Bagust, 1986, Avian Pathol 15, 581-595). The causative pathogen, ILTV, is a member of the genus Iltovirus in the family Herpesviridae (Bagust et al., 2000, supra; Fuchs et al., 2007, Vet Res 38, 261-279). Currently, live attenuated vaccines are used to control ILT infections. However, the live-attenuated vaccines are not satisfactory since they can revert to virulence after bird-to-bird passage (Guy et al., 1991, Avian Dis 35, 348-355) and can induce latent infections (Hughes et al., 1991, Arch Virol 121, 213-218). Several alternative strategies have been used to develop improved ILTV vaccines (Mauricio et al., 2013, Avian Pathol 42, 195-205). One of the strategies has been the creation of ILTV deletion mutants for use as attenuated live-virus vaccines (Mauricio et al., 2013, supra). Two of the concerns of using gene deleted ILTV vaccine are the establishment of latency and the possibility that the gene-deleted vaccine virus could become virulent after recombination with different attenuated vaccine used in the same region (Sang-Won et al, 2012, Science 337, 188; Henderson et al., 1991, Am J Vet Res 52, 820-825). All studies conducted to date suggest that a virus-vectored ILTV vaccine will be most effective for prevention and control of ILT (Tong et al., 2001, Avian pathol 30, 143-148; Sun et al., 2008, Avian Dis 52, 111-117; Vagnozzi et al., 2012, Avian Pathol 41, 21-31). A vectored-vaccine will be safe and not lead to reversion to virulence or establishment of latency. However, current live virus vectored vaccines against ILT have limitations (Mauricio et al., 2013, supra; Vagnozzi et al. 2012, supra): (i) route of administration to large number of one-day old chicks, (ii) effective delivery of vaccine antigen to the mucosal surface, (iii) production cost, and (iv) incomplete protection. Therefore, there is a need to evaluate additional viral vectors to deliver ILTV antigens to chickens.

SUMMARY OF THE INVENTION

Of the eleven glycoproteins on the envelope of ILTV (Fuchs et al., 2007, supra), only glycoprotein B has been shown to be a major protective immunogen (Tong et al., 2001, supra; Sun et al., 2008, supra; York et al., 1991, Avian Pathol 20, 693-704), but the role of other glycoproteins in immunity and protection has not been evaluated. In this study, the inventors have evaluated the role of three major surface proteins (gB, gC, and gD) of ILTV in induction of neutralizing antibodies and protection in chickens using Newcastle disease virus (NDV) as a vaccine vector.

It has previously been shown that NDV expressing protective antigens of highly-pathogenic avian influenza virus and infectious bursal disease virus of chicken provided complete protection against respective challenge viruses (Nayak et al., 2009, PLoS One 4, e6509; Zhuhui et al., 2004, J Virol 78, 10054-10063). In the Examples below, three recombinant NDVs (rNDVs) which express and incorporate gB, gC, and gD of ILTV, individually, were constructed and used to immunize chickens. Results indicate that rNDV expressing ILTV gD is a safe and effective bivalent vaccine that would provide protection against both of these economically important diseases.

Reverse-genetic techniques were used in making the recombinant NDVs of the present invention from cloned cDNA. This approach involves co-expression of the cloned cDNA of full length NDV genome and nucleocapsid proteins (the NP, P and L proteins) from transfected plasmids using the vaccinia virus/T7 RNA polymerase expression system. Within the scope of the present invention, recombinant NDV can be recovered from cDNA and the genome of NDV can be manipulated at the cDNA level. The production of infectious NDV from cloned cDNA can be used to engineer NDV carrying foreign genes. With the manipulation of the genome of NDV, one can insert foreign sequences into the NDV genome for co-expression. For example, the gene for a protective antigen of another avian pathogen or the genes for avian cytokines can be inserted into the NDV genome for co-expression.

Thus, the present invention includes multivalent genetically engineered NDV vaccines carrying genes encoding immunogens (e.g. immunogenic proteins) for pathogens of interest, such as for influenza virus, infectious bursal disease virus, rotavirus, infectious bronchitis virus, infectious laryngotracheitis virus, chicken anemia virus, Marek's disease virus, avian Leukosis virus, avian adenovirus and avian pneumovirus.

The present invention also is directed toward a genetically engineered NDV carrying avian cytokine genes. A NDV carrying at least one gene encoding an avian cytokine, e.g. an interleukin such as IL-2 and IL-4, can be used as a vaccine.

The recombinant NDV prepared by insertion of foreign genes into the NDV genome can express the foreign genes in cells infected by the recombinant NDV. As a result, the recombinant NDV can be used to express proteins of non-avian pathogens or other avian pathogens.

One of the objects of the invention is to provide a recombinant Newcastle disease virus (rNDV) comprising NP gene, P gene, M gene, F gene, HN gene and L gene. In one embodiment of the invention, the Newcastle disease virus contains a tyrosine to alanine substitution in the fusion or "F" gene at amino acid position 527. This tyrosine has been found to be conserved among different strains of NDV. The tyrosine can be substituted to any hydrophobic amino acid selected from the group: alanine, glycine, proline, methionine, leucine, etc. The inventors have found that the NDV with a 527 substitution has a higher replication magnitude than wild type NDV, results in larger plaques compared to wild type counterparts, and when a gene encoding a foreign antigen was inserted between the P and M genes, surface expression of the foreign antigen increased. Therefore, the mutation favors enhanced surface distribution of the expressed foreign protein and in turn, increases immunogenicity of the resulting vaccine. In the description that follows, it is understood that by NDV F gene is meant use of either the wild-type or the mutant form unless expressly stated.

Another object of the present invention is a recombinant antigenomic RNA or cDNA of Newcastle disease virus, comprising NP gene, P gene, M gene, F gene, HN gene and L gene in this order from a 5' to 3' direction, said antigenomic RNA further comprising n foreign nucleotide complexes inserted (a) before the NP gene, (b) between the P and M genes, and/or (c) between the HN and L genes, wherein n is 1, 2, 3 or 4;

each of the foreign nucleotide complexes comprising a Newcastle disease virus gene start sequence, an open reading frame of a foreign gene and a Newcastle disease virus gene end sequence in this order from the 5' to 3' direction, wherein the foreign gene is a gene not found naturally in the Newcastle disease virus;

wherein when n is 1, 2, 3 or 4, the foreign nucleotide complexes are the same or different; and wherein when 1, 2, 3 or 4 the foreign nucleotide complexes are inserted together or separately before the NP gene, between the P and M genes, or between the HN and L genes, the foreign nucleotide complexes are sequentially linked directly or indirectly.

Since each foreign nucleotide complex has a NDV gene start signal, i.e. GS sequence motif, upstream of the open reading frame (ORF) of the foreign gene and a NDV gene end signal, i.e. GE sequence motif, downstream of the ORF of the foreign gene, each foreign nucleotide complex forms a transcriptional unit or a gene cassette.

The recombinant antigenomic RNA or cDNA of NDV of the present invention preferably further comprises NP-P intergenic region between the NP gene and P gene, P-M intergenic region between the P gene and M gene, M-F intergenic region between the M gene and F gene, F-HN intergenic region between the F gene and HN gene, and/or HN-L intergenic region between the HN gene and L gene.

When one or more of the foreign nucleotide complexes are inserted between the P and M genes, the foreign nucleotide complexes can be inserted into the P-M intergenic region if present. Similarly, when one or more of the foreign nucleotide complexes are inserted between the HN and L genes, the foreign nucleotide complexes can be inserted into the HN-L intergenic region. Optionally, one or more of the NP-P intergenic region, P-M intergenic region, M-F intergenic region, F-HN intergenic region, and HN-L intergenic region are replaced with a single nucleotide, dinucleotide or an oligonucleotide of 3-80 nucleotides (preferably 4-60 nucleotides) in length, wherein the oligonucleotide optionally contains one or more restriction sites.

When one or more of the foreign nucleotide complexes are inserted before the NP gene, the foreign nucleotide complexes preferably are inserted into a non-coding region immediately before the ORF of the NP gene, so that the ORF of the foreign gene in each of the foreign nucleotide complexes is flanked by NDV gene start and gene end signals and the ORF of the NP gene is preceded by a NDV gene start signal, with the GS-foreign gene ORF-GE structure preceding the GS signal for the NP ORF. Within the scope of the invention is a recombinant antigenomic RNA of NDV having one or more foreign nucleotide complexes inserted between P and M genes.

The antigenomic RNA or cDNA can be made by inserting the one or more foreign nucleotide complexes into the noncoding region of P gene after the stop codon, but before the NDV gene end signal of the P gene. When only one foreign nucleotide complex is inserted into the noncoding region of P gene after the stop codon, the ORF of the foreign gene is preceded by a NDV gene end and NDV gene start signals, resulting in the ORF of the P gene being preceded by a NDV gene end signal, which is followed by a NDV gene start signal, the ORF of the foreign gene, and a NDV gene end signal in that order (the ORF of the following M gene is preceded by a NDV gene start signal). More foreign gene complexes can be inserted after this foreign gene complex. Similarly, the recombinant antigenomic RNA or cDNA of NDV having one or more foreign nucleotide complexes inserted between P and M genes can be made by inserting the one or more foreign nucleotide complexes into the noncoding region of M gene before the ORF of the M gene.

The present invention is also directed toward a process of preparing the recombinant antigenomic RNA of the invention, comprising the following steps:

(i) providing a cDNA comprising NP gene, P gene, M gene, F gene, HN gene and L gene in this order, said cDNA further comprising n foreign nucleotide complexes inserted (a) before the NP gene, (b) between the P and M genes, and/or (c) between the HN and L genes, wherein n is 1, 2, 3 or 4;

each of the foreign nucleotide complexes comprising a Newcastle disease virus gene start sequence, an open reading frame of a foreign gene and a Newcastle disease virus gene end sequence in this order from the 5' to 3' direction, wherein the foreign gene is a gene not found naturally in the Newcastle disease virus;

wherein when n is 1, 2, 3 or 4, the foreign nucleotide complexes are the same or different; and wherein when 1, 2, 3 or 4 foreign nucleotide complexes are inserted together before the NP gene, between the P and M genes, or between the HN and L genes, the foreign nucleotide complexes are sequentially linked directly or indirectly;

(ii) transcribing the antigenomic cDNA to form a mixture containing an antigenomic RNA; and thereafter (iii) isolating the antigenomic RNA.

In some embodiments of the process of preparing the recombinant antigenomic RNA of the invention, the cDNA used in step (i), comprising NP gene, P gene, M gene, F gene, HN gene and L gene having the n foreign nucleotide complexes inserted, is prepared by (I) constructing a cDNA comprising the NP gene, P gene, M gene, F gene, HN gene and L gene in this order; and thereafter (II) inserting the n foreign nucleotide complexes (a) before the NP gene, (b) between the P and M genes, and/or (c) between the HN and L genes. Preferably, the cDNA constructed in step (I) and/or the cDNA constructed in step (II) are in a plasmid, such as pBR322 or pGEM-7Z. In step (ii), the cDNA preferably is transcribed in cells expressing a RNA polymerase, such as T7 RNA polymerase.

The present invention is also directed toward a recombinant NDV (rNDV) comprising a recombinant antigenomic RNA carrying one or more foreign genes of the present invention. The recombinant NDV can be produced by a process comprising the following steps:

(i) providing cells capable of synthesizing T7 RNA polymerase;

(ii) cotransfecting the cells with a plasmid comprising the cDNA encoding the antigenomic RNA having one or more foreign genes inserted according to the invention, a plasmid encoding NP protein, a plasmid encoding P protein, and a plasmid encoding L protein to obtain cotransfected cells in a medium; and thereafter (iii) isolating Newcastle disease virus from a supernatant of the medium of step (ii) to obtain the recombinant Newcastle disease virus.

The cells capable of synthesizing T7 RNA polymerase provided in step (i) can be animal cells of an avian or mammalian species, plant cells, or cells from a cell line expressing T7 RNA polymerase.

Within the scope of the present invention are a cDNA encoding a recombinant NDV antigenomic RNA having one or more foreign genes inserted according to the invention, a cell containing the cDNA, a plasmid comprising the cDNA, a cell containing the plasmid, a cell containing the recombinant antigenomic RNA, and a recombinant NDV containing the recombinant antigenomic RNA of the invention, e.g. a recombinant NDV carrying one or more foreign genes recovered from transcription of the cDNA or the plasmid in a competent cell. The recombinant NDV containing the recombinant antigenomic RNA of the invention is preferably substantially purified. Also preferred is a substantially purified recombinant antigenomic RNA of NDV carrying one or more foreign genes prepared according to the invention.

In one embodiment, the present invention provides a cDNA encoding a recombinant antigenomic NDV RNA having one or more genes from ILTV inserted according to the invention, a cell containing the cDNA, a plasmid comprising the cDNA, a cell containing the plasmid, a cell containing the recombinant antigenomic RNA, and a recombinant NDV containing the recombinant antigenomic RNA of the invention, e.g. a recombinant NDV carrying one or more ILTV genes recovered from transcription of the cDNA or the plasmid in a competent cells.

The recombinant NDV, or rNDV, containing the one or more inserted foreign genes can be used as a monovalent vaccine to provide immunity and protection against NDV challenge, a bivalent vaccine protective against NDV and challenge with the pathogen source of the inserted foreign nucleic acid encoding one or more immunogenic protein, or a multivalent vaccine protective against NDV and challenge with the more than one pathogen source of the inserted foreign nucleic acid encoding one or more immunogenic protein.

In another aspect, the present invention includes a bivalent vaccine to provide immunity and protection against NDV and ILTV challenge, the vaccine comprising rNDV having one or more genes from ILTV, gB, gC, gD, preferably gD.

The present invention also includes a method of vaccinating an avian animal against Newcastle disease, wherein the avian animal is in need of the vaccination, comprising administering an effective amount of the recombinant NDV optionally carrying one or more foreign genes according to the invention to the avian animal.

One of the objects of the invention is a method of treating an avian animal with an avian cytokine, wherein the avian animal is in need of the treatment, said method comprising administering an effective amount of the recombinant NDV of the invention carrying one or more foreign genes encoding one or more avian cytokines, such as avian interleukins (preferably IL-2 and/or IL-4) to the avian animal.

Another object of the invention is a method of immunizing an avian animal against an avian pathogen selected from the group consisting of influenza virus, infectious bursal disease virus, rotavirus, infectious bronchitis virus, infectious laryngotracheitis virus, chicken anemia virus, Marek's disease virus, avian Leukosis virus, avian adenovirus and avian pneumovirus, wherein the avian animal is in need of the immunization, said method comprising administering an effective amount of the recombinant NDV of the invention to the avian animal, wherein one or more the recombinant NDV carries one or more foreign genes encoding one or more immunogenic proteins of the avian pathogen against which the avian animal is immunized.

In another object, the present invention provides a method of immunizing an avian animal against ILTV, said method comprising administering an effective amount of the recombinant NDV of the present invention, wherein the NDV carries one or more ILTV genes encoding one or more immunogenic ILTV proteins. In one embodiment, the ILTV genes are gB, gC, and gD, in any combination.

Also within the scope of the invention is a method of immunizing a mammal against a non-avian pathogen, wherein the mammal is in need of the immunization, said method comprising administering an effective amount of the one or more recombinant NDV of the invention to the mammal, wherein the recombinant NDV carries one or more foreign genes encoding one or more immunogenic proteins of the non-avian pathogen, e.g. influenza virus, SARS-causing virus, human respiratory syncytial virus, human immunodeficiency virus, hepatitis A virus, hepatitis B virus, hepatitis C virus, poliovirus, rabies virus, Hendra virus, Nipah virus, human parainfluenza 3 virus, measles virus, mumps virus, Ebola virus, Marburg virus, West Nile virus, Japanese encephalitis virus, Dengue virus, Hantavirus, Rift Valley fever virus, Lassa fever virus, herpes simplex virus and yellow fever virus, against which the mammal is immunized.

In this study, for the first time, the inventors have evaluated the protective efficacy of gD against ILTV challenge and demonstrate that ILTV gD is a major protective immunogen capable of inducing a protective immune response against ILTV in chickens. Immunization with rNDV expressing ILTV gD induced a higher level of neutralizing antibodies and offered complete protection to chickens against lethal ILTV challenge. The complete protection offered by gD can be attributed to its superior envelope incorporation and cell surface expression leading to induction of a protective immune responses.

Therefore, the ILTV gD protein can be exploited as an effective vaccine antigen for the development of safe vectored vaccines against ILT using viral and nonviral vectors. Examples of viral vectors include adenovirus, adeno-associated virus, herpesvirus, pox virus, influenza virus, retrovirus, and other recombinant viral vectors known to a person in the art.

Therefore, in another object, the present invention provides an ILTV vaccine comprising gD. Also provided is a method for eliciting in a subject an immune response against ILTV, the method comprising administering to a subject a nucleic acid comprising a gD encoding nucleic acid. The nucleic acid comprising a gD encoding nucleic acid can be part of a vector such as a viral vector, capable of producing gD in an immunized avian or non-avian animal. In another aspect, a composition comprising gD can be administered to a subject in need thereof.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 2-1 and 2-2. Western blot and flow cytometry analysis of the rNDVs expressing ILTV proteins. FIG. 2-1: Expression of ILTV gB, gC, and gD in DF1 cells and their incorporation into rNDV virions. FIG. 2-2: Flow cytometry analysis of the surface expression of ILTV proteins. DF1 cells were infected with rNDV gB (panel A), rNDV gC (panel B) or rNDV gD (panel C) viruses at a MOI of 5, in parallel with cells that were mock-infected or infected with the rNDV LaSota empty vector. At 24 h post-infection, the cells were probed with rabbit anti-ILTV sera, followed by incubation with Alexa Fluor 488 conjugated goat anti-rabbit IgG antibody and analyzed by Flowjo program of FACSRIA II flow cytometer. Values represent averages of the results obtained from two independent experiments.

FIGS. 4-1 and 4-2. Multicycle growth kinetics of rNDVs expressing ILTV proteins and NDV-specific serum antibody responses in chickens at 21 days following two oculonasal immunizations with rNDVs administered either individually or in combination. FIG. 4-1: Multicycle growth kinetics of rNDVs in nine-day-old SPF embryonated chicken eggs. Nine-day-old embryonated chicken eggs were inoculated with 100 PFU of each virus, and allantoic fluids from three eggs were harvested at different time points (12 h, 24 h, 36 h, 48 h, 60 h, and 72 h) after inoculation. The virus titer in allantoic fluid was determined by TCID50 assay in DF-1 cells. Values represent averages of the results obtained from two independent experiments. FIG. 4-2: NDV-specific serum antibody response was determined by HI assay and all antibody titers are expressed as mean reciprocal log 2 titer ±SEM (standard error of the mean). Statistical differences were calculated by one-way ANOVA with $P<0.05$.

FIGS. 5A and 5B. ILTV-neutralizing antibody response post-vaccination and clinical signs score evaluation post-ILTV challenge. 5A. Chickens were immunized by the oculonasal route with rNDVs either individually or in combination. Sera were taken on days 12 (12 days following primary immunization) and 21 (7 days following booster immunization) post-vaccination and analyzed for the ability to neutralize USDA strain of ILTV in vitro. The serum-neutralizing antibody titers were expressed as mean reciprocal log 2 titer (means±SEM). Statistical differences were calculated by one-way ANOVA with $P<0.05$. 5B. Total clinical signs were recorded daily until 14 days post-ILTV challenge for chickens immunized with rNDVs individually (panel a) or in combination (panel b). For comparison, clinical score of birds vaccinated with Trachivax CEO and HVT-LT were also included.

DETAILED DESCRIPTION OF THE INVENTION

Figure 1:
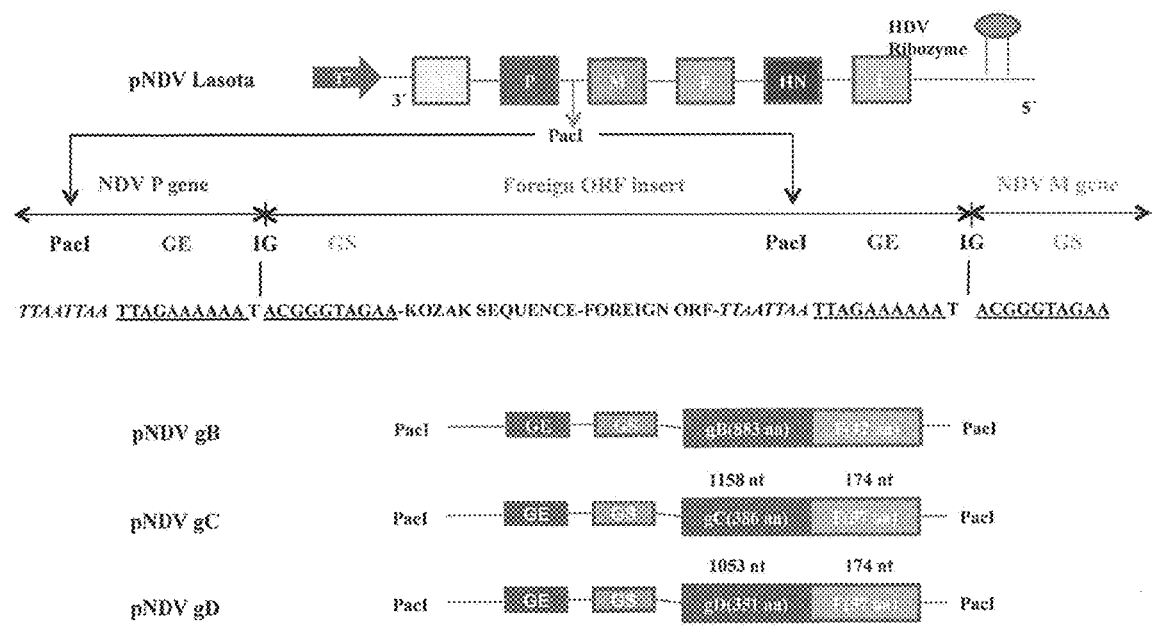
FIG. 1. Construction of recombinant NDVs expressing ILTV gB, gC, and gD. Schematic diagram depicting the full length antigenome of NDV strain LaSota with insertion of an added gene engineered to express the ILTV gB consisting of the complete ORF of gB fused to last 12 amino acids of NDV F protein cytoplasmic tail, gC or gD consisting of the ectodomain of gC or gD respectively, fused to the transmembrane and cytoplasmic tail of the NDV F protein. The inserted foreign ORF was placed under the control of a set of NDV transcriptional gene end (GE) and gene start (GS) signals such that each was expressed as a separate mRNA. nt-nucleotides, aa-amino acids, IG-intergenic.

In some embodiments of the invention, the recombinant antigenomic RNA is from a paramyxovirus, Newcastle disease virus strain LaSota. Other NDV strains, for example, Hitchner-B1 (B1), Clone-30, Strain-F, Strain V4, Strain V4-HR, Strain-I2 and Ulster (U) can also be used.

In some embodiments of the recombinant antigenomic RNA of the present invention, n is 1, 2, 3 or 4 (preferably 2 or 3, and more preferably 2) and the foreign nucleotide complexes are different. In some embodiments of the recombinant antigenomic RNA, n is 1, 2, 3 or 4 (preferably 2 or 3, and more preferably 2) and the foreign nucleotide complexes are the same. In still some embodiments of the recombinant antigenomic RNA, n is 1 or 2.

In some of the recombinant antigenomic RNAs of the invention, the ORF of each of the foreign genes in the inserted foreign nucleotide complexes is no more than about 3000 nucleotides, no more than about 2000 nucleotides, no more than about 1500 nucleotides, no more than about 1000 nucleotides, no more than about 800 nucleotides, no more than about 500 nucleotides, or no more than about 300 nucleotides in length.

In some of the embodiments of the recombinant antigenomic RNA of the present invention, where 1, 2, 3 or 4 foreign nucleotide complexes are inserted together before the NP gene, between the P and M genes, or between the HN and L genes, the foreign nucleotide complexes are sequentially linked directly or indirectly, and the foreign nucleotide complexes have a combined length of no more than about 5000 nucleotides, no more than about 4000 nucleotides, no more than about 3000 nucleotides, no more than about 2000 nucleotides, no more than about 1000 nucleotides, or no more than about 800.

The foreign gene inserted in the recombinant antigenomic RNA of the invention preferably encode a substance selected from the group consisting of chloramphenical acetyltransferase, GFP, an avian cytokine, and an immunogenic protein of influenza virus, infectious bursal disease virus, rotavirus, infectious bronchitis virus, infectious laryngotracheitis virus, chicken anemia virus, Marek's disease virus, avian leukosis virus, avian adenovirus, or avian pneumovirus. The foreign gene may encode an immunogenic protein of a non-avian pathogen, e.g. influenza virus, SARS-causing virus, human respiratory syncytial virus, human immunodeficiency virus, hepatitis A virus, hepatitis B virus, hepatitis C virus, poliovirus, rabies virus, Hendra virus, Nipah virus, human parainfluenza 3 virus, measles virus, mumps virus, Ebola virus, Marburg virus, West Nile disease virus, Japanese encephalitis virus, Dengue virus, Hantavirus, Rift Valley fever virus, Lassa fever virus, herpes simplex virus and yellow fever virus.

When more than one foreign gene encoding the avian cytokine is inserted, the foreign genes may encode the same or different avian cytokines, such as avian interleukins, e.g. IL-2 and IL-4.

Examples of the foreign gene encoding an immunogenic protein of an avian pathogen are HA or NA gene of influenza virus, VP2 or polyprotein gene of infectious bursal disease virus, S or S1 gene of infectious bronchitis virus, glycoprotein gene of infectious laryngotracheitis virus, e.g. gB, gC, gD, the complete genome of chicken anemia virus, glycoprotein gene of Marek's disease virus, envelope gene of avian leukosis virus, avian adenovirus, and G or F gene of avian pneumovirus.

Examples of the foreign gene encoding an immunogenic protein of a non-avian pathogen are HA or NA gene of influenza virus, S or S1 gene of SARS-causing virus, G or F gene of human respiratory syncytial virus, gp60, gp120 or gp41 gene of human immunodeficiency virus, surface antigen gene of hepatitis A virus, surface antigen gene of hepatitis B virus, surface antigen of hepatitis C virus, capsid proteins gene of poliovirus, G protein gene of rabies virus, G or F protein gene of Hendra virus, G or F protein gene of Nipah virus, HN or F protein gene of human parainfluenza 3 virus, H or F protein gene of measles virus, HN or F protein gene of mumps virus, G protein gene of Ebola virus, G protein gene of Marburg virus, envelope protein gene of West Nile disease virus, envelope protein gene of Japanese encephalitis virus, envelope protein gene of Dengue virus, glycoprotein gene of Hantavirus, glycoprotein gene of Rift Valley fever virus, G1 or G2 protein gene of Lassa fever virus, glycoprotein genes of herpes simplex virus, and glycoprotein gene of yellow fever virus.

The present invention is also directed toward an antigenomic RNA of NDV carrying one or more foreign genes inserted before the NP gene, between the P and M genes, and/or between the HN and L genes, wherein at least one of the foreign genes encodes a tumor antigen, such as pg100, MAGE1, MAGE3 and CDK4.

In the recombinant antigenomic RNA of the invention, the foreign nucleotide complexes preferably are inserted before the NP gene, and/or between the P and M genes. More preferably, at least one of the foreign nucleotide complexes is inserted before the NP gene. In some embodiments of the recombinant antigenomic RNA, at least one of the foreign nucleotide complexes is inserted before the NP gene and at least one of the foreign nucleotide complexes is inserted between the P and M genes. In some embodiments, at least one of the foreign nucleotide complexes is inserted before the NP gene and at least one of the foreign nucleotide complexes is inserted between the HN and L genes. In still some embodiments, at least one of the foreign nucleotide complexes is inserted before the NP gene, at least one of the foreign nucleotide complexes is inserted between the P and M genes, and at least one of the foreign nucleotide complexes is inserted between the HN and L genes. In yet some embodiments, at least one of the foreign nucleotide complexes is inserted between the P and M genes. Most preferably, the foreign nucleotide complexes are inserted only before the NP gene.

NDV grows to very high titers ($<10^9$ PFU/ml) in many cell lines and eggs and elicits strong humoral and cellular immune responses in vivo. NDV naturally infects via respiratory and alimentary tract mucosal surfaces. NDV replicates in the cytoplasm of infected cells and does not undergo genetic recombination, making vaccine vectors based on the recombinant NDV carrying foreign genes stable and safe. Due to these characteristics of NDV described herein, recombinant NDVs that can express foreign genes carried in the recombinant NDVs are good vaccines, wherein the foreign genes encode immunogenic proteins of pathogens.

The recombinant NDV of the invention carrying one or more inserted foreign genes show robust expression of the foreign genes. Moreover, the recombinant NDV expressing one or more of the foreign gene can replicate in cell culture and in vivo. NDV recombinants expressing heterologous proteins could be used as multivalent vaccines.

The recombinant NDV generated from the recombinant antigenomic RNA carrying one or more foreign genes inserted according to the invention can also be used as an inactivated vaccine. The vaccine or vaccine vector based on the recombinant NDV generated from the recombinant antigenomic RNA carrying one or more foreign genes inserted according to the invention can be administered topically, via the respiratory route, orally or via an injection. The dose of the vaccine or vaccine vector to be used can be readily determined by a person skilled in the art based on the disease, the host subject species, and the age, sex and/or health condition of the host subject involved.

This study demonstrates for the first time that ILTV gD is a major protective immunogen capable of inducing protective immune responses against ILTV infection in chickens.

As used herein, the term gD also includes analogs and truncated forms that are immunologically cross-reactive with natural gD. By gD is intended gD from other strains of ILTV, or any other newly identified strain or field isolate of ILTV.

gD can be used as a homo-oligomer, containing more than one gD monomer, e.g. gD dimers, trimers or tetramers, or any higher-order homo-oligomers of gD. The oligomers may contain one, two, or several different monomers of gD obtained from different strains of ILTV including for example USDA strain, ILTV strain 63140/C/08/BR, Strain A489, Australian CSW-1 ILTV strain, SA-2 ILTV, A-20 ILTV, Serva-ILTV, Strain V1-99, Strain Q1-96, Strain N3-04, Strain S2-04, Trachivax ILTV vaccine strain, and other strains and field isolates. Such mixed oligomers are still homo-oligomers within the scope of this invention, and may allow more universal diagnosis, prophylaxis or treatment of ILTV.

In one embodiment, ILTV gD can be recombinantly expressed, isolated and purified using methods well known in the art. The term 'purified' as applied to proteins herein refers to a composition wherein the desired protein comprises at least 35% of the total protein component in the composition. The desired protein preferably comprises at least 40%, more preferably at least about 50%, more preferably at least about 60%, still more preferably at least about 70%, even more preferably at least about 80%, even more preferably at least about 90%, and most preferably at least about 95% of the total protein component. The composition may contain other compounds such as carbohydrates, salts, lipids, solvents, and the like, without affecting the determination of the percentage purity as used herein. An 'isolated' protein intends a composition that is at least 35% pure.

The term 'essentially purified proteins' refers to proteins purified such that they can be used for in vitro diagnostic methods and as a prophylactic compound. These proteins are substantially free from cellular proteins, vector-derived proteins or other ILTV components. The proteins of the present invention are purified to homogeneity, at least 80% pure, preferably, 90%, more preferably 95%, more preferably 97%, more preferably 98%, more preferably 99%, even more preferably 99.5%.

The term 'recombinantly expressed' used within the context of the present invention refers to the fact that the proteins of the present invention are produced by recombinant expression methods be it in prokaryotes, or lower or higher eukaryotes.

Therefore, the present invention relates to a DNA or cDNA segment which encodes ILTV gD as described above. Genome sequences from different strains of ILTV have been published and are publicly available. DNA or nucleic acid sequences to which the invention also relates include fragments of the gD gene containing protective epitopes or antigenic determinants. The sequence of nucleic acids encoding antigens may be generated in any manner, including for example, chemical synthesis or DNA replication or reverse transcription or transcription, which are based on the information provided by the sequence bases in the region(s) from which the polynucleotide is derived. In addition, combinations of regions corresponding to that of the designated sequence may be modified in ways known in the art to be consistent with an intended use. It is understood in the art that certain advantageous steps can be taken to increase the antigenicity of an encoded protein by modifying its amino acid composition. Such changes in amino acid composition can be introduced by modifying the genetic sequence encoding the protein. It is contemplated that all such modifications and variations of the ILTV gD gene are equivalents within the scope of the present invention.

The DNA encoding the desired antigen can be introduced into the cell in any suitable form including, the fragment alone, in a vector such as a linearized plasmid, a circular plasmid, a plasmid capable of replication, an episome, RNA, a viral vector, an expression vector, etc. Individual expression vectors capable of expressing the genetic material can be produced using standard recombinant techniques. Please see e.g., Maniatis et al., 1985 *Molecular Cloning: A Laboratory Manual or DNA Cloning*, Vol. I and II (D. N. Glover, ed., 1985) for general cloning methods.

The DNA, alone or in a vector, can be delivered by injection into the tissue of the recipient, oral or pulmonary delivery. Any of these methods can be used to deliver DNA as long as the DNA is expressed and the desired antigen is made in the cell.

The present invention more particularly relates to a composition comprising at least one of the above-specified peptides or a recombinant gD protein composition as defined above, for use as a vaccine for immunizing avian subject against ILT, comprising administering a sufficient amount of the composition possibly accompanied by pharmaceutically acceptable adjuvant(s), to produce an immune response. The vaccine composition of the present invention is expected to provide cross-protection against infection from other ILTV strains, since the immunogenic antigen gD is highly conserved between strains.

Immunogenic compositions can be prepared according to methods known in the art. The present compositions comprise an immunogenic amount of a recombinant protein or peptides as defined above, usually combined with a pharmaceutically acceptable carrier, preferably further comprising an adjuvant.

Pharmaceutically acceptable carriers include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers; and inactive virus particles. Such carriers are well known to those of ordinary skill in the art.

The immunogenic compositions typically will contain pharmaceutically acceptable vehicles, such as water, saline, glycerol, ethanol, etc. Additionally, auxiliary substances, such as wetting or emulsifying agents, pH buffering substances, preservatives, and the like, may be included in such vehicles.

Typically, the immunogenic compositions are prepared as liquid solutions or suspensions; solid forms suitable for solution in, or suspension in, liquid vehicles prior to administration may also be prepared. Immunogenic compositions used as vaccines comprise a 'sufficient amount' or 'an immunologically effective amount' of the protein gD or a vector which will produce a sufficient amount of the gD protein in the subject. 'Immunologically effective amount', means that the administration of that amount to an individual, either in a single dose or as part of a series, is effective for treatment, as defined above. This amount varies depending upon the health and physical condition of the subject to be treated, the formulation of the vaccine, and other relevant factors. It is expected that the amount will fall in a relatively broad range that can be determined through routine trials. Usually, the amount will vary from 0.01 to 1000 ug/dose, more particularly from about 1.0 to 100 ug/dose most preferably from about 10 to 50 ug/dose.

Administration of the compounds or vaccines, disclosed herein may be carried out by any suitable means, including parenteral injection (such as intraperitoneal, subcutaneous, or intramuscular injection), in ova injection of birds, orally, oculonasal, or by topical application to an airway surface carried out by inhalation administration, such as by creating respirable particles of a pharmaceutical formulation (including both solid particles and liquid particles) as an aerosol suspension, and then causing the subject to inhale the respirable particles. Methods and apparatus for administering respirable particles of pharmaceutical formulations are well known, and any conventional technique can be employed. Oral administration may be in the form of an ingestable liquid or solid formulation.

The treatment may be given in a single dose schedule, or preferably a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, (v) 0 and 14 days, or other schedules sufficient to elicit the desired responses expected to reduce disease symptoms, or reduce severity of disease.

The present invention also provides kits which are useful for carrying out the present invention. The present kits comprise a first container means containing the above-described antibodies. The kit also comprises other container means containing solutions necessary or convenient for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means. The container means may be in another container means, e.g. a box or a bag, along with the written information.

All publications, including, but not limited to patents and patent applications, cited in this specification are herein incorporated by reference as if each individual publication were specifically and individually indicated to be incorporated by reference herein as though fully set forth.

The invention is further described in detail to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided therein.

The following Materials and Methods were used in the following Examples.

Materials and Methods

Cells, Viruses, Adjuvants and Antisera Production in Rabbits

Human epidermoid carcinoma, chicken embryo fibroblast, and Vero cells were grown in Dulbecco's modified Eagle medium (DMEM) containing 10% fetal bovine serum (FBS) and maintained in DMEM with 5% FBS. Chicken embryo liver cells (CELi) and chicken embryo kidney cells (CEK) were harvested from 11-12 day-old and 18-19 day-old specific pathogen free embryonated chicken eggs, respectively, by conventional trypsin disaggregation method and were grown in Eagle's minimal essential medium (EMEM) containing 10% FBS. The chicken-embryo-origin ILTV vaccine Trachivax was obtained from the Schering-Plough Animal Health Corp, Millsboro, Del. The Vectormune HVT-LT vaccine was obtained from the Ceva Animal Health, Lenexa, Kans. The USDA challenge strain of ILTV was obtained from the National Veterinary Services Laboratory, Ames, Iowa, USA. The USDA ILTV challenge strain was propagated on monolayers of chicken embryo liver cells. Recombinant NDV strains were grown in 9-day-old specific-pathogen-free (SPF) embryonated chicken eggs. The modified vaccinia virus Ankara strain expressing T7 RNA polymerase was grown in primary chicken embryo fibroblast cells. The Freund's complete and the Freund's incomplete adjuvants were obtained from the Sigma-Aldrich, St-Louis, Mo. The anti-ILTV antiserum was raised in rabbits against the synthetic peptides of gB, gC, and gD of ILTV. Synthetic peptides of ILTV gB, gC, and gD were obtained from GenScript USA Inc., Piscataway, N.J., USA. The sequences of the synthetic peptides used are shown in table below. Briefly, rabbits were injected with the synthetic peptides of gB, gC, and gD initially, and followed by two booster doses at 14 day interval time. Synthetic peptides were homogenized with the Freund's complete adjuvant in equal proportion for the initial dose, and for the subsequent booster doses, mixture of synthetic peptides and Freund's incomplete adjuvant in equal proportion was used. The rabbits were bled after the final booster and the serum samples were collected. The specificity of the antiserum (designated as anti-ILTV gB, gC, and gD antisera) was determined by Western blot analysis.

TABLE 1

Sequences of the synthetic peptides used for the production of rabbit polyclonal anti-ILTV sera and their respective anti-ILTV antibody titers.

| Peptide | Sequence | Anti-ILTV antibody titers[a] after 2nd booster |
|---|---|---|
| gB1 | LPRGRERRQAAGRRT 432 to 445 of SEQ ID NO: 2 | Anti-ILTV- gB- : 6582 |
| gB2 | AIGSGAPKEPQIRNR 59 to 73 of SEQ ID NO: 2 | |
| gB3 | RNLFRRKPRTKEDDY 854 to 868 of SEQ ID NO: 2 | |

TABLE 1-continued

Sequences of the synthetic peptides used for the production of rabbit polyclonal anti-ILTV sera and their respective anti-ILTV antibody titers.

| Peptide | Sequence | Anti-ILTV antibody titers[a] after 2nd booster |
|---|---|---|
| gC1 | ELEIRGEASQPLPSK 234 to 248 of SEQ ID NO: 4 | Anti-ILTV- gC- : 5394 |
| gC2 | WTPPEDFEMLRPETR 255 to 269 of SEQ ID NO: 4 | |
| gC3 | FSDRPLTHEESVKVE 46 to 60 of SEQ ID NO: 4 | |
| gD1 | LRKKNPSAPDPRPDS 246 to 260 of SEQ ID NO: 6 | Anti-ILTV- gD- : 5987 |
| gD2 | PEDTEHDDPNSDPDY 314 to 328 of SEQ ID NO: 6 | |
| gD3 | MISAAKEKEKGGPFE 75 to 89 of SEQ ID NO: 6 | |

[a]Anti ILTV titers were determined by ELISA (ProFLOCK® LT ELISA Kit, Synbiotics Corp., San Diego, CA) following the manufacturer's instructions.

Construction and Generation of rNDVs Containing ILTV gB, gC, and gD Genes

The ILTV gB, gC, and gD (GenBank accession number NC_06623) open reading frames were PCR amplified from the purified ILTV DNA and were subsequently cloned into the pCR 4 TOPO vector (Invitrogen). The nucleic acid sequence of gB is shown in SEQ ID NO:1, and the amino acid sequence is shown in SEQ ID NO:2. The nucleic acid sequence of gC in SEQ ID NO:3, and the amino acid sequence is shown in SEQ ID NO:4. The nucleic acid sequence of gD is shown in SEQ ID NO:5, and the amino acid sequence is shown in SEQ ID NO:6. The integrity of the gB, gC, and gD genes was confirmed by sequence analysis. To construct an insert encoding the modified gB glycoprotein, the complete ORF (excluding the stop codon) of the gB gene was fused to the last 12 amino acids of the NDV F protein cytoplasmic tail (amino acids 542-553). The gB open reading frame (ORF) was amplified by PCR using forward primer (gBF)

(SEQ ID NO: 7)
5'GATC*TTAATTAA*TTAGAAAAAATACGGGTAGAAGCCACCatgcaatc ctacatcgccgtg3'

(The primer contains a PacI site (italicized), the NDV gene end transcriptional signal (italicized, underlined), the NDV gene start transcriptional signal (underlined), the T intergenic nucleotide (boldface), additional nucleotide in order to maintain the genome length as a multiple of six (italicized and bold), a six nucleotide Kozak sequence for efficient translation (bold, underlined) and the ILTV specific sequence is in small case) and a reverse primer (gBR)

(SEQ ID NO: 8)
5'GATC*TTAATTAA*TCACATTTTTGTAGTGGCTCTCATCTGATCTAGAGT

ATTttcgtcttcgctttcttc3'

(The primer contains a PacI site (italicized), sequence specific to last 12 amino acids of the NDV F gene (underlined) and sequence specific to ILTV gB gene (small case) and a stop codon (bold face)). After amplification, the 2688 base pair product was cloned into pCR 4-Topo vector (Invitrogen) and sequenced to confirm the correct gB gene structure and the absence of any mutations. The glycoprotein gC and gD inserts were constructed by fusing the ectodomain of glycoproteins to the transmembrane domain and cytoplasmic tail (amino acids 497-553) of the NDV F protein by overlapping PCR. Briefly, the gC gene of ILTV was amplified by PCR using a forward primer (gCF)

(SEQ ID NO: 9)
5'GATC*TTAATTAA*TTAGAAAAAATACGGGTAGAAGCCACCatgcagca tcagagtactgcg 3'

(The primer and its constituents are notated similarly as described for the gBF primer) and a reverse primer (gC1) 5"-GACTGCGGGGAATCCTTGCCGCATTG-3" (sequence represents the sequence specific to ILTV gC gene ORF at position 1133-1158 of SEQ ID NO:3). The transmembrane domain and cytoplasmic tail sequences of the NDV F gene was PCR amplified using forward primer (gC2) 5"-CAATGCGGCAAGGATTCCCCGCAGTCagcacatct-gctctcattac-3" (SEQ ID NO:10) (sequence specific to ILTV gC gene overlap is in uppercase and NDV F gene transmembrane-specific sequence is in lower case) and a reverse primer (gCR) 5"-gatcTTAATTAATCACAT TTTTG-TAGTGGCTCTCATCTGATC-3" (SEQ ID NO:11)(the PacI site is italicized and NDV F gene cytoplasmic tail-specific sequence is in uppercase). Both the fragments were ligated by overlapping PCR by using forward primer gCF and reverse primer gCR. After amplification, 1332-bp PCR product was cloned into pCR-4 Topo vector (Invitrogen) and sequenced to confirm the correct gC gene structure and absence of any mutations. To make an insert that encodes for the ILTV gD protein, the ILTV gD gene was amplified by PCR using a forward primer (gDF)

(SEQ ID NO: 12)
5'-GATC*TTAATTAA*TTAGAAAAAATACGGGTAGAAGCCGCCACCatgg accgccatttattttgag-3'

(The primer and its constituents are notated similarly as described for gBF primer) and a reverse primer (gD1) 5"-GGGCATGGA GACGGCATTAGAACT-3" (SEQ ID NO:13)(sequence represents the sequence specific to ILTV gD gene ORF at position (1030-1053). The transmembrane domain and cytoplasmic tail sequences of the NDV F gene was PCR amplified using forward primer (gD2) 5"-AGT-TCTAATGCCGTCTCCATG CCCagcacatctgctctcattacct-3" (SEQ ID NO:14) (sequence specific to ILTV gD gene overlap is in uppercase and NDV F gene transmembrane-specific sequence is in lower case) and a reverse primer (gDR) 5"-gatcTTAATTAATCACATTTTTGTAGTG-GCTCTCATCTGATC-3"(SEQ ID NO:15)(the PacI site is italicized and NDV F gene cytoplasmic tail-specific sequence is in uppercase). Both the fragments were ligated by overlapping PCR by using forward primer gDF and reverse primer gDR. After amplification, 1227-bp PCR product was cloned into pCR-4 Topo vector (Invitrogen) and sequenced to confirm the correct gD gene structure and the absence of any mutations.

Statistical Analysis

Statistically significant differences in data from serological analysis of different immunized chicken groups were evaluated by one-way analysis of variance (ANOVA) (for more than two groups) and t-test (between two groups) with the use of Prism 5.0 (Graph Pad Software Inc., San Diego, Calif.) at a significance level of P<0.05. The significant differences in mean tracheal viral load post-ILTV challenge between experimental groups were determined by one-way ANOVA with Bonferroni post-test for multiple comparisons at 95% confidence intervals. The total clinical scores obtained for different groups at different days post ILTV challenge were entered into a prism 5.0 data sheet and statistically significant differences in data from clinical sign scores at different days post challenge within each group were evaluated by one-way ANOVA. Multiple pair-wise comparisons were made using Bonferroni test with 95% confidence intervals to limit the overall type-I error to 5%.

Immunofluorescence Analysis of the Expression of ILTV Proteins

Immunofluorescence assay was performed to evaluate the cell surface and intracellular expression of ILTV glycoproteins. Briefly, confluent monolayers of vero cells on 4 well Lab-Tek chamber slides were infected with the recombinant viruses at a multiplicity of infection (MOI) of 0.1. At 24 h post-infection, the infected cells were either fixed with 4% paraformaldehyde for 20 min at room temperature for detection of cell surface expression, or fixed in the same manner and permeabilized with 0.2% Triton X-100 in PBS for 10 min for detection of intracellular expression. The cells were blocked for 30 min with 3% normal goat serum and incubated with 1:100 dilution of primary antibody (anti-ILTV gB, gC and gD antisera) for 1 h. The cells were then rinsed with PBS and incubated with 1:1000 dilution of Alexa Fluor 488 conjugated goat anti-rabbit immunoglobulin G antibody (Invitrogen, Carlsbad, Calif.) for 45 min. Subsequently, the cells were washed with PBS and analyzed with a confocal microscope. Immunofluorescence analysis of vero cells infected with rNDV LaSota (data not shown), rNDV gB, rNDV gC, and rNDV gD and processed for intracellular expression of ILTV proteins: gB, gC and gD), as well as surface expression of ILTV proteins: gB, gC and gD using rabbit anti-ILTV antisera.

Construction and Generation of rNDVs Containing ILTV gB, gC, and gD Genes

All the vaccine constructs in the present study were based on the recombinant avirulent NDV strain LaSota. The construction of a full-length cDNA of the antigenomic RNA of NDV strain LaSota has been described previously (Huang et al., 2001, J Gen Virol 82, 1729-1736). In the present study, we have used a previously-described NDV derivative that had been modified to contain a unique PadI site between P and M genes. ILTV gB gene is 2652 nucleotides in length and has a guanine plus cytosine ratio of 44.53%. Detailed scanning of ILTV gB gene demonstrated sequence similarities to NDV strain LaSota gene end signals at nucleotide positions (ORF positions) 564-573 which contains poly A tail consisting of more than six repeated adenine bases flanked by "AG" nucleotides in the upstream region. These signals could be potentially read as gene ends by viral RNA polymerase leading to premature termination of transcription. Therefore, we have modified the gB gene at above said nucleotide positions by overlapping PCR methodology and without altering the amino acid sequence of the encoded protein. The wild type and modified gB with the modified nucleotides and their positions is shown in the Table 2 below. To construct an insert encoding the modified gB, the complete ORF (excluding the stop codon) of the gB gene was fused to the last 12 amino acids of the NDV F protein cytoplasmic tail (amino acids 542-553). The gC and gD inserts were constructed by fusing the ectodomain of glycoproteins to the transmembrane domain and cytoplasmic tail (amino acids 497-553) of the NDV F protein. The inserts bearing the gB, gC, and gD gene of ILTV were cloned at the unique PadI site between P and M genes of full-length NDV plasmid. The resulting plasmids were designated as pNDV gB (SEQ ID NO: 16), pNDV gC (SEQ ID NO:17), and pNDV gD (SEQ ID NO:18), respectively, (FIG. 1) which were used to recover recombinant viruses designated rNDV gB (SEQ ID NO:19), rNDV gC (SEQ ID NO: 20), and rNDV gD (SEQ ID NO:21), respectively, following the procedure described (Huang et al., 2001, supra).

TABLE 2

Modification of gB gene

Mutagenesis at 567, 570 and 573 ORF positions of ILTV gB gene

5'-AAT GAT GAA GCA GAa AAa AAa TTG CCC
CTG GTT CCA TCA CTG-3' (SEQ ID NO: 22)

5'-AAT GAT GAA GCA GAg AAg AAg TTG CCC
CTG GTT CCA TCA CTG-3' (SEQ ID NO: 23)

(Nucleotides at positions 567, 570 and 573 in unmodified gB (top row) are shown in lower case and their modifications are shown in modified gB (bottom row) in lower case italicized. Underlined sequence in the unmodified gB (top row) indicates the sequence showing close similarities to NDV transcriptional gene end signal: TTA GAA AAA A (SEQ ID NO: 24)(NDV gene end transcriptional signal).

Expression and Incorporation of ILTV gB, gC, and gD by rNDVs

The expression of ILTV gB, gC, and gD was examined by Western blot, immunofluorescence, and flow cytometry while their incorporation by rNDVs was evaluated by Western blot and immunoelectron microscopy assays as described (Nayak et al., 2009, supra; Khattar et al., 2010, Vaccine 28, 3159-70; Khattar et al., 2011, J Virol 85, 10529-41; Nayak et al., 2010, J Virol 84, 2408-20), using anti-peptide antisera raised in rabbits against ILTV gB, gC, and gD.

DF1 cells were infected with the individual rNDV constructs and 48 h later the cells were collected and processed to prepare cell lysates. Allantoic fluid from embryonated eggs infected with the individual constructs was clarified and subjected to centrifugation on sucrose gradients to make partially purified preparations of virus particles. For purification of ILT virions, infected Chicken embryo liver cell lysates were cleared by centrifugation at 4500×g for 15 min followed by sedimentation of ILTV by centrifugation through a cushion of 40% sucrose in phosphate buffered saline (PBS), and purified in a continuous 20-50% sucrose gradient at 25,000 rpm and 4° C. for 1 and half hour. The virions were resuspended in PBS. Total CEK cell lysates were prepared 24 h after infection with ILTV at a multiplicity (MOI) of 5 PFU per cell. These samples were analyzed by Western blot analysis using rabbit anti-ILTV gB, gC, and gD antisera (see text for details).

Flow cytometry analysis of the surface expression of ILTV proteins. DF1 cells were infected with the rNDV gB (panel A), rNDV gC (panel B) or rNDV gD (panel C) viruses at a MOI of 5, in parallel with cells that were mock-infected or infected with the rNDV LaSota empty vector. At 24 h post-infection, the cells were probed with rabbit anti-ILTV sera, followed by incubation with Alexa Fluor 488 conjugated goat anti-rabbit IgG antibody and analyzed by Flowjo program of FACSRIA II flow cytometer. Values represent averages of the results obtained from two independent experiments.

Biological Characterization of the Recombinant Viruses

The multicycle growth kinetics of rNDVs expressing ILTV gB, gC, and gD were determined in SPF embryonated chicken eggs (Nayak et al., 2010 supra). The pathogenicity of recombinant viruses was determined by the mean death time (MDT) test in 9-day-old SPF embryonated chicken eggs (Nayak et al., 2010, supra).

Immunization and Challenge Experiments in Chickens

The immunogenicity and protective efficacy of the recombinant viruses against virulent ILTV and virulent NDV challenges were evaluated in specific pathogen free (SPF) chickens obtained from Charles River Laboratories, Wilmington, Mass., USA. A total of 140 two-week-old SPF white leghorn chickens were assigned to 10 groups of 14 chickens each and received a prime-boost immunization on days 0 and 14 with the indicated virus by the indicated routes as described below (the day 0 and day 14 doses are identical). Briefly, the control group remained unvaccinated and served later as challenge controls. Group CEO and HVT-LT were vaccinated with the ILTV-CEO vaccine Trachivax and the recombinant herpes virus of turkey expressing laryngotracheitis antigens vaccine HVT-LT respectively, as per the manufacturer's recommendations. The groups gB, gC, and gD received a virus rNDV gB, rNDV gC, and rNDV gD, respectively, by oculonasal route with a dose of $10^6$ TCID$_{50}$/mL, whereas the groups gB+gC, gB+gD, gC+gD, and gB+gC+gD were immunized through the same route with a multivalent vaccine consisting of a mixture of $10^6$ TCID$_{50}$/mL each of rNDV gB and rNDV gC, a mixture of $10^6$ TCID$_{50}$/mL each of rNDV gB and rNDV gD, a mixture of $10^6$ TCID$_{50}$/mL each of rNDV gC and rNDV gD, and a mixture of $10^6$ TCID$_{50}$/mL each of rNDV gB, rNDV gC, and rNDV gD respectively. Each oculonasal immunization involved administration of allantoic fluid containing the indicated rNDVs in a total volume of 200 µL (50 µL in each eye and nostril). Blood was collected on days 12 and 21 and sera were separated from the blood samples for analyzing antibody response. Two weeks following booster immunization, chickens in each group were divided into two subgroups of 7 chickens each, one subgroup was transferred to enhanced BSL3 facility for virulent NDV challenge. The remaining chickens were kept in a BSL-2+ facility for virulent ILTV challenge. For virulent NDV challenge, each bird in all groups (n=7) was challenged by oculonasal route with $10^{4.5}$EID$_{50}$ of velogenic NDV strain Texas GB. All birds were observed daily for 2 weeks for clinical signs (death, paralysis, and torticollis) of neurotropic NDV. In order to determine the replication of challenge virus, two chickens from each group were sacrificed on $3^{rd}$ day post challenge. Tissue sample (trachea, lungs, and brain) were collected, homogenized in cell culture medium (1 gm/10 ml) and clarified by centrifugation. The challenge virus titers in tissue samples were determined by limiting dilution in DF-1 cells. For virulent ILTV challenge, each bird in all groups (n=7) were challenged with $6.3 \times 10^4$ TCID$_{50}$ of a USDA ILT challenge virus in a total volume of 200 µL (100 µL intratracheally and 50 µL in each nostril). All birds were observed daily for 14 days post challenge for clinical signs of dyspnea, conjunctivitis, depression, and mortality. A daily total clinical sign score was calculated for each group following the scoring system described by Oldoni et al. (Oldoni et al., 2009, Avian Pathol 38, 47-53). In order to determine the replication of challenge virus as well as to assess the viability of trachea, two chickens from each group were sacrificed on 4th day post challenge. A part of the tracheal tissue was collected in buffered formalin for histopathology and the remaining tissue was collected in cell culture medium (1 g/mL) and homogenized. The homogenate was used to determine the challenge virus titers by limiting dilutions in chicken embryo liver cells. The remaining five chickens in each group were observed daily for 14 days for disease signs and mortality following challenge. Virulent NDV Texas-GB challenge experiment was carried out in an enhanced BSL3 containment facility certified by the USDA, with the investigators wearing appropriate protective equipment. All of the animals used in this study were cared for in accordance with established guidelines, and the experimental protocols were performed with the approval of Institutional Animal Care and Use Committee (IACUC) of the University of Maryland and under Animal Welfare Association (AWA) regulations.

Scoring of Clinical Signs

Blind scoring of clinical signs was performed following the scoring system described by Oldoni et al. (supra).

Virological and Serological Assays

Limiting dilution (TCID50), virus neutralization test (VNT) and hemagglutination inhibition (HI) assays were performed following standard protocols (Nayak et al., 2010, supra; Hierholzer and Killington, 1996, In Mahy and Kangro Eds. Virology Methods Manual, Academic Press, London).

Histopathology Examination

Tracheal tissues collected from the birds 4th day post ILTV challenge were processed for sections. The sections were stained with hematoxylin and eosin and the blind histological scoring was performed based on the severity of inflammation, necrosis, ulceration, and the presence of viral inclusions in the tracheal epithelium. Inflammatory, necrotic, and ulcerative lesions were scored as 0 (no lesions), + (minimal lesions), ++ (mild lesions), +++ (moderate lesions), and ++++ (severe lesions). Inclusion bodies were scored as either + (present) or − (absent). An overall histological score was given to each bird on a 0 to ++++ scale as described above.

Transfection and Recovery of Recombinant NDV

Transfection was carried out as described previously (Krishnamurthy et al., 2000, Virol 278, 168-182). Briefly, HEp-2 cells (6-well plates) were infected at 1 p.f.u. per cell with modified vaccinia virus (MVA/T7) expressing T7 RNA polymerase. A mixture of three plasmids containing NDV NP, P and L gene ORFs under the control of the T7 promoter (2.5, 1.5 and 0.5 µg per well, respectively) and a fourth plasmid encoding either the NDV or NDV plus foreign genes, antigenome (5 µg) was transfected with Lipofectamine Plus (Life Technologies). Four h after transfection, cells were washed and the medium was replaced with 2 ml fresh medium (DMEM with 0% fetal calf serum and 1 µg/ml acetyl trypsin). Three days post-transfection, the supernatant was harvested for virus, clarified and used to infect fresh HEp-2 cells. Three days later, 100 µl supernatant was taken to inoculate into the allantoic cavity of 10-day-old embryonated SPF eggs. After 96 h, allantoic fluid was harvested and tested for haemagglutinating (HA) activity.

Recovery of Infectious Recombinant NDV from cDNA

A recombinant vaccinia virus-based transfection system was used to recover infectious recombinant NDV from cDNA. HEp-2 cells were infected with recombinant vaccinia virus (MVA/T7) capable of synthesizing T7 RNA polymerase. Simultaneously, the cells were transfected with the recombinant NDV encoding the desired foreign antigen, along with plasmids encoding proteins of RNP complex, namely NP (pNP), P (pP), and L (pL). In a parallel transfection, plasmid pL was excluded in the experiment to serve as a negative control. Four days after transfection, the supernatant was used in either of two different ways to recover the virus. The supernatant was either injected into the allantoic cavities of 9-day-old embryonated eggs or amplified further in HEp-2 cells and DF1 cells (chicken embryo fibroblast cell line). The allantoic fluid of the eggs injected with the transfectant gave a positive hemagglutination (HA) titer ranging from 32 to 2048. The cell culture-amplified supernatant gave NDV titers slightly in excess of 104 plaque-forming units (PFU)/ml at the end of passage 1 and slightly in excess of 108 PFU/ml at the end of passage 2. Thus, the cotransfection method of rescue resulted in efficient recovery of NDV. After passage 2, the cell culture passaged virus was plaque purified to eliminate vaccinia virus and then individual plaques were used to inject 9-day-old embryonated eggs. No plaques were visualized nor HA titer quantified in the case of negative controls, further confirming the specificity of recovery of NDV from cDNA. The recovered virus was designated, for example rNDVgB, when the foreign antigen was gB, to distinguish it from the parental wild-type NDV, or in this case, pNDV gB.

Example 1

Distinguishing Features of Vector Lasota Having 527 Mutation (Y527A) in its F Gene Over the Wild Type Lasota (WT) Vector The Newcastle disease virus Fusion protein (F) is a major contributor to the protective immunity of the NDV vaccine and also the primary determinant of NDV virulence and pathogenicity in chickens. The cytoplasmic tail of the NDV fusion protein contains a tyrosine amino acid at position 527 (of the "F" protein, SEQ ID NO:25) which is found to be conserved among different strains of NDV. To evaluate the effect of point mutation at this conserved tyrosine residue, tyrosine was substituted to alanine, cloned into PBR322 to produce pNDVY527A (SEQ ID NO:26) and the resulting Newcastle disease virus, rNDVY527A (SEQ ID NO:27), with phenotype designated "Y527A" was compared with the wild type Lasota (WT) virus for its ability to multiply in cell culture, fusogenicity, levels of surface expression of a foreign protein, pathogenicity to chicken eggs and chicken embryos, and immunogenicity and protective efficacy in chickens against virulent NDV challenge.

Growth Characteristics and Fusion Activity of Y527A:

The multistep growth kinetics and magnitudes of replication of the Y527A and the WT viruses were determined in DF1 cells (data not shown). Both the viruses replicated exponentially until ~40 hpi, after which replication was at a plateau. The magnitudes of replication were similar for WT and the Y527A, however, the titer of the Y527A virus was approximately 1.75 log 10 higher than that of WT at 24 hpi. These results suggest that the mutagenesis in Y527A virus did not compromise its ability to multiply in cell culture but the same has been improved slightly over the WT virus. We further evaluated the fusogenicity of the Y527A virus by measuring the plaque sizes of the mutated virus on DF-1 cell monolayers and comparing them with those of the WT virus (data not shown). We observed significantly larger plaques for Y527A virus compared to their WT counterparts. These results indicated that added mutation in the Y527A virus provides for the enhanced fusogenicity compared to that of the WT virus.

Levels of Surface Expression of a Foreign Protein by Recombinant Viruses:

In our previous study we found that the level of surface expression of a vaccine antigen is the main contributor to the immunogenicity and protective efficacy of the vaccine (Kanabagatte Basavarajappa et al., 2014, Vaccine 32, 3555-63). Therefore, to quantify and compare the levels of surface expression of a foreign antigen by the recombinant viruses, the human respiratory syncytial virus (hRSV) "F" gene was cloned into Y527A and WT viruses at a unique PmeI site present between their P and M genes. Surface expression of the foreign protein was quantified by flowcytometry using DF-1 cells and commercially available monoclonal antibodies against hRSV "F" protein. We observed approximately 5% more surface expression of the hRSV "F" by Y527A virus compared to the surface expression of the foreign protein by the WT virus (data not shown). These results suggest that the mutation in the Y527A virus favors the enhanced surface distribution of the expressed foreign protein on the virus infected cells and presumably this would increase the immunogenicity of the vaccine.

Pathogenicity of the CT Mutant Viruses in Embryonated Chicken Eggs and 1-day-old chicks.

We evaluated the effect of the added mutation on viral pathogenicity using two standard pathogenicity assays, namely, the mean embryo death time (MDT) assay and the intracerebral pathogenicity index (ICPI) test. MDT values were determined in 9-day-old embryonated chicken eggs (data not shown). NDV strains are categorized into three pathotypes on the basis of their MDT values: velogenic (less than 60 h), mesogenic (60 to 90 h), and lentogenic (greater than 90 h). The MDT value of the Y527A mutant (90.60 h) was reduced by 10 h compared to that for WT (100.60 h), which is suggestive of modest increases in virulence but still they were the lentogenic viruses. The pathogenicity of the recombinant viruses was also evaluated by the ICPI test in 1-day-old chicks (data not shown). Lentogenic strains give values close to 0. The ICPI value of Y527A virus was 0.2 which is slightly higher than that for WT (0.11) which is indicative of increased pathogenicity, although the increases was modest.

Immunogenicity and Protective Efficacy of Recombinant Viruses in Chickens.

The immunogenicity and protective efficacy of the recombinant viruses against virulent NDV challenge was evaluated in specific pathogen free (SPF) chickens obtained from Charles River Laboratories, Wilmington, Mass., USA. A total of 21 two-week-old SPF white leghorn chickens were assigned to 3 groups of 6 chickens each and received a immunization on days 0 with the indicated virus by the indicated routes as described below. The control group remained unvaccinated and served later as challenge controls. The groups Y527A and WT received a virus Y527A and WT, respectively, by oculonasal route with a dose of $10^6$ TCID50/mL. Each oculonasal immunization involved administration of allantoic fluid containing the indicated recombinant viruses in a total volume of 200 μL (50 μL in each eye and nostril). Blood was collected on day 21 and sera were separated from the blood samples for analyzing antibody response. After 21 days, birds were transferred to enhanced BSL3 facility for virulent NDV challenge. For virulent NDV challenge, each bird in all groups (n=7) were challenged by oculonasal route with $10^{4.5}$EID50 of velogenic NDV strain Texas GB. All birds were observed daily for 2 weeks for clinical signs (death, paralysis, and torticollis) of neurotropic NDV. In order to determine the replication of challenge virus, two chickens from each group were sacrificed on 3rd day post challenge. Tissue sample (trachea, lungs, and brain) were collected, homogenized in cell culture medium (1 gm/10 ml) and clarified by centrifugation. The challenge virus titers in tissue samples were determined by limiting dilution in DF-1 cells. NDV-specific antibody responses in the sera collected on $21^{st}$ day post immunization was assayed using HI test. High levels of NDV-specific serum antibodies were detected for both Y527A and WT groups (data not shown). However, the Y527A group possessed approximately 0.5 log 2 higher HI titers than WT group indicating the enhanced immunogenicity of the mutated Y527A virus. Upon challenge on 22nd day post immunization with highly-virulent NDV strain Texas-GB, all of the chickens that had been immunized with recombinant viruses were completely protected from NDV challenge without any disease signs and with no evidence of challenge virus replication in the organs collected 3rd day post challenge. These results suggest that the added mutation in Y527A virus does not reduce its protective efficacy against virulent NDV challenge.

In the present study, we have investigated the effect of mutagenesis of the conserved tyrosine residue in the NDV "F" protein cytoplasmic tail by substituting alanine for tyrosine. The resulting recombinant virus was compared with wild-type Lasota virus for its ability to replicate in cell culture, fusogenicity and levels of surface expression of the foreign protein in vitro. The pathogenicities of the recombinant viruses were evaluated in vivo in embryonated chicken eggs, 1-day-old chicks and 2-week old SPF chickens. Our results indicated that the mutated Y527A virus is superior to WT virus in all of the parameters evaluated in vitro and in vivo. Briefly, Y527A virus showed enhanced replication in cell culture, higher fusogenicity and surface expression of the foreign protein, boosted immunogenicity and protective efficacy compared to the WT virus yet maintaining the lentogenic phenotype similar to the WT virus. Therefore, the hyperfusogenic virus developed in this study may be useful in developing NDV as a better vaccine vector and as an oncolytic agent.

Example 2

Modification of the ILTV gD Gene for Improved Incorporation in NDV Envelope

In the present study, we have generated rNDV expressing and incorporating ILTV gD protein. It has been reported that expression of foreign envelope glycoprotein by recombinant negative sense non-segmented viruses (NNSV) can result in incorporation of the foreign protein into the envelope of NNSV (DiNapoli et al., PNAS, June 2007, 1049788-9793). However, in our study, incorporation of the ILTV gD protein into envelopes of rNDV particles was not found when its intact ORF was cloned into NDV genome, but significant incorporation of gD protein into NDV particles was detected only when its ectodomain (amino acids 1-351) was fused to the NDV F protein cytoplasmic tail and transmembrane domain (amino acids 497-553), suggesting that native ILTV gD protein lack the packaging signals necessary for their incorporation into NDV particles. These results were consistent with the previous study, which has shown that replacement of the transmembrane domain and cytoplasmic tail of the foreign envelope protein with those of a NDV envelope protein increased incorporation of the foreign glycoprotein into the NDV virion (Nayak et al., 2009, supra).

Example 3

Generation of rNDVs Expressing gB, gC, and gD Genes of ILTV

In order to obtain a NDV recombinant which will express and incorporate gB in its envelope, several rNDVs containing chimeric gB were generated (data not shown). However, it was found that when the complete ORF of gB fused to the last 12 amino acids of NDV F protein cytoplasmic tail in a recombinant rNDV gB (FIG. 1), the gB was incorporated into the envelope of NDV. The expression and incorporation of ILTV gC and gD were achieved when their ectodomain was fused to the cytoplasmic tail and transmembrane domain of NDV F protein creating rNDV gC and rNDV gD (described above, FIG. 1), respectively. The genetic stability of the ILTV genes was confirmed by passaging the recombinant viruses in embryonated chicken eggs. Our results showed that the integrity of the added genes and the expression of the foreign proteins were preserved even after 10 egg passages.

Example 4

Expression and Incorporation of ILTV Glycoproteins by Recombinant Viruses

Figure 3:
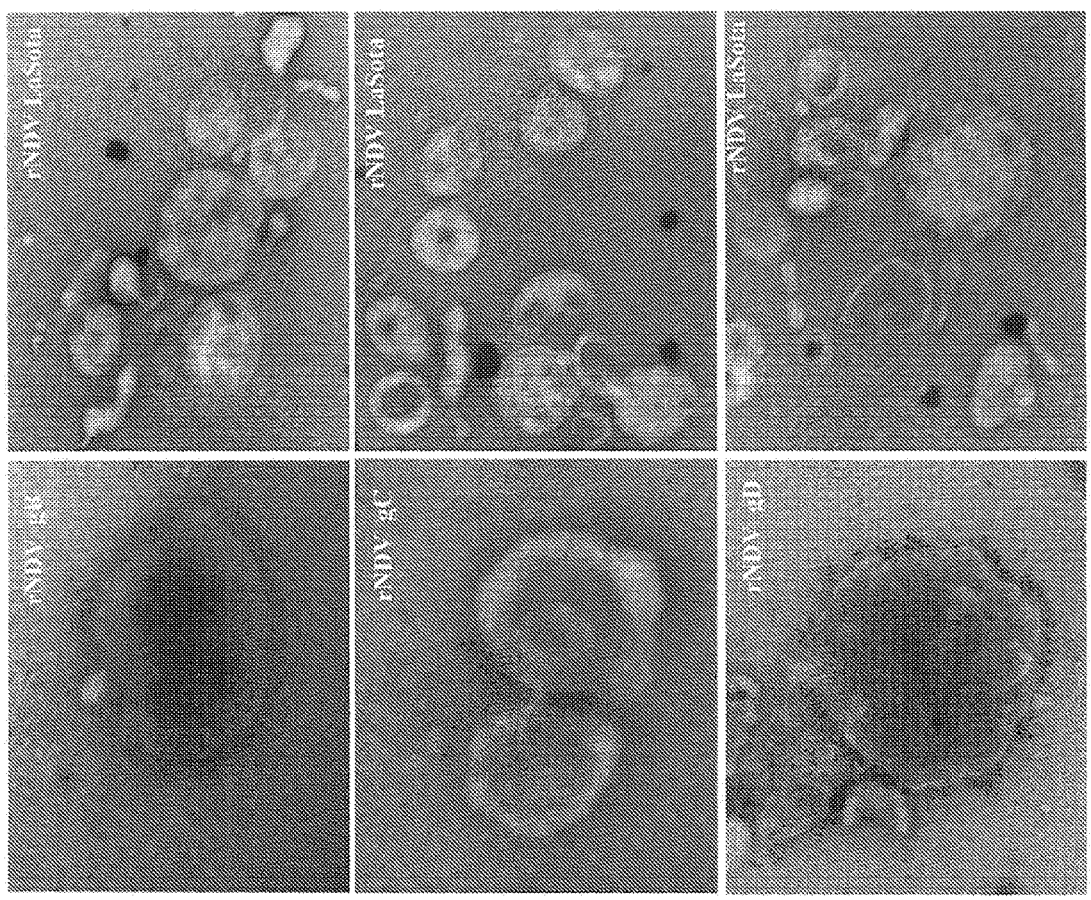
FIG. 3. Immunoelectron microscopy of purified virions of rNDV LaSota, rNDV gB, rNDV gC, and rNDV gD, analyzed using rabbit anti ILTV serum against gB (upper panel), gC (middle panel) or gD (lower panel).

The expression and incorporation of ILTV glycoproteins by recombinant viruses were analyzed by western blot using rabbit anti-ILTV peptide sera. All the three proteins of ILTV that were expressed and incorporated by rNDVs reacted in western blot with the anti-ILTV gB, gC and gD antisera (FIG. 2-1). Western blot analysis detected two bands in purified virus preparations and lysates of cells infected with ILTV and rNDV gB viruses (FIG. 2-1A): these represented (i) the uncleaved monomeric precursor form of gB with an apparent molecular weight of >100 kDa and (ii) C-terminal cleavage product of gB with an apparent molecular weight of 58 kDa (Poulsen and Keeler, 1997, J Gen Virol 78, 2945-2951). Western blot analysis detected 60 kDa band of gC and 42 kDa band of gD (FIGS. 2-1B and C) in ILTV infected cell lysate and ILTV purified virus. However, a band slightly higher than ILTV control was detected in lysates of cell infected with rNDV gC and rNDV gD and purified virus preparations of rNDV gC (FIGS. 2-1B and C), which was likely due to the fused cytoplasmic tail and transmembrane domains of NDV F protein. Approximately 50 kDa band of gD was detected in the lysate of cells infected with rNDV gD virus. Further, the increase in molecular weight to ~65 to 70 kDa of the chimeric gD observed in rNDV gD purified virions (FIG. 2-1C) was presumably due to an artificial aggregation of gD with itself or other proteins occurring during virion preparation. As expected, the ILTV gB, gC, and gD were not detected in lysate of cells infected with rNDV LaSota virus. Immunofluorescence studies showed expression of gB, gC and gD in the cytoplasm and surface of vero cells confirming the internal and surface expression of the foreign proteins. Flowcytometry results indicated a higher level of cell surface expression of gD than cell surface expression of gB and gC (FIG. 2-2). The magnitude of surface expression is in the order: gD>gC>gB with 11-fold and 1.5-fold more surface expression of gD and gC, respectively, compared to the surface expression of gB on infected DF-1 cells. In parallel with the flowcytometry results, the results of immunoelectron microscopy indicated the enhanced incorporation of gD into the envelopes of recombinant viruses compared to the incorporation of gB and gC into the NDV particles (FIG. 3).

Example 5

Biological Characterization of rNDVs Expressing ILTV Proteins

The results of multicycle growth kinetics of rNDVs (FIG. 4-1) indicated the similar growth patterns for rNDV LaSota, rNDV gD, and rNDV gB viruses. At 72 hour post-inoculation, the maximum titers for rNDV LaSota and rNDV gD viruses were similar, but the rNDV gB virus achieved the final titer which was approximately one half log lower compared to rNDV LaSota virus. The rNDV gC grew more slowly and attained the final titer which was approximately two logs lower than that of rNDV LaSota virus. The pathogenicities of the rNDVs were evaluated by MDT test in 9-day old embryonated SPF chicken eggs. The MDTs for the recombinant viruses were 110 h (rNDV LaSota), 125 h (rNDV gB), 124 h (rNDV gC), and 122 h (rNDV gD) which indicated that the rNDVs expressing ILTV proteins were lentogenic viruses (an NDV strain is considered lentogenic or avirulent, if the MDT value is >90 h (Alexander, D J, 1989, Newcastle disease, p. 114-120. In, HG Purchase et al., Eds. A Laboratory Manual for the Isolation and Identification of Avian Pathogens, $3^{rd}$ Ed. American Association for Avian Pathologists, Inc. Kennett Square. PA) and the addition of ILTV genes further decreased the virulence of the NDV vector.

Example 6

Immunogenicity and Protective Efficacies of rNDVs Against Virulent NDV Challenge NDV-specific antibody responses in the sera collected on $21^{st}$ day post immunization was assayed using HI test. High levels of NDV-specific serum antibodies with no statistically significant differences (P<0.05) were detected for all of the immunized groups except control, CEO, and HVT-LT vaccinated birds (FIG. 4-2). Upon challenge on $42^{nd}$ day post immunization with highly-virulent NDV strain Texas-GB, all of the chickens that had been immunized with rNDVs either individually or in combination were completely protected from NDV challenge without any disease signs and with no evidence of challenge virus replication in the organs collected $3^{rd}$ day post challenge. In contrast, all of the chickens in the unvaccinated control group, CEO, and HVT-LT vaccinated groups died within 3 days after chal-
lenge. Therefore, these results suggested that expression of the ILTV glycoproteins does not interfere with protective immunity of NDV LaSota vaccine.

Example 7

ILTV Specific Serum Neutralizing Antibody (NAb) Responses Following Immunization with rNDVs The ability of sera taken after primary and secondary immunization to neutralize the virulent USDA ILTV strain was evaluated by virus neutralization test (VNT) (FIG. 5A). The salient findings are that vector-expressed ILTV gB and gC do not or barely induce detectable virus neutralizing antibodies, whereas gD alone induces higher titers than any combination or an attenuated whole virus ILTV vaccine. Furthermore, it is remarkable that the gD-expressing HVT-based vaccine does not induce detectable neutralizing antibodies. In addition, negligible and inconsistent presence of NAbs were found for CEO, gB, gB+gD, gC+gD and gB+gC+gD vaccinated groups with some birds in each group completely lacking the NAb response, while all birds vaccinated with rNDV gD vaccine showed the presence of neutralizing antibody activity in various titers differed from bird to bird. These results suggested that gD expressed by rNDV gD induce a very good neutralizing antibody response in chickens.

Example 8

Protective Efficacy of rNDVs Against Virulent ILTV Replication in Trachea

To determine the protective efficacy of rNDVs vaccines against virulent ILTV challenge, the challenge virus titers in the tracheal tissue collected from birds on $4^{th}$ day post-challenge were titrated by limiting dilution and are shown in table 1. Our results suggested that rNDV gD and rNDV gB+rNDV gD vaccines were very efficient in preventing challenge virus replication in trachea. The kinetics of challenge virus replication in the trachea was monitored by taking tracheal swabs for the recovery of challenge virus from the remaining 5 birds in each group on $5^{th}$ and $7^{th}$ days post-challenge. Surprisingly, none of the tracheal swabs were positive for ILTV, indicating peak challenge virus titers occurs in trachea up to 4th day post-challenge.

Example 9

Histopathology Examination

Histopathological scoring of tracheal tissue collected on $4^{th}$ day post challenge with ILTV is shown in table 2. Our results suggested that gD expressed by rNDV is very efficient in preventing challenge virus replication in trachea which is reflected by the absence of histopathology as well as viral inclusions in the tracheal epithelium.

TABLE 3

Histopathological characterization of tracheal tissue samples from chickens after challenge with USDA strain of ILTV.

| Group | Animal ID | Overall score | Necrosis | Ulceration | Inflammation | Viral Inclusions |
|---|---|---|---|---|---|---|
| Control group | Bird 1 | ++++ | ++++ | ++++ | +++ | + |
| | Bird 2 | ++++ | ++++ | ++++ | +++ | + |
| CEO | Bird 1 | + | 0 | 0 | + | 0 |
| | Bird 2 | + | 0 | 0 | + | 0 |

TABLE 3-continued

Histopathological characterization of tracheal tissue samples from chickens after challenge with USDA strain of ILTV.

| Group | Animal ID | Overall score | Necrosis | Ulceration | Inflammation | Viral Inclusions |
|---|---|---|---|---|---|---|
| HVT-LT | Bird 1 | ++ | 0 | 0 | ++ | 0 |
|  | Bird 2 | 0 | 0 | 0 | 0 | 0 |
| gB | Bird 1 | +++ | + | +++ | ++ | + |
|  | Bird 2 | +++ | ++ | +++ | +++ | + |
| gC | Bird 1 | ++ | + | + | ++ | +few[a] |
|  | Bird 2 | ++ | 0 | 0 | ++ | 0 |
| gD | Bird 1 | ++ | 0 | 0 | ++ | 0 |
|  | Bird 2 | 0 | 0 | 0 | 0 | 0 |
| gB + gC | Bird 1 | ++ | 0 | 0 | +++ | +few |
|  | Bird 2 | + | 0 | 0 | + | 0 |
| gB + gD | Bird 1 | +++ | 0 | 0 | +++ | 0 |
|  | Bird 2 | +++ | 0 | 0 | +++ | +few |
| gC + gD | Bird 1 | +++ | 0 | 0 | +++ | +few |
|  | Bird 2 | ++ | 0 | 0 | ++ | 0 |
| gB + gC + gD | Bird 1 | ++ | 0 | 0 | +++ | +few |
|  | Bird 2 | +++ | ++ | ++ | +++ | + |

Histology scoring:
0, no lesions;
+, minimal;
++, mild;
+++, moderate;
++++, severe;
+, viral intra-nuclear inclusions present.
[a]Tracheas with few inclusions usually had only focal lesions with the inclusions Example 10

Clinical Signs Score Evaluation

Clinical sign scores were recorded for all of the experimental groups from day 1 to 14 post-challenge and are summarized in FIG. 5B. Briefly, all of the chickens in the control and gB groups showed severe clinical signs until 9$^{th}$ and 6th dpi, respectively. Birds in the gC group showed mild disease signs on 3rd and 4th dpi with signs recorded until 6th dpi. The birds immunized with rNDV gD and multivalent vaccines consisting of combinations of rNDVs did not show disease signs until 14$^{th}$ dpi with the exception of gB+gC+gD group showed severe disease signs between 3rd to 5th dpi. Total clinical scores of gB or gC group were statistically significantly ($P<0.05$) differed while those for gD and multivalent vaccinated groups did not differ significantly from total clinical scores obtained for CEO and HVT-LT groups. The birds immunized with CEO and HVT-LT vaccines showed optimum protection with few birds in HVT-LT group displayed respiratory dyspnea and depression until 5$^{th}$ dpi. The detailed summary of the mortalities in each experimental group following ILTV challenge is given in table 4. These results suggested that rNDV gD and multivalent vaccines consisting of combinations of two rNDVs offered optimal protection without apparent clinical signs and mortality.

TABLE 4

Tracheal viral load in chickens on 4th day post challenge with USDA strain of ILTV and survival of chickens after ILTV challenge.

| Group | Mean tracheal viral load at 4 day post challenge for the indicated groups | No. of survivors on day 14 post-challenge with USDA ILTV/ total no. of birds |
|---|---|---|
| Control | 6.0$^a$ (±0.50)$^A$ | 2/5 |
| Trachivax | 0.0$^B$ | 5/5 |
| HVT-LT | 0.0$^B$ | 5/5 |
| gB | 5.5 (±0.50)$^A$ | 4/5 |
| gC | 2.2 (±2.2)$^A$ | 4/5 |
| gD | 0.0$^B$ | 5/5 |
| gB + gC | 2.3 (±2.3)$^A$ | 5/5 |
| gB + gD | 0.0$^B$ | 5/5 |
| gC + gD | 1.8 (±1.8)$^A$ | 5/5 |
| gB + gC + gD | 1.0 (±1.0)$^A$ | 5/5 |

Discussion

ILT is a highly contagious and economically important disease of poultry world-wide. Currently available vaccine strategies against ILT are not ideal and the knowledge about the protective antigens of ILTV is limited. Therefore, we have used recombinant NDV to evaluate the role of three major ILTV envelope glycoproteins gB, gC, and gD in immunity and protection. These three envelope proteins of ILTV were chosen because they were found to be the major protective antigens in other herpesviruses (Fischer et al., 1003, Vaccine 21, 1732-1741; Hong et al., 2002, Vaccine 20, 1205-1214; Lukacs et al., 1985, J Virol 53, 166-173; Hampl et al., 1984, J Virol 52, 583-590; Zuckermann et al., 1990, J Virol 64, 802-812; Ober et al., 1998, J Virol 72, 4866-4873; Babiuk et al., 1987, Virology 159, 57-66; Chase et al., 1989, J Gen Virol 70, 1561-1569; van Drunen Little-van den Hurk et al., 1990, Vaccine 8, 358-368; Gao et al., 1994, Vaccine 12, 145-152, Zhu and Letchworth, 1996, Vaccine 14, 61-69).

Glycoprotein B (gB) has previously been shown to be an important target for cellular and humoral immune responses capable of conferring protective immunity against ILTV infection (Tong et al, 2001, supra; Sun et al., 2008, supra; York and Fahey, 1991, Avian Pathol 20, 693-704). Likewise, gC in other herpesviruses has been shown to be a target for cellular and humoral immune responses capable of inducing neutralizing antibodies and T-cell immune responses (Fischer et al., 2003, Vaccine 21, 1732-1741; Hong et al., 2002, Vaccine 20, 1205-1214; Lukas et al., 1985, J Virol 53, 166-173; Hampl et al., 1984, J Virol 52, 583-590). However, in this study, immunization with rNDV gB or rNDV gC vaccine did not induce the immune response sufficient to offer complete protection against ILTV challenge. We presume that the incomplete protection offered by these vaccines was due to inefficient envelope incorporation and cell surface expression of gB or gC which might have led to inadequate immune activation leading to partial protection, since there has been a previous report correlating the levels of foreign protein expression and the extent of protection offered by the recombinant viral vaccine (Roberts et al., 2004, J Virol 78, 3196-3199). Further, previous studies with recombinant fowl pox virus (rFPV) vector expressing gB gene of ILTV provided variable protection against morbidity but 100% protection against mortality after virulent ILTV challenge in chickens (Tong et al., 2001, supra; Chen et al., 2011, FEMS Immunol Med Microbiol 63, 289-295). In addition, in another study with rFPV co-expressing NDV fusion (F) and hemagglutinin proteins (HN) and ILTV gB induce detectable ELISA antibody titers against NDV and ILTV, but failed to elicit significant HI titers against NDV (Sun et al., 2008, supra). The immunization of chickens with rFPV based bivalent vaccine against ND and ILT offered 70% protection from death against NDV challenge and 100% protection against ILTV induced mortality, but 70% protection against ILTV induced clinical signs. In our study, immunization of chickens with rNDV based ILTV gB vaccine induces higher levels of HI antibody titers against NDV and detectable levels of NAb titers against ILTV.

Following challenge, the vaccine offered complete protection against NDV challenge and 80% protection against ILTV induced mortality, but failed to protect chickens against ILTV associated respiratory signs. The discrepancy in results between these studies could be due to the differences in the vector systems used to express the ILTV gB. The poor protective efficacy of rNDV gB vaccine against ILTV challenge was attributed to its poor immunogenicity which is represented by the presence of lower neutralizing antibody titers in chickens immunized with rNDV gB vaccine.

In this study, for the first time, we have evaluated the protective efficacy of gD against ILTV challenge. Immunization with rNDV expressing ILTV gD induced a higher level of neutralizing antibodies and offered complete protection to chickens against lethal ILTV challenge. The complete protection offered by gD can be attributed to its superior envelope incorporation and cell surface expression leading to induction of protective immune responses.

Our results are consistent with the results of previous studies reported in other herpesviruses in which glycoprotein D provided higher level of protection against the respective challenge viruses (Khattar et al., 2010, supra; Bennett et al., 1999, J Med Virol 57, 47-56; Zakhartchouk et al., 1999, J Gen Virol 80, 1263-9; Heineman et al., 2004, Vaccine 30, 2558-65). However, it is important to mention that the commercial vectored vaccine HVT-LT also express ILTV gD together with ILTV gI in one virus recombinant (Vagnozzi et al., 2012, supra), but only immunization with rNDV gD induce detectable neutralizing antibodies, and confers better protection than HVT-LT. This observed discrepancy can be explained by the fact that the herpes virus of turkey is a strong inducer of cell-mediated immunity (Fabienne et al., 2010, Vaccine 28, 823-833), but NDV elicits strong humoral and cellular immune responses (Di-Napoli et al., 2007, J Virol 81, 11560-11568) which is reflected by the presence of higher levels of neutralizing antibodies in chickens immunized with rNDV gD vaccine.

Further, our results indicated that, neutralizing antibodies against gD were highly effective in blocking ILTV attachment and entry, as was shown by the absence of histopathology and viral inclusions in the tracheal epithelium post-ILTV challenge. In addition, the intranasal immunization of rNDV gD vaccine might have induced robust mucosal immunity at the respiratory tract, the portal of entry for ILTV, and hence preventing ILTV colonization and replication in the tracheal tissue.

In the present study, the apparent inability of the multivalent vaccines where gD is a part of the combination to completely prevent the challenge virus replication in trachea could be due to interference or competition for growth among the rNDVs expressing gB, gC or gD. These results were consistent with the results of previous study in which rNDV expressing HPAIV M2 protein interfered with the replication of rNDV expressing HA or NA proteins when administered to chickens as a multivalent vaccine (Nayak et al., 2010, supra). In our study, failure to achieve similar levels of envelope incorporation of gB, gC and gD into NDV particles render us unable to clearly evaluate the role of each of these proteins in immunity and protection against virulent ILTV challenge. It is notable that immunization with rNDV gB+rNDV gC or HVT-LT vaccine did not induce a neutralizing antibody response but protected 100% of chickens against virulent ILTV challenge. This is consistent with the fact that humoral antibody response cannot stand alone to provide complete protection against ILT infection (York and Fahey, 1990, Arch Virol 115, 289-297; Fahey and York, 1990, J Gen Virol 2401-2405; Fahey et al., 1983, Avian Pathol 12, 505-514; Honda et al., 1994, J Vet Med Sci 56, 1051-1055). Therefore, to thoroughly assess the immunogenicity and protective efficacy of rNDV vectored ILTV vaccines, the mucosal and cell-mediated immunity would need to be evaluated.

In summary, for the first time we have evaluated the potential of recombinant NDV as a vaccine vector for ILTV. Our study showed that rNDV gD elicited immune response specific to NDV and ILTV and provided complete protection against highly virulent NDV and ILTV challenges. These results demonstrated that ILTV gD is a major protective antigen capable of inducing neutralizing antibodies. The immune response induced by rNDV gC or rNDV gB or multivalent rNDV combinations was not adequate enough to confer complete protection against virulent ILTV challenge. Further, the NDV-vectored vaccine expressing gD alone was superior to a combination vaccine consisting of rNDVs expressing gB, gC, and gD. Therefore, the rNDV-based ILTV gD vaccine generated in this study for the protection of both NDV and ILTV will be highly beneficial to the poultry industry worldwide and could be the promising vaccine candidate to replace the existing ILTV vaccines.

What is claimed is:

1. A cDNA comprising:
a recombinant Newcastle disease virus (NDV) polynucleotide encoding NDV proteins NP, P, M, F, HN and L wherein the F protein contains a tyrosine to alanine substitution at position 527 of SEQ ID NO: 25, and wherein the NDV proteins are positioned between a T7 promoter and a hepatitis delta virus ribozyme sequence.

2. A vector comprising the cDNA of claim 1.

3. The vector of claim 2 wherein said vector is pNDVY527A identified in SEQ ID NO: 26.

4. A cell comprising the vector of claim 3.

5. A method for producing recombinant Newcastle disease virus comprising:
(i) providing cells capable of synthesizing T7 RNA polymerase;
(ii) cotransfecting the cells with a plasmid comprising the cDNA of claim 1, and a mixture of plasmids encoding NP, P, and L proteins; and
(iii) isolating recombinant Newcastle disease virus from medium of cotransfected cells.

6. The method of claim 5, wherein said plasmid in (ii) is pNDVY527A identified in SEQ ID NO: 26.

7. A recombinant Newcastle disease virus (rNDV) produced by the method of claim 6, wherein said rNDV is rNDVY527A identified in SEQ ID NO: 27.

8. A cDNA comprising:
(i) a recombinant Newcastle disease virus (NDV) polynucleotide encoding NDV proteins NP, P, M, F, HN and L wherein the F protein contains a tyrosine to alanine substitution at position 527 of SEQ ID NO: 25, and wherein the NDV proteins are positioned between a T7 promoter and a hepatitis delta virus ribozyme sequence;
and
(ii) one or more polynucleotide encoding an antigen of interest, wherein said one or more polynucleotide is inserted before the NP gene, between the P and M genes, and/or between the HN and L genes.

9. The cDNA of claim 8 wherein said one or more polynucleotide encoding an antigen is inserted between the P and M genes.

10. The cDNA of claim 9 wherein the antigen of interest is from a virus selected from the group consisting of influenza virus, infectious bursal disease virus, rotavirus, infectious bronchitis virus, infectious laryngotracheitis virus, chicken anemia virus, Marek's disease virus, avian leukosis virus, avian adenovirus and avian pneumovirus.

11. The cDNA of claim 10 wherein said antigen is a surface glycoprotein from Infectious Laryngotracheitis virus (ILTV).

12. The cDNA of claim 11 wherein said antigen is one or more ILTV antigen gB, gC, and/or gD, in any combination.

13. A vector comprising the cDNA of claim 12.

14. The vector of claim 13 wherein the vector is a plasmid.

15. The vector of claim 14 wherein said vector is pNDVgB identified in SEQ ID NO: 16, pNDVgC identified in SEQ ID NO: 17, or pNDVgD identified in SEQ ID NO: 18.

16. A cell comprising one or more vector of claim 15.

17. A method for producing recombinant Newcastle disease (rNDV) virus comprising:
(i) providing cells capable of synthesizing T7 RNA polymerase;
(ii) cotransfecting the cells with one or more plasmid of claim 15, and a mixture of plasmids encoding NP, P and L proteins; and
(iii) isolating rNDV from medium of cotransfected cells.

18. The method of claim 17, wherein the amount of the rNDV isolated from step (iii) is higher than a reference value.

\* \* \* \* \*